(12) United States Patent
Beard et al.

(10) Patent No.: US 6,887,896 B1
(45) Date of Patent: May 3, 2005

(54) 7-[(7-ALKOXY)-CHROM-3-EN-6-YL]-HEPTATRIENOIC ACID AND 7-[(3-ALKOXY)-5,6-DIHYDRONAPHTHALEN-2-YL]-HEPTATRIENOIC ACID DERIVATIVES HAVING SERUM GLUCOSE REDUCING ACTIVITY

(75) Inventors: Richard L. Beard, Newport Beach, CA (US); Tien T. Duong, Irvine, CA (US); Janet A. Takeuchi, Anaheim, CA (US); Ling Li, Irvine, CA (US); Kwok Yin Tsang, Irvine, CA (US); Xiaoxia Liu, Tustin, CA (US); Jayasree Vasudevan, Anaheim, CA (US); Liming Wang, Irvine, CA (US); Santosh C. Sinha, Irvine, CA (US); Haiqing Yuan, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/696,748

(22) Filed: Oct. 29, 2003

(51) Int. Cl.$^7$ ............... A61K 31/35; A61K 31/235; A61K 31/19

(52) U.S. Cl. ............... 514/456; 514/532; 514/569; 560/56; 562/466

(58) Field of Search ............... 549/399, 407; 560/56; 562/466; 514/456, 532, 569

(56) References Cited

U.S. PATENT DOCUMENTS

| | | | |
|---|---|---|---|
| 5,445,265 A | 8/1995 | Herr et al. | |
| 5,667,320 A | 9/1997 | Ambrose et al. | |
| 5,721,103 A | 2/1998 | Boehm et al. | |
| 5,801,253 A | 9/1998 | Klaus et al. | |
| 5,917,082 A | 6/1999 | Vuligonda et al. | |
| 6,048,873 A | 4/2000 | Vasudevan et al. | |
| 6,114,533 A | 9/2000 | Vuligonda et al. | |
| 6,147,224 A | 11/2000 | Vuligonda et al. | |
| 6,326,397 B1 | 12/2001 | Bollag et al. | |
| 6,613,917 B1 | 9/2003 | Beard et al. | |

FOREIGN PATENT DOCUMENTS

| WO | WO 93/11755 | 6/1993 |
|---|---|---|
| WO | WO 97/12853 | 4/1997 |
| WO | WO 01/19770 | 3/2001 |

OTHER PUBLICATIONS

Mangelsdorf, et al., The Retinoid Receptors, The Retinoids, 1994, 319–349, Raven Press, Ltd., New York.
Dawson, et al., Chemistry and Bilogy of Synthetic Retinoids, 1990, 324–356, CRC Press, Inc.
Mukherjee, et al., Sensitization of Diabetic and Obese Mice to Insulin by retinoid X Receptor Agonists, Nature, 1997, 407–410, 386.
Feigner, et al., Focus, 1989, 21–25, 11, 2.
Heyman, et al., Cell, 1992, 397–406, 68.
Cheng, et al., Biochemical Pharmacology, 1973, 3099–3108, 22.
Allegretto, et al., Transactivation Properties of Retinoic acid and Retinoid X Receptors in Mammalian Cells and Yeast, 1993, 26625–26633, 268, 35.
Piers, et al. ,Synthesis, 1995, 47–55.

Primary Examiner—Amelia A. Owens
(74) Attorney, Agent, or Firm—Gabor L. Szekeres

(57) ABSTRACT

Compounds of the formula

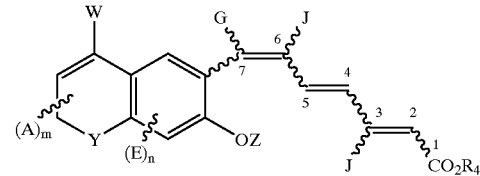

where the variations have the meaning defined in the specification are capable of reducing serum glucose levels in diabetic mammals without the undesirable side effects of transiently increasing triglyceride levels and reducing serum thyroxine levels.

68 Claims, No Drawings

7-[(7-ALKOXY)-CHROM-3-EN-6-YL]-HEPTATRIENOIC ACID AND 7-[(3-ALKOXY)-5,6-DIHYDRONAPHTHALEN-2-YL]-HEPTATRIENOIC ACID DERIVATIVES HAVING SERUM GLUCOSE REDUCING ACTIVITY

BACKGROUND OF THE INVENTION

Field of Invention

The present invention relates to compounds that have the property of reducing serum glucose and serum triglyceride levels in diabetic mammals without the undesirable properties of reducing serum thyroxine levels and transiently raising triglyceride levels. More particularly, the present invention relates to 7-[(7-alkoxy)-chrom-3-en-6-yl]-heptatrienoic acid and 7-[(3-alkoxy)-5,6-dihydronaphthalen-2-yl)-heptatrienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAP_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see *Dawson and (?)Okamura*, Chemistry and Biology of Synthetic Retinoids, published by CRC Press Inc., 1990, pages 324–356.

The following United States patents and other references disclose compounds that include a pentadienoic acid or heptatrienoic acid moiety attached to a chroman, chromene, tetrahydronaphthalene or dihydronaphthalene group, or related compounds with retinoid or like biological activity: U.S. Pat. Nos. 6,048,873; 6,147,224; 5,917,082, 5,677,320; 5721,103; 5,801,253; 6,326,397 and PCT Publications WO 97/12853 and WO 01/19770.

Relatively recently it has become known that certain retinoid compounds are capable of reducing serum glucose levels in diabetic mammals. Mukherjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists, *Nature* 1997, 386 (6623), 407–410. The compound (2E,4E, 1'S,2'S)-3-methyl-5-[2'-methyl-2'-(5,5,8,8-tetramethyl-5,6, 7,8-tetrahydro-naphthalen-2-yl)-cyclopropyl]-penta-2,4-dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds that do not have one or both of these undesirable side effects.

SUMMARY OF THE INVENTION

The present invention generally relates to compounds of Formula 1

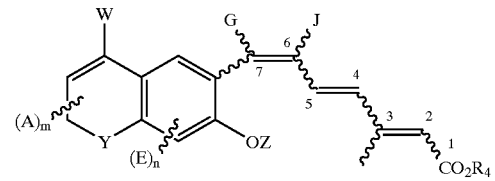

Formula 1 where

A is independently an alkyl group of 1 to 6 carbons, halogen, or alkoxy of 1 to 6 carbons;

m is an integer having the values of 0 to 3;

W is H, alkyl of 1 to 8 carbons or phenyl;

E is independently an alkyl group of 1 to 0.6 carbons, halogen, or alkoxy of 1 to 6 carbons;

n is an integer having the values of 0 to 2;

Z is an alkyl group of 1 to 8 carbons;

G is H or an alkyl group of 1 to 8 carbons;

J is independently H, halogen, or alkyl of 1 to 6 carbons;

Y is O, or $[C(R_3)_2]$ where $R_3$ independently is H or alkyl of 1 to 6 carbons and o is an integer having the value of zero (0) or one (1), and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more compounds of Formula 1 to reduce serum glucose levels in said mammals.

The present invention also relates to the methods of using the compounds of the invention to treat diseases and conditions which are responsive to treatment by retinoids.

DETAILED DESCRIPTION OF THE INVENTION GENERAL EMBODIMENTS AND SYNTHETIC METHODOLOGY

Definitions

The term alkyl refers to and covers any and all groups which are known as normal alkyl and branched-chain alkyl. In the case of an alkyl group of three carbons (propyl) the definition of "alkyl" also includes cyclopropyl that is abbreviated in the schemes and formulas, as applicable, as "cPr".

A pharmaceutically acceptable salt may be prepared for any compound in this invention having a functionality capable of forming a salt, for example an acid functionality.

A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. All orientations with regard to the olephinic bonds are within the scope of the invention, as is indicated by wavy lines in Formula 1. Nevertheless specific examples of the compounds of the present invention have the specific orientations of substituents relative to the double bonds as is indicated in the name of the respective compound, and/or by specific showing in the structural formula of the orientation of the substituents relative to the respective double bonds.

The compounds of the present invention may also contain one or more chiral centers and therefore may exist in enantiomeric and diastereomeric forms. With regard to the chiral centers which may exist in the compounds, the scope of the invention is intended to cover all possible orientations of the substituents relative to the chiral center or centers, thus including pure enantiomers (optical isomers), diastereomers, mixtures of diastereomers and racemic mixtures of enantiomers.

Generally speaking the compound of the invention can be obtained as shown un Reaction Schemes 1 and Reaction Scheme 1

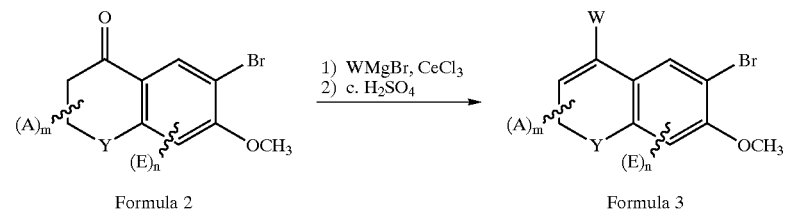

Formula 2    Formula 3

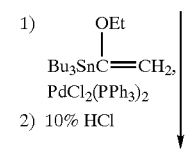

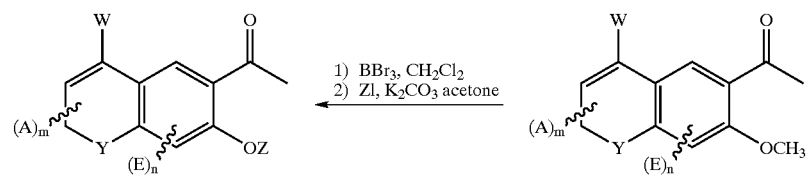

Formula 5    Formula 4

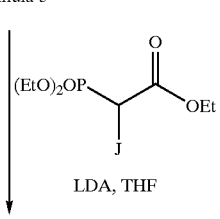

LDA, THF

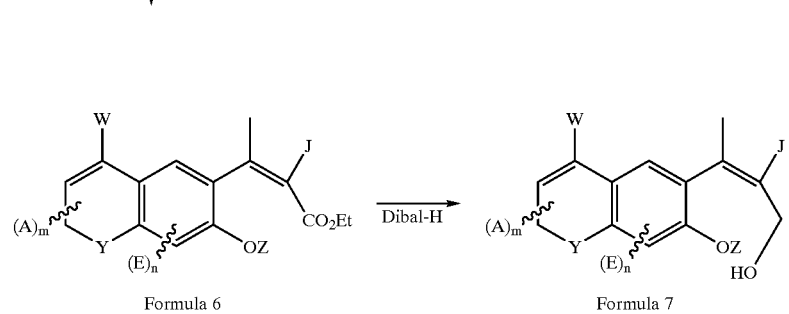

Formula 6    Formula 7

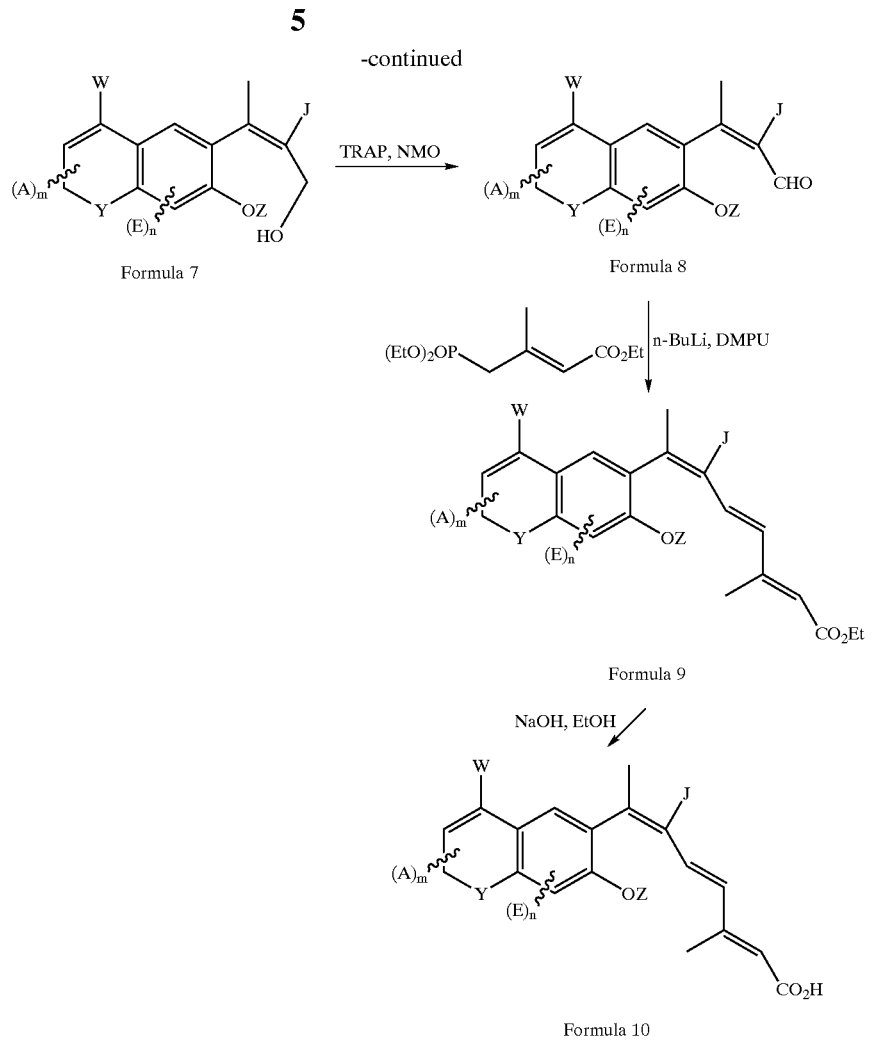

In accordance with Reaction Scheme 1 a chroman, tetrahydrohydronaphthalene or indane derivative of Formula 2 is reacted with a Grignard reagent of the formula WMgBr, preferably in the presence of cerium (III) chloride (CeCl$_3$), and thereafter with acid to form a chromene, dihydronaphthalene or indene derivative of Formula 3. The variables A, Y, E, m, n and W are defined as in Formula 1 with the exception that in this scheme W is not H. The starting compounds of Formula 2 are either available in accordance with the chemical scientific or patent literature, or by such modifications of these literature procedures which are well within the skill of the practicing organic chemist. Also, description of the specific embodiments below provide examples for obtaining exemplary compounds of Formula 2 by literature procedure or by synthesis. Additional compounds within the scope of Formula 2 can also be made by such modifications of the below described examples which will be within the skill of the practicing organic chemist in light of this disclosure.

Inasmuch as the presently preferred exemplary compounds of the invention are chromene and dihydronaphthalene derivatives, only these two condensed ring structures are mentioned further in connection with the further description of the invention, although it should be understood that the reactions shown in Reaction Schemes 1 and 2 are also applicable to the synthesis of indene derivatives within the broad scope of the invention.

The bromo substituted chromene or dihydronaphthalene derivative of Formula 3 is then reacted with tributyl(1-ethoxyvinyl)tin in the presence of dichlorobis(triphenylphosphine)palladium(II) and thereafter with acid to introduce an acetyl group in place of the bromo group and obtain a chromene or dihydronaphthalene derivative of Formula 4. Treatment of the compound of Formula 4 with boron tribromide removes the methyl group from the 7-position of the chromene, or from the 3 position of the dihydronaphthalene compound, as applicable, and provides a free hydroxyl function in its place. Treatment of this hydroxyl compound with an alkyl iodide (or other halide) of the formula ZI introduces the alkyl group Z (defined as in connection with Formula 1) into the molecule and provides the 7-alkoxy-chromene or 3-alkoxy-dihydronaphthalene derivative, as applicable, of Formula 5. Instead of the alkyl halide ZI other types of alkylating agents can also be used to introduce the alkyl group Z.

The compound of Formula 5 is then subjected to a Horner-Emmons reaction with the reagent triethyl-2-phosphonoacetate, triethyl-2-fluoro-2-phosphonoacetate, or like reagent shown in the scheme where the variable J represents hydrogen, halogen (preferably fluoro) or an alkyl group, as defined in connection with Formula 1. The reagents triethyl-2-phosphonoacetate and triethyl-2-fluoro-2-phosphonoacetate are available commercially (Aldrich).

The Horner-Emmons reaction is conducted in the presence of strong base, such as lithium di-iso-propylamide (LDA) as is indicated in the scheme, or n-butyllithium, in the presence of an inert solvent, such as tetrahydrofuran (THF) as indicated in the scheme, or in hexane. The product of the Horner-Emmons reaction is a carboxylic acid ester compound of Formula 6 which is thereafter reduced to the primary alcohol level with a suitable reducing agent such as diisobutylaluminum hydride (DIBAL-H) to give a compound in accordance with Formula 7. The primary alcohol of Formula 7 is then oxidized to the aldehyde level by treatment with 4-methylmorpholine N-oxide (NMO) and tetrapropylammonium perruthenate (TPAP) to give a compound in accordance with Formula 8.

The aldehyde compound of Formula 8 is then subjected to still another Horner-Emmons reaction conducted in the presence of strong base (n-butyllithium) and 1,3-dimethyl-3,4,5,6-tetrahydro-2(1H)-pyrimidinone (DMPU) with the reagent ethyl 4-(diethoxyphosphoryl)-3-methylbut-2-enoate in THF or in other suitable inert solvent, to provide a 7-[(7-alkoxy)-chrom-3-en-6-yl)-heptatienoic acid ethyl ester or 7-[(3-alkoxy)-5,6-dihydronaphthalen-2-yl)-heptatrienoic acid ethyl ester, as applicable, in accordance with Formula 9. Ethyl 4-(diethoxyphosphoryl)-3-methylbut-2E-enoate can be obtained in accordance with the literature reference: JOC, 1974, 39, 821, incorporated herein. Sometimes this reagent is also referred to as triethylphosphono-3-methyl-2E-butenoate. The compounds of Formula 9 are within the scope of the invention. They are saponified by treatment of sodium hydroxide (or other suitable base) to give free acid compounds, or their pharmaceutically acceptable salts in accordance with Formula 10. The free acids of Formula 10 can also be esterified by procedures well known in the art to obtain ester compounds, within the full scope of the variable $R_4$ in Formula 1.

It should be noted that Reaction Scheme 1 and all other reactions schemes of this specification, for the sake of simplicity and clarity of illustration, indicate the presently preferred specific orientation (cis) or (trans) of the applicable groups relative to each olephinic bond in the intermediate and final compounds. A person having ordinary skill in the art can obtain the compounds with different orientations based on the present description coupled with state-of-the-art knowledge regarding analogous reagents, reaction and separation techniques. Also, for the sake of simplicity and clarity of illustration the variable G in the 7 position of the heptatrienoic acid moiety of the compounds of Formula 1 is shown as methyl in Reaction Scheme 1. The variable J in the 3 position of the heptatrienoic acid moiety of the compounds of Formula 1 is also shown as methyl in Reaction Scheme 1 and in all other reactions schemes of this specification. Some of the specific reactions schemes below provide examples for the preparation of compounds of the invention where the variable G in the 7 position of the heptatrienoic acid moiety of the compounds of the invention is an alkyl group other than methyl.

Reaction Scheme 2 discloses an alternative general method for obtaining compounds of the invention. In accordance with this scheme an iodo-substituted allyl alcohol of Formula 11 serves as a starting material. In Formula 11 the variables G and J are defined as in connection with Formula 1. Examples for compounds of Formula 11 where the variable J is H and the variable G is methyl or ethyl are utilized for the synthesis of several preferred compounds of the invention. These examples are described in the specification of U.S. Pat. No. 6,147,224 which is expressly incorporated herein by reference.

The allyl alcohol of Formula 11 is oxidized to the aldehyde level by treatment with 4-methylmorpholine N-oxide (NMO) and tetrapropylammonium perruthenate (TRAP) and the resulting aldehyde is subjected to a Horner-Emmons reaction with the reagent ethyl 4 (diethoxyphosphoryl)-3-methylbut-2E-enoate in THF, hexane or in other suitable inert solvent, to provide a 7-iodo-substituted heptatrienoic acid ester of Formula 12.

Another starting material in this reaction scheme is a 6-bromo-substituted-chroman-4-one derivative, or a 2-bromo-substituted tetrahydronaphthalen-8-one derivative, as applicable, of Formula 2, which can be obtained as described in connection with Reaction Scheme 1.

Reaction Scheme 2

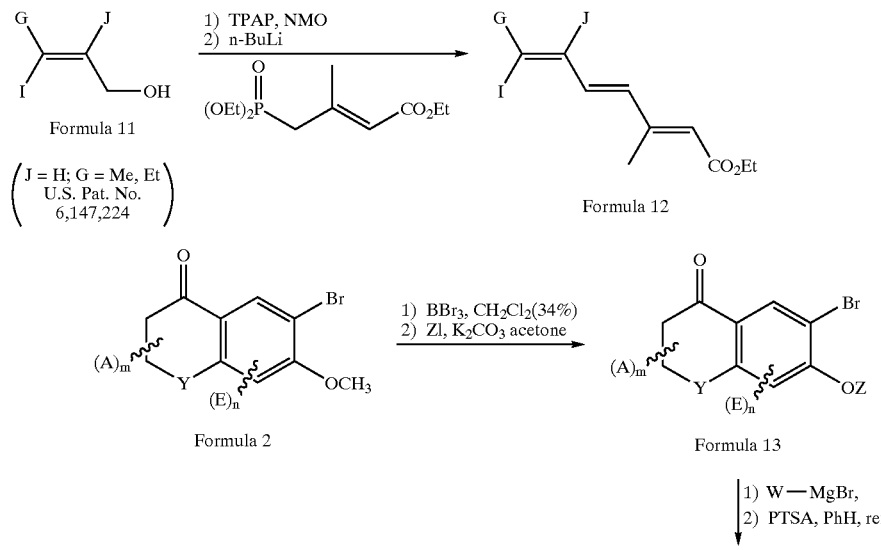

-continued

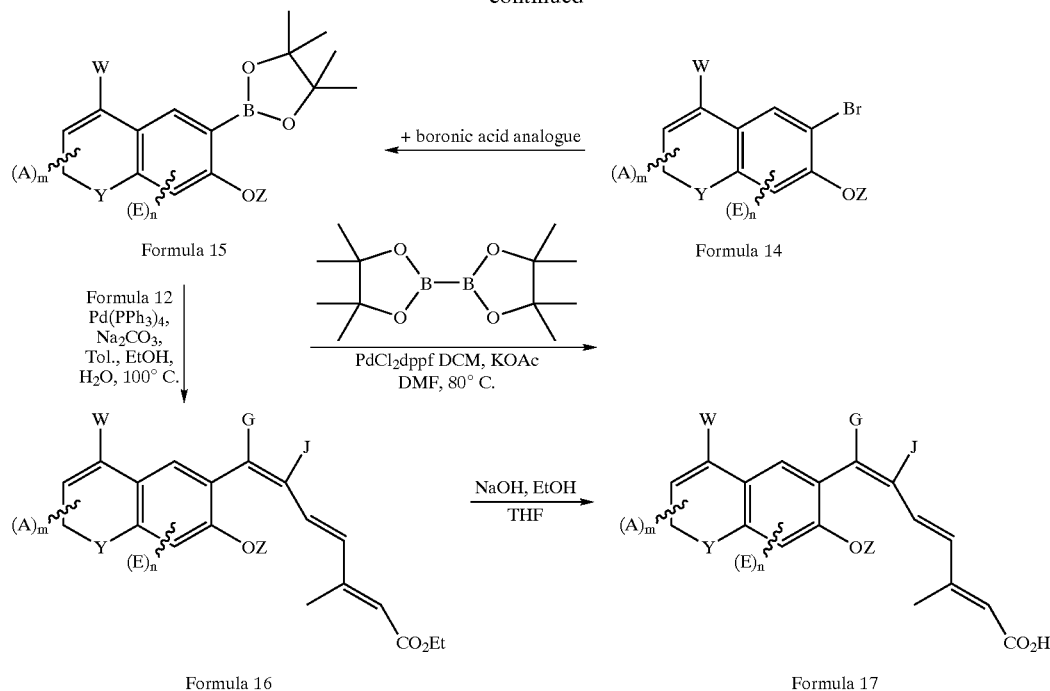

The bromo compound of Formula 2 is reacted with boron tribromide to remove the methyl group from the 7-position of the chroman-4-one or from the 3 position of the tetrahydronaphthalen-8-one derivative, as applicable, and the resulting free hydroxyl group is reacted with an alkyl iodide (or other halide) of the formula ZI to introduce the alkyl group Z (defined as in connection with Formula 1) into the molecule and to provide a 7-alkoxy-chroman-4-one or 3-alkoxy-tetrahydronaphthalen-8-one derivative, as applicable, in accordance with Formula 13. Instead of the alkyl halide ZI other types of alkylating agents can also be used to introduce the alkyl group Z.

The compound of Formula 13 is reacted with a Grignard reagent of the formula WMgBr, and thereafter with acid, such as para-toluenesulfonic acid (PTSA) to form a 6-bromo-chromene, or 2-bromodihydronaphthalene derivative, as applicable, in accordance with Formula 14. The bromo compound of Formula 14 is reacted with bis(pinacolato)diboron in the presence of potassium acetate and [1,1'-bis(disphenylphosphino)-ferrocene]dichloropalladium (II) complex in dichloromethane and dimethylformamide under an inert gas (argon) atmosphere. This reaction yields a mixture of the boronic ester compound of Formula 15 and the boronic acid analogue that is not shown in the reaction scheme. The mixture of the boronic ester compound of Formula 15 and of the boronic acid analogue is reacted with the reagent of Formula 12 in the presence of tetrakis(triphenylphosphine)palladium(0) and sodium carbonate in toluene and ethanol to provide a 7-[(7-alkoxy)-chrom-3-en-6-yl-heptatrienoic acid ethyl ester or 7-[(3-alkoxy)-5,6-dihydronaphthalen-2-yl]-heptatrienoic acid ethyl ester, as applicable, in accordance with Formula 16. The compounds of Formula 16 are within the scope of the invention. They are saponified by treatment of sodium hydroxide (or other suitable base) to give free acid compounds, or their pharmaceutically acceptable salts in accordance with Formula 17.

BIOLOGICAL ACTIVITY, MODES OF ADMINISTRATION

It has been discovered in accordance with the present invention that compounds of this invention are capable of significantly reducing serum glucose levels and reducing or maintaining serum triglyceride levels in diabetic mammals, without the undesirable side effects of transiently raising triglyceride levels (hypertriglyceridemia) and in some cases without reducing serum thyroxine levels (hypothyroidism). The compounds of the invention were tested in certain assays for activity as agonists of RAR and RXR retinoid receptors. These assays demonstrated that the compounds of the invention are partial agonists of the RXR receptors.

Specifically, one such assay is a chimeric receptor transactivation assay which tests for agonist-like activity in the R RAPE and $RAR_7$ receptor subtypes, and which is based on work published by Feigner, P. L. and Holm, M (1989) Focus, 112 is described in detail in U.S. Pat. No. 5,455,265. The specification of U.S. Pat. No. 5,455,265 is hereby expressly incorporated by reference. A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of the ligand binding assay are expressed in Ki numbers. (See Cheng et al. Biochemical Pharmacology Vol. 22 pp 3099–3108, expressly incorporated herein by reference.)

Efficacy in a transactivation assay is expressed as a percentage of the maximum potency attained by the compound compared to a standard which, in this case, is the compound named (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

The specification of this application for patent is organized in several sections in accordance with structural Formulas A through F each of which discloses a group of preferred compounds within the scope of the invention. Tables that disclose the activity of certain exemplary compounds of the invention in the above-described RXR receptor transactivation and binding assays are found in the corresponding sections. Generally speaking, in the chimeric receptor transactivation assay the compounds were essentially inactive in activating $RAR_\alpha$, $RAR_\beta$ and $RAR_\gamma$ receptors. The transactivation data pertaining to the activation of RXR receptors were obtained in the holoreceptor assay.

Generally speaking, in the tables disclosing the results of transactivation and binding assays the numbers in parentheses indicate efficacy as a percentage compared to the standard compound, (2E,4E,1'S,2'S)-3-methyl-5-[2'-methyl-2'-(5,5,8,8-tetramethyl-5,6,7,8-tetrahydro-naphthalen-2-yl) cyclopropyl]-penta-2,4-dienoic acid and the other numbers indicate the measured $EC_{50}$ and K; in nanomolar concentration.

An assay described below tests the effect of compounds of the invention on serum glucose, triglyceride and thyroxine levels in female 9–10 weeks old db/db mice.

Description of Assay.

Female diabetic db/db (9–10 weeks old) mice were maintained on standard laboratory food and treated by oral gavage with vehicle (corn oil), standard compound (2E,4E, 1'S,2'S)-3-methyl-5-[2'-methyl-2'-(5,5,8,8-tetramethyl-5,6, 7,8-tetrahydro-naphthalen-2-yl)-cyclopropyl]-penta-2,4 dienoic acid (5 mg/kg) or the test compound (5–100 mg/kg, as described in Table 2) daily for seven days at 8:00 AM. Blood samples (70 µl) were taken by orbital bleeding at 11:00 AM on day 0 (pre-treatment), day 3, and day 6. On day 7, a blood sample (700 µl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were supplied in commercially available kits (glucose and T4: Boehringer Manheim; triglycerides: Roche Diagnostics). Seven animals were treated in each group. As noted above, the specification of this application for patent is organized in several sections in accordance with structural Formulas A through F each of which discloses a group of preferred compounds within the scope of the invention. Tables that disclose the activity of certain exemplary compounds of the invention in the above-described assay testing the effect of compounds of the invention on serum glucose, triglyceride and thyroxine levels are found in the corresponding sections. Any modification of the assay procedure, if applicable, is also indicated in the corresponding section.

As the data in the tables below indicate the compounds of the invention not only cause significant decrease in serum glucose levels and maintain or reduce triglyceride levels in diabetic mammals but, in contrast with the prior art standard compound (2E,4E, 1'S,2'S)-3-methyl-5-[2'-methyl-2'-(5,5,8, 8-tetramethyl-5,6,7,8-tetrahydro-naphthalen-2-yl)- cyclopropyl]-penta-2,4-dienoic acid, do not have the undesirable side effect of reducing serum thyroxine levels.

MODES OF ADMINISTRATION, DOSING

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as MinoxidilR, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

SPECIFIC EMBODIMENTS OF THE COMPOUNDS OF THE INVENTION

Referring now to Formula 1, in the preferred compounds of the invention the variable Y represents 0 (chromene derivatives) or Y is $[C(R_3)_o$ where o represents the integer one (1) (dihydronaphthalene derivatives). Even more preferably when the compounds are dihydronaphthalene derivatives, then Y represents $C(CH_3)_2$.

Referring now to the variable group $(A)_m$, in the presently preferred compounds of the invention $(A)_m$ represents a geminal dimethyl group when Y is O (chromene derivatives). When the compounds are dihydronaphthalene derivatives then in the preferred compounds m is zero (0).

In the preferred compounds of the invention the group $(E)_n$ either represents a single halogen or alkyl substituent in the 8-position of chromenes, or in the 4-position of dihydronaphthalenes, as applicable, or the variable n is zero (0), that is, there is no E substituent.

Referring now to the variable W, it is preferred as an alkyl group of 1 to 6 carbons, or phenyl. Alkyl groups of 1 to 4 carbons are even more preferred, and in several preferred compounds of the invention W represents a branch-chained allyl group of 3 or 4 carbons.

The variable Z preferably represents an alkyl group of 1 to 4 carbons.

Referring now to the variable G, in the preferred compounds of the invention G represents an alkyl group of 1 to 4 carbons, even more preferably an alkyl group of 1 to 3 carbons.

The variable J in the 7-position of the heptatrienoic acid moiety is preferably fluoro (F) or hydrogen (H). In the 3 position of the heptatrienoic acid moiety the variable J preferably represents an alkyl group, even more preferably methyl.

The presently preferred configurations E or Z (cis or trans) relative to the olephinic bonds are shown in the structures of the exemplary compounds.

The presently most preferred compounds of the invention are shown below in Sections A through F by general Formulas A through F, and the syntheses of these preferred compounds is also described below in detail.

Section a of Specific Embodiments

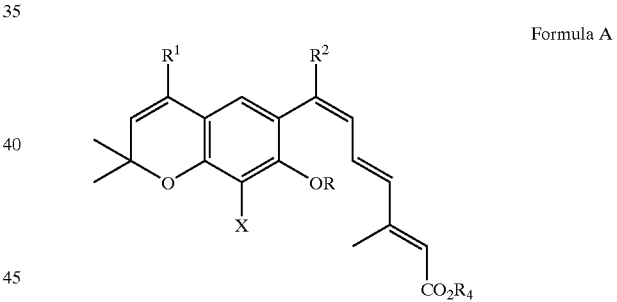

Formula A

Formula A discloses a specific class of preferred and exemplary compounds of the invention. In Formula A:

R represents alkyl of 1 to 8 carbons, more preferably alkyl of 1 to 4 carbons, and most preferably alkyl of 1 to 2 carbons;

$R^1$ represents alkyl of 1 to 8 carbons, more preferably alkyl of 1 to 4 carbons, and most preferably alkyl of 1 to 3 carbons;

$R^2$ represents alkyl of 1 to 8 carbons, more preferably alkyl of 1 to 4 carbons, and most preferably alkyl of 1 to 2 carbons;

$R_4$ represents H, alkyl of 1 to 6 carbons, $CH_2OR_5$ or $CH_2OCOR_5$ where $R_5$ is alkyl of 1 to 3 carbons, and X represents H or halogen, more preferably H or Cl, or a pharmaceutically acceptable salt of said compound.

The synthetic schemes and the experimental procedures for obtaining compounds within the scope of Formula A are provided below

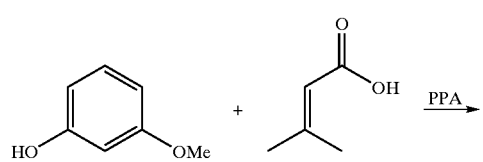
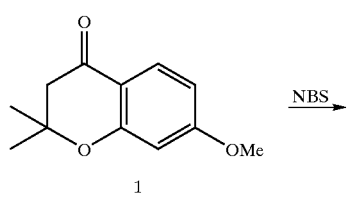
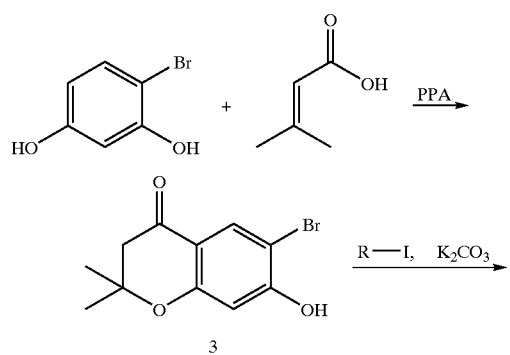
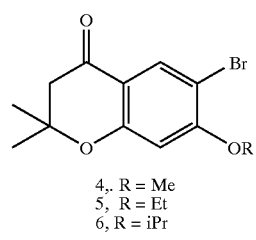
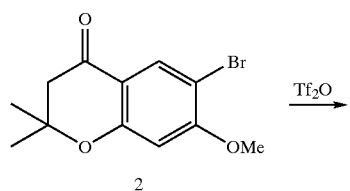
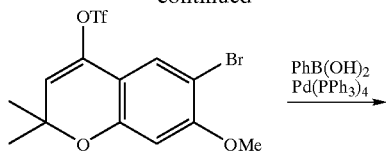
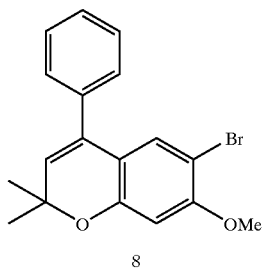
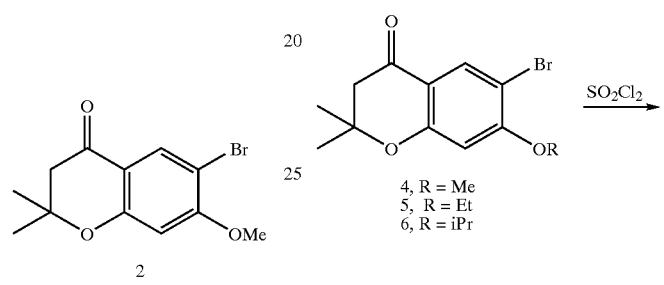
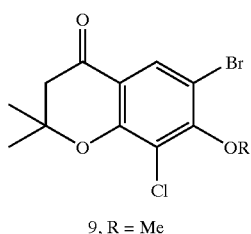
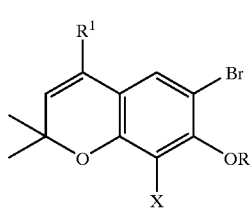

17

-continued

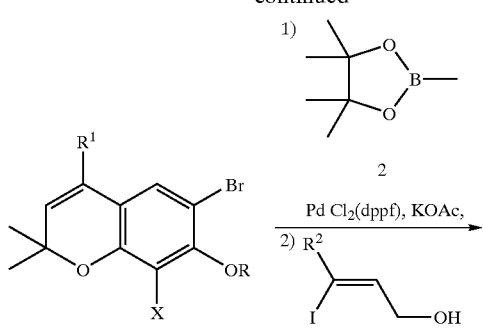

13 (R = Me, R$^1$ = Et, X = H)
14 (R = Me, R$^1$ = iPr, X = H)
16 (R = Et, R$^1$ = Et, X = H)
17 (R = Et, R$^1$ = Me, X = H)
18 (R = Et, R$^1$ = iPr, X = H)
19 (R = Me, R$^1$ = iPr, X = Cl)
20 (R = Et, R$^1$ = iPr, X = Cl)

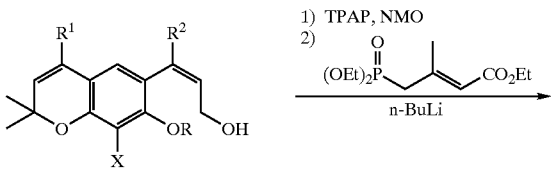

22 (R = Me, R$^1$ = Et, R$^2$ = Me, X = H)
23 (R = Me, R$^1$ = iPr, R$^2$ = Me, X = H)
24 (R = Me, R$^1$ = iPr, R$^2$ = Et, X = H)
25 (R = Et, R$^1$ = Et, R$^2$ = Me, X = H)
26 (R = Et, R$^1$ = Me, R$^2$ = Et, X = H)
27 (R = Et, R$^1$ = iPr, R$^2$ = Me, X = H)
28 (R = Et, R$^1$ = iPr, R$^2$ = Et, X = H)
29 (R = Me, R$^1$ = iPr, R$^2$ = Me, X = Cl)
30 (R = Et, R$^1$ = iPr, R$^2$ = Me, X = Cl)
31 (R = Et, R$^1$ = iPr, R$^2$ = Et, X = Cl)

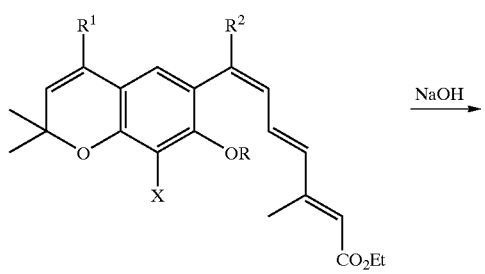

32 (R = Me, R$^1$ = Et, R$^2$ = Me, X = H)
33 (R = Me, R$^1$ = iPr, R$^2$ = Me, X = H)
34 (R = Me, R$^1$ = iPr, R$^2$ = Et, X = H)
35 (R = Et, R$^1$ = Et, R$^2$ = Me, X = H)
36 (R = Et, R$^1$ = Me, R$^2$ = Et, X = H)
37 (R = Et, R$^1$ = iPr, R$^2$ = Me, X = H)
38 (R = Et, R$^1$ = iPr, R$^2$ = Et, X = H)
39 (R = Me, R$^1$ = iPr, R$^2$ = Me, X = Cl)
40 (R = Et, R$^1$ = iPr, R$^2$ = Me, X = Cl)
41 (R = Et, R$^1$ = iPr, R$^2$ = Et, X = Cl)

18

-continued

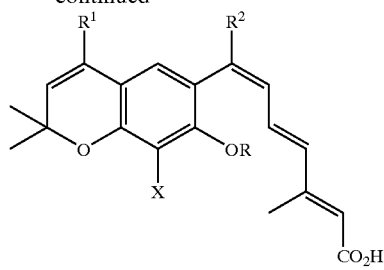

42 (R = Me, R$^1$ = Et, R$^2$ = Me, X = H)
43 (R = Me, R$^1$ = iPr, R$^2$ = Me, X = H)
44 (R = Me, R$^1$ = iPr, R$^2$ = Et, X = H)
45 (R = Et, R$^1$ = Et, R$^2$ = Me, X = H)
46 (R = Et, R$^1$ = Me, R$^2$ = Et, X = H)
47 (R = Et, R$^1$ = iPr, R$^2$ = Me, X = H)
48 (R = Et, R$^1$ = iPr, R$^2$ = Et, X = H)
49 (R = Me, R$^1$ = iPr, R$^2$ = Me, X = Cl)
50 (R = Et, R$^1$ = iPr, R$^2$ = Me, X = Cl)
51 (R = Et, R$^1$ = iPr, R$^2$ = Et, X = Cl)

7-Methoxy-2,2-dimethyl-chroman 4-one
(Compound 1)

A mixture of 3-methoxyphenol (5.00 g, 40.3 mmol) and 3,3-dimethylacrylic acid (4.03 g, 40.3 mmol) were ground in a mortar. The mixture was then added portion-wise into polyphosphoric acid (8 g) at 90° C. After stirring at 90° C. for 30 min, the reaction mixture was quenched with ice, then extracted with diethyl ether. The organic layers were washed with water; brine, and dried over Na$_2$SO$_4$. The filtered solvent was concentrated in vacuo and purified by column chromatography (silica gel, 10% ethyl acetate in hexane) to give the title compound as a yellow solid.

$^1$H NMR (300 MHz, CDCl$_3$): δ 1.41 (s, 6H), 2.82 (s, 2H), 3.80 (s, 3H), 6.39 (d, J=2.3 Hz, 1H), 6.55 (dd, J=2.6, 8.8 Hz, 1H), 7.80 (d, J=8.8 Hz, 1H).

6-Bromo-7-methoxy-2,2-dimethyl-chroman-4-one
(Compound 2)

To a solution of 7-methoxy-2,2-dimethyl-chroman-4-one (Compound 1, 5.81 g, 28.2 mmol) in anhydrous N,N-dimethylformamide (15 mL) under argon at 25° C. was added N-bromosuccinimide (5.02 g, 33.8 mmol). The mixture was stirred at ambient temperature for 12 h. The product was extracted with diethyl ether. The organic layers were washed with water, brine, and dried over Na$_2$SO$_4$. The filtered solvent was concentrated in vacuo and purified by column chromatography (silica gel, 5% ethyl acetate in hexane) to give the title compound as a white solid.

$^1$H NMR (300 MHz, CDCl$_3$): δ 1.46 (s, 6H), 2.65 (s, 2H), 3.91 (s, 3H), 6.41 (s, 1H), 8.03 (s, 1H).

6-Bromo-7-hydroxy-2,2-dimethyl-chroman-4-one (Compound 3)

A mixture of 4-bromoresorcinol (5.00 g, 26.5 mmol) and 3,3-dimethylacrylic acid (2.64 g, 26.5 mmol) were ground in a mortar. The mixture was then added portion-wise into polyphosphoric acid (8 g) at 90° C. After stirred at 90° C. for 15 min, the reaction mixture was cooled to room temperature and quenched with water. The mixture was then extracted with diethyl ether. The organic layer was separated, washed with water, brine, dried ($MgSO_4$) and concentrated at reduced pressure to give a yellow residue. Purification by recrystallization (methanol and water) afforded the title compound as a yellow solid.

$^1$H NMR (300 MHz, $CDCl_3$): δ 8.02 (s, 1H), 6.58 (s, 1H), 5.93 (s, 1H), 2.68 (s, 2H), 1.46 (s, 6H).

6-Bromo-7-methoxy-2,2-dimethyl-chroman-4-one (Compound 4)

General Procedure A

To a solution of 6-bromo-7-hydroxy-2,2-dimethyl-chroman-4-one (Compound 3, 2.00 g, 7.4 mmol) in acetone (100 mL) were added potassium carbonate (500 mg) and iodomethane (5.22 g, 36.8 mmol). The mixture was then heated to reflux for 2 h. After cooling to room temperature, water was added to the mixture until all solids dissolved. The resulting solution was then extracted with diethyl ether, washed with brine, dried ($MgSO_4$) and concentrated at reduced pressure to give a yellow residue. Purification by flash chromatography (silica gel, 95:5 hexane/ethyl acetate) gained the title compound as a white solid.

$^1$H NMR (300 MHz, $CDCl_3$): δ 8.03 (s, 1H), 6.41 (s, 1H), 3.91 (s, 3H), 2.65 (s, 2H), 1.46 (s, 6H).

6-Bromo-7-ethoxy-2,2-dimethyl-chroman-4-one (Compound 5)

As described in General Procedure A, 6-bromo-7-hydroxy-2,2-dimethyl-chroman-4-one (Compound 3, 2.0 g, 7.35 mmol) was treated with potassium carbonate (500 mg) and iodoethane (1.5 mL, 18.75 mmol) to give rise to the title compound as a white solid after purification by flash chromatography (silica gel, 5% ethyl acetate in hexanes).

$^1$H NMR (300 MHz, $CDCl_3$): δ 8.04 (s, 1H), 6.38 (s, 1H), 4.11 (q, J=6.9 Hz, 2H), 2.66 (s, 2H), 1.49 (t, J=6.9 Hz, 3H), 1.45 (s, 6H).

6-Bromo-7-isopropoxy-2,2-dimethyl-chroman-4-one (Compound 6)

As described in General Procedure A, 6-bromo-7-hydroxy-2,2-dimethyl-chroman-4-one, (Compound 3, 1.0 g, 3.8 mmol) in acetone (50 mL) was treated with anhydrous potassium carbonate (2.1 g, 14.9 mmol) and 2-iodopropane (0.7 mL, 7.5 mmol) to give the title compound as a white solid after purification by flash chromatography (silica gel, 10% ethyl acetate in hexanes).

$^1$H NMR (300 MHz, $CDCl_3$): δ 8.03 (s, 1H), 6.39 (s, 1H), 4.59 (sept, J=5.9 Hz, 1H) 2.66 (s, 2H, 1.45 (s, 6H), 1.41 (d, J=5.9 Hz, 6H).

Trifluoro-methanesulfonic acid 6-bromo-7-methoxy-2,2-dimethyl-2H-chromen-4-yl ester (Compound 7)

To a solution of 6-bromo-7-methoxy-2,2-dimethyl-chroman-4-one (Compound 2, 1.00 g, 3.52 mmol) in 20 mL of anhydrous dichloromethane under argon at 25° C. was added trifluoromethanesulfonic anhydride (2.38 g, 8.45 mmol) and 2,6-di-tert-butyl-4-methyl-pyridine (1.08 g, 5.28 mmol). The mixture was heated to 45° C. for 2 h. The mixture was then cooled to 25° C. and quenched with water. The product was extracted with dichloromethane. The organic layers were washed with water, brine, and dried over $Na_2SO_4$. The filtered solvent was concentrated in vacuo and purified by column chromatography (silica gel, 5% ethyl acetate in hexane) to give the title compound as a red oil.

$^1$H NMR (300 MHz, $CDCl_3$): δ 1.51 (s, 6H), 3.87 (s, 3H), 5.51 (s, 1H), 6.44 (s, 1H), 7.37 (s, 1H).

6-Bromo-7-methoxy-2,2-dimethyl-4-phenyl-2H-chromene (Compound 8)

A solution of trifluoro-methanesulfonic acid 6-bromo-7-methoxy-2,2-dimethyl-2H-chromen-4-yl ester (Compound 7, 2.14 g, 5.30 mmol) in 35 mL of anhydrous toluene was first degassed by bubbling with argon for 15 min. Phenylboronic acid (650 mg, 5.30 mmol), potassium carbonate (1.47 g, 10.6 mmol), lithium chloride (632 mg, 14.8 mmol), and tetrakis(triphenylphosphine)palladium(0) (270 mg, 0.53 mmol) were added. After stirring at 90° C. for 12 h, the mixture was cooled to room temperature and quenched with water. The product was extracted with ethyl acetate. The organic layer was washed with water, brine, and dried over $Na_2SO_4$. The filtered solvent was concentrated in vacuo and purified by column chromatography (silica gel, 5% ethyl acetate in hexane) to give the title compound as a foam.

$^1$H NMR (300 MHz, $CDCl_3$): δ 1.49 (s, 6H), 3.86 (s, 3H), 5.51 (s, 1H), 6.50 (s, 1H), 7.15 (s, 1), 7.38 (m, 5H).

6-Bromo-8-chloro-7-methoxy-2,2-dimethyl-chroman-4-one (Compound 9)

General Procedure B

To a solution of 6-bromo-7-methoxy-2,2-dimethyl-chroman-4-one (Compound 4, 2.80 g, 9.8 mmol) in methylene chloride (50 nL) at 0° C. were added sulfuryl chloride (1.59 g, 11.7 mmol) followed by treatment with pyridine (0.87 g, 11.7 mmol). After stirring at 0° C. and slow warning room temperature over 3 h, the reaction was quenched with ice water. The resulting mixture was extracted with dichloromethane and then the combined organic layers were washed with water and brine, dried ($MgSO_4$), filtered, and concentrated under reduced pressure. The crude residue was purified by flash chromatography (silica gel, 95:5 hexane/ethyl acetate) to afford the title compound as a colorless oil.

$^1$H NMR (300 MHz, $CDCl_3$) δ 8.01 (s, 1H), 3.92 (s, 3H), 2.73 (s, 2H), 1.51 (s, 6H).

6-Bromo-8-chloro-7-ethoxy-2,2-dimethyl-chroman-4-one (Compound 10)

Following General Procedure B, 6-bromo-7-ethoxy-2,2-dimethyl-chroman-4-one (Compound 5, 2.8 g, 9.33 mmol) and sulfuryl chloride (1.51 g, 11.2 mmol) in dichloromethane were reacted to yield the title compound as a colorless oil.

$^1$H NMR (300 MHz, $CDCl_3$): δ 7.99 (s, 1H), 4.16 (q, J=6.9 Hz, 2H), 2.73 (s, 2H), 1.47–1.52 (m, 9H).

6-Bromo-8-chloro-7-isopropoxy-2,2-dimethyl-chroman-4-one (Compound 11)

Following General Procedure B, 6-bromo-7-isopropoxy-2,2-dimethyl-chroman-4-one, (Compound 6, 2.2 g, 7.0 mmol) and sulfuryl chloride (0.84 mL, 10.5 mmol) in dichloromethane were reacted to yield the title compound as white trapezoidal plates after recrystallization from hexanes.

$^1$H NMR (300 MHz, $CDCl_3$): δ 7.90 (s, 1H), 4.72 (sept, J=6.2 Hz, 1H) 2.66 (s, 2H), 1.44 (s, 6H), 1.32 (d, J=6.2 Hz, 6H).

6-Bromo-7-methoxy-2,2,4-trimethyl-2H-chromene (Compound 12)

General Procedure C

A solution of methylmagnesium bromide (3.0 M in THF, 1.67 mL, 5.0 mmol) was added slowly into a solution of 6-bromo-7-methoxy-2,2-dimethyl-chroman-4-one (Compound 4, 710 mg, 2.5 mmol) in 10 mL of THF at −30° C. The mixture was stirred and warmed to 10° C. for 2 h. The reaction mixture was quenched with 10% HCl and extracted with ethyl acetate. The combined organic layers were washed with a saturated solution of $NH_4Cl$, dried ($MgSO_4$) and concentrated at reduced pressure to give a crude oil, which was then dissolved in 10 mL of dichloromethane and cooled to 0° C. with an ice bath. To this solution was added p-toluenesulfonic acid (100 mg). After stirring for 3 h at 0° C., the reaction mixture was quenched with water, extracted with dichloromethane, washed with brine, dried ($MgSO_4$) and concentrated at reduced pressure to give a colorless oil. Purification by flash chromatography (silica gel, 95.5 hexane/ethyl acetate) gave the title compound as a colorless oil.

$^1$H NMR (300 MHz, $CDCl_3$): δ 7.26 (s, 1H, 6.42 (s, 1H), 5.30 (s, 1H), 3.85 (s, 3H), 1.95 (s, 3H), 1.38 (s, 6H).

6-Bromo-4-ethyl-7-methoxy-2,2-dimethyl-2H-chromene (Compound 13)

Following General Procedure C, ethylmagnesium bromide (2.0 M in THF, 4.7 mL, 14.08 mmol) was added to a solution of 6-bromo-7-methoxy-2,2-dimethyl-chroman-4-one (Compound 4, 800 mg, 2.81 mmol) in THF. The crude alcohol was treated with p-toluenesulfonic acid to afford the title compound as a colorless oil.

$^1$H NMR (300 MHz, $CDCl_3$): δ 7.28 (s, 1H), 6.42 (s, 1H), 5.27 (s, 1H), 3.82 (s, 3H), 2.30 (q, J=7.2 Hz, 2H), 1.38 (s, 6H), 1.12 (t, J=7.2 Hz, 3H).

6-Bromo-4-isopropyl-7-methoxy-2,2-dimethyl-2H-chromene (Compound 14)

Following General Procedure C, isopropylmagnesium chloride (2.0 M in THF, 6.1 mL, 21.3 mmol) was added to a solution of 6-bromo-7-methoxy-2,2-dimethyl-chroman-4-one (Compound 4, 700 mg, 2.46 mmol) in THF. The crude alcohol was treated with p-toluenesulfonic acid to afford the title compound as a colorless oil.

$^1$H NMR (300 MHz, $CDCl_3$): & 7.33 (s, 1H), 6.43 (s, 1H), 5.28 (s, 1H), 3.84 (s, 3H), 2.70–2.79 (m, 1H), 1.38 (s, 6H), 1.13 (d, J=9.0 Hz, 61).

6-Bromo-4-tert-butyl-7-methoxy-2,2-dimethyl-2H-chromene (Compound 15)

Following General Procedure C, tert-butylmagnesium chloride (1.0 M in THF, 45.5 mL, 45.5 mmol) was added to a solution of 6-bromo-7-methoxy-2,2-dimethyl-chroman-4-one (Compound 4, 2.6 g, 9.1 mmol) in THF. The crude alcohol was treated with p-toluenesulfonic acid to afford the title compound as a colorless oil.

$^1$H NMR (300 MHz, $CDCl_3$): δ 7.69 (s, 1H), 6.45 (s, 1H), 5.39 (s, 1H), 3.84 (s, 3H), 1.36 (s, 6H), 1.28 (s, 9H).

6-Bromo-4-ethyl-7-ethoxy-2,2-dimethyl-2H-chromene (Compound 16)

Following General Procedure C, ethylmagnesium bromide (3.0 M in THF, 7.04 mL, 21.1 mmol) was added to a solution of 6-bromo-7-ethoxy-2,2-dimethyl-chroman-4-one (Compound 5, 1.2 g, 4.2 mmol) in THF. The crude alcohol was treated with p-toluenesulfonic acid to afford the title compound as a colorless oil.

$^1$H NMR (300 MHz, $CDCl_3$): δ 7.21 (s, 1H), 6.40 (s, 1H), 5.27 (s, 1H), 4.08 (q, J=7.2 Hz, 2H), 2.30 (q, J=7.2 Hz, 2H), 1.38 (s, 6H), 1.12 (t, J=7.2 Hz, 3H), 0.89 (t, J=7.2 Hz, 3H).

6-Bromo-4-methyl-7-ethoxy-2,2-dimethyl-2H-chromene (Compound 17)

Following General Procedure C, methylmagnesium chloride (3 M in THF, 1.38 mL, 4.14 mmol) was added to a solution of 6-bromo-7-ethoxy-2,2-dimethyl-chroman-4-one (Compound 5, 588 mg, 2.07 mmol) in THF. The crude alcohol was treated with p-toluenesulfonic acid to afford the title compound as a colorless oil.

$^1$H NMR (300 MHz, $CDCl_3$): δ 7.29 (s, 1H), 6.41 (s, 1H), 5.28 (s, 1H), 4.04 (q, J=7.2 Hz, 2H), 1.81 (s, 3H), 1.41 (s, 6H), 1.36 (t, J=7.2 Hz, 3H).

6-Bromo-7-ethoxy-4-isopropyl-2,2-dimethyl-2H-chromene (Compound 18)

Following General Procedure C, isopropylmagnesium chloride (2.0 M in THF, 3.3 mL, 6.6 mmol) was added to a solution of 6-bromo-7-ethoxy-2,2-dimethyl-chroman-4-one (Compound 5, 1.0 g, 3.3 mmol) in THF. The crude alcohol was treated with p-toluenesulfonic acid to afford the title compound as a colorless oil.

$^1$H NMR (300 MHz, $CDCl_3$): δ 7.28 (s, 1H), 6.31 (s, 1H), 5.21 (s, 1H), 3.99 (s, 3H), 3.99 (q, J=7.5 Hz, 2H), 2.61–2.70 (m, 1H), 1.36 (t, J=7.5 Hz, 3H), 1.34 (s, 6H), 1.05 (d, J=6.9 Hz, 6H).

6-Bromo-8-chloro-4-isopropyl-7-methoxy-2,2-dimethyl-2H-chromene (Compound 19)

Following General Procedure C, isopropylmagnesium chloride (2.0 M in THF, 3.15 mL, 6.29 mmol), 6-bromo-8-chloro-7-methoxy-2,2-dimethyl-chroman-4-one (Compound 9, 400 mg, 1.26 mmol) and 1,3-dimethyl-3,4,5,6-tetrahydro-2(1H)-pyrimidinone (DMPU, 2 mL) in THF was reacted then quenched with 10% HCl, and stored at room temperature for 12 h. Purification by flash chromatography (silica gel, 95:5 hexane/ethyl acetate) afforded the title compound as a yellow oil.

$^1$H NMR (300 MHz, $CDCl_3$): δ 7.27 (s, 1H), 5.43 (s, 1H), 3.89 (s, 1H), 2.79–2.82 (m, 1H), 1.43 (s, 6H), 0.14 (d, J=6.8 Hz, 6H).

6-Bromo-8-chloro-4-isopropyl-7-ethoxy-2,2-dimethyl-2H-chromene (Compound 20)

Following General Procedure C, isopropylmagnesium chloride (2.0 M in THF, 111 mL, 22 mmol), 6-bromo-8-chloro-7-ethoxy-2,2-dimethyl-chroman-4-one (Compound 10, 1.5 g, 4.5 mmol), and 1,3-dimethyl-3,4,5,6-tetrahydro-2(1H)pyrimidinone (DMPU, 2.6 mL) in THF was reacted then quenched with 10% HCl, and stored at room temperature for 12 h.

Purification by flash chromatography (silica gel, 95:5 hexane/ethyl acetate) gained the title compound as a yellow oil.

$^1$H NMR (300 MHz, $CDCl_3$): δ 7.27 (s, 1H), 5.42 (s, 1H), 4.09 (q, J=7.0 Hz, 2H), 2.79–2.82 (m, 1H), 1.45–1.48 (m, 9H), 1.14 (d, J=6.8 Hz, 6H).

6-Bromo-8-chloro-7-isopropoxy-4-isopropyl-2,2-dimethyl-2H-chromene (Compound 21)

Following General Procedure C, isopropylmagnesium chloride (2.0 M in THF, 18.8 mL, 37.6 mmol), 6-bromo-8- chloro-7-isopropoxy-2,2-dimethyl-chroman-4-one, (Compound 11, 2.6 g, 7.5 mmol) and 1,3-dimethyl-3,4,5,6-tetrahydro-2(]-pyrimidinone (DMPU, 4.5 mL, 37.6 mmol) in THF was reacted to afford the title compound as a yellow oil after purification by flash chromatography (silica gel, 5% to 10% ethyl acetate in hexanes).

$^1$H NMR (300 MHz, CDCl$_3$): δ 7.27 (s, 1H), 5.39 (s, 1H), 4.65 (sept, J=6.4 Hz, 1H), 2.73 (sept, J=6.6 Hz, 1H), 1.40 (s, 6H), 1.35 (d, J=6.4 Hz, 6H), 1.10 (d, J=6.6 Hz, 6H).

(2Z)-3-(4-Ethyl-7-methoxy-2,2-dimethyl-2H-chromen-6-yl)-but-2-en-1-ol (Compound 22)

General Procedure D

A solution of 6-bromo-4-ethyl-7-methoxy-2,2-dimethyl-2H-chromene (Compound 13,200 mg, 0.67 mmol), bis(pinacolato)diboron (254 mg, 1.0 mmol), and potassium acetate (198 mg, 2.0 mmol) in N,N-dimethylformamide (10 mL) was purged with argon for 15 min. The reaction mixture was then treated with [1,1'-bis(disphenylphosphino)-ferrocene]dichloropalladium(1) (1:1 complex with dichloromethane, 50 mg) and purged with argon for another 5 min. The reaction was continuously stirred at 80° C. for 4 days under argon. After the reaction was cooled to room temperature, the boronic ester mixture was treated with 3-iodo-but-2E-en-1-ol (U.S. Pat. No. 6,147,224, 266 mg, 1.34 mmol), [1,1'-bis(disphenylphosphino)ferrocene] dichloropalladium(II) (1:1 complex with dichloromethane, 50 mg) and 2 M sodium carbonate (1.3 mL, 2.6 mmol) in N,N-dimethylformamide (2 mL). After heating the reaction mixture to 50° C. for 24 h, the mixture was cooled to room temperature and extracted with ethyl acetate. The combined organic layers were washed with brine, dried over Na$_2$SO$_4$, and concentrated in vacuo. Purification by flash column chromatography (silica gel, 10 to 20% ethyl acetate in hexane) yielded the title compound as a yellow solid.

$^1$H NMR (300 MHz, CDCl$_3$): δ 6.82 (s, 1H), 6.41 (s, 1H), 5.65–5.71 (m, 1H), 5.26 (s, 1H), 3.89 (d, J=7.5 Hz, 2H), 3.75 (s, 3H), 2.34 (q, J=7.2 Hz, 2H), 2.00 (s, 3H), 1.32 (s, 6H), 1.20 (t, J=7.2 Hz).

(2Z)-3-(4-Isopropyl-7-methoxy-2,2-dimethyl-2H-chromen-6-yl)-but-2-en-1-ol (Compound 23)

As described by General Procedure D, 6-bromo-4-isopropyl-7-methoxy-2,2-dimethyl-2H-chromene (Compound 14, 138 mg, 0.45 mmol), bis(pinacolato)diboron (173 mg, 0.68 mmol), and potassium acetate (133 mg, 1.35 mmol) in N,N-dimethylformamide was treated with [1,1'-bis(disphenylphosphino)-ferrocene]dichloropalladium(II) (1:1 complex with dichloromethane, 50 mg) to give rise to the corresponding boronic ester. The crude mixture was treated with 3-iodo-but-2E-en-1-ol (178 mg, 0.90 mmol) to yield the title compound as a yellow solid after purification by flash column chromatography (silica gel, 10 to 20% ethyl acetate in hexane).

$^1$H NMR (300 MHz, CDCl$_3$): δ 6.95 (s, 1H), 6.42 (s, 1H), 5.70–5.80 (m, 1H), 5.26 (s, 1H), 3.90 (d, J=6.9 Hz, 2H), 3.76 (s, 3H), 2.73–2.82 (m, 1H), 2.03 (s, 3H), 1.39 (s, 6H), 1.11 (d, J=6.9 Hz, 6H).

(2Z)-3-(4-Isopropyl-7-methoxy-2,2-dimethyl-2H-chromen-6-yl)-pent-2-en-1-ol (Compound 24)

As described by General Procedure D, 6-bromo-4-isopropyl-7-methoxy-2,2-dimethyl-2H-chromene (Compound 14, 83 mg, 0.27 mmol), bis(pinacolato)diboron (102 mg, 0.40 mmol), and potassium acetate (80 mg, 0.81 mmol) in N,N-dimethylformamide was treated with [1,1'-bis(disphenylphosphino)-ferrocene]dichloropalladium(II) (1:1 complex with dichloromethane, 50 mg) to give rise to the corresponding boronic ester. The crude mixture was treated with 3-iodo-pent-2E-en-1-ol (Synthesis, 1995, 47, 128 mg, 6.6 mmol) to yield the title compound as a yellow solid after purification by flash column chromatography (silica gel, 10 to 20% ethyl acetate in hexane).

$^1$H NMR (300 MHz, CDCl$_3$): δ 6.85 (s, 1H), 6.41 (s, 1H), 5.70–5.80 (m, 1H), 5.23 (s, 1H), 4.01 (d, J=7.0 Hz, 2H), 3.90 (q, J=7.5 Hz, 2H), 2.70–2.81 (m, 1H), 2.01 (s, 3H), 1.39 (s, 6H), 1.30 (t, J=7.5 Hz, 3H), 1,13 (d, J=6.9 Hz, 6H).

(2Z)-3-(7-Ethoxy-4-ethyl-2,2-dimethyl-2H-chromen-6-yl)-but-2-en-1-ol (Compound 25)

As described by General Procedure D, 6-bromo-4-ethyl-7-methoxy-2,2-dimethyl-2H-chromene (Compound 16,355 mg, 1.14 mmol), bis(pinacolato)diboron (402 mg, 1.70 mmol), and potassium acetate. (336 mg, 3.42 mmol) in N,N-dimethylformamide was treated with [1,1'-bis(disphenylphosphino)-ferrocene]dichloropalladium(II) (1:1 complex with dichloromethane, 60 mg) to give rise to the corresponding boronic ester. The crude mixture was treated with 3-iodo-but-2E-en-1-ol (U.S. Pat. No. 6,147,224, 451 mg, 2.28 mmol) to yield the title compound as a yellow solid after purification by flash column chromatography (silica gel, 20% ethyl acetate in hexane).

$^1$H NMR (300 MHz, CDCl$_3$): δ 6.85 (s, 1H), 6.29 (s, 1H), 5.60–5.70 (m, 1H), 5.19 (s, 1H), 4.01 (d, J=7.0 Hz, 2H), 3.90 (q, J=7.5 Hz, 2H), 2.27 (q, 7.5 Hz, 2H), 1.96 (s, 3H), 1.32 (s, 6H), 1.32 (s, 6H), 1.01 (t, J=7.5 Hz, 3H). (2Z)-3-(7-Ethoxy-2,2,4-trimethyl-2H-chromen-6-yl)-pent-2-en-1-ol (Compound 26)

As described by General Procedure D, 6-bromo 4-methyl-7-methoxy-2,2-dimethyl-2H-chromene (Compound 17, 58 mg, 0.24 mmol), bis(pinacolato)diboron (93 mg, 0.36 mmol), and potassium acetate (54 mg, 0.55 mmol) in N,N-dimethylformamide was treated with [1,1'-bis(disphenylphosphino)ferrocene]dichloropalladium(II) (1:1 complex with dichloromethane, 20 mg) to give rise to the corresponding boronic ester. The crude mixture was treated with 3-iodo-pent-2E-en-1-ol (95 mg, 0.48 mmol) to yield the title compound as a yellow solid after purification by flash column chromatography (silica gel, 10 to 20% ethyl acetate in hexane).

$^1$H NMR (300 MHz, CDCl$_3$): δ 6.76 (s, 1H), 6.31 (s, 1H), 5.60–5.70 (m, 1H), 5.21 (s, 1H), 4.01 (q, J=7.5 Hz, 2H), 3.82 (d, J=7 Hz, 2H), 2.21–2.38 (m, 2H), 1.98 (s, 3H), 1.36 (s, 6H) 1.30 (t, J=7.5 Hz, 3H), 0.89 (t, l=7.5 Hz, 3H).

(2Z)-3-(7-Ethoxy-4-isopropyl-2,2-dimethyl-2H-chromen-6-yl)-but-2-en-1-ol (Compound 27)

As described by General Procedure D, 6-bromo-7-ethoxy-4 isopropyl-2,2-dimethyl-2H-chromene (Compound 18,274 mg, 0.85 mmol), bis(pinacolato)diboron (325 mg, 1.30 mmol), and potassium acetate (255 mg, 2.6 mmol) in N,N-dimethylformamide was treated with [1,1'-bis(disphenylphosphino)-ferrocene]dichloropalladium(II) (1:1 complex with dichloromethane, 50 mg) to give rise to the corresponding boronic ester. The crude mixture was treated with 3-iodo-but-2E-en-1-ol (335 mg, 1.68 mmol) to yield the title compound as a yellow solid after purification by flash column chromatography (silica gel, 10 to 20% ethyl acetate in hexane).

$^1$H NMR (300 MHz, CDCl$_3$): δ 6.82 (s, 1H), 6.33 (s, 1H), 5.60–5.78 (m, 1H), 5.17 (s, 1H), 4.28 (d, J=6.6 Hz, 2H), 3.98

(q, J=7.0 Hz, 2H), 3.66 (s, 3H), 2.66–2.76 (m, 1H), 2.01 (s, 3H), 1.39 (s, 6H), 1.30 (t, J=7.5 Hz, 3H), 1.13 (d, J=6.9 Hz, 6H).

(2Z)-3-(7-Ethoxy-4-isopropyl-2,2-dimethyl-2H-chromen-6-yl)-pent-2-en-1-ol (Compound 28)

As described by General Procedure D, 6-bromo-7-ethoxy-4 isopropyl-2,2-dimethyl-2H-chromene (Compound 18, 130 mg, 0.40 mmol), bis(pinacolato)diboron (152 mg, 0.60 mmol), and potassium acetate (118 mg, 1.2 mmol) in N,N-dimethylformamide was treated with [1,1'-bis(disphenylphosphino)-ferrocene]dichloropalladium(II) (1:1 complex with dichloromethane, 50 mg) to give rise to the corresponding boronic ester. The crude mixture was treated with 3-iodo-pent-2E-en-1-ol (170 mg, 0.80 mmol) to yield the title compound as a yellow solid.

$^1$H NMR (300 MHz, CDCl$_3$): δ 6.74 (s, 1H), 6.33 (s, 1H), 5.66–5.71 (m, 1H), 5.19 (s, 1H), 3.92 (q, J=7.0 Hz, 2H), 3.82(d, J=7.2 Hz, 2H), 2.66–2.75 (m, 1H), 2.28 (q, J=7.5 Hz, 2H), 1.33 (s, 6H), 1.27 (t, J=7.0 Hz, 3H), 1.06 (d, J=6.9 Hz, 6H), 0.98 (t, J=7.5 Hz, 3H).

(2Z)-3-(8-Chloro-4-isopropyl-7-methoxy-2,2-dimethyl-2H-chromen-6-yl)-but-2-en-1-ol (Compound 29)

General Procedure E

To a solution of 6-bromo-8-chloro-4-isopropyl-7-methoxy-2,2-dimethyl-2H-chromene (Compound 19, 334 mg, 0.97 mmol) in THF (25 mL) at −78° C. tert-butyllithium (1.7 M in pentane, 1.1 mL, 1.93 mmol) was added dropwise. After stirring for 30 min, trimethyl borate (0.2 mL, 1.93 mmol) was added. The reaction mixture was slowly warmed to room temperature and stirred for 2 h. The reaction mixture was quenched with a saturated solution of NH$_4$Cl and extracted with diethyl ether. The combined organic layers were washed with water and brine, dried (MgSO$_4$), filtered and concentrated under reduced pressure. The crude boronic acid was treated with 3-iodo-but-2E-en-1-ol (334 mg, 1.93 mmol), 2 M sodium carbonate (2 mL), and tetrakis(triphenylphosphine)palladium (0) (30 mg) in toluene (101 mL) and methanol (1 mL). The reaction mixture was degassed via bubbling argon for 5 min. After heating to 100° C. for 6 h, the black solution was cooled to room temperature and quenched with a saturated solution of NH$_4$Cl and extracted with diethyl ether. The combined organic layers were washed with water and brine, dried (MgSO$_4$), filtered and concentrated under reduced pressure. Purification of the residue by flash chromatography (silica gel, 5% to 20% ethyl acetate in hexanes) gave rise to the title compound as a brown oil.

$^1$H NMR (300 MHz, CDCl$_3$): δ 6.82 (s, 1H), 5.79–5.85 (m, 1H), 5.40 (s, 1H), 3.87–3.90 (m, 2H), 3.74 (s, 3H), 2.742.84 (m, 1H), 2.08 (s, 3H), 1.45 (s, 6H), 1.14 (d, J=7.1 Hz, 6H).

(2Z)-3-(8-Chloro-4-isopropyl-7-ethoxy-2,2-dimethyl-2H-chromen-6-yl)-but-2-en-1-ol (Compound 30)

As described by General Procedure E, 6-bromo-8-chloro-4-isopropyl-7-ethoxy-2,2-dimethyl-2H-chromene (Compound 20, 364 mg, 1.01 mmol) was treated with tert-butyllithium (1.7 M in pentane, 1.2 mL, 2.02 mmol) and trimethyl borate (0.2 mL, 2.02 mmol) to give rise to the boronic acid. The crude mixture was treated with 3-iodo-but-2E-en-1-ol (400 mg, 2.02 mmol), tetrakis(triphenylphosphine)palladium(0) (30 mg), and sodium carbonate (2M solution in water, 2 mL) to yield the title compound as a brown oil.

$^1$H NMR (300 MHz, CDCl$_3$): δ 6.82 (s, 1H), 5.80–5.85 (m, 1H), 5.40 (s, 1H), 3.86–3.94 (m, 4H), 2.74–2.84 (m, 1H), 2.08 (s, 1H), 1.45 (s, 6H), 1.37 (t, J=7.2 Hz, 3H), 1.14 (d, J=7.2 Hz, 6H).

(2Z)-3-(8-Chloro-4-isopropyl-7-ethoxy-2,2-dimethyl-2H-chromen-6-yl)-pent-2-en-1-ol (Compound 31)

As described by General Procedure E, 6-bromo-8-chloro-4-isopropyl-7-ethoxy-2,2-dimethyl-2H-chromene (Compound 20, 1.30 g, 3.61 mmol) was treated with tert-butyllithium (1.7 M in pentane, 6.4 mL, 10.8 mmol) and trimethyl borate (1.2 mL, 10.8 mmol) to give rise to the boronic acid. The crude mixture was treated 3-iodo-pent-2E-en-1-ol (1.0 g, 1.08 mmol), tetrakis(triphenylphosphine)palladium(0) (100 mg), and sodium carbonate (2M solution, 5 mL) to yield the title compound as a brown oil.

$^1$H NMR (300 MHz, CDCl$_3$): δ 6.80 (s, 1H), 5.79–5.82 (m, 1H), 5.40 (s, 1H), 3.87–3.94 (m, 4H), 2.73–2.83 (m, 1H), 2.36 (q, J=7.0 Hz, 2H), 1.45 (s, 6H), 1.36 (t, J=7.0 Hz, 3H), 1.00–1.14 (m, 9H).

Ethyl 7-(4-ethyl-7-methoxy-2,2-dimethyl-2H-chromen-6-yl)-3-methyl-octa-2E,4E,6Z-trienoate (Compound 32)

General Procedure F

A solution of (2Z)-3-(4-ethyl-7-methoxy-2,2-dimethyl-2H-chromen-6-yl)-but-2-en-1-ol (Compound 22, 118 mg, 0.41 mmol), 4 Å molecular sieves (100 mg), and dichloromethane (5 mL) was treated with tetrapropylammonium perruthenate (5 mg) and 4-methylmorpholine N-oxide (102 mg, 0.84 mmol). The solution was stirred under argon for 30 min and filtered through a silica gel plug (20% ethyl acetate in hexanes). The filtrate was concentrated under vacuum to give the corresponding aldehyde.

A solution of n-butyllithium (1.6 M in hexanes, 0.78 mL, 1.96 mmol) was added over 10 min down the side of the flask to a −78° C. solution of ethyl 4-(diethoxyphosphoryl)-3-methylbut-2E-enoate (545 mg, 2.0 mmol), 1,3-dimethyl-3,4,5,6-tetrahydro-2(1H)-pyrimidinone (DMPU, 3 mL) and THF (6 mL). After 10 min, a solution of the above aldehyde in THF (1 mL) was added, and the resulting solution was warmed to 0° C. and stirred until the reaction was completed (<2 h). The mixture was diluted with water, and the product was extracted with diethyl ether. The combined ether extracts were washed with brine, and dried over MgSO$_4$, and filtered. The solvent was removed under reduce pressure, and the residue was purified by flash column chromatography (silica gel, 2% ethyl acetate in hexanes) to produce the title compound as a yellow oil.

$^1$H NMR (300 MHz, CDCl$_3$): δ 6.84 (s, 1H), 6.54 (dd, J=10.5, 15.0 Hz, 1H), 6.44 (s, 1H), 6.19–6.25 (m, 2H), 5.71 (s, 1H), 5.28 (s, 1H), 4.15 (q, J 7.0 Hz, 2H), 3.76 (s, 3H), 2.33 (q, J=7.0 Hz, 2H), 2.12 (s, 3H), 1.42 (s6H), 1.26 (t, J=7.0 Hz, 3H), 1.12 (t, J=7.0 Hz, 3H), 1.09 (s, 3H).

Ethyl 7-(4-isopropyl-7-methoxy-2,2-dimethyl-2H-chromen-6-yl)-3-methyl-octa-2E,4E,6Z-trienoate (Compound 33)

As described in General Procedure F, 3-(4-isopropyl-7-methoxy-2,2-dimethyl-2H-chromen-6-yl)-but-2-en-1-ol (Compound 23, 66 mg, 0.22 mmol), tetrapropylammonium perruthenate (50 mg) and 4-methylmorpholine N-oxide (52 mg, 0.44 mmol) were reacted to produce the corresponding aldehyde. A solution of the resulting aldehyde in THF was added to the ylide of ethyl 4-(diethylphosphoryl)-3-methylbut-2Z-enoate (204 mg, 1.00 mmol), in THF and DMPU to produce the title compound as a yellow oil after purification by flash column chromatography (silica gel, 2% ethyl acetate in hexanes).

$^1$H NMR (300 MHz, CDCl$_3$): 36.89 (s, 1H), 6.45 (dd, J=10.5, 15.0 Hz, 1H), 6.37 (s, 1H), 6.12–6.20 (m, 2H), 5.64 (s, 1H), 5.20 (s, 1H), 4.07 (q, J=7.0 Hz, 2H), 3.70 (s, 3H), 2.67–2.70 (m, 1H), 2.05 (s, 3H), 2.04 (s, 3H), 1.34 (s, 6H), 1.20 (t, J=7.0 Hz, 3H), 1.04 (d, J=7.0 Hz, 6H), 0.81 (t, J=7.0 Hz, 3H).

Ethyl 7-(4-isopropyl-7-methoxy-2,2-dimethyl-2H-chromen-6-yl)-3-methyl-nona-2E,4E,6Z-trienoate (Compound 34)

As described in General Procedure F, 3-(4-isopropyl-7-methoxy-2,2-dimethyl-2H-chromen-6-yl)-pent-2-en-1-ol (Compound 24, 62 mg, 0.20 mmol), tetrapropylammonium perruthenate (5 mg) and 4-methylmorpholine N-oxide (46 mg, 0.39 mmol) were reacted to produce the corresponding aldehyde. A solution of the resulting aldehyde in THF was added to the ylide of ethyl 4-(diethylphosphoryl)-3-methylbut-2Z-enoate (233 mg, 0.88 mmol) to produce the title compound as a yellow oil after purification by flash column chromatography (silica gel, 2% ethyl acetate in hexanes).

$^1$H NMR (300 MHz, CDCl$_3$): δ 6.85 (s, 1H), 6.49 (dd, J=10.5, 15.0 Hz, 1H), 6.46 (s, 1H), 6.106.24 (m, 2H), 5.70 (s, 1H, 5.26 (s, 1H), 4.07 (q, J=7.2 Hz, 2H), 3.70 (s, 3H), 2.67–2.74 (m, 1H), 2.42 (q, J=7.2 Hz, 2H), 2.05 (s, 3H), 2.03 (s, 3H), 1.38 (s, 6H), 1.20 (t, J=7.0 Hz, 3H), 1.05 (d, J=6.0 Hz, 6H), 0.85 (t, J=7.2 Hz, 3H).

Ethyl 7-(7-ethoxy-4-ethyl-2,2-dimethyl-2H-chromen-6-yl)-3-methyl-octa-2E,4E,6Z-trienoate (Compound 35)

As described in General Procedure F, 3-(7-ethoxy-4-ethyl-2,2-dimethyl-2H-chromen-6-yl)-but-2-en-1-ol (Compound 25, 55 mg, 0.18 mmol), tetrapropylammonium perruthenate (5 mg) and 4-methylmorpholine N-oxide (50 mg, 0.36 mmol) were reacted to produce the corresponding aldehyde. A solution of the resulting aldehyde in THF was added to the ylide of ethyl 4-(diethylphosphoryl)-3-methylbut-2Z-enoate (159 mg, 0.60 mmol) to produce the title compound as a yellow oil after purification by flash column chromatography (silica gel, 2% ethyl acetate in hexanes).

$^1$H NMR (300 MHz, CDCl$_3$): δ 6.85 (s, 1H), 6.55 (dd, J=10.5, 15 Hz, 1H), 6.50–6.58 (m, 2H), 6.41 (s, 1H), 5.71 (s, 1H), 5.27 (s, 1H), 4.14 (q, J=7.0 Hz, 2H), 3.98 (q, J=7.0 Hz, 2H), 2.33 (q, J=7.0 Hz, 2H), 2.14 (s, 3H), 1.42 (s, 6H), 1.35 (t, J=7.0 Hz, 3H), 1.26 (t, J=7.0 Hz, 3H), 1.12 (t, J=7.0 Hz, 3H).

Ethyl 7-(7-ethoxy-2,2,4-trimethyl-2H-chromen-6-yl)-3-methyl-nona-2E,4E,6Z-trienoate (Compound 36)

As described in General Procedure F, 3-(7-ethoxy-2,2,4-trimethyl-2H-chromen-6-yl)-pent-2-en-1-ol (Compound 26, 37 mg, 0.16 mmol), tetrapropylammonium perruthenate (3 mg) and 4-methylmorpholine N-oxide (21 mg, 0.20 mmol) were reacted to produce the corresponding aldehyde. A solution of the resulting aldehyde in THF was added to the ylide of ethyl 4-(diethylphosphoryl)-3-methylbut-2Z-enoate (204 mg, 1.0 mmol) to produce the title compound as a yellow oil after purification by flash column chromatography (silica gel, 2% ethyl acetate in hexanes).

$^1$H NMR (300 MHz, CDCl$_3$): δ 6.80 (s, 1H), 6.55 (dd, J=10.5, 15.0 Hz, 1H), 6.10–6.20 (m, 2H), 6.40 (s, 1H), 5.66 (s, 1H, 5.28 (s, 1H), 4.16 (q, J=7.2 Hz, 2H), 4.01 (q, J=7.2 Hz, 2H), 2.43–2.50 (q, 2H, J=7.2 Hz), 2.10 (s, 3H), 1.95 (s, 3H), 1.41 (s, 6H), 1.30 (s, 3H), 1.25 (t, J=7.2 Hz, 3H), 0.96 (t, J=7.5 Hz, 3H).

Ethyl 7-(7-ethoxy-4-isopropyl-2,2-dimethyl-2H-chromen-6-yl)-3-methyl-octa-2E,4E,6Z-trienoate (Compound 37)

As described in General Procedure F, 3-(7-ethoxy-4-isopropyl-2,2-dimethyl-2H-chromen-6-yl)but-2-en-1-ol (Compound 27, 57 mg, 0.18 mmol), tetrapropylammonium perruthenate (5) and 4-methylmorpholine N-oxide (44 mg, 0.36 mmol) were reacted to produce the corresponding aldehyde. A solution of the resulting aldehyde in THF was added to the ylide of ethyl 4-(diethylphosphoryl)-3-methylbut-2Z-enoate (238 mg, 0.90 mmol) to produce the title compound as a yellow oil after purification by flash column chromatography (silica gel, 2% ethyl acetate in hexanes).

$^1$H NMR (300 MHz, CDCl$_3$): δ 6.87 (s, 1H), 6.55 (dd, J=10.5 Hz, 15 Hz, 1H), 6.41 (s, 1H), 6.10–6.20 (m, 2H), 5.70 (s, 1H), 5.25 (s, 1H), 4.10 (q, J=7.2 Hz, 2H), 3.96 (q, J=7.2 Hz, 2H), 2.64–2.76 (m, 1H), 2.07 (s, 3H), 2.04 (s, 3H), 1.39 (s, 6H), 1.30 (t, J=7.2 Hz, 3H), 1.25 (d, J=7.2 Hz, 6H), 1.10 (d, J=6.6 Hz, 6H).

Ethyl 7-(7-ethoxy-4-isopropyl-2,2-dimethyl-2H-chromen-6-yl)$_3$-methyl-nona-2E,4E,6Z-trienoate (Compound 38)

As described in General Procedure F, 3-(7-ethoxy-4-isopropyl-2,2-dimethyl-2H-chromen-6-yl)-pent-2-en-1-ol (Compound 28, 25 mg, 0.08 mmol), tetrapropylammonium perruthenate (5 mg) and 4-methylmorpholine N-oxide (19 mg, 0.16 mmol) were reacted to produce the corresponding aldehyde. A solution of the resulting aldehyde in THF was added to the ylide of ethyl 4-(diethylphosphoryl)-3-methylbut-2Z-enoate (101 mg, 0.38 mmol) to produce the title compound as a yellow oil after purification by flash column chromatography (silica gel, 2% ethyl acetate in hexanes).

$^1$H NMR (300 MHz, CDCl$_3$): δ 6.85 (s, 1H), 6.50 (dd, J=10.5, 15.0 Hz, 1H), 6.41 (s, 1H), 6.10–6.20 (m, 2H), 5.70 (s, 1H, 5.21 (s, 1H), 4.11 (q, J=7.0 Hz, 2H), 3.95 (q, J=7.0 Hz, 2H), 2.642.75 (m, 1H), 2.40 (q, J=7.0 Hz, 2H), 2.06 (s, 3H), 1.38 (s, 6H), 1.30 (t, J=7.0 Hz, 3H), 1.11 (d, J=6.6 Hz, 6H), 0.87 (t, J=7.0 Hz, 3H).

Ethyl 7-(8-chloro-4-isopropyl-7-methoxy-2,2-dimethyl-2H-chromen-6-yl) 3-methyl-octa-2E,4E, 6Z-trienoate (Compound 39)

As described in General Procedure F, 3(8-chloro-4-isopropyl-7-methoxy-2,2-dimethyl-2H-chromen-6-yl)-but-2-en-1-ol (Compound 29, 73 mg, 0.21 mmol), tetrapropylammonium perruthenate (10 mg) and 4-methylmorpholine N-oxide (57 mg, 0.43 mmol) were reacted in acetonitrile and dichloromethane to produce the corresponding aldehyde. A solution of the resulting aldehyde in THF was added to the ylide of ethyl 4-(diethylphosphoryl)-3-methylbut-2Z-enoate (230 mg, 0.87 mmol) to produce the title compound as a yellow oil after purification by flash column chromatography (silica gel, 10% ethyl acetate in hexanes).

¹H NMR (300 MHz, CDCl₃): δ 6.82 (s, 1H), 6.44–6.52 (m, 1H), 6.21–6.28 (m, 2H), 5.74 (s, 1H), 5.40 (s, 1H), 4.16 (q, J=7.0 Hz, 2H), 3.72 (s, 3H), 2.74–2.84 (m, 1H), 2.16 (s, 3H), 2.10 (s, 3H), 1.45 (s, 6H), 1.27 (t, J=7.0 Hz, 3H), 1.14 (d, J=6.8 Hz, 6H).

Ethyl 7-(8-chloro-4-isopropyl-7-ethoxy-2,2-dimethyl-2H-chromen-6-yl)-3-methyl-octa-2E,4E,6Z-trienoate (Compound 40)

As described in General Procedure F, 3-(8-chloro-4-isopropyl-7-ethoxy-2,2-dimethyl-2H-chromen-6-yl)-but-2-en-1-ol (Compound 30, 51 mg, 0.15 mmol), tetrapropylammonium perruthenate (10 mg) and 4-methylmorpholine N-oxide (34 mg, 0.29 mmol) were reacted in acetonitrile and dichloromethane to produce the corresponding aldehyde. A solution of the resulting aldehyde in THF was treated with the ylide of ethyl 4-(diethylphosphoryl)-3-methylbut-2Z-enoate (151 mg, 0.57 mmol), in THF and DMPU to produce the title compound as a white solid after purification by flash column chromatography (silica gel, 10% ethyl acetate in hexanes).

¹H NMR (300 MHz, CDCl₃): δ 6.81 (s, 1H), 6.46–6.52 (m, 1H), 6.21–6.26 (m, 2H), 5.74 (s, 1H), 5.40 (s, 1H), 4.16 (q, J=7.0 Hz, 2H), 3.90 (q, J=7.3 Hz, 2H), 2.74–2.84 (m, 1H), 2.17 (s, 3H), 2.11 (s, 3H), 1.45 (s, 6H), 1.24–1.34 (m, 6H), 1.13 (d, J=6.8 Hz, 6H).

Ethyl 7-(8-chloro-4-isopropyl-7-ethoxy-2,2-dimethyl-2H-chromen-6-yl)-3-methyl-nona-2E,4E,6Z-trienoate (Compound 41)

As described in General Procedure F, 3-(8-chloro-4-isopropyl-7-ethoxy-2,2-dimethyl-2H-chromen-6-yl)-pent-2-en-1-ol (Compound 31, 699 mg, 1.88 mmol), tetrapropylammonium perruthenate (20 mg) and 4 methylmorpholine N-oxide (440 mg, 3.76 mmol) were reacted in acetonitrile and dichloromethane to produce the corresponding aldehyde. A solution of the resulting aldehyde in THF was treated with the ylide of ethyl 4-(diethylphosphoryl)-3-methylbut-2Z-enoate(2.0 g, 7.52 mmol), in THF and DMPU to produce the title compound as a white solid after purification by flash column chromatography (silica gel, 10% ethyl acetate in hexanes).

¹H NMR (300 MHz, CDCl₃): δ 6.81 (s, 1H), 6.48–6.55 (m, 1H), 6.21–6.30 (m, 2H), 5.74 (s, 1H), 5.40 (s, 1H), 4.16 (q, J=7.0 Hz, 2H), 3.75–3.95 (m, 2H), 2.742.83 (m, 1H), 2.42–2.55 (m, 2H), 2.12 (s, 3H), 1.45 (s, 6H), 1.21–1.36 (m, 6H), 1.14 (d, J=6.8 Hz, 6H), 1.00 (d, J=7.0 Hz, 3H).

7-(4-Ethyl-7-methoxy-2,2-dimethyl-2H-chromen-6-yl)-3-methyl-octa-2E,4E,6Z-trienoic acid (Compound 42)

General Procedure G

To a solution of ethyl 7-(4-ethyl-7-methoxy-2,2-dimethyl-2H-chromen-6-yl)₃-methyl-octa-2E,4E,6Z-trienoate (Compound 32, 50 mg, 0.13 mmol) in ethanol (5 mL) and THF (2 mL) was added 1M NaOH (1.0 mL, 1.0 mmol). The mixture was heated to 60° C. for 5 h and was cooled to room temperature, acidified with 1M HCl, and extracted with ethyl acetate. The organic layer was washed with brine, dried over Na₂SO₄, and concentrated in vacuo. The residue was purified by flash column chromatography (silica gel, 30% ethyl acetate in hexanes) followed by recrystallization from acetonitrile to give the title compound as a light yellow solid.

¹H NMR (300 MHz, CDCl₃): δ 6.85 (s, 1H), 6.56 (dd, J=10.5, 15.0 Hz, 1H), 6.44 (s, 1H), 6.11–6.26 (m, 2H), 5.73 (s, 1H), 5.28 (s, 1H), 3.79 (s, 3H), 2.33 (q, J=7.5 Hz, 2H), 2.13 (s, 3H), 2.12 (s, 3H), 1.43 (s, 6H), 1.12 (t, J=7.5 Hz, 3H).

7-(4-Isopropyl-7-methoxy-2,2-dimethyl-2H-chromen-6-yl)-3-methyl-octa-2E,4E,6Z-trienoic acid (Compound 43)

Following General Procedure G, ethyl 7-(4-isopropyl-7-methoxy-2,2-dimethyl-2H-chromen-6-yl)-3-methyl-octa-2E,4E,6Z-trienoate (Compound 33, 60 mg, 0.15 mmol) was hydrolyzed with 1 M NaOH. Purification by column chromatography (silica gel, 30% ethyl acetate in hexanes) followed by recrystallization from acetonitrile yielded the title compound as a yellow solid.

¹H NMR (300 MHz, CDCl₃): δ 6.87 (s, 1H), 6.57 (dd, J=10.5, 15.0 Hz, 1H), 6.45 (s, 1H), 6.10–6.26 (m, 2H),5.73 (s, 1H), 5.28 (s, 1H), 3.77 (s, 3H), 2.74–2.78 (m, 1H), 2.14 (s, 3H), 2.11 (s, 3H), 1.42 (s, 6H), 1.12 (d, J=6.8 Hz, 6H).

7-(4-Isopropyl-7-methoxy-22-dimethyl-2H-chromen-6-yl)-3-methyl-nona-2E,4E,6Z-trienoic acid (Compound 44)

Following General Procedure G, ethyl 7-(4-isopropyl-7-methoxy-2,2-dimethyl-2H-chromen-6-yl)-3-methyl-nona-2E,4E,6Z-trienoate (Compound 34, 37 mg, 0.09 mmol) was hydrolyzed with 1M NaOH. Purification by column chromatography (silica gel, 30% ethyl acetate in hexanes) followed by recrystallization from acetonitrile yielded the title compound as a light yellow solid.

¹H NMR (300 MHz, CDCl₃): δ 6.83 (s, 1H), 6.56 (dd, J=10.5, 15.0 Hz, 1H), 6.44 (s, 1H), 6.11–6.27 (m, 2H), 5.71 (s, 1H), 5.26 (s, 1H), 3.74 (s, 3H), 2.68–2.78 (m, 1H), 2.44 (q, J=7.5 Hz, 2H), 2.09 (s, 3H), 1.40 (s, 6H), 1.11 (d, J=6.8 Hz, 6H), 0.98 (t, J=7.5 Hz, 3H).

7-(7-Ethoxy-4-ethyl-2,2-dimethyl-2H-chromen-6-yl)-3-methyl-octa-2E,4E,6Z-trienoic acid (Compound 45)

Following General Procedure G, ethyl 7-(7-ethoxy-4-ethyl-2,2-dimethyl-2H-chromen-6-yl)-3-methyl-octa-2E,4E,6Z-trienoate (Compound 35,23 mg, 0.058 mmol) was hydrolyzed with 1M NaOH. Purification by column chromatography (silica gel, 30% ethyl acetate in hexanes) followed by recrystallization from acetonitrile gave rise to the title compound as a light yellow solid.

¹H NMR (300 MHz, CDCl₃): δ 6.85 (s, 1H), 6.62 (dd, J=10.5, 15.0 Hz, 1H), 6.42 (s, 1H), 6.20–6.25 (m,2H), 5.73 (s, 1H), 5.28 (s, 1H), 4.01 (q, J=7.5 Hz, 2H), 2.33 (q, J=7.5 Hz, 2H), 2.15 (s, 3H), 2.12 (s, 3H), 1.42 (s, 6H), 1.33 (t, J=7.5 Hz, 3H), 1.13 (t, J=7.5 Hz, 3H).

7-(7-Ethoxy-2,2,4-trimethyl-2H-chromen-6-yl)-3-methyl-nona-2E,4E,6Z-trienoic acid (Compound 46)

Following General Procedure G, ethyl 7-(7-ethoxy-2,2,4-trimethyl-2H-chromen-6-yl)-3-methyl-nona-2E,4E,6Z-trienoate (Compound 36, 33 mg, 0.086 mmol) was hydrolyzed with 1M NaOH. Purification by column chromatography (silica gel, 30% ethyl acetate in hexanes) followed by recrystallization from acetonitrile gave rise to the title compound as a light yellow solid.

¹H NMR (300 MHz, CDCl₃): δ 6.77 (s, 1H), 6.60 (dd, J=10.5, 15.0 Hz, 1H), 6.41 (s, 1H), 6.20–6.35 (m, 2H), 5.77(s, 1H), 5.23 (s, 1H), 3.99 (q, J=7.2 Hz, 2H), 2.46–2.49 (q, J=7.2 Hz, 2H), 2.13 (s, 3H), 1.94 (s, 3H), 1.45 (s, 6H), 1.32 (t, J=7.5 Hz, 3H), 1.00 (t, J=7.5 Hz, 3H).

7-(7-Ethoxy-4-isopropyl-2,2-dimethyl-2H-chromen-6-yl)-3-methyl-octa-2E,4E,6Z-trienoic acid (Compound 47)

Following General Procedure G, ethyl 7-(7-ethoxy-4-isopropyl-2,2-dimethyl-2H-chromen-6-yl)-3-methyl-octa-2E,4E,6Z-trienoate (Compound 37, 55 mg, 0.13 mmol) was hydrolyzed with 1M NaOH to yield the title compound as a yellow solid after purification by column chromatography (silica gel, 30% ethyl acetate in hexanes) followed by recrystallization from acetonitrile to yield the title compound as a light yellow solid.

$^1$H NMR (300 MHz, CDCl$_3$): δ 6.86 (s, 1H), 6.60 (dd, J=10.5, 15.0 Hz, 1H), 6.41 (s, 1H), 6.14–6.20 (m, 2H), 5.72 (s, 1H), 5.26 (s, 1H), 3.98 (q, J=7.0 Hz, 2H), 2.64–2.76 (m, 1H), 2.13 (s, 3H), 2.10 (s, 3H), 1.36 (s, 6H), 1.33 (t, J=7.0 Hz, 3H), 1.10 (d, J=7.0 Hz, 6H).

7-(7-ethoxy-4-isopropyl-2,2-dimethyl-2H-chromen-6-yl)-3-methyl-nona-2E,4E,6Z-trienoic acid (Compound 48)

Following General Procedure G, ethyl 7-(7-ethoxy-4-isopropyl-2,2-dimethyl-2H-chromen-6-yl)-3-methyl-nona-2E,4E,6Z-trienoate (Compound 38, 30 mg, 0.70 mmol) was hydrolyzed with 1M NaOH. Purification by column chromatography (silica gel, 30% ethyl acetate in hexanes) followed by recrystallization from acetonitrile gave rise to the title compound as a light yellow solid.

$^1$H NMR (300 MHz, CDCl$_3$): δ 6.82 (s, 1H), 6.60 (dd, J=10.5, 15.0 Hz, 1H), 6.40 (s, 1H), 6.05–6.33 (m, 2H), 5.73 (s, 1H), 5.26 (s, 1H), 3.98 (q, J=7.0 Hz, 2H), 2.60–2.77 (m, 1H), 2.46 (q, J=7.0 Hz, 2H), 2.26 (s, 3H), 1.37 (s, 6H), 1.32 (t, J=7.0 Hz, 3H), 1.10 (d, J=7.0 Hz, 6H), 0.87 (t, J=7.0 Hz, 3H).

7-(8-Chloro-4-isopropyl-7-methoxy-2,2-dimethyl-2H-chromen-6-y)-3-methyl-octa-2E,4E,6Z-trienoic acid (Compound 49)

Following General Procedure G, ethyl 7-(8-chloro-4-isopropyl-7-methoxy-2,2-dimethyl-2H-chromen-6-yl)-3-methyl-octa-2E,4E,6Z-trienoate (Compound 39, 53 mg, 0.12 mmol) was hydrolyzed with 1M NaOH. Purification by column chromatography (silica gel, 20% to 30% ethyl acetate in hexanes) followed by recrystallization from acetonitrile gave rise to the title compound as a light yellow solid.

$^1$H NMR (300 MHz, CDCl$_3$): δ 6.81 (s, 1H), 6.45–6.54 (m, 1H), 6.24–6.29 (m, 2H), 5.76 (s, 1H), 5.41 (s, 1H), 3.72 (s, 3H), 2.74–2.84 (m, 1H), 2.17 (s, 3H), 2.11 (s, 3H), 1.46 (s, 6H), 1.13 (d, J=6.8 Hz, 6H).

7-(8-Chloro-4-isopropyl-7-ethoxy-2,2-dimethyl-2H-chromen-6-yl)-3-methyl-octa-2E,4E,6Z-trienoic acid (Compound 50)

Following General Procedure G, ethyl 7-(8-chloro-4-isopropyl-7-ethoxy-2,2-dimethyl-2H-chromen-6-yl)-3-methyl-octa-2E,4E,6Z-trienoate (Compound 40, 42 mg, 0.092 mmol) was hydrolyzed with 1M NaOH. Purification by column chromatography (silica gel, 25% ethyl acetate in hexanes) followed by recrystallization from acetonitrile gave rise to the title compound as a light yellow solid.

$^1$H NMR (300 MHz, CDCl$_3$): δ 6.81 (s, 1H), 6.44–6.52 (m, 1H), 6.24–6.28 (m, 2H), 5.76 (s, 1H), 5.40 (s, 1H), 3.88 (q, J=7.3 Hz, 2H), 2.74–2.84 (m, 1H), 2.17 (s, 3H), 2.11 (s, 3H), 1.46 (s, 6H), 1.32 (t, J=7.3 Hz, 3H), 1.13 (d, J=6.8 Hz, 6H).

Ethyl 7-(8-chloro-isopropyl-7-ethoxy-2,2-dimethyl-2H-chromen-6-yl)-3-methyl-nona-2E,4E,6Z-trienoate (Compound 51)

Following General Procedure G, ethyl 7-(8-chloro-4-isopropyl-7-ethoxy-2,2-dimethyl-2H-chromen-6-yl)-3-methyl-nona-2E,4E,6Z-trienoate (Compound 41, 296 mg, 0.63 mmol) was hydrolyzed with 1M NaOH. Purification by column chromatography (silica gel, 10% ethyl acetate in hexanes) followed by recrystallization from acetonitrile gave rise to the title compound as a light yellow solid.

$^1$H NMR (300 MHz, CDCl$_3$): δ 6.80 (s, 1H), 6.51–6.61 (m, 1H), 6.25–6.31 (m, 2H) 5.76 (s, 1H), 5.41 (s, 1H), 3.86 (s, 2H), 2.74–2.84 (m, 1H), 2.45–2.55 (s, 2H), 2.11 (s, 3H), 1.46 (s, 6H), 1.30 (t, J=7.0 Hz, 3H), 1.13 (d, J=6.8 Hz, 6H), 1.01 (t, J=7.3 Hz, 3H).

TABLE 1

Receptor Transactivation, Efficacy and Binding Data for Exemplary Compounds of Formula A

| Compound Number | Structure | RAR Trans. EC$_{50}$ nM / RAR Bind. K$_i$ nM | | | RXR Trans. EC$_{50}$ nM / RXR Bind K$_i$ nM | | |
|---|---|---|---|---|---|---|---|
| | | α | β | γ | α | β | γ |
| 42 | | NA | 845 (34) | NA | 6 (99) | 55 (98) | 13 (125) |
| | | 8.9k | 9.9k | >10k | 49 | 228 | ND |

TABLE 1-continued

Receptor Transactivation, Efficacy and Binding Data for Exemplary Compounds of Formula A

| Compound Number | Structure | RAR Trans. $EC_{50}$ nM RAR Bind. $K_i$ nM | | | RXR Trans. $EC_{50}$ nM RXR Bind $K_i$ nM | | |
|---|---|---|---|---|---|---|---|
| | | α | β | γ | α | β | γ |
| 43 | 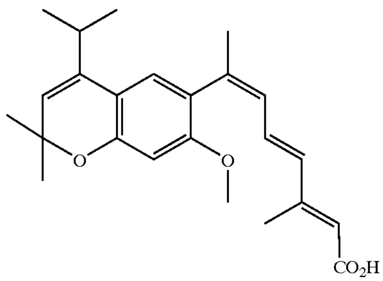 | 13 (5) 243 | 57 (37) 378 | NA 2.5k | 2 (89) 6 | 16 (96) 78 | 3 (95) ND |
| 44 | 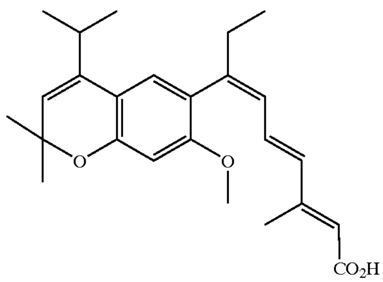 | NA 215 | 75 (25) 617 | NA 3.5k | 0.3 (89) 4 | 4.4 (94) 38 | 0.4 (97) ND |
| 45 | 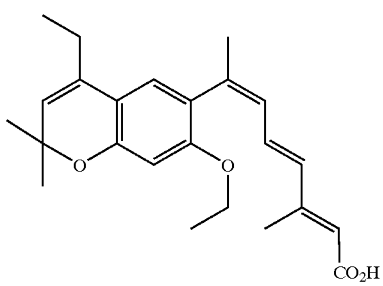 | 121 (6) 3 | >1k 196 | NA 2.3k | 78 (5) 52 | >1k 343 | NA ND |
| 46 | 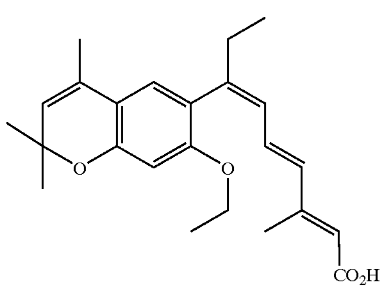 | NA 623 | 305 (6) 614 | NA 3.4k | >1k 199 | >1k 1.7k | >1k ND |
| 47 | 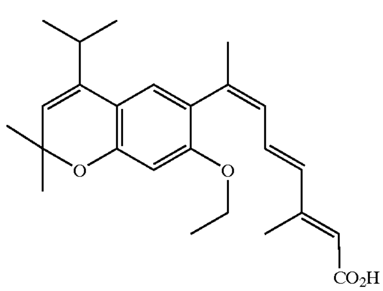 | NA >10k | NA 3.9k | NA ND | NA 15 | 288 (6) 150 | NA ND |

TABLE 1-continued

Receptor Transactivation, Efficacy and Binding Data for Exemplary Compounds of Formula A

| Compound Number | Structure | RAR Trans. $EC_{50}$ nM RAR Bind. $K_i$ nM | | | RXR Trans. $EC_{50}$ nM RXR Bind $K_i$ nM | | |
|---|---|---|---|---|---|---|---|
| | | α | β | γ | α | β | γ |
| 49 | 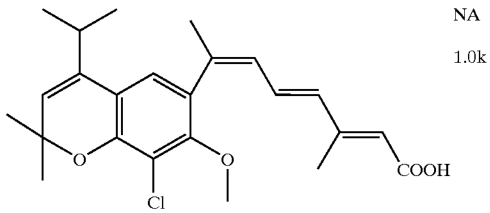 | NA | 132 (12) | NA | 0.1 (93) | 0.9 (98) | 0.3 (97) |
| | | 1.0k | 4.1k | >10k | 2 | 20 | ND |
| 50 | 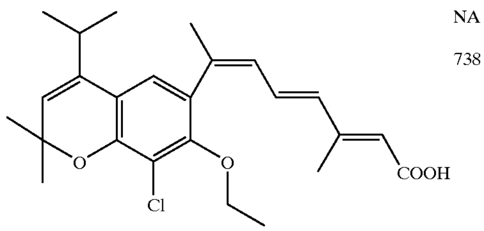 | NA | NA | NA | 2 (56) | 19 (57) | 5 (47) |
| | | 738 | 1.3k | 5.9k | 4 | 76 | ND |
| 51 | 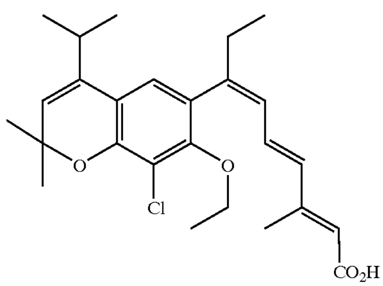 | NA | NA | NA | 9 (25) | 88 (26) | 22 (13) |
| | | 422 | 1.4k | 4.9k | 13 | 112 | ND |

TABLE 2

In vivo Data (in ob/ob mice) for Exemplary Compounds of Formula A

| Treatment (dose) | Glucose (mg/dl) | | | Triglycerides (mg/dl) | | T4 (μg/dL) |
|---|---|---|---|---|---|---|
| | Day 0 | Day 3, 3 h | Day 6, 3 h | Day 0 | Day 3, 3 h | Day 7 |
| Vehicle (Control Diet) | 296 ± 123 | 279 ± 97 | 367 ± 116 | 90 ± 42 | 98 ± 17 | 3.8 ± 0.3 |
| Standard compound (2.5 mg/kg) | 246 ± 49 | 107 ± 27 | 136 ± 28 | 92 ± 41 | 55 ± 23 | 0.8 ± 0.2 |
| Compound 50 (30 mg/kg) | 288 ± 109 | 209 ± 72 | 237 ± 42 | 122 ± 72 | 90 ± 33 | 4.5 ± 0.5 |

In this in vivo assay, the drug was mixed in a control diet and fed to the animals over 7 days. The dose indicates the average amount of drug consumed by each animal per day.

In this assay the transient hypertriglyceridemia caused by full RXR agonists is not observed when animals are dosed by this method. Hypothyroidism is the only observed toxicity of RXR full agonists in this assay.

Section B of Specific Embodiments

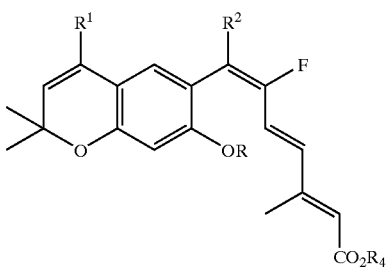

Formula B

Formula B discloses a specific class of preferred and exemplary compounds of the invention. In Formula B:

R represents alkyl of 1 to 8 carbons, more preferably alkyl of 1 to 4 carbons;

$R^1$ represents phenyl, alkyl of 1 to 8 carbons, more preferably alkyl of 1 to 4 carbons;

$R^2$ represents alkyl of 1 to 8 carbons, more preferably alkyl of 1 to 4 carbons, and most preferably alkyl of 1 to 2 carbons, and $R_4$ represents H, alkyl of 1 to 6 carbons, $CH_2OR_5$ or $CH_2OCOR_5$ where $R_5$ is alkyl of 1 to 3 carbons, or a pharmaceutically acceptable salt of said compound.

The synthetic schemes and the experimental procedures for obtaining compounds within the scope of Formula B are provided below.

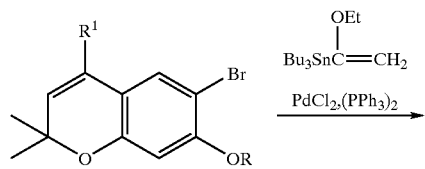

8, (R = Me, R¹ = Ph)
13 (R = Me, R¹ = Et)
14 (R = Me, R¹ = iPr)
15 (R = Me, R¹ = t-Bu)
16 (R = Et, R¹ = Et)

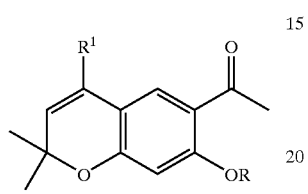

52, (R = Me, R¹ = Ph)
53 (R = Me, R¹ = Et)
54 (R = Me, R¹ = iPr)
55 (R = Me, R¹ = t-Bu)
56 (R = Et, R¹ = Et)

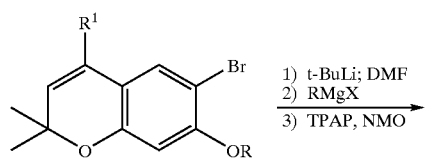

12 (R = Me, R¹ = Me)
14 (R = Me, R¹ = iPr)
15 (R = Me, R¹ = t-Bu)
17 (R = Et, R¹ = Me)

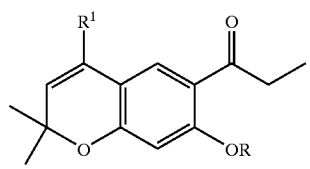

57 (R = Me, R¹ = Me)
58 (R = Me, R¹ = iPr)
59 (R = Me, R¹ = t-Bu)
60 (R = Et, R¹ = Me)

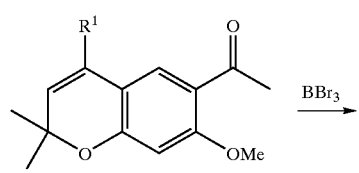

52, (R¹ = Ph)
54 (R¹ = iPr)

-continued

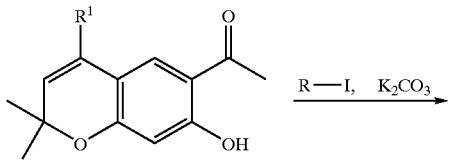

61, (R¹ = Ph)
62 (R¹ = iPr)

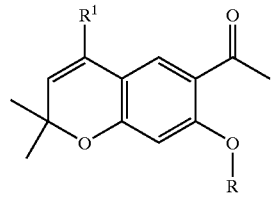

63 (R = Et, R¹ = iPr)
64 (R = n-Pr, R¹ = iPr)
65 (R = n-Bu, R¹ = iPr)
66 (R = Et, R¹ = Ph)
67 (R = n-Pr, R¹ = Ph)

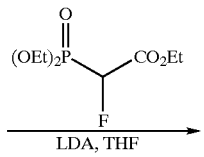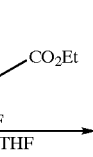

53 (R = Me, R¹ = Et, R² = Me)
54 (R = Me, R¹ = iPr, R² = Me)
55 (R = Me, R¹ = t-Bu, R² = Me)
56 (R = Et, R¹ = Et, R² = Me)
63 (R = Et, R¹ = iPr, R² = Me)
64 (R = n-Pr, R¹ = iPr, R² = Me)
65 (R = n-Bu, R¹ = iPr, R² = Me)
66 (R = Et, R¹ = Ph, R² = Me)
67 (R = n-Pr, R¹ = Ph, R² = Me)
57 (R = Me, R1 = Me, R² = Et)
58 (R = Me, R1 = iPr, R² = Et)
59 (R = Me, R1 = t-Bu, R² = Et)
60 (R = Et, R1 = Me, R² = Et)

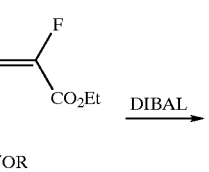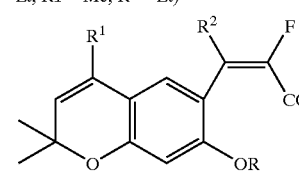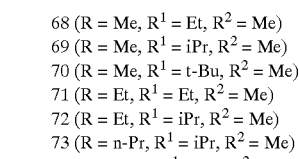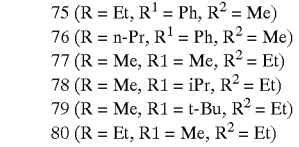

68 (R = Me, R¹ = Et, R² = Me)
69 (R = Me, R¹ = iPr, R² = Me)
70 (R = Me, R¹ = t-Bu, R² = Me)
71 (R = Et, R¹ = Et, R² = Me)
72 (R = Et, R¹ = iPr, R² = Me)
73 (R = n-Pr, R¹ = iPr, R² = Me)
74 (R = n-Bu, R¹ = iPr, R² = Me)
75 (R = Et, R¹ = Ph, R² = Me)
76 (R = n-Pr, R¹ = Ph, R² = Me)
77 (R = Me, R1 = Me, R² = Et)
78 (R = Me, R1 = iPr, R² = Et)
79 (R = Me, R1 = t-Bu, R² = Et)
80 (R = Et, R1 = Me, R² = Et)

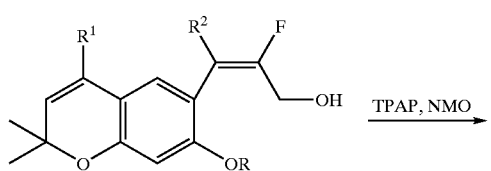

TPAP, NMO →

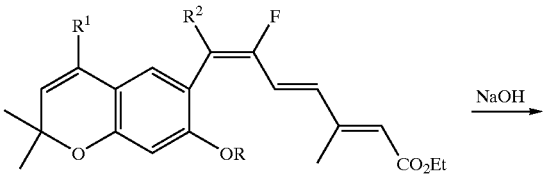

NaOH →

81 (R = Me, R¹ = Et, R² = Me)
82 (R = Me, R¹ = iPr, R² = Me)
83 (R = Me, R¹ = t-Bu, R² = Me)
84 (R = Et, R¹ = Et, R² = Me)
85 (R = Et, R¹ = iPr, R² = Me)
86 (R = n-Pr, R¹ = iPr, R² = Me)
87 (R = n-Bu, R¹ = iPr, R² = Me)
88 (R = Et, R¹ = Ph, R² = Me)
89 (R = n-Pr, R¹ = Ph, R² = Me)
90 (R = Me, R1 = Me, R² = Et)
91 (R = Me, R1 = iPr, R² = Et)
92 (R = Me, R1 = t-Bu, R² = Et)
93 (R = Et, R1 = Me, R² = Et)

107 (R = Me, R¹ = Et, R² = Me)
108 (R = Me, R¹ = iPr, R² = Me)
109 (R = Me, R¹ = t-Bu, R² = Me)
110 (R = Et, R¹ = Et, R² = Me)
111 (R = Et, R¹ = iPr, R² = Me)
112 (R = n-Pr, R¹ = iPr, R² = Me)
113 (R = n-Bu, R¹ = iPr, R² = Me)
114 (R = Et, R¹ = Ph, R² = Me)
115 (R = n-Pr, R¹ = Ph, R² = Me)
116 (R = Me, R1 = Me, R² = Et)
117 (R = Me, R1 = iPr, R² = Et)
118 (R = Me, R1 = t-Bu, R² = Et)
119 (R = Et, R1 = Me, R² = Et)

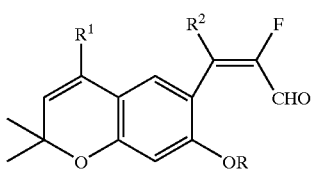

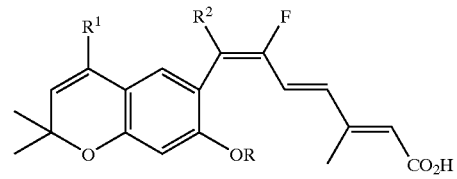

94 (R = Me, R¹ = Et, R² = Me)
95 (R = Me, R¹ = iPr, R² = Me)
96 (R = Me, R¹ = t-Bu, R² = Me)
97 (R = Et, R¹ = Et, R² = Me)
98 (R = Et, R¹ = iPr, R² = Me)
99 (R = n-Pr, R¹ = iPr, R² = Me)
100 (R = n-Bu, R¹ = iPr, R² = Me)
101 (R = Et, R¹ = Ph, R² = Me)
102 (R = n-Pr, R¹ = Ph, R² = Me)
103 (R = Me, R1 = Me, R² = Et)
104 (R = Me, R1 = iPr, R² = Et)
105 (R = Me, R1 = t-Bu, R² = Et)
106 (R = Et, R1 = Me, R² = Et)

120 (R = Me, R¹ = Et, R² = Me)
121 (R = Me, R¹ = iPr, R² = Me)
122 (R = Me, R¹ = t-Bu, R² = Me)
123 (R = Et, R¹ = Et, R² = Me)
124 (R = Et, R¹ = iPr, R² = Me)
125 (R = n-Pr, R¹ = iPr, R² = Me)
126 (R = n-Bu, R¹ = iPr, R² = Me)
127 (R = Et, R¹ = Ph, R² = Me)
128 (R = n-Pr, R¹ = Ph, R² = Me)
129 (R = Me, R1 = Me, R² = Et)
130 (R = Me, R1 = iPr, R² = Et)
131 (R = Me, R1 = t-Bu, R² = Et)
132 (R = Et, R1 = Me, R² = Et)

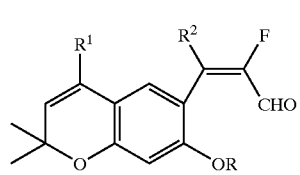
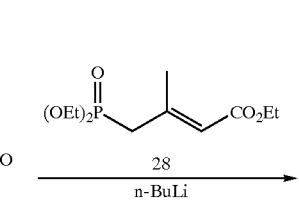

94 (R = Me, R¹ = Et, R² = Me)
95 (R = Me, R¹ = iPr, R² = Me)
96 (R = Me, R¹ = t-Bu, R² = Me)
97 (R = Et, R¹ = Et, R² = Me)
98 (R = Et, R¹ = iPr, R² = Me)
99 (R = n-Pr, R¹ = iPr, R² = Me)
100 (R = n-Bu, R¹ = iPr, R² = Me)
101 (R = Et, R¹ = Ph, R² = Me)
102 (R = n-Pr, R¹ = Ph, R² = Me)
103 (R = Me, R1 = Me, R² = Et)
104 (R = Me, R1 = iPr, R² = Et)
105 (R = Me, R1 = t-Bu, R² = Et)
106 (R = Et, R1 = Me, R² = Et)

1-(7-Methoxy-2,2-dimethyl-4-phenyl-2H-chromen-6-yl-ethanone) (Compound 52)

General Procedure H

A solution of 6-bromo-7-methoxy-2,2-dimethyl-4-phenyl-2H-chromene (Compound 8, 1.58 g, 4.60 mmol) in THF (8 mL) was first degassed by bubbling with argon for 15 min. To the solution tributyl(1-ethoxyvinyl)tin (3.10 mL, 9.19 mmol) and dichlorobis(triphenylphosphine)palladium (II) (322 mg) were added. After stirring at 80° C. for 12 h, the mixture was cooled to room temperature and 10% HCl (4 mL) was added. The resulting mixture was stirred at 25° C. for 30 min. The product was extracted with ethyl acetate. The organic layer was washed with water, brine, and dried over $Na_2SO_4$. The filtered solvent was concentrated in vacuo and purified by column chromatography (silica gel, 5% ethyl acetate in hexane) to give the title compound as a yellow oil.

$^1$H NMR (300 MHz, $CDCl_3$): δ 1.50 (s, 6H), 1.14 (s, 3H), 2.52 (s, 3H), 3.90 (s, 3H), 5.52 (s, 1H), 6.49 (s, 1H), 7.35 9 m, 5H), 7.56 (s, 1H). 1-(4-Ethyl-7-methoxy-2,2-dimethyl-2H-chromen-6-yl)-ethanone Compound 53)

Following General Procedure H, a solution of 6-bromo-4-ethyl-7-methoxy-2,2-dimethyl-2H-chromene (Compound 13, 690 mg, 2.42 mmol) in THF was treated with tributyl (1-ethoxyvinyl)tin (1.74 g, 4.84 mmol) to give the title compound as a colorless oil after purification by flash chromatography (silica gel, 80:20 hexane/ethyl acetate).

$^1$H NMR (300 MHz, CDCl$_3$): δ 7.75 (s, 1H), 6.31 (s, 1H), 5.26 (s, 10H), 3.82 (s, 3H), 2.49 (s, 3H), 2.40 (q, J=7.2 Hz, 2H), 1.40 (s, 6H), 1.10 (t, J=7.2 Hz, 3H).

1-(4-Isopropyl-7-methoxy-2,2-dimethyl-2H-chromen-6-yl)-ethanone (Compound 54)

Following General Procedure H, a solution of 6-bromo-4-isopropyl-7-methoxy-2,2-dimethyl-2H-chroman-4-one (Compound 14, 290 mg, 0.94 mmol) in THF was treated with tributyl(1-ethoxyvinyl)tin (0.63 mL, 1.88 mmol) to give the title compound as a colorless oil.

$^1$H NMR (300 MHz, CDCl$_3$): δ 1.11 (s, 3H), 1.14 (s, 3H), 1.40 (s, 6H), 2.59 (s, 3H), 2.85 (m, If), 3.85 (s, 3H), 5.37 (s, 1H), 6.41 (s, 1H), 7.77 (s, 1H).

1-(4-tert-Butyl-7-methoxy-2,2-dimethyl-2H-chromen-6-yl)-ethanone (Compound 55)

Following General Procedure H, a solution of 6-bromo-4-tert-butyl-7-methoxy-2,2-dimethyl-2H-chromene (Compound 15, 280 mg, 0.86 mmol) in THF was treated with tributyl(1-ethoxyvinyl)tin (0.58 mL, 1.7 mmol) to give the title compound as a colorless oil.

$^1$H NMR (300 MHz, CDCl$_3$): δ 8.14 (s, if), 6.41 (s, 1H), 5.41 (s, 1H), 3.85 (s, 3H), 2.56 (s, 3H), 1.37 (s, 6H), 1.29 (s, 9H).

1-(7-Ethoxy-4-ethyl-2,2-dimethyl-2H-chromen-6-yl)-ethanone (Compound 56)

Following General Procedure H, a solution of 6-bromo-4-ethyl-7-ethoxy-2,2-dimethyl-2H-chromene (Compound 16, 595 mg, 2.08 mmol) in THF was treated with tributyl (1-ethoxyvinyl)tin (1.50 g, 4.17 mmol) to give the title compound as a yellow solid.

$^1$H NMR (300 MHz, CDCl$_3$): δ 7.66 (s, 1H), 6.29 (s, 1H), 5.24 (s, 1H), 4.03 (q, J=7.2 Hz, 2H), 2.51 (s, 3H), 2.35 (q, J=7.2 Hz, 2H), 1.33 (s, 6H), 1.09 (t, J 57.2 Hz, 3H), 0.84 (t, J=7.2 Hz, 3H).

1-(7-Methoxy-2,2,4-trimethyl-2H-chromen-6-yl)-propan-1-one (Compound 57)

General Procedure I

A solution of tert-butyllithium (1.7 M in pentane, 1.7 mL, 4.4 mmol) was added to a solution of 6-bromo-7-methoxy-2,2,4-trimethyl-2H-chromene (Compound 12, 626 mg, 2.2 mmol) in THF (10 mL) at −78 DC. After stirring for 10 min, DMF (1 mL) was added and the mixture was allowed to warm to room temperature for 30 min. The reaction mixture was quenched with water, extracted with ethyl acetate, washed with brine, dried (MgSO$_4$) and concentrated at reduced pressure to give the corresponding aldehyde. The crude mixture was dissolved in THF (10 mL) and cooled to 0° C. with an ice bath. To this solution ethylmagnesium bromide (2.0 μM in THF, 2.2 mL, 4.4 mmol) was added and stirred at room temperature for 20 min. The reaction mixture was quenched with water, extracted with ethyl acetate, washed with brine, dried (MgSO$_4$) and concentrated at reduced pressure to give the crude alcohol. To a solution of the residue in dichloromethane (10 mL) was added 4-methylmorpholine N-oxide (514 mg, 4.4 mmol) and tetrapropylammonium perruthenate (5 mg). After stirring at room temperature for 10 min, the solvent was removed under reduced pressure and the residue was purified by flash chromatography (silica gel, 80:20 hexane/ethyl acetate) to obtain the title compound as a colorless oil.

$^1$H NMR (300 MHz, CDCl$_3$): δ 7.59 (s, 1H), 6.32 (s, 1H), 5.26 (s, 1H), 3.80 (s, 3H), 2.90 (q, J=7.2 Hz, 2H), 1.94 (s, 3H), 1.33 (s, 6H), 1.08 (t, J=7.2 Hz, 3H).

1-(Isopropyl-7-methoxy-2,2-dimethyl-2H-chromen-6-yl)-propan-1-one (Compound 58)

Following General Procedure I, 6-bromo-4-isopropyl-7-methoxy-2,2-dimethyl-2H-chromene (Compound 14, 146 mg, 0.50 mmol) afforded the title compound as a colorless oil.

$^1$H NMR (300 MHz, CDCl$_3$): δ 7.76 (s, 1H), 6.40 (s, 1H), 5.30 (s, 1H), 3.86 (s, 3H), 2.86–2.97 (m, 5H), 0.93–1.40 (m, 6H).

1-[(4-tert-Butyl-7-methoxy-2,2-dimethyl-2H-chromen-6-yl) propan-1-one (Compound 59)

Following General Procedure I, 6-bromo-4-tert-butyl-7-methoxy-2,2-dimethyl-2H-chromene (Compound 15, 118 mg, 0.39 mmol) afforded the title compound as a colorless oil.

$^1$H NMR (300 MHz, CDCl$_3$): δ 8.09(s, 1H), 6.35 (s, 1H), 5.34 (s, 1H), 3.79 (s, 3H), 2.91 (q, J=7.2 Hz, 2H), 1.31 (s, 6H), 1.23 (s, 9H), 1.08 (t, J=7.2 Hz, 3H).

1-(7-Ethoxy-2,2,4-trimethyl-2H-chromen-6-yl)-propan-1-one (Compound 60)

Following General Procedure I, 6-bromo-4-methyl-7-ethoxy-2,2-dimethyl-2H-chromene (Compound 17, 505 mg, 1.54 mmol) afforded the title compound as a yellow solid.

$^1$H NMR (300 MHz, CDCl$_3$): δ 7.61 (s, 1H), 6.28 (s, 1H), 5.21 (s,1H), 4.04 (q, J=7.2 Hz, 2H), 2.85 (q, J=7.2 Hz, 2H), 1.80 (s, 3H), 1.41 (s, 6H), 1.36 (t, J=7.2 Hz, 3H), 0.88 (t, J=7.2 Hz, 3H).

6-Bromo-2,2-dimethyl-4-phenyl-2H-chromen-7-ol (Compound 61)

General Procedure J

To a solution of 6-bromo-7-methoxy-2,2-dimethyl-4-phenyl-2H-chromene (Compound 52, 992 mg, 3.22 mmol) in dichloromethane (20 mL) under argon at 0° C. was added boron tribromide (1M in dichloromethane, 3.8 mL, 3.8 mmol). The mixture was stirred at 0° C. for 1 h, then quenched with ice. The product was extracted with ethyl acetate. The organic layer was washed with water and brine, and dried over Na$_2$SO$_4$. The filtered solvent was concentrated in vacuo and purified by column chromatography (silica gel, 5% ethyl acetate in hexane) to produce the title compound as a white solid.

$^1$H NMR (300 MHz, CDCl$_3$): δ 1.51 (s, 6H), 2.36 (s, 3H), 5.57 (s, 1H), 6.44 (s, If), 7.34 (m, 6H), 12.7 (s, OH).

1-(7-Hydroxy-4-isopropyl-2,2-dimethyl-2H-chromen-6-yl)-ethanone (Compound 62)

As described in General Procedure J, a solution of 1-(4-isopropyl-7-methoxy-2,2-dimethyl-2H-chromen-6-yl)-ethanone (Compound 54, 752 mg, 2.43 mmol) in dichloromethane was treated with boron tribromide (1M in dichloromethane, 3.64 mL, 3.64 mmol) to afford the title compound as a bright yellow oil.

¹H NMR (300 MHz, CDCl₃): δ 1.16 (s, 3H), 1.18 (s, 3H), 1.40 (s, 6H), 2.59 (s, 3H), 2.80 (m, 1H), 5.40 (s, 1H), 6.40 (s, 1H), 7.50 (s, 1H), 12.6 (s, OH).

1-(4-Isopropyl-7-ethoxy-2,2-dimethyl-2H-chromen-6-yl)ethanone (Compound 63)

As described in General Procedure A, a solution of 1-(7-hydroxy-4 isopropyl-2,2-dimethyl-2H-chromen-6-yl)-ethanone (Compound 62, 205 mg, 0.69 mmol) in acetone were added ethyl iodide (0.3 mL, 3.45 mmol) and potassium carbonate (476 mg, 3.45 mmol) to give rise to the title compound as a colorless oil after purification by flash chromatography (silica gel, 5% ethyl acetate in hexanes).

¹H NMR (300 MHz, CDCl₃): δ 1.11 (s, 3H), 1.14 (s, 3H), 1.40 (s, 6H), 1.45 (t, J=6.9 Hz, 3H), 2.59 (s, 3H), 2.85 (m, 1H), 4.13 (q, J=6.9 Hz, 2H), 5.31 (s, 1H), 6.38 (s, 1H), 7.78 (s, 1H).

1-(4-Isopropyl-2,2-dimethyl-7-propoxy-2H-chromen-6-yl)-ethanone (Compound 64)

Following General Procedure A, 1-(7-hydroxy-4-isopropyl-2,2-dimethyl-2H-chromen-6-yl)ethanone (Compound 62, 400 mg, 1.38 mmol) and 1-iodopropane (0.70 mL, 6.90 mmol) were reacted to produce the title compound as a colorless oil.

¹H NMR (300 MHz, CDCl₃): δ 1.08 (t, J=6.9 Hz, 3H), 1.11 (s, 3H), 1.14 (s, 3H), 1.40 (s, 6H), 1.85 (m, 2H), 2.60 (s, 3H), 2.90 (m, 1H), 4.08 (q, J=6.9 Hz, 2H), 5.31 (s, 1H), 6.39 (s, 1H), 7.79 (s, 1H).

1-(7-Butoxy-4-isopropyl-2,2-dimethyl-2H-chromen-6-yl)-ethanone (Compound 65)

Following General Procedure A, 1-(7-hydroxy-4-isopropyl-2,2-dimethyl-2H-chromen-6-yl)ethanone (Compound 62, 205 mg, 0.65 mmol) and 1-iodobutane (0.35 mL, 3.24 mmol) were reacted to produce the title compound as a yellow oil.

¹HNMR (300 MHz, CDCl₃): δ 1.00 (t, J=6.9 Hz, 3H), 1.11 (s, 3H), 1.14 (s, 3H), 1.40 (s, 6H), 1.57 (m, 2H), 1.84 (m, 2H), 2.60 (s, 3H), 2.90 (m, 1H), 4.04 (q, J=6.9 Hz, 2H), 5.31 (s, 10H), 6.39 (s, 1H), 7.79 (s, 1H).

1-(7-Ethoxy-2,2-dimethyl-4-phenyl-2H-chromen-6-yl)-ethanone (Compound 66)

Following General Procedure A, 1-(7-hydroxy-2,2-dimethyl-4-phenyl-2H-chromen-6-yl)-ethanone (Compound 61, 992 mg, 3.08 nmol) and 1-iodoethane (1.67 mL, 15.4 mmol) were reacted to produce the title compound as a white solid ¹H NMR (300 MHz, CDCl₃): δ 1.48 (m, 9H), 2.60 (s, 3H), 4.11 (q, J=6.9 Hz, 2H), 5.51 (s, 1H), 6.46 (s, 1H), 7.35 (m, 5H), 7.57 (s, 1H).

1-(2,2-Dimethyl-4-phenyl-7-propoxy-2H-chromen-6-yl)-ethanone (Compound 67)

Following General Procedure A, 1-(7-hydroxy-2,2-dimethyl-4-phenyl-2H-chromen-6-yl)-ethanone (Compound 61, 170 mg, 0.51 mmol) and 1-iodopropane (0.30 mL, 2.55 mmol) were reacted to produce the title compound as a colorless oil.

¹H NMR (300 MHz, CDCl₃): δ 1.08 (t, J=6.9 Hz, 3H), 1.50 (s, 6H), 1.89 (m, 2H), 2.60 (s, 3H), 4.01 (q, J=6.9 Hz, 2H), 5.51 (s, 1H), 6.46 (s, 1H), 7.35 (m, 5H), 7.57 (s, 1H).

Ethyl (2E)-3-(4-ethyl-7-methoxy-2,2-dimethyl-2H-chromen-6-yl)-2-fluoro-but-2-enoate (Compound 68)

General Procedure K

To a solution of n-butyllithium (2.5 M in hexanes, 1.3 mL, 3.28 mmol) in THF (5 mL) at 0° C. was slowly added triethyl-2-fluoro-2-phosphonoacetate (700 mg, 2.89 mmol). The solution was stirred for 10 min at −40° C. The mixture was cooled to −78° C., and a solution of 1-(4-ethyl-7-methoxy-2,2-dimethyl-2H-chromen-6-yl)-ethanone (Compound 53, 222 mg, 0.97 mmol) in THF (5 mL) was added by cannula. After stirring at 0° C. for 4 h, the reaction mixture was quenched with water. The product was extracted with ethyl acetate and the combined extracts were washed with water and brine, and dried over Na₂SO₄. The solution was filtered and concentrated in vacuo. The residue was purified by column chromatography (silica gel, 10% ethyl acetate in hexane) to produce the title compound as a colorless oil.

¹H NMR (300 MHz, CDCl₃): δ 6.74 (s, 1H), 6.38 (s, 1H), 5.27 (s, 1H), 4.04 (q, J=7.2 Hz, 2H), 2.32 (q, J=7.2 Hz, 2H), 2.05 (d, J=3.3 Hz, 3H), 1.40 (s, 6H), 1.10 (t, J=7.2 Hz, 3H), 0.89 (t, J=7.2 Hz, 3H).

Ethyl (2E)-2-fluoro-3-(4-isopropyl-7-methoxy-2,2-dimethyl-2H-chromen-6-yl)-but-2-enoate (Compound 69)

Following General Procedure K, triethyl-2-fluoro-2-phosphonoacetate (0.44 mL, 2.18 mmol) and 1-(4-isopropyl-7-methoxy-2,2-dimethyl-2H-chromen-6-yl)-ethanone (Compound 54, 199 mg, 0.73 mmol) were reacted to give the title compound as a colorless oil after purification by flash chromatography (silica gel, 1:9 ethyl acetate/hexane).

¹H NMR (300 MHz, CDCl₃) δ 1.04 (t, J=7.0 Hz, 3H), 1.10 (s, 3H), 1.13 (s, 3H), 1.40 (s, 6H), 2.07 (d, J=4.4 Hz, 3H), 2.70 (m, 1H), 4.04 (q, J=7.2 Hz, 2H), 5.25 (s, 1H), 6.40 (s, 1H), 6.85 (s, 1H).

Ethyl (2E)-2-fluoro-3-(4-tert-butyl-7-methoxy-2,2-dimethyl-2H-chromen-6-yl)-but-2-enoate (Compound 70)

Following General Procedure K, triethyl-2-fluoro-2-phosphonoacetate (0.47 mL, 2.3 mmol) and 1-(4-tert-butyl-7-methoxy-2,2-dimethyl-2H-chromen-6-yl)-ethanone (Compound 55, 133 mg, 0.46 mmol) were reacted to give the title compound as a colorless oil after purification by flash chromatography (silica gel, 1:9 ethyl acetate/hexane).

¹H NMR (300 MHz, CDCl₃): δ 7.23 (s, 1H), 6.37 (s, 1H), 5.30 (s, 1H), 3.96 (q, J=7.2 Hz, 2H), 3.73 (s, 3H), 2.29 (d, J=3.3 Hz, 3H), 1.31 (s, 6H), 1.20 (s, 9H), 0.95 (t, J=7.2 Hz, 3H).

Ethyl (2E)-3-(7-ethoxy-4-ethyl-2,2-dimethyl-2H-chromen-6-yl)-2-fluoro-but-2-enoate (Compound 71)

Following General Procedure K, triethyl-2-fluoro-2-phosphonoacetate (173 mg, 7.15 mmol) and 1-(7-ethoxy-4-ethyl-2,2-dimethyl-2H-chromen-6-yl)-ethanone (Compound 56, 394 mg, 1.43 mmol) were reacted to give the title compound as a yellow oil after purification by flash chromatography (silica gel, 1:9 ethyl acetate/hexane).

¹H NMR (300 MHz, CDCl₃): δ 6.78 (s, 1H), 6.25 (s, 1H), 5.21 (s, 1H), 3.85 (q, J=7.2 Hz, 2H), 2.01 (q, J=7.2 Hz, 2H), 2.21 (q, J=7.2 Hz, 2H), 2.01 (d, J=3.3 Hz, 3H), 1.38 (s, 6H), 1.25 (t, J=7.2 Hz, 3H), 1.10 (t, J=7.2 Hz, 3H), 0.89 (t, J=7.2 Hz, 3H).

Ethyl (2E)-3-(7-ethoxy-isopropyl-2,2-dimethyl-2H-chromen-6-yl)-2-fluoro-but-2-enoate (Compound 72)

Following General Procedure K, triethyl-2-fluoro-2-phosphonoacetate (0.40 mL, 1.74 mmol) and 1-(4-isopropyl-7-ethoxy-2,2-dimethyl-2H-chromen-6-yl)-ethanone (Compound 63, 167 mg, 0.58 mmol) were reacted to give the title compound as a colorless oil after purification by flash chromatography (silica gel, 1:9 ethyl acetate/hexane).

$^1$H NMR (390 MHz, CDCl$_3$): δ 1.01 (t, J=7.0 Hz, 3H), 1.10 (s, 3H), 1.12 (s, 3H), 1.40 (s, 6H), 1.32 (t, J=7.0 Hz, 3H), 2.07 (d, J=4.4 Hz, 3H), 2.75 (m, 1H), 4.10 (m, 4H), 5.24 (s, 1H), 6.38 (s, 1H), 6.86 (s, 1H).

Ethyl (2E)-2-fluoro-3-[(4-isopropyl-2,2-dimethyl-7 yl)-but-2-enoate (Compound 73)

Following General Procedure K, triethyl-2-fluoro-2-phosphonoacetate (0.32 mL, 1.56 mmol) and 1-(4-isopropyl-2,2-dimethyl-7-propoxy-2H-chromen-6-yl)-ethanone (Compound 64, 157 mg, 0.52 mmol) were reacted to give the title compound as a colorless oil after purification by flash chromatography (silica gel, 1:9 ethyl acetate/hexane).

$^1$HNMR(300 MHz, CDCl$_3$) δ 1.01 (t, J=7.0 Hz, 3H), 1.10 (s, 3H), 1.12 (s, 3H), 1.26 (t, J=7.0 Hz, 3H), 1.40 (s, 6H), 1.79 (q, J=7.0 Hz, 2H), 2.09 (d, J=4.4 Hz, 3H), 2.75 (m, 1H), 3.86 (t, J=7.0. Hz, 2H), 4.03 (q, J=7.0 Hz, 2H), 5.24 (s, 1H), 6.41 (s, 1H), 6.85 (s, 1H).

Ethyl (2E)-3-(7-butoxy-4-isopropyl-2,2-dimethyl-2H-chromen-6-yl)-2-fluoro-but-2-enoate (Compound 74)

Following General Procedure K, triethyl-2-fluoro-2-phosphonoacetate (0.44 mL, 1.75 mmol) and 1-(7-butoxy-4-isopropyl-2,2-dimethyl-2H-chromen-6-yl)-ethanone (Compound 65, 184 mg, 0.58 mmol) were reacted to give the title compound as a pink oil after purification by flash chromatography (silica gel, 1:9 ethyl acetate/hexane).

$^1$H NMR (300 MHz, CDCl$_3$) δ 0.95 (t, J=7.0 Hz, 3H), 1.01 (t, J=7.0 Hz, 2H), 1.10 (s, 3H), 1.12 (s, 3H), 1.40 (s, 6H), 1.43 (m, 2H), 2.08 (d, J=4.4 Hz, 3H), 2.71 (m, 1H), 3.90 (t, J=7.0 Hz, 2H), 4.03 (q, J=7.0 Hz, 2H), 5.24 (s, 1 μl), 6.39 (s, 1H), 6.85 (s, 1H).

Ethyl (2E)$_3$-(7-ethoxy-2,2-dimethyl-4-phenyl-2H-chromen-6-yl)-2-fluoro-but-2-enoate (Compound 75)

Following General Procedure K, triethyl-2-fluoro-2-phosphonoacetate (0.42 mL, 1.70 mmol) and 1-(7-ethoxy-2,2-dimethyl-4-phenyl-2H-chromen-6-yl)-ethanone (Compound 66, 183 mg, 0.57 mmol) were reacted to give the title compound as a colorless oil after purification by flash chromatography (silica gel, 1:9 ethyl acetate/hexane).

$^1$H NMR (300 MHz, CDCl$_3$): δ 1.07 (t, J=7.0 Hz, 3H), 1.34 (t, J=7.0 Hz, 3H), 1.50 (s, 6H), 2.01 (d, J=4.4 Hz, 3H), 4.04 (m, 4H), 5.47 (s, 1H), 6.48 (s, 1H), 6.69 (s, 1H), 7.35 (m, 5H).

Ethyl (2E)-3-(2,2-dimethyl-4-phenyl-7-propoxy-2H-chromen-6-yl)-2-fluoro-but-2-enoate (Compound 76)

Following General Procedure K, triethyl-2-fluoro-2-phosphonoacetate (0.41 mL, 1.61 mmol) and 1-(2,2-dimethyl-4-phenyl-7-propoxy-2H-chromen-6-yl)-ethanone (Compound 67, 180 mg, 0.54 mmol) were reacted to give the title compound as a colorless oil after purification by flash chromatography (silica gel, 1:9 ethyl acetate/hexane).

$^1$H NMR (300 MHz, CDCl$_3$): δ 0.97 (t, J=7.0 Hz, 3H), 1.07 (t, J=7.0 Hz, 3H), 1.50 (s, 6H), 1.75 (m, 2H), 2.01 (d, J=4.4 Hz, 3H), 3.87 (q, J=7.0 Hz, 2H), 4.03 (q, J=7.0 Hz, 2H), 5.47 (s, 1H), 6.48 (s, 1H), 6.69 (s, 1H), 7.35 (m, 5H).

Ethyl (2E)$_2$-fluoro-3-(7-methoxy-22,4-trimethyl-2H-chromen-6-yl)-pent-2-enoate (Compound 77)

Following General Procedure K, triethyl-2-fluoro-2-phosphonoacetate (530 mg, 2.2 mmol) and 1-(7-methoxy-2,2,4-trimethyl-2H-chromen-6-yl)-propan-1-one (Compound 57, 189 mg, 0.73 mmol) were reacted to give the title compound as a colorless oil after purification by flash chromatography (silica gel, 5% ethyl acetate in hexanes).

$^1$H NMR (300 MHz, CDCl$_3$): δ (6.74 (s, 1H), 6.38 (s, 1H, 5.27 (s, 1H), 4.04 (q, J=7.2 Hz, 2H), 3.73 (s, 3H), 2.46–2.55 (m, 2H), 1.94 (s, 3H), 1.40 (s, 6H), 1.01 (t, J=7.2 Hz, 3H).

Ethyl (2E)-2-fluoro-3-(4-isopropyl-7-methoxy-2,2-dimethyl-2H-chromen-6-yl)-pent-2-enoate (Compound 78)

Following General Procedure K, triethyl-2-fluoro-2-phosphonoacetate (605 mg, 2.50 mmol) and 1-(4-isopropyl-7-methoxy-2,2-dimethyl-2H-chromen-6-yl)-propan-1-one (Compound 58, 148 mg, 0.50 mmol) were reacted to give the title compound as a colorless oil after purification by flash chromatography (silica gel, 5% ethyl acetate in hexanes).

$^1$H NMR (300 MHz, CDCl$_3$): δ 6.73 (s, 1H), 6.33 (s, 1H), 5.18 (s, 1H), 3.95 (q, J=7.5 Hz, 2H), 3.66 (s, 3H), 2.66–2.70 (m, 1H), 2.39–2.48 (m, 2H), 1.32 (s, 6H), 1.04 (d, J=9.0 Hz, 6H), 0.84–0.96 (m, 6H).

Ethyl (2E)-2-fluoro-3-(4-tert-butyl-7-methoxy-2,2-dimethyl-2H-chromen-6-yl)-pent-2-enoate (Compound 79)

Following General Procedure K, triethyl-2-fluoro-2-phosphonoacetate (431 mg, 1.78 mmol) and 1-(4-tert-butyl-7-methoxy-2,2-dimethyl-2H-chromen-6-yl)-propan-1-one (Compound 59, 107 mg, 0.35 mmol) were reacted to give the title compound as a colorless oil after purification by flash chromatography (silica gel, 5% ethyl acetate in hexanes)

$^1$H NMR (CDCl$_3$, 300 MHz): δ 7.08 (s, 1H), 6.35 (s, 1H), 5.29 (s, 1H), 3.94 (q, J=7.2 Hz, 2H), 3.66 (s, 3H), 2.42–2.49 (m, 2H), 1.31 (s, 6H), 1.19 (s, 9H), 0.84–0.95 (m, 6H).

Ethyl (2E)-3-(7-ethoxy-2,2,4-trimethyl-2H-chromen-6-yl)-2-fluoro-pent-2-enoate (Compound 80)

Following General Procedure K, triethyl-2-fluoro-2-phosphonoacetate (993 mg, 4.11 mmol) and 1-(7-ethoxy-4-methyl-2,2-dimethyl-2H-chromen-6-yl)-propan-1-one (Compound 60, 225 mg, 0.82 mmol) were reacted to give the title compound as a colorless oil after purification by flash chromatography (silica gel, 5% ethyl acetate in hexanes).

$^1$H NMR (300 MHz, CDCl$_3$): δ 6.74 (s, 1H), 6.38 (s, 1H), 5.21 (s, 1H), 3.82–4.01 (m, 4H), 2.38–2.42 (m, 2H), 1.85 (s, 3H), 1.39 (s, 6H), 1.24 (t, J=7.2 Hz, 3H), 0.89–0.99 (m, 6H).

(2E)-3-(4-Ethyl-7-methoxy-2,2-dimethyl-2H-chromen-6-yl)-2-fluoro-but-2-en-1-ol (Compound 81)

General Procedure L

To a solution of ethyl (2E)-3-(4-ethyl-7-methoxy-2,2-dimethyl-2H-chromen-6-yl)-2-fluoro-but-2-enoate (Compound 68, 349 mg, 0.96 mmol) in THF (15 mL) under argon at 0° C. was added diisobutylaluminum hydride (1.0 M in hexanes, 2.9 mL, 2.9 mmol). The resulting mixture was stirred at −78° C. for 4 h. The reaction was quenched slowly with saturated NH$_4$Cl, celite, and diluted with diethyl ether. The resulting mixture was stirred at 25° C. for 1 h. The product was filtered through a pad of celite. The solution was dried over Na$_2$SO$_4$ and concentrated in vacuo. The residue was purified by flash column chromatography (silica gel, 1:4 ethyl acetate/hexane) to yield the title compound as a yellow solid.

$^1$H NMR (300 MHz, CDCl$_3$) δ 7.08 (s, 1H), 6.81 (s, 1H), 5.25 (s, 1H), 3.90 (d, J=22.0 Hz, 2H), 3.68 (s, 3H), 2.40 (bs, 1H), 2.28–2.35 (m, 2H), 1.96 (s, 3H), 1.33 (s, 6H), 1.08 (t, J=7.2 Hz, 3H).

(2E)-2-Fluoro-3-(4-isopropyl-7-methoxy-2,2-dimethyl-2H-chromen-6-yl)-but-2-en-1-ol (Compound 82)

Following General Procedure L, ethyl (2E)-2-fluoro-3-(4-isopropyl-7-methoxy-2,2-dimethyl-2H-chromen-6-yl)-but-2-enoate (Compound 69, 145 mg, 0.40 mmol) and a diisobutylaluminum hydride (1M in hexanes, 1.60 mL, 1.60 mmol) were reacted to give the title compound as a colorless oil after purification by flash chromatography (silica gel, 1:9 to 1:4 ethyl acetate/hexane).

$^1$H NMR (300 MHz, CDCl$_3$): δ 1.10 (s, 3H), 1.13 (s, 3H), 1.40 (s, 6H), 1.94 (d, J=4.4 Hz, 3H), 2.80 (m, 10H), 3.80(s, 1H), 4.03 (dd, J=6.2 Hz, J=18.4 Hz, 2H), 5.27 (s, 1H), 6.41 (s, 1H), 6.93 (s, 1H).

(2E)-3-(4-tert-Butyl-7-methoxy-2,2-dimethyl-2H-chromen-6-yl)-2-fluoro-but-2-en-1-ol (Compound 83)

Following General Procedure L, ethyl (2E)-fluoro-3-(4-tert-butyl-7-methoxy-2,2-dimethyl-2H-chromen-6-yl)but-2-enoate (Compound 70, 148 mg, 0.39 mmol) and diisobutylaluminum hydride (1 M in dichloromethane, 1.1 mL, 1.1 mmol) were reacted to give the title compound as yellow solid after purification by flash chromatography (silica gel, 1:9 to 1:4 ethyl acetate/hexane).

$^1$H NMR (300 MHz, CDCl$_3$): δ 7.27 (s, 1H), 6.40 (s, 1H), 5.37 (s, 1H), 4.03 (d, J=22.0 Hz, 2H), 3.74 (s, 3H), 1.93 (d, J=3.9 Hz, 3H), 1.31 (s, 6H), 1.21 (s, 9H).

(2E)-3-(7-Ethoxy-4-ethyl-2,2-dimethyl-2H-chromen-6-yl)-2-fluoro-but-2-en-1-ol (Compound 84)

Following General Procedure L, ethyl (2E)-3-(7-ethoxy-4-ethyl-2,2-dimethyl-2H-chromen-6-yl)-2-fluoro-but-2-enoate (Compound 71, 348 mg, 0.96 mmol) and diisobutylaluminum hydride (1 M dichloromethane, 2.9 mL, 2.88 mmol) were reacted to give the title compound as yellow solid after purification by flash chromatography (silica gel, 1:9 to 1:4 ethyl acetate/hexane).

$^1$H NMR (300 MHz, CDCl$_3$): δ 6.82 (s, 1H), 6.32 (s, 1H), 5.23 (s, 1H), 3.89–3.94 (m, 4H), 2.36 (br s, 1H), 2.26–2.28 (m, 2H), 1.96 (d, J=3.3 Hz, 3H), 1.33 (s, 6H), 1.10 (t, J=7.2 Hz, 3H), 0.89 (t, J=7.2 Hz, 3H).

(2E)-3-(7-Ethoxy-4-isopropyl-2,2-dimethyl-2H-chromen-6-yl)-2-fluoro-but-2-en-]-ol (Compound 85)

Following General Procedure L, ethyl (2E)-3-(7-ethoxy-4-isopropyl-2,2-dimethyl-2H-chromen-6-yl)-2-fluoro-but-2-enoate (Compound 72, 163,mg, 0.44 mmol) and diisobutylaluminum hydride (1M in hexanes, 1.74 mL, 1.74 mmol) were reacted to give the title compound as a colorless oil after purification by flash chromatography (silica gel, 1:9 to 1:4 ethyl acetate/hexane).

$^1$H NMR (300 MHz, CDCl$_3$): δ 1.10 (s, 3H), 1.13 (s, 3H), 1.37 (t, J=7.2 Hz, 3H), 1.40 (s, 6H), 1.94 (d, J=4.4 Hz, 3H), 2.80 (m, 1H), 3.80(s, 1H), 4.03 (m, 4H), 5.27 (s, 1H), 6.41 (s, 1H), 6.93 (s, 1H).

(2E)-2-Fluoro-3-(4-isopropyl-2,2-dimethyl-7-propoxy-2H-chromen-6-yl)-but-2-en-1-ol (Compound 86)

Following General Procedure L, ethyl (2E)-2-fluoro-3-(4-isopropyl-2,2-dimethyl-7-propoxy-2H-chromen-6-yl)-but-2-enoate (Compound 73, 130 mg, 0.33 mmol) and diisobutylaluminum hydride (1M in hexanes, 1.34 mL, 1.34 mmol) were reacted to give the title compound as a colorless oil after purification by flash chromatography (silica gel, 1:9 ethyl acetate/hexane).

$^1$H NMR (300 MHz, CDCl$_3$): δ 1.00 (t, J=7.0 Hz, 3H), 11.0 (s, 3H), 1.13 (s, 3H), 1.40 (s, 6H), 1.79 (q, J.=7.0 Hz, 2H), 1.94 (d, J=4.4 Hz, 3H), 2.80 (m, 1H), 3.85 (t, J=7.0 Hz, 2H), 4.03 (dd, J=6.2 Hz, J=18.4 Hz, 2H), 5.27 (s, 1H), 6.41 (s, 1H), 6.93 (s, 1H).

(2E)-3-(7-Butoxy-4-isopropyl-2,2-dimethyl-2H-chromen-6-yl)-2-fluoro-but-2-en-1-ol (Compound 87)

Following General Procedure L, ethyl (2E)-3-(7-butoxy-4-isopropyl-2,2-dimethyl-2H-chromen-6-yl)-2-fluoro-but-2-enoate (Compound 74, 133 mg, 0.34 mmol) and diisobutylaluminum hydride (1 M in hexanes, 1.37 mL, 1.37 mmol) were reacted to give the title compound as a colorless oil after purification by flash chromatography (silica gel, 1:9 ethyl acetate/hexane).

$^1$H NMR (300 MHz, CDCl$_3$): δ 1.00 (t, J=7.0 Hz, 3H), 1.10 (s, 3H), 1.13 (s, 3H), 1.40 (s, 6H), 1.45(m, 2H), 1.79 (m, 2H), 1.94 (d, J=4.4 Hz, 3H), 2.80 (m, 1H), 3.85 (t, J=7.0 Hz, 2H), 4.03 (dd, J=6.2 Hz, J=18.4 Hz, 2H), 5.27 (s, 1H), 6.41 (s, 1H), 6.93 (s, 1H.

(2E)-3-(7-Ethoxy-2,2-dimethyl-4-phenyl-2H-chromen-6-yl)$_2$-fluoro-but-2-en-1-ol (Compound 88)

Following General Procedure L, ethyl (2E)-3-(7-ethoxy-2,2-dimethyl-4-phenyl-2H-chromen-6-yl)-2-fluoro-but-2-enoate (Compound 75, 160 mg, 0.38 mmol) and diisobutylaluminum hydride (1 M in hexanes, 1.51 mL, 1.51 mmol) were reacted to give the title compound as a colorless oil after purification by flash chromatography (silica gel, 1:4 ethyl acetate/hexane).

$^1$H NMR (300 MHz, CDCl$_3$): δ 1.40 (t, J=7.0 Hz, 3H), 1.50 (s, 6H), 1.86 (d, J=4.4 Hz, 3H), 4.02 (m, 4H), 5.50 (s, 1H), 6.50 (s, 1H), 6.72 (s, 1H), 7.38 (m, 5H).

(2E)-3-[(2,2-Dimethyl-4-phenyl-7-propoxy-2H-chromen-6-yl)-2-fluoro-but-2-en-1-ol (Compound 89)

Following General Procedure L, ethyl (2E)-3-(2,2-dimethyl-4-phenyl-7-propoxy-2H-chromen-6-yl)-2-fluorobut-2-enoate (Compound 76, 213 mg, 0.49 mmol) and diisobutylaluminum hydride (1M in hexanes, 1.95 mL, 1.95 mmol) were reacted to give the title compound as a colorless oil after purification by flash chromatography (silica gel, 1:4 ethyl acetate/hexane).

$^1$H NMR (300 MHz, CDCl$_3$): δ 1.00 (t, J=7.0 Hz, 3H), 1.50 (s, 6H), 1.78 (q, J=7.0 Hz, 2H), 1.86(d, J=4.4 Hz, 3H), 4.00 (m, 4H), 5.48 (s, 1H), 6.47 (s, 1H), 6.71 (s, 1H), 7.38 (m, 5H).

(2E)-2-Fluoro-3-(7-methoxy-2,2,4-trimethyl-2H-chromen-6-yl)-pent-2-en-1-ol (Compound 90)

Following General Procedure L, ethyl 2-fluoro-3-(7-methoxy-2,2,4-trimethyl-2H-chromen-6-yl)-pent-2-enoate (Compound 77, 195 mg, 0.56 mmol) and a diisobutylaluminum hydride (1 M in hexanes, 1.68 mL, 1.68 mmol) were reacted to give the title compound as yellow solid after purification by flash chromatography (silica gel, 1:4 ethyl acetate/hexane).

$^1$H NMR (300 MHz, CDCl$_3$): δ 6.74 (s, 1H), 6.33 (s, 1H), 5.23 (s, 1H), 3.89 (d, J=22.0 Hz, 2H), 3.68 (s, 3H), 2.28–2.40 (m, 2H), 1.96 (s, 3H), 1.33 (s, 6H),0.84(t, J=7 Hz, 3H).

(2E)-2-Fluoro-3-(isopropyl-7-methoxy-2,2-dimethyl-2H-chromen-6-yl)-pent-2-en-1-ol (Compound 91)

Following General Procedure L, ethyl 2-fluoro-3-(4-isopropyl-7-methoxy-2,2-dimethyl-2H-chromen-6-yl)-pent-2-enoate (Compound 78, 128 mg, 0.34 mmol) and a diisobutylaluminum hydride (1 M in dichloromethane, 1.0 mL, 1.0 mmol) were reacted to give the title compound as yellow solid after purification by flash chromatography (silica gel, 1:4 ethyl acetate/hexane).

$^1$H NMR (300 MHz, CDCl$_3$): δ 6.87 (s, 1H), 6.40 (s, 1H), 5.26 (s, 1H), 3.90 (d, J=22.0 Hz, 2H), 3.69 (s, 3H), 2.68–2.73 (m, 1H), 2.29–2.37 (m, 2H), 1.33 (s, 6H), 1.05 (d, J=6.0 Hz, 6H), 0.83 (t, J=7.8 Hz, 3H).

(2E)-3-(4-tert-Butyl-7-methoxy-2,2-dimethyl-2H-chromen-6-yl)-2-fluoro-pent-2-en-1-ol (Compound 92)

Following General Procedure L, ethyl 2-fluoro-3-(4-tert-butyl-7-methoxy-2,2-dimethyl-2H-chromen-6-yl)-pent-2-enoate (Compound 79, 90 mg, 0.23 mmol) and diisobutylaluminum hydride (1 M in dichloromethane, 0.7 mL, 0.7 mmol) were reacted to give the title compound as yellow solid after purification by flash chromatography (silica gel, 1:4 ethyl acetate/hexane).

$^1$H NMR (300 MHz, CDCl$_3$): δ 7.27 (s, 1H), 6.44 (s, 1H), 5.39 (s, 1H), 4.05 (d, J=22.0 Hz, 2H), 3.77 (s, 3H), 2.37–2.43 (m, 2H), 1.38 (s, 6H), 1.27 (s, 9H), 0.89 (t, J=6.9 Hz, 3H).

(2E)-3-(7-Ethoxy-2,2,4-trimethyl-2H-chromen-6-yl)-2-fluoro-pent-2-en-1-ol (Compound 93)

Following General Procedure L, ethyl 3-(7-ethoxy-2,2,4-trimethyl-2H-chromen-6-yl)-2-fluoro-but-2-enoate (Compound 80,226 mg, 0.62 mmol) and diisobutylaluminum hydride (1 M in dichloromethane, 1.87 mL, 1.87 mmol) were reacted to give the title compound as yellow solid after purification by flash chromatography (silica gel, 1:4 ethyl acetate/hexane).

$^1$H NMR (300 MHz, CDCl$_3$): δ 6.81 (s, 1H),6.39 (s, 1H),5.21 (s, 1H), 3.90–4.00 (m, 4H), 2.21–2.38 (m, 3H), 1.93 (s, 3H), 1.34 (s, 6H) 1.33 (t, J=7.2 Hz, 3H), 0.89 (t, J=7.2 Hz, 3H).

(2E)-2-Fluoro-3-(4-isopropyl-7-methoxy-2,2-dimethyl-2H-chromen-6-yl)-but-2-enal (Compound 95)

General Procedure M

To a solution of (2E)-2-fluoro-3-(4-isopropyl-7-methoxy-2,2-dimethyl-2H-chromen-6-yl)-but-2-en-1-ol (Compound 82, 117 mg, 0.37 mmol) in dichloromethane/acetonitrile (6:1, 7 mL) at 25° C. were added 4-methylmorpholine N-oxide (85 mg, 0.74 mmol), tetrapropylammonium perruthenate (12 mg, 0.04 mmol), and 4 Å molecular sieve powder (60 mg). The mixture was stirred at 25° C. for 1 h and applied directly to chromatography. Flash chromatography (silica gel, 100% hexane to 5% ethyl acetate in hexanes) gave rise to the title compound as a colorless oil.

$^1$H NMR (300 MHz, CDCl$_3$): δ 1.10 (s, 3H), 1.13 (s, 3H), 1.42 (s, 6H), 2.20 (d, J=3.8 Hz, 3H), 2.76 (m, 1H), 3.78 (s, 1H), 5.30 (s, If), 6.5 1H), 6.95 (s, 1H), 9.23 (d, J=19.3 Hz, 1H).

(2E)-3-(7-Ethoxy-4-isopropyl-2,2-dimethyl-2H-chromen-6-yl)-2-fluoro-but-2-enal (Compound 98)

Following General Procedure M, (2E)-3-(7-ethoxy-4-isopropyl-2,2-dimethyl-2H-chromen-6-yl)-2-fluoro-but-2-en-1-ol (Compound 85, 114 mg, 0.36 mmol) and 4-methylmorpholine N-oxide (85 mg, 0.72 mmol) were reacted to give the title compound as a yellow oil.

$^1$H NMR (300 MHz, CDCl$_3$): δ 1.10 (s, 3H), 1.13 (s, 3H), 1.34 (t, J=7.0 Hz, 3H), 1.41 (s, 6H), 2.07 (d, J=3.8 Hz, 3H), 2.76 (m, 1H), 4.00 (q, J=7.0 Hz, 2H), 5.30 (s, 1H), 6.50 (s, 1H), 6.93 (s, 1H), 9.25 (d, J=19.3 Hz, 1H).

(2E)-2-Fluoro-3-(4-isopropyl-2,2-dimethyl-7-propoxy-2H-chromen-6-yl)-but-2-enal (Compound 99)

Following General Procedure M, (2E)-2-fluoro-3-(4-isopropyl-2,2-dimethyl-7-propoxy-2H-chromen-6-yl)-but-2-en-1-ol (Compound 86, 100 mg, 0.27 mmol) and 4-methylmorpholine N-oxide (75 mg, 0.57 mmol) were reacted to give the title compound as a yellow oil.

$^1$H NMR (300 MHz, CDCl$_3$): δ 1.00 (t, J=7.0 Hz, 3H), 1.10 (s, 3H), 1.13 (s, 3H), 1.42 (s, 6H), 1.78 (q, J=7.0 Hz, 2H), 2.10 (d, J=3.8 Hz, 3H), 2.76 (m, 1H), 3.90 (t, J=7.0 Hz, 2H), 5.30 (s, 1H), 6.50 (s, 1H), 6.95 (s, 1H), 9.25 (d, J=19.3 Hz, 1H).

(2E)-3-(7-Butoxy-4-isopropyl-2,2-dimethyl-2H-chromen-6-yl)-2-fluoro-but-2-enal (Compound 100)

Following General Procedure M, (2E)-3-(7-butoxy 4-isopropyl-2,2-dimethyl-2H-chromen-6-yl)-2-fluoro-but-2-en-1-ol (Compound 87, 109 mg, 0.30 mmol) and 4-methylmorpholine N-oxide (70 mg, 0.60 mmol) were reacted to give the title compound as a yellow oil.

$^1$H NMR (300 MHz, CDCl$_3$): δ 0.97 (t, J=7.0 Hz, 3H), 1.10 (s, 3H), 1.13 (s, 3H), 1.40 (s, 6H), 1.42 (m, 2H), 1.68 (m, 2H), 2.20 (d, J=3.8 Hz, 3H), 2.78 (m, 1H), 3.95 (t, J=7.0 Hz, 2H), 5.30 (s, 1H), 6.43 (s, 1H), 6.94 (s, 1H), 9.25 (d, J=19.3 Hz, 1H).

(2E)-3-(7-Ethoxy-2,2-dimethyl-4-phenyl-2H-chromen-6-yl)-2-fluoro-but-2-enal (Compound 101)

Following General Procedure M, (2E)-3-(7-ethoxy-2,2-dimethyl-4 phenyl-2H-chromen-6-yl)-2-fluoro-but-2-en-1-ol (Compound 88, 137 mg, 0.37 mmol) and 4-methylmorpholine N-oxide (87 mg, 0.74 mmol) were reacted to give the title compound as a yellow oil.

¹H NMR (300 MHz, CDCl₃): δ 1.39 (t, J=7.0 Hz, 3H), 1.51 (s, 3H), 1.55 (s, 3H), 2.15 (d, J=3.8 Hz, 3H), 4.04 (q, J=7.0 Hz, 2H), 5.50 (s, 1H), 6.50 (s, 1H, 6.76 (s, 1H), 7.38 (m, 5H), 9.20 (d, J=19.3 Hz, 1H).

(2E)-3-(2,2-Dimethyl-4-phenyl-7-propoxy-2H-chromen-6-yl)-2-fluoro-but-2-enal (Compound 102)

Following General Procedure M, (2E)-3-(2,2-dimethyl-4-phenyl-7-propoxy-2H-chromen-6-yl)-2-fluoro-but-2-en-1-ol (Compound 89, 145 mg, 0.38 mmol) and 4-methylmorpholine N-oxide (90 mg, 0.76 mmol) were reacted to give the title compound as a yellow oil.

¹H NMR (300 MHz, CDCl₃): δ 1.00 (t, J=7.0 Hz, 3H), 1.51 (s, 3H), 1.55 (s, 3H), 1.79 (m, 2H), 2.15 (d, J=3.8 Hz, 3H), 3.93 (t, J=7.0 Hz, 2H), 5.50 (s, 1H), 6.50 (s, 1H), 6.76 (s, 1H), 7.38 (m, 5H), 9.20 (d, J=19.3 Hz, 1H).

Ethyl 7-(4-ethyl-7-methoxy-2,2-dimethyl-2H-chromen-6-yl)-6-fluoro-3-methyl-octa-2E,4E,6-E-trienoate (Compound 107)

General Procedure N

To a solution of 3-(4-ethyl-7-methoxy-2,2-dimethyl-2H-chromen-6-yl)-2-fluoro-but-2-en-1-ol (Compound 81, 115 mg, 0.36 mmol) in dichloromethane/acetonitrile (1:1, 10 mL) was added 4-methylmorpholine N-oxide (48 mg, 0.43 mmol) and tetrapropylammonium perruthenate (10 mg). After stirring at room temperature for 30 min, the solvent was removed under reduced pressure and the residue was purified by flash chromatography (silica gel, 80:20 hexane/ethyl acetate) to give the corresponding aldehyde (Compound 94).

To a solution of ethyl 4-(diethoxyphosphoryl)-3-methylbut-2E-enoate (462 mg, 2.89 mmol) in THF (20 mL) and 1,3-dimethyl-3,4,5,6-tetrahydro-2(1H-pyrimidinone (DMPU, 6 mL) at −78° C. was slowly added n-butyllithium (1.6 M in hexane, 1.6 mL, 2.6 mmol). After stirring for 5 min, a solution of the crude aldehyde in THF (6 mL) was added to the reaction mixture via cannula. The resulting solution was stirred and warmed up to room temperature for 2 h before quenching with saturated NH₄C] solution. The reaction mixture was extracted with ethyl acetate, washed with brine, dried (MgSO₄) and concentrated under reduced pressure. Purification by flash chromatography (silica gel, 90:10 hexane/ethyl acetate) afforded the title compound as a yellow oil.

¹H NMR (300 MHz, CDCl₃): δ 6.80 (s, 1H), 6.50 (d, J=15.0 Hz, 1H), 6.41 (s, 1H), 6.28 (dd, J=15.6, 25.5 Hz, 1H), 5.75 (s, 1H), 5.27 (s, 1H), 4.10 (q, J=7.2 Hz, 2H), 3.70 (s, 3H), 2.20–2.37 (m, 2H), 2.05 (s, 3H), 1.95 (d, J=3.0 Hz, 3H), 1.42 (s, 3H), 1.38 (s, 6H), 1.20 (t, J=7.2 Hz, 3H), 1.05 (t, J=7.5 Hz, 3H).

Ethyl (2E,4E,6-E)-6-fluoro-7-(4-isopropyl-7-methoxy-2,2-dimethyl-2H-chromen-6-yl)-3-methyl-octa-2,4,6-trienoate (Compound 108)

General Procedure O

To a solution of ethyl 4-(diethoxyphosphoryl)-3-methyl-but-2E-enoate (240 mg, 0.91 mmol) in THF (10 mL), and 1,3-dimethyl-3,4,5,6-tetrahydro-2(1H)-pyrimidinone (DMPU, 0.13 mL) under argon at −78° C. was slowly added n-butyl lithium (1.6 M in hexanes, 0.60 mL, 0.96 mmol). The resulting mixture was stirred at −78° C. for 15 min before a solution of (2E)-2-fluoro-3-(4-isopropyl-7-methoxy-2,2-dimethyl-2H-chromen-6-yl)-but-2-enal (Compound 95, 100 mg, 0.31 mmol) and THF (3 mL) was added via cannula. The resulting mixture was stirred at 0° C. for 1 h. The reaction was quenched with saturated NH₄Cl and the product was extracted with diethyl ether. The combined ethereal layers were washed with water and brine, dried over Na₂SO₄, filtered and concentrated in vacuo. The residue was purified by flash column chromatography (silica gel, 5% ethyl acetate in hexane) to yield the title compound as a yellow oil.

¹H NMR (300 MHz, CDCl₃): δ 1.12 (d, J=6.7 Hz, 6H), 1.27 (t, J=7.0 Hz, 3H), 1.42 (s, 6H), 2.04 (m, 6H), 2.76 (m, 1H), 3.77 (s, 3H), 4.16 (q, J=7.0 Hz, 2H), 5.28 (s, 1H), 5.82 (s, 1H), 6.31 (dd, J=15.5 Hz, J=25.5 Hz, 1H), 6.43 (s, 1H), 6.47 (d, J=15.5 Hz, 1H), 6.89 (s, 1H).

Ethyl 7-(4-tert-butyl-7-methoxy-2,2-dimethyl-2H-chromen-6-yl)6-fluoro-3-methyl-octa-2E,4E,6-E-trienoate (Compound 109)

Following General Procedure N, 3-(4-tert-butyl-7-methoxy-2,2-dimethyl-2H-chromen-6-yl)-2-fluoro-but-2-en-1-ol (Compound 83, 55 mg, 0.16 mmol) and 4-methylmorpholine N-oxide (39 mg; 0.33 mmol) were reacted to give the corresponding aldehyde (Compound 96). Treatment with the ylide of ethyl 4-(diethoxyphosphoryl)-3-methyl-but-2E-enoate (382 mg, 1.40 mmol) gave rise to the title compound as a colorless oil after purification by flash chromatography (silica gel, 5% ethyl acetate in hexanes).

¹H NMR (300 MHz, CDCl₃): δ 7.20 (s, 1H), 6.46 (d, J=15.5 Hz, 1H), 6.44 (s, 1H), 6.35 (dd, J=15.5, 25.5 Hz, 1H), 5.75 (s, 1H), 5.31 (s, 1H), 4.09 (q, J=7.2 Hz, 2H), 3.70 (s, 3H), 2.01–2.03 (m, 6H), 1.32 (s, 6H), 1.17–1.22 (m, 12H).

Ethyl 7-(7-ethoxy-4-ethyl-2,2-dimethyl-2H-chromen-6-yl)-6-fluoro-3-methyl-octa-2E,4E,6-E-trienoate (Compound 110)

Following General Procedure N, 3-(7-ethoxy-4-ethyl-2,2-dimethyl-2H-chromen-6-yl)-2-fluoro-but-2-en-1-ol (Compound 84, 166 mg, 0.52 mmol) and 4-methylmorpholine N-oxide (67 mg, 0.62 mmol) were reacted to give the corresponding aldehyde (Compound 97). Treatment with the ylide of ethyl 4(diethoxyphosphoryl)-3-methyl-but-2Eenoate (1.25 g, 4.76 mmol) afforded the title compound as a yellow oil after purification by flash chromatography (silica gel, 5% ethyl acetate in hexanes).

¹H NMR(300 MHz, CDCl₃) δ 6.78 (s, 1H), 6.41 (d, J=15.0 Hz, 1H), 6.38 (s, 1H), 6.25 (dd, J=15.6, 25.5 Hz, 1H), 5.79 (s, 1H), 5.21 (s, 1H), 4.15 (q, J=7.8 Hz, 2H), 3.91 (q, J=7.8 Hz, 2H), 2.21–2.30 (m, 2H), 2.10 (s, 3H), 2.01 (d, J=3.3 Hz, 3H), 1.35 (s, 614), 1.29 (t, J=7.8 Hz, 3H), 1.21 (t, J=7.8 Hz, 3H), 1.02 (t, J=7.8 Hz, 3H).

Ethyl (2E,4E,6E)-7-(7-ethoxy-4-isopropyl-2,2-dimethyl-2H-chromen-6-yl)-6-fluoro-3-methyl-octa-2,4,6-trienoate (Compound 111)

Following General Procedure O, ethyl 4-(diethoxyphosphoryl)-3-methyl-but-2E-enoate (230 mg, 0.84 mmol) and (2E)-3-(7-ethoxy-4-isopropyl-2,2-dimethyl-2H-chromen-6-yl)-2-fluoro-but-2-enal (Compound 98, 96 mg, 0.29 mmol) were reacted to give the title compound as a yellow oil after purification by column chromatography (silica gel, 5% ethyl acetate in hexane).

¹H NMR (300 MHz, CDCl₃): δ 1.12 (d, J=,6.7 Hz, 6H), 1.27 (m, 3H), 1.35 (t, J=7.0 Hz, 3H), 1.41 (s, 6H), 2.07 (m, 6H), 2.80 (m, 1H), 3.77 (s, 3H), 4.00 (q, J=7.0 Hz, 2H), 4.16 (q, J=7.0 Hz, 2H), 5.28 (s, 1H), 5.82 (s, 1H), 6.34 (dd, J=15.5 Hz, J=25.5 Hz, 1H), 6.42 (s, 1 μl), 6.47 (d, J=15.5 Hz, 1H), 6.89 (s, 1H).

Ethyl (2E,4E,6E)-6-fluoro-7-(4-isopropyl-2,2-dimethyl-7-propoxy-2H-chromen-6-yl)-3-methyl-octa-2,4,6-trienoate (Compound 112)

Following General Procedure O, ethyl 4-(diethoxyphosphoryl)-3-methyl-but-2E-enoate (159 mg, 0.60 mmol) and (2E)-2-fluoro-3-(4-isopropyl-2,2-dimethyl-7-propoxy-2H-chromen-6-yl)but-2-enal (Compound 99, 72 mg, 0.21 mmol) were reacted to give the title compound as a yellow oil after purification by flash chromatography (silica gel, 5% ethyl acetate in hexane).

$^1$H NMR (300 MHz, CDCl$_3$): δ 0.98 (t, J=7.0 Hz, 3H), 1.13 (d, J=6.7 Hz, 6H), 1.27 (t, J=7.0 Hz, 3H), 1.41 (s, 6H), 1.74 (m, 2H), 2.07 (m, 6H), 2.80 (m, 1H), 3.86 (t, J=7.0 Hz, 21), 4.16 (q, J=7.0 Hz, 2H), 5.27 (s, 1H), 5.82 (s, 1H), 6.34 (dd, J 15.5, 25.5 Hz, 1H), 6.42 (s, 1H), 6.47 (d, J=15.5 Hz, 1H), 6.89 (s, 1H).

Ethyl (2E,4E,6E)-7-(7-butoxy-4-isopropyl-2,2-dimethyl-2H-chromen-6-yl)-6-fluoro-3-methyl-octa-2,4,6-trienoate (Compound 113)

Following General Procedure O, ethyl 4-(diethoxyphosphoryl)-3-methyl-but-2E-enoate (183 mg, 0.70 mmol) and (2E)-3-(7-butoxy-4-isopropyl-2,2-dimethyl-2H-chromen-6-yl)-2-fluoro-but-2-enal (Compound 100, 86 mg, 0.24 mmol) were reacted to give the title compound as a yellow oil after purification by flash chromatography (silica gel, 5% ethyl acetate in hexane).

$^1$H NMR (300 MHz, CDCl$_3$): δ 0.93 (t, l=7.0 Hz, 3H), 1.11 (d, J=6.7 Hz, 6H), 1.27 (m, 3H), 1.40 (s, 6H), 1.70 (m, 2H), 2.11 (m, 6H), 2.78 (m, 1H), 3.86 (t, J=7.0 Hz, 2H), 4.16 (q, J=7.0 Hz, 2H), 5.27 (s, 1H), 5.82 (s, 1H), 6.34 (dd, J=15.5, 25.5 Hz, 1H), 6.42 (s, 1H), 6.47 (d, J=15.5 Hz, 1H), 6.89 (s, 1H).

Ethyl (2E,4E,6E)-7-(7-ethoxy-2,2-dimethyl-4-phenyl-2H-chromen-6-yl)-6 fluoro-3-methyl-octa-2,4,6-trienoate (Compound 114)

Following General Procedure O, ethyl 4-(diethoxyphosphoryl)-3-methyl-but-2E-enoate (237 mg, 0.90 mmol) and (2E)-3-(7-ethoxy-2,2-dimethyl-4-phenyl-2H-chromen-6-yl)-2-fluoro-but-2-enal (Compound 101, 113 mg, 0.31 mmol) were reacted to give the title compound as a yellow oil after purification by flash chromatography (silica gel, 5% ethyl acetate in hexane).

$^1$H NMR (300 MHz, CDCl$_3$): δ 1.26 (t, J=7.0 Hz, 3H), 1.37 (t, J=7.0 Hz, 3H), 1.51 (s, 6H), 2.00 (m, 3H), 2.19 (s, 3H), 4.03 (t, J=7.0 Hz, 2H), 4.13 (q, J=7.0 Hz, 2H), 5.48 (s, 1H), 5.82 (s, 1H), 6.37 (d, J=14.0 Hz, 1H), 6.40 (m, 1H), 6.48 (s, 1H), 6.70 (s, 1H), 7.32 (m, 5H).

Ethyl (2E,4E,6E)-7-(2,2-dimethyl-4-phenyl-7-propoxy-2H-chromen-6-yl)-6-fluoro-3-methyl-octa-2,4,6-trienoate (Compound 115)

Following General Procedure O, ethyl 4-(diethoxyphosphoryl)-3-methyl-but-2E-enoate (237 mg, 0.83 mmol) and (2E)-3-(2,2-dimethyl-4-phenyl-7-propoxy-2H-chromen-6-yl)-2-fluoro-but-2-enal (Compound 102, 107 mg, 0.29 mmol) were reacted to give the title compound as a yellow oil after purification by flash chromatography (silica gel, 5% ethyl acetate in hexane).

$^1$H NMR (300 MHz, CDCl$_3$): δ 1.00 (t, J=7.0 Hz, 3H), 1.27 (t, J=7.0 Hz, 3M), 1.56 (s, 61), 1.79 (m, 2H), 2.00 (m, 3H), 2.19 (s, 3H), 3.91 (t, J=7.0 Hz, 2H), 4.16 (q, J=7.0 Hz, 2H), 5.48 (s, 1H), 5.82 (s, 1H), 6.37 (d, J=14.0 Hz, 1H), 6.40 (m, 1H), 6.48 (s, 1H), 6.70 (s, 1H), 7.32 (m, 5H).

Ethyl 6-fluoro-7-(7-methoxy-2,2,4-trimethyl-2H-chromen-6-yl)-3-methyl-nona-2E,4E,6E-trienoate (Compound 116)

Following General Procedure N, a solution of 2-fluoro-3-(7-methoxy-2,2,4-trimethyl-2H-chromen-6-yl)-pent-2-en-1-ol (Compound 90, 171 mg, 0.56 mmol) in THF, 4-methylmorpholine N-oxide (132 mg, 1.12 mmol) and tetrapropylammonium perruthenate (5 mg) were reacted to give the corresponding aldehyde, Compound 103. Treatment with the ylide of ethyl 4-(diethoxyphosphoryl)-3-methyl-but-2E-enoate (1.48 g, 5.60 mmol) afforded the title compound as a colorless oil after purification by flash chromatography (silica gel, 10% ethyl acetate in hexanes).

$^1$H NMR (300 MHz, CDCl$_3$): δ 6.80 (s, 1H), 6.50 (d, J=15.0 Hz, 1H), 6.41 (s, 1H), 6.28 (dd, J=15.6, 25.5 Hz, 1H), 5.81 (s, 1H), 5.30 (s, 1H), 4.15 (q, J=7.2 Hz, 2H), 3.75 (s, 3H), 2.41–2.59 (m, 2H), 2.10 (s, 3H), 1.95 (s, 3H), 1.42 (s, 6H), 1.26 (t, J=7.2 Hz, 3H), 0.94 (t, J=7.5 Hz, 3H).

Ethyl 6-fluoro-7-(4-isopropyl-7-methoxy-2,2-dimethyl-2H-chromen-6-yl)-3-methyl-nona-2E,4E,6E-trienoate (Compound 117)

Following General Procedure N, (2E)-2-fluoro-3-(4-isopropyl-7-methoxy-2,2-dimethyl-2H-chromen-6-yl)-pent-2-en-1-ol (Compound 91, 112 mg, 0.34 mmol) and 4-methylmorpholine N-oxide (80 mg, 0.68 mmol) were reacted to give the corresponding aldehyde, Compound 104. Treatment with the ylide ofethyl 4-(diethoxyphosphoryl)-3-methyl-but-2E-enoate (762 mg, 2.89 mmol) afforded the title compound as a colorless oil after purification by flash chromatography (silica gel, 5% ethyl acetate in hexanes).

$^1$H NMR (300 MHz, CDCl$_3$): δ 6.78 (s, 1H), 6.39 (d, J=15.5 Hz, 1H), 6.30 (s, 1H), 6.22 (dd, J=15.5, 25.5 Hz, 1H), 5.74 (s, 1H), 5.21 (s, 1H), 4.07 (q, J=7.2 Hz, 2H), 3.68 (s, 3H), 2.66–2.71 (m, 1H), 2.40–2.59 (m, 2H), 2.01 (s, 3H), 1.34 (s, 6H), 1.19 (t, J=7.2 Hz, 3H), 1.04 (d, J=7.2 Hz, 6H), 0.86 (t, J=7.2 Hz, 3H).

Ethyl 7-(4-tert-butyl-7-methoxy-2-dimethyl-2H-chromen-6-yl)-6-fluoro-3-methyl-nona-2E,4E,6E-trienoate (Compound 118)

Following General Procedure N, (2E)-3-(4-tert-butyl-7-methoxy-2,2-dimethyl-2H-chromen-6-yl)-2-fluoro-pent-2-en-1-ol (Compound 92, 75 mg, 0.21 mmol) and 4-methylmorpholine N-oxide (50 mg, 0.42 mmol) were reacted to give the corresponding aldehyde, Compound 105. Treatment with the ylide ofethyl 4(diethoxyphosphoryl)-3-methyl-but-2E-enoate (554 mg, 2.10 mmol) afforded the title compound as a colorless oil after purification by flash chromatography (silica gel, 5% ethyl acetate in hexanes).

$^1$H NMR (CDCl$_3$, 300 MHz): δ 7.19 (s, 1H), 6.46 (d, J=15.5 Hz, 1H), 6.43 (s, 1H), 6.30 (dd, J=15.5, 25.5 Hz, 1H), 5.80 (s, If), 5.37 (s, 1H), 4.15 (q, J=7.2 Hz, 2H), 3.74 (s, 3H), 2.35–2.40 (m, 2H), 2.05 (s, 3H), 1.32 (s, 6H), 1.17–1.23 (m, 12H), 0.87 (t, J=7.2 Hz, 3H).

Ethyl 7-(7-ethoxy-2,2,4-trimethyl-2H-chromen-6-yl)-6-fluoro-3-methyl-nona-2E,4E,6E-trienoate (Compound 119)

Following General Procedure N, (2E)-3-(7-ethoxy-2,2,4-trimethyl-2H-chromen-6-yl)-2-fluoro-pent-2-en-1-ol (Compound 93, 152 mg, 0.475 mmol) and 4-methylmorpholine N-oxide (63 mg, 0.57 mmol) were reacted to give the corresponding aldehyde, Compound 106.

Treatment with the ylide ofethyl 4-(diethoxyphosphoryl)-3-methylbut-2E-enoate (2.06 g, 7.82 mmol) afforded the title compound as a yellow oil after purification by flash chromatography (silica gel, 5% ethyl acetate in hexanes).

$^1$H NMR (300 MHz, CDCl$_3$): δ 6.80 (s, 1H), 6.50 (d, J=15.0 Hz, 1H), 6.41 (s, 1H), 6.25 (dd, J=15.6, 25.5 Hz, 1H), 5.81 (s, 1H), 5.25 (s, 1H), 4.18 (q, J=7.2 Hz, 2H), 4.01 (q, J=7.2 Hz, 2H), 2.43–2.58 (in, 2H), 2.10 (s, 3H), 1.95 (s, 3H), 1.45 (s, 6H), 1.40 (s, 3H), 1.29 (t, J=7.2 Hz, 3H), 0.89 (t, J=7.5 Hz, 3H).

7-(4Ethyl-7-methoxy-2,2-dimethyl-2H-chromen-6-yl)-6-fluoro-3-methyl-octa-2E,4E,6E-trienoic acid (Compound 120) Following General Procedure G, a solution of ethyl 7-(4-ethyl-7-methoxy-2,2-dimethyl-2H-chromen-yl)-6-fluoro-3-methyl-octa-2E,4E,6E-trienoate (Compound 107, 19 mg, 0.08 mmol) in ethanol and THF was hydrolyzed with 1M NaOH. Purification by flash chromatography (silica gel, 75:25 hexane/ethyl acetate) afforded the title compound as a white solid.

$^1$H NMR (CDCl$_3$, 300 MHz) δ 11.25 (br s, 1H), 6.80 (s, 1H), 6.50 (d, J=15.0 Hz, 1H), 6.41 (s, 1H), 6.28 (dd, J=15.6, 25.5 Hz, 1H), 5.75 (s, 1H), 5.27 (s, 1H), 3.70 (s, 3H), 2.20–2.37 (in, 21), 2.05 (s, 31), 1.95 (d, J=3.0 Hz, 3H), 1.42 (s, 3H), 1.38 (s, 6H), 1.05 (t, J=7.5 Hz, 3H).

(2E,4E,6E)-6-Fluoro-7-(4-isopropyl-7-methoxy-2,2-dimethyl-2H-chromen-6-yl)-3-methyl-octa-2,4,6-trienoic acid (Compound 121).

Following General Procedure G, a solution of ethyl (2E, 4E,6E)-6-fluoro-7-(4-isopropyl-7-methoxy-2,2-dimethyl-2H-chromen-6-yl)-3-methyl-octa-2,4,6-trienoate (Compound 108, 116 mg, 2.71 mmol) in ethanol and THF was hydrolyzed with NaOH to yield a yellow oil after purification by column chromatography (silica gel, 100% hexane to 5% to 50% ethyl acetate in hexanesethyl). The resulting oil was recrystallized from acetonitrile to produce the title compound as a yellow solid.

$^1$H NMR (300 MHz, CDCl$_3$): 1.13 (d, J=6.4 Hz, 6H), 1.43 (s, 6H), 2.09 (m, 6H), 2.78 (m, 114), 3.79 (s, 3H), 5.29 (s, 1H), 5.87 (s, 1H), 6.32 (dd, J=15.5 Hz, J=25.5 Hz, 1H), 6.44 (s, 1H), 6.47 (d, J=15.5 Hz, 1H), 6.91 (s, 1H).

7-(4-tert-Butyl-7-methoxy-2,2-dimethyl-2H-chromen-6-yl)-6-fluoro-3-methyl-octa-2E,4E,6E-trienoic acid (Compound 122)

Following General Procedure G, a solution of ethyl 7-(4-tert-butyl-7-methoxy-2,2-dimethyl-2H-chromen-6-yl)-6-fluoro-3-methyl-octa-2E,4E,6E-trienoate (Compound 109, 32 mg, 0.07 mmol) in ethanol and THF was hydrolyzed with 1M NaOH. Purification by flash chromatography (silica gel, 75:25 hexane/ethyl acetate) afforded the title compound as a light yellow solid.

$^1$H NMR (300 M-z, CDCl$_3$): δ 11.35 (bs, 1H), 7.20 (s, 1H), 6.52 (d, J=15.6 Hz, 1H), 6.44 (s, 1H), 6.32 (dd, J=15.6, 25.5 Hz, 1H), 5.83 (s, 1H), 5.38 (s, 1H), 3.77 (s, 3H), 2.04–2.09 (m, 6H), 1.42 (s, 6H), 1.25 (s, 9H).

7-(7-Ethoxy-4-ethyl-2,2-dimethyl-2H-chromen-6-yl)-6-fluoro-3-methyl-octa-2E,4E,6E-trienoic acid (Compound 123)

Following General Procedure G, a solution of ethyl 7-(7-ethoxy-4-ethyl-2,2-dimethyl-2H-chromen-6-yl)-6-fluoro-3-methyl-octa-2E,4E,6E-trienoate (Compound 110, 9.0 mg, 0.02 mmol) in ethanol and THF was hydrolyzed with 1M NaOH. Purification by flash chromatography (silica gel, 75:25 hexane/ethyl acetate) afforded the title compound as a white solid.

$^1$H NMR (300 MHz, CDCl$_3$): δ 11.25 (br s, 1H), 6.78 (s, 1H), 6.41 (d, J=15.0 Hz, 1H), 6.38 (s, 1H), 6.25 (dd, J=15.6, 25.5 Hz, 1H), 5.79 (s, 1H), 5.21 (s, 1H), 4.15 (q, J=7.8 Hz, 2H), 2.21–2.30 (m, 2H), 2.10 (s, 3H), 2.01 (d, J=3.3 Hz, 3H), 1.35 (s, 6H), 1.19 (t, J=7.8 Hz, 3H), 1.02 (t, J=7.8 Hz, 3H).

(2E,4E,6E)-7-(7-Ethoxy-4-isopropyl-2,2-dimethyl-2H-Chromen-6-yl)-6-fluoro-3-methyl-octa-2.46-trienoic acid (Compound 124)

Following General Procedure G, a solution of ethyl (2E, 4E,6E)-7-(7-ethoxy-isopropyl-2,2-dimethyl-2H-chromen-6-yl)-6-fluoro-3-methyl-octa-2,4,6-trienoate (Compound 111, 6 mg, 0.27 mmol) in ethanol and THF was hydrolyzed with NaOH to yield a yellow oil after purification by column chromatography (silica gel, 100% hexane to 5% to 50% ethyl acetate in hexanes). The resulting oil was recrystallized from acetonitrile to produce the title compound as a yellow solid.

$^1$H NMR (300 MHz, CDCl$_3$): δ 1.11 (d, J=6.7 Hz, 6H), 1.35 (t, J=7.0 Hz, 3H), 1.41 (s, 6H), 2.07 (m, 6H), 2.76 (m, 1H), 3.98 (q, J=7.0 Hz, 2H), 4.16 (q, J=7.0 Hz, 2H), 5.27 (s, 1H), 5.85 (s, 1H), 6.34 (dd, J=15.5, 25.5 Hz, 1H), 6.42 (s, 1H), 6.47 (d, J=15.5 Hz, 1H), 6.89 (s, 1H).

(2E,4E,6E) 6-Fluoro-7-(4-isopropyl-2,2-dimethyl-7-propoxy-2H-chromen-6-yl)-3-methyl-octa-2,4,6-trienoic acid (Compound 125)

Following General Procedure G, a solution of ethyl (2E, 4E,6E)-6-fluoro-7-(4-isopropyl-2,2-dimethyl-7-propoxy-2H-chromen-6-yl)-3-methyl-octa-2,4,6-trienoate (Compound 112, 73 mg, 0.16 mmo) in ethanol and THF was hydrolyzed with NaOH to yield the title compound as a yellow solid after recrystallized from acetonitrile.

$^1$H NMR (300 MHz, CDCl$_3$): δ 0.98 (t, J=7.0 Hz, 3H), 1.13 (d, J=6.7 Hz, 6H), 1.41 (s, 6H), 1.74 (m, 2H), 2.07 (m, 6H), 2.80 (m, 1H), 3.86 (t, J=7.0 Hz, 2H), 5.27 (s, 1H), 5.82 (s, 1H), 6.34 (dd, J=15.5 Hz, J=25.5 Hz, 1H), 6.42 (s, 1H), 6.47 (d, J=15.5 Hz, 1H), 6.89 (s, 1H).

(2E,4E,6E)-7-(7-Butoxy-4-isopropyl-2,2-dimethyl-2H-chromen-6-yl)-6-fluoro-3-methyl-octa-2,4,6-trienoic acid (Compound 126)

Following General Procedure G, a solution of ethyl (2E, 4E,6E)-7-(7-butoxy-4-isopropyl-2,2-dimethyl-2H-chromen-6-yl)-6-fluoro-3-methyl-octa-2,4,6-trienoate (Compound 113, 95 mg, 0.20 mmol) was hydrolyzed with NaOH to yield the title compound as a yellow solid after recrystallized from acetonitrile.

$^1$H NMR (300 MHz, CDCl$_3$): δ 0.93 (t, J=7.0 Hz, 3H), 1.11 (Id, J=6.7 Hz, 6H), 1.40 (s, 6H), 1.41 (r, 2H), 1.71 (m, 2H), 2.11 (m, 2H), 2.78 (m, 1H), 3.86 (t, J=7.0 Hz, 2H), 5.27 (s, 1H), 5.82 (s, 1H), 6.34 (dd, J=15.5, 25.5 Hz, 1H), 6.42 (s, 1H), 6.47 (d, J=15.5 Hz, 1H), 6.89 (s, 1H).

(2E,4E,6E)-7-(7-Ethoxy-2,2-dimethyl-4-phenyl-2H-chromen-6-yl)-6-fluoro-3-methyl-octa-2,4,6-trienoic acid (Compound 127)

Following General Procedure G, a solution of ethyl (2E, 4E,6E)-7-(7-ethoxy-2,2-dimethyl-4-phenyl-2H-chromen-6-yl)-6-fluoro-3-methyl-octa-2,4,6-trienoate (Compound 114, 147 mg, 0.31 mmol) was hydrolyzed with NaOH to yield a yellow oil after purification by column chromatography (silica gel, 100% hexane to 5% to 50% ethyl acetate in hexanes). The resulting oil was recrystallized from acetonitrile to produce the title compound as a yellow solid.

¹H N (300 MHz, CDCl₃): δ 1.37 (t, J=7.0 Hz, 3H), 1.51 (s, 6H), 2.00 (m, 3H), 2.19 (s, 3H), 4.03 (t, J=7.0 Hz, 2H), 5.48 (s, 1H), 5.82 (s, 1H), 6.37 (d, J=14.0 Hz, 1H), 6.40 (m, 1H), 6.48 (s, 1H), 6.70 (s, 1H), 7.32 (m, 5H).

(2E,4E,6E)-7-(2,2-Dimethyl-4-phenyl-7-propoxy-2H-chromen-6-yl)-6-fluoro-3-methyl-octa-2,4,6-trienoic acid (Compound 128)

Following General Procedure G, ethyl (2E,4E,6E)-7-(2,2-dimethyl-4-phenyl-7-propoxy-2H-chromen-6-yl)-6-fluoro-3-methyl-octa-2,4,6-trienoate (Compound 115, 131 mg, 0.27 mmol) was hydrolyzed with NaOH to yield a yellow oil after purification by column chromatography (silica gel, 100% hexane to 5% to 50% ethyl acetate in hexanes). The resulting oil was recrystallized from acetonitrile to produce the title compound as a yellow solid.

¹H NMR (300 MHz, CDCl₃): δ 1.00 (t, J=7.0 Hz, 3H), 1.56 (s, 6H), 1.79(m, 2H), 2.00 (m, 3H), 2.19 (s, 3H), 3.91 (t, J=7.0 Hz, 2H), 5.48 (s, 1H), 5.82 (s, 1H), 6.37 (s, 1H), 6.40 (m, 1H), 6.48 (s, 1H), 6.70 (s, 1H), 7.32 (m, 5H).

6-Fluoro-7-(7-methoxy-2,2,4-trimethyl-2H-chromen-6-yl)-3-methyl-nona-2E,4E,6E-trienoic acid (Compound 129)

Following General Procedure G, a solution of ethyl 6-fluoro-7-(7-methoxy-2,2,4-trimethyl-2H-chromen-6-yl)-3-methyl-nona-2E,4E,6E-trienoate (Compound 116, 204 mg, 0.51 mmol) in ethanol and THF was hydrolyzed with 1M NaOH. Purification by flash chromatography (silica gel, 75:25 hexane/ethyl acetate) afforded the title compound as a light yellow solid.

¹H NMR (300 MHz, CDCl₃): δ 11.25 br s, 1H), 6.79 (s, 1H), 6.50 (d, J=15.5 Hz, 1H), 6.42 (s, 1H), 6.32 (dd, J=15.6, 25.5 Hz, 1H), 5.83 (s, 1H), 5.31 (s, 1H), 3.75 (s, 3H), 2.42–2.58 (m, 2H), 2.11 (s, 3H), 1.94 (s, 3H), 1.42 (s, 6H), 0.94 (t, J=7.5 Hz, 3H).

6-Fluoro-7-(4-isopropyl-7-methoxy-2,2-dimethyl-2H-chromen-6-yl)-3-methyl-nona-2E,4E,6E-trienoic acid (Compound 130)

Following General Procedure G, a solution of ethyl 6-fluoro-7-(4-isopropyl-7-methoxy-2,2-dimethyl-2H-chromen-6-yl)3-methyl-nona-2E,4E,6E-trienoate (Compound 117, 86 mg, 0.20 mmol) in ethanol and THF was hydrolyzed with 1M NaOH. Purification by flash chromatography (silica gel, 75:25 hexane/ethyl acetate) afforded the title compound as a light yellow solid.

¹H NMR (300 MHz, CDCl₃): δ 11.14 (br s, 1H), 6.85 (s, 1H), 6.51 (d, J=15.6 Hz, 1H), 6.44 (s, 1H), 6.30 (dd, J=15.6, 25.5 Hz, 1H), 5.83 (s,1H), 5.28 (s, 1H), 3.75 (s, 3H), 2.71–2.78 (m, 1H), 2.42–2.58 (m, 2H), 2.08 (s, 3H), 1.42 (s, 6H), 1.11 (d, J=6.0 Hz, 6H), 0.94 (t, J=7.5 Hz, 3H).

7-(4-tert-Butyl-7-methoxy-2,2-dimethyl-2H-chromen-6-yl)-6-fluoro-3-methyl-nona-2E,4E,6E-trienoic acid (Compound 131)

Following General Procedure G, a solution of ethyl 7-(4-ten-butyl-7-methoxy-2,2-dimethyl-2H-chromen-6-yl)-6-fluoro-3-methyl-nona-2E,4E,6E-trienoate (Compound 118, 54 mg, 0.11 mmol) in methanol and THF was hydrolyzed with 1M NaOH. Purification by flash chromatography (silica gel, 75:25 hexane/ethyl acetate) afforded the title compound as a light yellow solid.

¹H NMR (CDCl₃, 300 MHz) δ 11.34 (br s, 1H), 7.19 (s, 1H), 6.51 (d, J=15.6 Hz, 1H), 6.45 (s, 1H), 6.33 (dd, J=15.6, 25.5 Hz, 1H), 5.83 (s, 1H), 5.38 (s, 1H), 3.76 (s, 3H), 2.40 2.60 (m, 2H), 2.06 (s, 3H), 1.40 (s, 6H), 1.26 (s, 9H), 0.95 (t, J=7.5 Hz, 3H).

7-(7-Ethoxy-2,2,4-trimethyl-2H-chromen-6-yl)-6-fluoro-3-methyl-nona-2E,4E,6E-trienoic acid (Compound 132)

Following General Procedure G, a solution of ethyl 7-(7-ethoxy-2,2,4-trimethyl-2H-chromen-6-yl)-6-fluoro-3-methyl-nona-2E,4E,6E-trienoate (Compound 119, 103 mg, 0.24 mmol) in ethanol and THF was hydrolyzed with 1M NaOH. Purification by flash chromatography (silica gel, 75:25 hexane/ethyl acetate) afforded the title compound as a white solid.

¹H NMR (300 MHz, CDCl₃) δ 11.25 br s, 1H), 6.80 (s, 1H), 6.50 (d, J=15.0 Hz, 1H), 6.41 (s, 1H), 6.25 (dd, J=15.6, 25.5 Hz, 1H), 5.81 (s, 1H), 5.25 (s, 1H), 4.18 (q, J=7.2 Hz, 2H), 2.43–2.58 (m, 2H), 2.10 (s, 3H), 1.95 (s, 3H), 1.45 (s, 6H), 1.40 (s, 3H), 0.89 (t, J=7.5 Hz, 3H).

TABLE 3

Receptor Transactivation, Efficacy and Binding Data for Exemplary Compounds of Formula B

| Compound | | RAR Trans. EC₅₀ nM RAR Bind. Kᵢ nM | | | RXR Trans. EC₅₀ nM RXR Bind Kᵢ nM | | |
|---|---|---|---|---|---|---|---|
| Number | Structure | α | β | γ | α | β | γ |
| 120 | 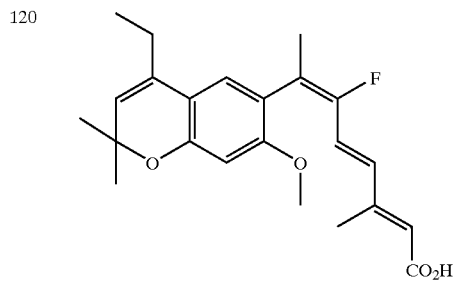 | NA 4.1k | NA 8.1k | NA >10K | >10K 277 | >10K 2.6k | >10K ND |

TABLE 3-continued

Receptor Transactivation, Efficacy and Binding Data for Exemplary Compounds of Formula B

| Compound Number | Structure | RAR Trans. $EC_{50}$ nM RAR Bind. $K_i$ nM | | | RXR Trans. $EC_{50}$ nM RXR Bind $K_i$ nM | | |
|---|---|---|---|---|---|---|---|
| | | α | β | γ | α | β | γ |
| 121 | | NA 692 | 46620 2.1k | NA 8.8k | 5 (59) 7 | 51 (72) 33 | 10 (79) ND |
| 122 | | NA 800 | NA 1.4k | NA 3.9k | 5 (36) 11 | 35 (61) 110 | 9 (52) ND |
| 123 | | NA >10k | NA >10k | NA >10k | >10k 833 | NA >10k | >1k ND |
| 124 | | NA 523 | NA 1.0k | NA 3.3k | NA 6 | NA 42 | NA ND |
| 125 | | NA 12 | NA 3 | NA 43 | NA 8 | NA 73 | NA ND |

TABLE 3-continued

Receptor Transactivation, Efficacy and Binding Data for Exemplary Compounds of Formula B

| Compound Number | Structure | RAR Trans. EC$_{50}$ nM / RAR Bind. K$_i$ nM | | | RXR Trans. EC$_{50}$ nM / RXR Bind K$_i$ nM | | |
|---|---|---|---|---|---|---|---|
| | | α | β | γ | α | β | γ |
| 126 | 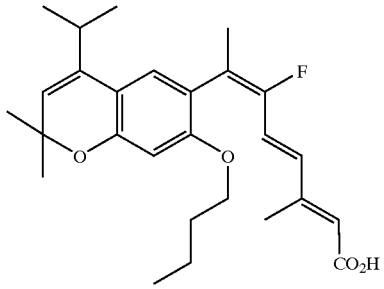 | NA<br>860 | NA<br>522 | NA<br>3.0k | NA<br>8 | NA<br>59 | NA<br>ND |
| 127 | 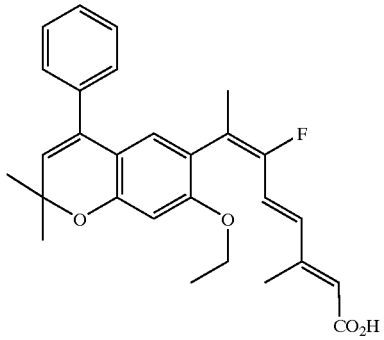 | 245<br>(26)<br>3.7k | 227<br>(17)<br>1.4k | NA<br><br>2.6k | NA<br><br>97 | NA<br><br>554 | NA<br><br>ND |
| 128 | 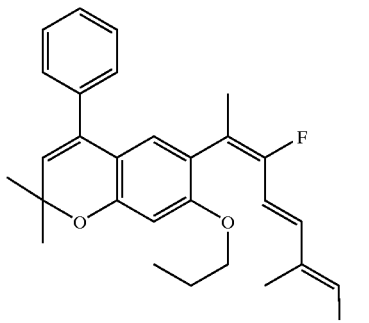 | 14<br>(25)<br>302 | 90<br>(22)<br>388 | NA<br><br>759 | NA<br><br>53 | NA<br><br>289 | NA<br><br>ND |
| 129 | 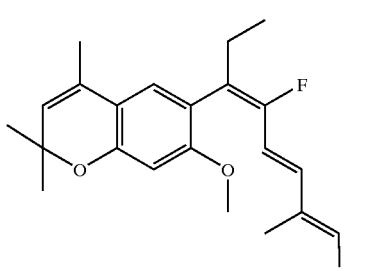 | >10k<br><br>177 | 563<br>(24)<br>490 | NA<br><br>4.7k | 44<br>(99)<br>69 | 843<br>(151)<br>625 | 53<br>(108)<br>ND |

TABLE 3-continued

Receptor Transactivation, Efficacy and Binding Data for Exemplary Compounds of Formula B

| Compound | | RAR Trans. EC$_{50}$ nM RAR Bind. K$_i$ nM | | | RXR Trans. EC$_{50}$ nM RXR Bind K$_i$ nM | | |
|---|---|---|---|---|---|---|---|
| Number | Structure | α | β | γ | α | β | γ |
| 130 | | 218 (8) 133 | 65 (31) 547 | NA 2.7k | 0.5 (80) 3 | 3.1 (73) 24 | 0.6 (86) ND |
| 131 | | NA 837 | 116 (13) 843 | NA 3.3k | 6 (37) 10 | 64 (47) 94 | 8 (53) ND |
| 132 | | NA 148 | 710 (8) 548 | NA 2.4k | 759 (15) 124 | >10k 1.1k | >1k ND |

Section C of Specific Embodiments

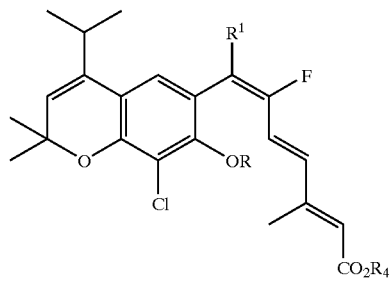

Formula C

Formula C discloses a specific class of preferred and exemplary compounds of the invention. In Formula C:

R represents alkyl of 1 to 8 carbons, more preferably alkyl of 1 to 4 carbons, and most preferably alkyl of 1 to 3 carbons;

$R^1$ represents alkyl of 1 to 8 carbons, more preferably alkyl of 1 to 4 carbons, and most preferably alkyl of 1 to 2 carbons, and $R^4$ represents H, alkyl of 1 to 6 carbons, $CH_2OR_5$ or $CH_2OCOR_5$ where $R_5$ is alkyl of 1 to 3 carbons, or a pharmaceutically acceptable salt of said compound.

The synthetic schemes and the experimental procedures for obtaining compounds within the scope of Formula C are provided below.

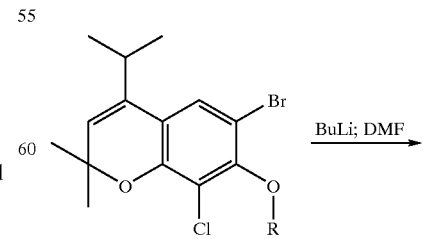

19, (R = Me)
20, (R = Et)
21, (R = i-Pr)

65
-continued

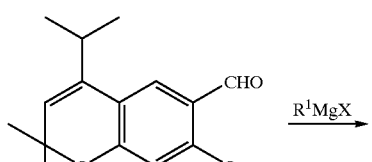

133, (R = Me)
134, (R = Et)
135, (R = i-Pr)

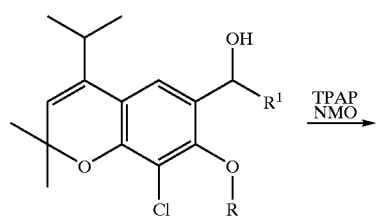

136, (R = Me, R¹ = Et)
137, (R = Et, R¹ = Et)
138, (R = i-Pr, R¹ = Me)
139, (R = i-Pr, R¹ = Et)

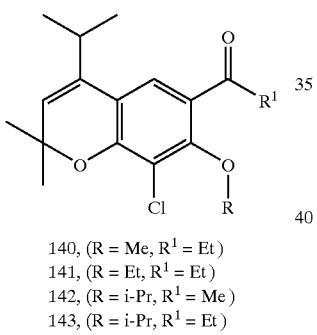

140, (R = Me, R¹ = Et)
141, (R = Et, R¹ = Et)
142, (R = i-Pr, R¹ = Me)
143, (R = i-Pr, R¹ = Et)

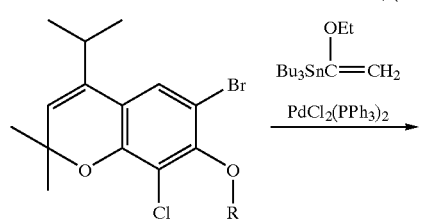

19, (R = Me)
20, (R = Et)

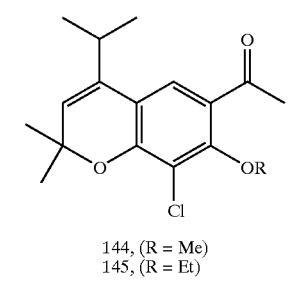

144, (R = Me)
145, (R = Et)

66
-continued

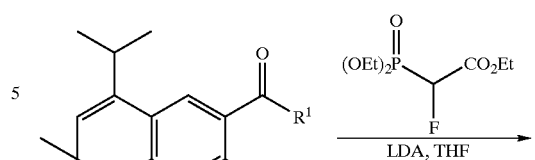

144, (R = Me, R¹ = Me)
140, (R = Me, R¹ = Et)
145, (R = Et, R¹ = Me)
141, (R = Et, R¹ = Et)
142, (R = i-Pr, R¹ = Me)
143, (R = i-Pr, R¹ = Et)

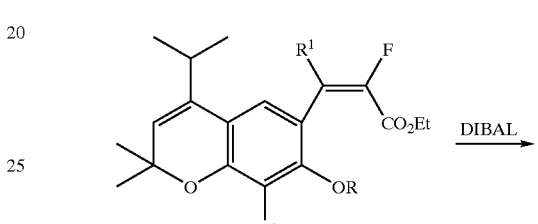

146, (R = Me, R¹ = Me)
147, (R = Me, R¹ = Et)
148, (R = Et, R¹ = Me)
149, (R = Et, R¹ = Et)
150, (R = i-Pr, R¹ = Me)
151, (R = i-Pr, R¹ = Et)

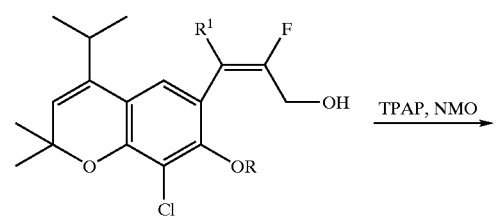

152, (R = Me, R¹ = Me)
153, (R = Me, R¹ = Et)
154, (R = Et, R¹ = Me)
155, (R = Et, R¹ = Et)
156, (R = i-Pr, R¹ = Me)
157, (R = i-Pr, R¹ = Et)

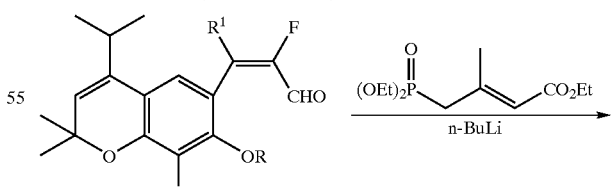

158, (R = Me, R¹ = Me)
159, (R = Me, R¹ = Et)
160, (R = Et, R¹ = Me)
161, (R = Et, R¹ = Et)
162, (R = i-Pr, R¹ = Me)
163, (R = i-Pr, R¹ = Et)

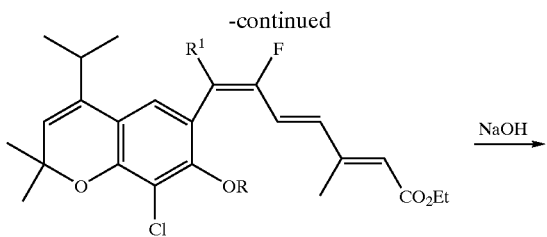

164, (R = Me, R¹ = Me)
165, (R = Me, R¹ = Et)
166, (R = Et, R¹ = Me)
167, (R = Et, R¹ = Et)
168, (R = i-Pr, R¹ = Me)
169, (R = i-Pr, R¹ = Et)

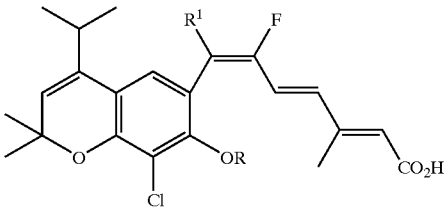

170, (R = Me, R¹ = Me)
171, (R = Me, R¹ = Et)
172, (R = Et, R¹ = Me)
173, (R = Et, R¹ = Et)
174, (R = i-Pr, R¹ = Me)
175, (R = i-Pr, R¹ = Et)

8-Chloro-7-isopropoxy-4-isopropyl-2,2-dimethyl-2H-chromene-6-carbaldehyde (Compound 135)

To a solution of 6-bromo-8-chloro-7-isopropoxy-4-isopropyl-2,2-dimethyl-2H-chromene, (Compound 21, 3.9 g, 10.3 mmol) in diethyl ether (100 mL) at −78° C. was added n-butyllithium (1.6 M in hexanes, 10.3 mL, 16.5 mmol). After stirring at −78° C. for 20 min, the reaction mixture was quenched with DMF (10 mL). After further stirring at −78° C. for 15 min, the reaction was allowed to warm to room temperature. The reaction mixture was poured into 1N HCl and extracted with ethyl acetate. The combined organic layers were washed with water and brine, dried (MgSO$_4$), filtered, and concentrated under reduced pressure. The crude residue was purified by flash chromatography (silica gel, 100% hexanes to 2% ethyl acetate in hexanes) to afford the title compound as a colorless oil.

$^1$H NMR (300 MHz, CDCl$_3$): δ 10.25 (s, 1H), 7.68 (s, 1H), 5.47 (s, 1H), 4.62 (sept, J=6.1 Hz, 1H), 2.90 (sept, J=6.7 Hz, 1H), 1.48 (s, 6H), 1.39 (d, J=6.1 Hz, 6H), 1.15 (d, J=6.7 Hz, 6H).

1-(8-Chloro-7-isopropoxy-4-isopropyl-2,2-dimethyl-2H-chromene-6-yl)-ethanol (Compound 138)
General Procedure P To a solution of 8-chloro-7-isopropoxy-4-isopropyl-2,2-dimethyl-2H-chromene-6-carbaldehyde, (Compound 135, 0.97 g, 3.0 mmol) in THF (15 mL) at was added methylmagnesium chloride (3M in THF, 1.6 mL, 4.8 mmol). After stirring at 0° C. for 30 min, the reaction was quenched with 1N HCl. The resulting mixture was diluted with water, extracted with ethyl acetate. The combined organic layers were washed with water and brine, dried (MgSO$_4$), filtered, and concentrated under reduced pressure to give the title compound as a yellow foam.

$^1$H NMR (300 MHz, CDCl$_3$): δ 7.21 (s, 1H), 5.35 (s, 1H), 5.18 (q, J=6.4 Hz, 114), 4.55 (sept, 36.2 Hz, 1H), 2.83 (sept, J=6.7 Hz, 1H), 1.39 (d, J=6.4 Hz, 3H), 1.37 (s, 6H), 1.28 (d; J=6.2 Hz, 6H), 1.10 (d, J=6.7 Hz, 6H).

1-(8-Chloro-7-isopropoxy-4-isopropyl-2,2-dimethyl-2H-chromene-6-yl)-propan-1-ol (Compound 139)

As described in General Procedure P, 8-chloro-7-isopropoxy-4-isopropyl-2,2-dimethyl-2H-chromene-6-carbaldehyde, (Compound 135, 0.98 g, 3.05 mmol) was treated with ethylmagnesium bromide (3 M in ether, 1.6 mL, 4.9 mmol) to give rise to the title compound as a yellow foam.

$^1$H NMR (300 MHz, CDCl$_3$): δ 7.20 (s, 1H), 5.39 (s, 1H), 4.96 (t, J=6.5 Hz, 1H), 4.60 (sept, J=6.2 Hz, 1H), 2.86 (sept, J=6.9 Hz, 1H), 2.01 (s, OH), 1.85–1.63 (m, 2H), 1.44 (s, 3H), 1.42 (s, 3H), 1.32 (d, J=6.2 Hz, 3H), 1.36 (d, J=6.2 Hz, 3H), 1.14 (d, J=6.7 Hz, 6H), 0.96 (t, J=7.5 Hz, 3H).

1-(8-Chloro-4-isopropyl-7-methoxy-2,2-dimethyl-2H-chromen-6-yl)-propan-1-one (Compound 140)

Following General Procedure I, 6-bromo-8-chloro-4-isopropyl-7-methoxy-2,2-dimethyl-2H-chromene (Compound 19, 660 mg, 1.91 mmol) afforded the title compound as a colorless oil.

$^1$H NMR (300 MHz, CDCl$_3$): δ 7.53 (s, 1H), 5.43 (s, 1H), 3.89 (s, 3H), 3.01 (q, J=7.3 Hz, 2H), 2.842.87 (m, 1H), 1.55 (s, 6H), 1.17–1.20 (m, 9H).

1-(8-Chloro-4-isopropyl-7-ethoxy-2,2-dimethyl-2H-chromen-6-yl)-propan-1-one (Compound 141)

Following General Procedure I, 6-bromo-8-chloro-4-isopropyl-7-ethoxy-2,2-dimethyl-2H-chromene (Compound 20, 965 mg, 2.68 mmol) afforded the title compound as a colorless oil.

$^1$H NMR (300 MHz, CDCl$_3$): δ 7.49 (s, 1H), 5.43 (s, 1H), 4.05 (q, J=7.3 Hz, 2H), 3.02 (q, J=7.3 Hz, 2H), 2.842.87 (m, 1H), 1.44–1.47 (m, 9H), 1.161.20 (m, 9H).

1-(8-Chloro-7-isopropoxy-4-isopropyl-2,2-dimethyl-2H-chromene-6-yl)-ethanone (Compound 142)

Following General Procedure M, 1-(8-chloro-7-isopropoxy-4-isopropyl-2,2-dimethyl-2H-chromene-6-yl)-ethanol (Compound 138, 0.92 g, 2.7 mmol), tetrapropylammonium perrunthenate (TPAP, 0.047 g, 0.14 mmol), and 4-methylmorpholine N-oxide (NMO, 0.47 g, 4.1 mmol) were reacted to give the title compound as a yellow oil.

$^1$H NMR (300 MHz, CDCl$_3$): δ 7.40 (s, 1H), 5.39 (br s, 1H), 4.42 (sept, J=6.1 Hz, 1H), 2.82 (sept, J=6.7 Hz, 1H), 2.57 (s, 3H), 1.41 (s, 6H), 1.26 (d, J=6.1 Hz, 6H), 1.09 (d, J=6.7 Hz, 6H).

1-(8-Chloro-7-isopropoxy-4-isopropyl-2,2-dimethyl-2H-chromene-6-yl]propan-1-one (Compound 143)

Following General Procedure M, 1-(8-chloro-7-isopropoxy-4-isopropyl-2,2-dimethyl-2H-chromene-6-yl)-propan-1-ol (Compound 139, 1.05 g, 2.96 mmol) and 4-methylmorpholine N-oxide (520 mg, 4.44 mmol) were reacted to give the title compound as a yellow oil.

$^1$H NMR (300 MHz, CDCl$_3$): δ 7.31 (s, 1H), 5.39 (s, 1H), 4.36 (sept, J=6.2 Hz, 1H), 2.97 (q, J=7.2 Hz, 2H), 2.81 (sept, J=6.7 Hz, 1H), 1.41 (s, 6H), 1.24 (d, J=6.2 Hz, 6H), 1.11 (t, J=7.2 Hz, 3H), 1.09 (d, J=6.7 Hz, 6H).

1-(8-Chloro-4-isopropyl-7-methoxy-2,2-dimethyl-2H-chromen-6-yl)-ethanone (Compound 144)

Following General Procedure H, 6-bromo-8-chloro-4-isopropyl-7-methoxy-2,2-dimethyl-2H-chromene (Compound 19, 410 mg, 1.19 mmol) afforded the title compound as a light yellow oil.

$^1$H NMR (300 MHz, CDCl$_3$): δ 7.60 (s, 1H, 5.42 (s, 1H), 3.90 (s, 3H), 2.81–2.84 (m, 1H), 2.60 (s, 3H), 1.43 (s, 6H), 1.14 (d, J=6.8 Hz, 6H).

1-(8-Chloro-4-isopropyl-7-ethoxy-2,2-dimethyl-2H-chromen-6-yl)-ethanone (Compound 145)

Following General Procedure H, 6-bromo-8-chloro-4-isopropyl-7-ethoxy-2,2-dimethyl-2H-chromene (Compound 20, 1.70 g, 4.73 mmol) afforded the title compound as a colorless oil.

$^1$H NMR (300 MHz, CDCl$_3$): δ 7.60 (s, 1H), 5.42 (s, 1H), 4.06 (q, J=7.0 Hz, 2H), 2.83–2.87 (m, 1H), 2.60 (s, 3H), 1.43–1.45 (m, 9H), 1.14 (d, J=6.8 Hz, 6H).

Ethyl (2E)-3-(8-chloro-4-isopropyl-7-methoxy-2,2-dimethyl-2H-chromen-6-yl)-2-fluoro-but-2-enoate (Compound 146)

Following General Procedure K, triethyl-2-fluoro-2-phosphonoacetate (0.2 mL, 1.07 mmol) and 1-(8-chloro-4-isopropyl-7-methoxy-2,2-dimethyl-2H-chromen-6-yl)-ethanone (Compound 144, 930 mg, 2.88 mmol) were reacted to give the title compound as a light yellow oil after purification by flash chromatography (silica gel, 1:9 ethyl acetate/hexane).

$^1$H NMR (300 MHz, CDCl$_3$): δ 6.80 (s, 1H), 5.40 (s, 1H), 4.07 (q, J=7.3 Hz, 2H), 3.80 (s, 3H), 2.78–2.82 (m, 1H), 2.13 (d, J=4.4 Hz, 3H), 1.44 (s, 6H), 1.10–1.18 (m, 9H).

Ethyl (2E)-3-(8-chloro-4-isopropyl-7-methoxy-2,2-dimethyl-2H-chromen-6-yl)-2-fluoro-pent-2-enoate (Compound 147)

Following General Procedure K, triethyl-2-fluoro-2-phosphonoacetate (0.4 mL, 2.14 mmol) and 1-(8-chloro-4-isopropyl-7-methoxy-2,2-dimethyl-2H-chromen-6-yl)-propan-1-one (Compound 140, 229 mg, 0.71 mmol) were reacted to give the title compound as a yellow oil after purification by flash chromatography (silica gel, 1:9 ethyl acetate/hexane).

$^1$H NMR (300 MHz, CDCl$_3$): δ 6.76 (s, 1H), 5.40 (s, 1H), 4.04 (q, J=7.0 Hz, 2H), 3.77 (s, 3H), 2.76–2.80 (m, 3H), 1.45 (s, 6H), 1.14 (d, J=6.8 Hz, 6H), 0.97–1.02 (m, 6H).

Ethyl (2E)-3-(8-chloro-4-isopropyl-7-ethoxy-2,2-dimethyl-2H-chromen-6-yl)-2-fluoro-but-2-enoate (Compound 148)

Following General Procedure K, triethyl-2-fluoro-2-phosphonoacetate (1.8 mL, 8.64 nmol) and 1-(8-chloro-4-isopropyl-7-ethoxy-2,2-dimethyl-2H-chromen-6-yl)-ethanone (Compound 145, 930 mg, 2.88 mmol) were reacted to give the title compound as a colorless oil after purification by flash chromatography (silica gel, 1:9 ethyl acetate/hexane).

$^1$H NMR (300 MHz, CDCl$_3$): δ 6.80 (s, 1H), 5.40 (s, 1H), 4.06 (q, J=7.0 Hz, 2H), 3.92 (q, J=7.0 Hz, 2H), 2.78–2.82 (m, 1H), 2.18 (d, J=4.4 Hz, 3H), 1.42–1.47 (m, 9H), 1.12–1.16 (m, 6H).

Ethyl(2E)-3-(8-chloro-4-isopropyl-7-ethoxy-2,2-dimethyl-2H-chromen-6-yl)-2-fluoro-pent-2-enoate (Compound 149)

Following General Procedure K, triethyl-2-fluoro-2-phosphonoacetate (0.14 mL, 0.67 mmol) and 1-(8-chloro-4-isopropyl-7-ethoxy-2,2-dimethyl-2H-chromen-6-yl)-propan-1-one (Compound 141, 75 mg, 0.23 mmol) were reacted to give the title compound as a yellow oil after purification by flash chromatography (silica gel, 1:9 ethyl acetate/hexane).

$^1$H NMR (300 MHz, CDCl$_3$): δ 6.76 (s, 1H), 5.39 (s, 1H), 3.98–4.02 (m, 4H), 2.74–2.76 (m, 3H), 1.45 (s, 6H), 1.36 (t, J=7.1 Hz, 3H), 1.14 (d, J=6.8 Hz, 6H), 0.99–1.02 (m, 6H).

(2E)-3-(8-Chloro-4-isopropyl-7-methoxy-2,2-dimethyl-2H-chromen-6-yl)-2-fluoro-but-2-en-1-ol (Compound 152)

Following General Procedure L, ethyl 3-(8-chloro-4-isopropyl-7-methoxy-2,2-dimethyl-2H-chromen-6-yl)-2-fluoro-but-2-enoate (Compound 146, 110 mg, 0.28 mmol) and diisobutylaluminum hydride (1 M in hexanes, 1.1 mL, 1.1 mmol) were reacted to give the title compound as a colorless oil after purification by flash chromatography (silica gel, 1:9 to 1:4 ethyl acetate/hexane).

$^1$H NMR (300 MHz, CDCl$_3$): δ 6.90 (s, 1H), 5.41 (s, 1H), 3.98–4.03 (m, 2H), 3.76 (s, 3H), 2.78–2.82 (m, 1H), 2.35 (t, J=6.4 Hz, 1H), 2.02 (d, J=4.0 Hz, 3H), 1.45 (s, 6H), 1.14 (d, J=6.8 Hz, 6H).

(2E)-3-(8-Chloro-4-isopropyl-7-methoxy-2,2-dimethyl-2H-chromen-6-yl)-2-fluoro-pent-2-en-1-ol (Compound 153)

Following General Procedure L, ethyl 3-(8-chloro-4-isopropyl-7-methoxy-2,2-dimethyl-4-chromen-6-yl)-2-fluoro-pent-2-enoate (Compound 147, 242 mg, 0.59 mmol 1) and diisobutylaluminum hydride (1M in hexanes, 2.4 mL, 2.4 mmol) were reacted to give the title compound as a colorless oil after purification by flash chromatography (silica gel, 1:9 to 1:4 ethyl acetate/hexane).

$^1$H NMR (300 MHz, CDCl$_3$): δ 6.87 (s, 1H), 5.42 (s, 1H), 3.98–4.03 (m, 2H), 3.78 (s, 3H), 2.78–2.82 (m, 1H), 2.48 (s, 1H), 2:28 (t, J=6.6 Hz, 1H), 1.45 (s, 6H), 1.14 (d, J=6.8 Hz, 6H), 1.19 (t, J=6.8 Hz, 3H).

(2E)-3-(8-Chloro-4-isopropyl-7-ethoxy-2,2-dimethyl-2H-chromen-6-yl)-2-fluoro-but-2-en-1-ol (Compound 154)

Following General Procedure L, ethyl 3-(8-chloro-4-isopropyl-7-ethoxy-2,2-dimethyl-2H-chromen-6-yl)-2-fluoro-but-2-enoate (Compound 148, 2.04 g, 5.66 mmol) and diisobutylaluminum hydride (1M in hexanes, 11.7 mL, 11.7 mmol) were reacted to give the title compound as a colorless oil after purification by flash chromatography (silica gel, 1:9 to 1:4 ethyl acetate/hexane).

$^1$H NMR (300 MHz, CDCl$_3$): δ 6.90 (s, 1H), 5.42 (s; 1H), 3.97–4.05 (m, 4H), 2.78–2.82 (m, 1H), 2.55(t, J=6.3 Hz, 1H), 2.00 (d, J=4.0 Hz, 3H), 1.42 (s, 6H), 1.40 (t, J=7.3 Hz, 3H), 1.14 (d, J=6.8 Hz, 6H).

(2E)-3-(8-Chloro-4-isopropyl-7-ethoxy-2,2-dimethyl-2H-chromen-6-yl)-2-fluoro-pent-2-en-1-ol (Compound 155)

Following General Procedure L, ethyl 3-(8-chloro-4-isopropyl-7-ethoxy-2,2-dimethyl-2H-chromen-6-yl)-2-fluoro-pent-2-enoate (Compound 149, 79 mg, 0.19 mmol) and diisobutylaluminum hydride (1M in hexanes, 1.4 mL, 1.4 mmol) were reacted to give the title compound as a colorless oil after purification by flash chromatography (silica gel, 1:9 to 1:4 ethyl acetate/hexane).

$^1$H NMR (300 MHz, CDCl$_3$): δ 6.88 (s, 1H), 5.41 (s, 1H), 3.97–4.05 (m, 4H), 2.78–2.82 (m, 1H), 2.56–2.60 (m, 2H), 2.41 (t, I=6.5 Hz, 1H), 1.45(s, 6H), 1.39 (t, J=7.1 Hz, 3H), 1.14(d, J=6.8 Hz, 6H), 0.97 (t, J=7.6 Hz, 3H).

(2E)-3-(8-Chloro-7-isopropoxy-4-isopropyl-2,2-dimethyl-2H-chromen-6-yl)-2-fluoro-but-2-en-1-ol (Compound 156)

Following General Procedure K, triethyl-2-fluoro-2-phosphonoacetate (1.6 mL, 7.9 mmol) and 1-(8-chloro-7-isopropoxy-4-isopropyl-2,2-dimethyl-2H-chromene-6-yl)-ethanone (Compound 142, 885 mg, 2.63 mmol) were reacted to give the ester (Compound 150) as a yellow oil after purification by flash chromatography (silica gel, 5% ethyl acetate in hexanes). Following General Procedure L, the resulting ester (Compound 150) and diisobutylaluminum hydride (1M in hexanes, 8.1 mL-8.08 mmol) were reacted to give the title compound as a white solid after purification by flash chromatography (silica gel, 10% ethyl acetate in hexanes).

$^1$H NMR (300 MHz, CDCl$_3$): δ 1.12 (d, J=6.7 Hz, 6H) 1.25 (br s, 6H) 1.43 (s, 6H) 1.99 (d, J=3.5 Hz, 3H) 2.70–2.84 (m, 2H) 3.89–4.07 (m, 2H) 4.37 (sept, J=6.2 Hz, 1H) 5.40 (br s, 1H) 6.90 (s, 1H).

(2E)-3-(8-Chloro-7-isopropoxy-4-isopropyl-2,2-dimethyl-2H-chromen-6-yl)-2-fluoro-pent-2-n-1-ol (Compound 157)

Following General Procedure K, triethyl-2-fluoro-2-phosphonoacetate (1.6 mL, 7.9 mmol) and 1-(8-chloro-7-isopropoxy-4-isopropyl-2,2-dimethyl-2H-chromene-6-yl)-propan-1-one (Compound 143, 1.22 g, 3.48 Mmol) were reacted to give the ester (Compound 151) as a yellow oil after purification by flash chromatography (silica gel, 10% ethyl acetate in hexanes). Following General Procedure L, the ester (Compound 151) and diisobutylaluminum hydride (1M in hexanes, 9.4 mL, 9.4 mmol) were reacted to give the title compound as a white solid after purification by flash chromatography (silica gel, 10% ethyl acetate in hexanes).

$^1$H NM (300 MHz, CDCl$_3$): δ 0.97 (t, J=7.6 Hz, 3H), 1.11 (d, J=6.8 Hz, 6-H), 1.24 (d, J=6.0 Hz, 6H), 1.43 (s, 6H), 2.26–2.33 (m,1H), 2.58–2.66 (m, 1H), 2.77 (sept, J=6.8 Hz,1H), 3.91–4.11 (m, 2H), 4.42 (sept, J=6.0 Hz, 1. H), 5.38 (s,1H), 6.87 (s, 1H).

(2E)-3-(8-Chloro-7-isopropoxy-4-isopropyl-2,2-dimethyl-2H-chromen-6-yl)-2-fluoro-but-2-enal (Compound 162)

Following General Procedure M, 3-(8-chloro-7-isopropoxy-4-isopropyl-2,2-dimethyl-2H-chromen-6-yl)-2-fluoro-but-2-en-1-ol (Compound 156,0.74 g, 1.9 mmol), tetrapropylammonium perrunthenate (TPAP, 0.034 g, 0.101 mmol), and 4-methylmorpholine N-oxide (NMO, 0.34 g, 2.9 mmol) were reacted to give the title compound as a pale yellow solid after purification by flash chromatography (silica gel column, 20% ethyl acetate in hexanes).

$^1$H NMR (300 MHz, CDCl$_3$): 8 ppm 1.14 (d, J=6.5 Hz, 6H), 1.23 (br s, 6H), 1.47 (s, 6H), 2.25 (d, J=3.8 Hz, 3H), 2.76 (sept, J=6.5 Hz, 1H), 4.44-(sept, J=6.7 Hz,1H), 5.45 (s,1H), 6.92 (s, 1H), 9.31 (d, J=19.4 Hz, CHO).

(2E)-3-(8-Chloro-7-isopropoxy-4-isopropyl-2,2-dimethyl-2H-chromen-6-yl)-2-fluoro-pent-2-enal (Compound 163)

Following General Procedure M, 3-(8-chloro-7-isopropoxy-4-isopropyl-2,2-dimethyl-2H-chromen-6-yl)-2-fluoro-pent-2-en-1-ol (Compound 157, 0.90 g, 2.26 mmol), tetrapropylammonium perrunthenate (TPAP, 0.04 g, 0.11 mmol), and 4-methylmorpholine N-oxide (NMO, 0.40 g, 3.4 mmol) were reacted to give the title compound as a pale yellow solid after purification by flash chromatography (silica gel, 10% ethyl acetate in hexanes).

$^1$H NMR (300 MHz, CDCl$_3$): δ ppm 1.02 (t, J=7.6 Hz, 3H), 1.13 (d, J=6.6 Hz, 3H), 1.14 (d, J=6.6 Hz, 3H), 1.19 (d, J=6.2 Hz, 3H), 1.29 (d, J=6.2 Hz, 3H), 1.47 (s,3H), 1.48 (s, 3H), 2.91–2.57 (m, 3H), 4.51 (sept, J=6.0 Hz, 1H), 5.45 (s, 1H), 6.88 (s,1H), 9.33 (d, J=19.4 Hz, 1H).

Ethyl 7-(8-chloro-4-isopropyl-7-methoxy-2,2-dimethyl-2H-chromen-6-yl)-fluoro-3-methyl-octa-2E,4E,6E-trienoate (Compound 164)

Following General Procedure N, a solution of 3-(8-chloro-4-isopropyl-7-methoxy-2,2-dimethyl-2H-chromen-6-yl)-2-fluoro-but-2-en-1-ol (Compound 152, 50 mg, 0.14 mmol) in THF was treated with 4-methylmorpholine N-oxide (33 mg, 0.28 mmol) and tetrapropylammonium perruthenate (10 mg) to give the corresponding aldehyde, Compound 158. Treatment with the ylide ofethyl 4-(diethoxyphosphoryl)-3-methyl-but-2E-enoate (149 mg, 0.57 mmol) afforded the title compound as a light yellow solid after purification by flash chromatography (silica gel, 10% ethyl acetate in hexanes).

$^1$H NMR (300 MHz, CDCl$_3$): δ 6.85 (s, 1H), 6.56 (d, J=15.3 Hz, 1H), 6.24–6.38 (m, 1H), 5.85 (s, 1H), 5.42 (s, 1H), 4.17 (q, J=7.3 Hz, 2H), 3.70 (s, 3H), 2.70–2.78 (m, 1H), 2.1 (s, 6H), 1.54 (s, 6H), 1.28 (t, J=7.3 Hz, 3H), 1.14 (d, J=6.8 Hz, 6H).

Ethyl 7-(8-chloro-isopropyl-7-methoxy-2,2-dimethyl-2H-chromen-6-yl)-6-fluoro-3-methyl-nona-2E,4E,6E-trienoate (Compound 165)

Following General Procedure N, a solution of 3-(8-chloro-4 isopropyl-7-methoxy-2,2-dimethyl-2H-chromen-6-yl)-2-fluoro-pent-2-en-1-ol (Compound 153, 180 mg, 0.49 mmol) in THF was treated with 4-methylmorpholine N-oxide (114 mg, 0.97 mmol) and tetrapropylammonium perruthenate (20 mg) to give the corresponding aldehyde (Compound 159). Treatment with the ylide ofethyl 4-(diethoxyphosphoryl)-3-methyl-but-2E-enoate (517 mg, 7.96 mmol) afforded the title compound as a light yellow oil after purification by flash chromatography (silica gel, 10% ethyl acetate in hexanes).

$^1$H NMR (300 MHz, CDCl$_3$): δ 6.81 (s, 1H), 6.56 (d, J=15.8 Hz, 1H), 6.20–6.34 (m, 1H), 5.85 (s, 1H), 5.42 (s, 1H), 4.16 (q, J=7.3 Hz, 2H), 3.70 (s, 3H), 2.65–2.81 (m, 2H), 2.50 (s, 1H), 2.09 (s, 3H), 1.51 (s, 3H), 1.43 (s, 3H), 1.28 (t, J=7.3 Hz, 3H), 1.12 (s, 6H), 0.96 (d, J=7.3 Hz, 3H).

Ethyl 7-(8-chloro-4-isopropyl-7-ethoxy-2,2-dimethyl-2H-chromen-6-Yl)-6-fluoro-3-methyl-octa-2E,4E,6E-trienoate (Compound 166)

Following General Procedure N, a solution of 3-(8-chloro-4-isopropyl-7-ethoxy-2,2-dimethyl-2H-chromen-6-yl)-2-fluoro-but-2-en-1-ol (Compound 154, 867 mg, 2.34 mmol) in THF was treated with 4-methylmorpholine N-oxide (548 mg, 4.69 mmol) and tetrapropylammonium perruthenate (50 mg) to give the corresponding aldehyde (Compound 160). Treatment with the ylide ofethyl 4-(diethoxyphosphoryl)-3-methyl-but-2E-enoate (2.07 g, 7.86 mmol) afforded the title compound as a yellow solid after purification by flash chromatography (silica gel, 10% ethyl acetate in hexanes).

¹H NMR (300 MHz, CDCl₃): δ 6.85 (s, 1H), 6.56 (d, J=15.3 Hz, 1H), 6.25–6.40 (m, 1H), 5.85 (s,1H), 5.40 (s, 1H), 4.18 (q, I=7.3 Hz, 2H), 3.95 (s, 3H), 2.72–2.80 (m, 1H), 2.10 (s, 6H), 1.56 (s, 6H), 1.22–1.36 (m, 6H), 1.14 (d, J=6.8 Hz, 6H).

Ethyl 7-(8-chloro-4-isopropyl-7-ethoxy-2,2-dimethyl-2H-chromen-6-yl)6-fluoro-3-methyl-nona-2E,4E,6E-trienoate (Compound 167)

Following General Procedure N, a solution of 3-(8-chloro-4 isopropyl-7-ethoxy-2,2-dimethyl-2H-chromen-6-yl)-2-fluoro-pent-2-en-1-ol (Compound 155, 49 mg, 0.13 mmol) in THF was treated with 4 methylmorpholine N-oxide (30 mg, 0.26 mmol) and tetrapropylammonium perruthenate (15 mg) to give the corresponding aldehyde (Compound 161). Treatment with the ylide ofethyl 4-(diethoxyphosphoryl)-3-methyl-but-2E-enoate (122 mg, 0.46 mmol) afforded the title compound as a light yellow solid after purification by flash chromatography (silica gel, 10% ethyl acetate in hexanes).

¹H NMR (300 MHz, CDCl₃): δ 6.80 (s, 1H), 6.56 (d, J=15.5 Hz, 1H), 6.20–6.34 (m, 1H), 5.84 (s, 1H), 5.40 (s, 1H), 4.16(q, J=7.3 Hz, 2H), 3.82–4.00 (m,2H), 2.70–2.76 (m, 21H), 2.51 (s, 1H),2.09 (s, 3H), 1.50 (s, 3H), 1.42 (s, 3H), 1.25–1.35 (m, 6H), 1.10–1.15 (m,6H), 0.97 (d, J=7.4 Hz, 3H).

Ethyl 7-(8-chloro-7-isopropoxy-4-isopropyl-2,2-dimethyl-2H-chromen-6-yl)-2-fluoro-3-methyl-octa-2E,4E,6E-trienoate (Compound 168)

Following General Procedure O, a solution of (2E)-3-(8-chloro-7-isopropoxy-4-isopropyl-2,2-dimethyl-2H-chromen-6-yl)-2-fluoro-but-2-enal (Compound 162, 0.63 g, 1.7 mmol) in THF was added to the ylide of ethyl 4(diethyoxyphosphoryl)-3-methylbut-2E-enoate (1.1 g, 4.1 mmol) to give the title compound as a yellow oil after purification by flash chromatography (silica gel, 1% to 5% ethyl acetate in hexanes).

¹HNMR(300 MHz, CDCl₃): 66.83 (s, 1H)6.52 (d, J=16.0 Hz, 1H), 6.37 (dd, J=25.0, 16.0 Hz, 1H), 5.84 (s, 1H), 5.39 (s, 1H), 4.39 (sept, J=6.5 Hz, 1H), 4.14 (q, J=7.1 Hz, 2H), 2.74 (sept, J=6.6 Hz, 1H), 2.10 (s, 6H), 1.50 (s, 3H), 1.38 (s, 3H), 1.25 (t, J=7.1 Hz, 3H), 1.30–1.04 (m, 12H).

Ethyl 7-(8-chloro-7-isopropoxy-4-isopropyl-2,2-dimethyl-2H-chromen-6-yl)-2-fluoro-3-methyl-nona-2E,4E,6E-trienoate (Compound 169)

Following General Procedure O, a solution of (2E)-3-(8-chloro-7 isopropoxy-4-isopropyl-2,2-dimethyl-2H-chromen-6-yl)-2-fluoro-pent-2-enal (Compound 163, 0.86 g, 2.17 mmol) in THF was added to the ylide of ethyl 4-(diethyoxyphosphoryl)-3-methylbut-2E-enoate (143 g, 5.42 mmol) to give the title compound as a yellow foam after purification by flash chromatography (silica gel, 1% to 5% to 10% ethyl acetate in hexanes).

¹H NMR (300 MHz, CDCl₃): δ 6.81 (s, 1H), 6.56 (d, J=15.6 Hz,1H), 6.36 (dd, J=25.2, 16.0 Hz, 1H), 5.86 (s, 1H), 5.42 (s, 1H), 4.44 (sept, J=6.2 Hz, 0.1H), 4.16 (q, J=7.1 Hz, 2H), 2.84–2.71 (m, 1H), 2.77 (sept, J=6.7 Hz, 1H), 2.51–2.38 (m, 1H), 2.11 (s, 3H), 1.53 (s, 3H), 1.41 (s, 3H), 1.28 (t, J=7.3 Hz, 3H), 1.25 (d, J=6.2 Hz, 3H), 1.18(d, J=6.2 Hz,3H), 1.15(d, J=6.7 Hz,3H), 1.10 (d, J=6.7 Hz,3H),0.93(t, J=7.5 Hz,3H).

7-(8-Chloro-4-isopropyl-7-methoxy-2,2-dimethyl-2H-chromen-6-yl)-6-fluoro-3-methyl-octa-2E,4E, 6E-trienoic acid (Compound 170)

Following General Procedure G, a solution of ethyl 7-(8-chloro-4-isopropyl-7-methoxy-2,2-dimethyl-2H-chromen-6-yl)-6-fluoro-3-methyl-octa-2E,4E,6E-trienoate (Compound 164, 38 mg, 0.082 mmol) in ethanol and THF was hydrolyzed with 1M NaOH to give rise to the title compound as a white solid.

¹H NMR (300 MHz, CDCl₃): δ 11.35 (br s, 1H), 6.85 (s, 1H), 6.53 (d, J=15.2 Hz, 1H), 6.33–6.42 (in 1H), 5.88 (s, 1H), 5.42 (s, 1H), 3.75-(s, 3H), 2.75–2.80 (m, 1H), 2.11 (s, 6H), 1.14 (d, J=6.8 Hz, 6H), 1.45 (s, 6H).

7-(8-Chloro-4-isopropyl-7-methoxy-2,2-dimethyl-2H-chromen-6-yl)-6-fluoro-3-methyl-nona-2E,4E, 6E-trienoic acid (Compound 171)

Following General Procedure G, a solution of ethyl 7-(8-chloro-4-isopropyl-7-methoxy-2,2-dimethyl-2H-chromen-6-yl)-6-fluoro-3-methyl-nona-2E,4E,6E-trienoate (Compound 165, 179 mg, 0.38 mmol) in ethanol and THF was hydrolyzed with 1M NaOH to give rise to the title compound as a white solid.

¹H NMR (300 MHz, CDCl₃): δ 11.28 (br s, 1H), 6.81 (s, 1H), 6.54 (d, J=15.5 Hz, 1H), 6.20–6.37 (m,1H), 5.87 (s, 1H), 5.42 (s, 1H),3.74 (s, 3H), 2.70–2.79 (m, 2H), 2.50 (s, 1H), 2.10 (s, 3H), 1.51 (s, 3H), 1.43 (s, 3H), 1.14 (s,6H), 0.96(t, J=7.6 Hz, 3H).

7-(8-Chloro-4-isopropyl-7-ethoxy-2,2-dimethyl-2H-chromen-6-yl)-6-fluoro-3-methyl-octa-2E,4E,6E-trienoic acid (Compound 172)

Following General Procedure G, a solution of ethyl 7L(8-chloro-4-isopropyl-7-ethoxy-2,2-dimethyl-2H-chromen-6-yl)-6-fluoro-3-methyl-octa-2E,4E,6E-trienoate (Compound 166, 874 mg, 1.95 mmol) in ethanol and THF was hydrolyzed with 1M NaOH to give rise to the title compound as a light yellow solid.

¹H NMR (300 MHz, CDCl₃): δ 11.21(br s, 1H), 6.85-(s, 1H), 6.53 (d, J=15.1 Hz, 1H), 6.24–6.41 (m, 1H), 5.88 (s, 1H), 5.42 (s, 1H), 3.90 (q,J=7.1 Hz, 2H),2.71–2.80 (m, 1H), 2.18 (s, 3H), 2.11 (s, 1H), 1.46 (s, 6H), 1.32 (t, J=7.1 Hz, 3H), 1.13 (d, J=6.8 Hz, 6H).

7-(8-Chloro-4-isopropyl)-7-ethoxy-2,2-dimethyl-2H-chromen-6-yl)-6-fluoro-3-methyl-nona-2E,4E,6E-trienoic acid (Compound 173)

Following General Procedure G, a solution of ethyl 7-(8-chloro-4-isopropyl-7-ethoxy-2,2-dimethyl-2H-chromen-6-yl)-6-fluoro-3-methyl-nona-2E,4E,6E-trienoate (Compound 167, 50 mg, 0.106 mmol) in ethanol and THF was hydrolyzed with 1M NaOH to give rise to the title compound as a white solid.

¹H NMR (300 MHz, CDCl₃): δ 11.27 (br s, 1H), 6.80 (s, 1H), 6.54 (d, J=15.5 Hz, 1H), 6.25–6.39 (m, 1H), 5.87 (s, 1H), 5.42 (s, 1H), 3.84–4.01 (m, 4H), 2.70–2.79 (m, 2H), 2.46 (s, 1H), 2.10 (s, 3H), 1.51 (s, 3H), 1.42 (s, 3H), 1.33 (t, J=7.0 Hz, 3H), 1.12–1.18 (m, 6H), 0.97 (t, J=7.6 Hz, 3H).

7-(8-Chloro-7-isopropoxy-7-isopropoxy-2,2-methyl-2H-chromen-6-yl)-2-fluoro-3-methyl-octa-2E,4E, 6E-trienoic acid (Compound 174)

Following General Procedure G, a solution of ethyl 7-(8-chloro-7-isopropoxy-4-isopropyl-2,2-dimethyl-2H-chromen-6-yl)-2-fluoro-3-methyl-octa-2,4,6-trienoate (Compound 168, 0.81 g, 1.6 mmol) in ethanol and THF was hydrolyzed with 1M NaOH. Purification by flash chromatography (silica gel, 30% ethyl acetate in hexanes) and recrystallization from acetonitrile gave rise to the title compound as short yellow needles.

¹H NMR (300 MHz, CDCl₃): δ 6.84 (s, 1H), 6.57 (d, J=15.4 Hz, 1H), 6.43 (dd, J=25.1, 15.8 Hz, 1H), 5.88 (s, 1H), 5.41 (s, 1H), 4.39 (sept, J=6.5 Hz, 1H), 2.76 (sept, J=6.5 Hz, 1H), 2.12 (s, 6H), 1.52 (s, 3H), 1.40 (s, 3H), 1.25 (d, J=5.6 Hz, 3H), 1.19 (d, J=5.6 Hz, 3H), 1.15 (d, J=6.6 Hz, 3H), 1.10 (d, J=6.6 Hz, 3H).

7-(8-Chloro-7-isopropoxy-4-isopropyl-2,2-dimethyl-2H-chromen-6-yl)-2-fluoro-3-methyl-nona-2,4,6-trienoic acid (Compound 175)

Following General Procedure G, a solution of ethyl 7-(8-chloro-7-isopropoxy-4-isopropyl-2,2-dimethyl-2H-chromen-6-yl)-2-fluoro-3-methyl-nona-2E,4E,6E-trienoate (Compound 169, 1.02 g, 2.01 mmol) in ethanol and THF was hydrolyzed with 1M NaOH. Purification by flash chromatography (silica gel, 30% to 50% ethyl acetate in hexanes) and recrystallization from acetonitrile gave rise to the title compound as a pale yellow solid.

¹H NMR (300 MHz, CDCl₃): δ 6.79 (s, 1H), 6.57 (d, J=15.3 Hz, 1H), 6.40 (dd, J=25.0, 15.7 Hz, 1H), 5.87 (s, 1H), 5.41 (s, 1H), 4.43 (sept, J=6.2 Hz, 1H), 2.85–2.69 (m, 2H), 2.52–2.37 (m, 1H), 2.11 (s, 3H), 1.52 (s, 3H), 1.40 (s,3H), 1.26(d,J=6.2 Hz,3H), 1.18(d,J=6.2 Hz,3H), 1.15(d,J=6.7 Hz, 3H), 1.09 (d, J=6.7 Hz, 3H), 0.93 (t, J=7.5 Hz, 3H).

TABLE 4

Receptor Transactivation, Efficacy and Binding Data for Exemplary Compounds of Formula C

| Compound number | Structure | RAR Trans. EC₅₀ nM RAR Bind. K$_i$ nM | | | RXR Trans. EC₅₀ nM RXR Bind K$_i$ nM | | |
|---|---|---|---|---|---|---|---|
| | | α | β | γ | α | β | γ |
| 170 | 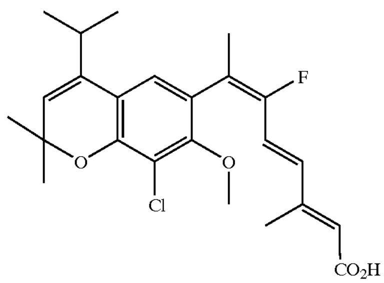 | NA | NA | NA | 0.8 (86) | 0.8 (88) | 0.2 (109) |
| | | 3.4k | 2.3k | 5.3k | 2 | 7 | ND |
| 171 | 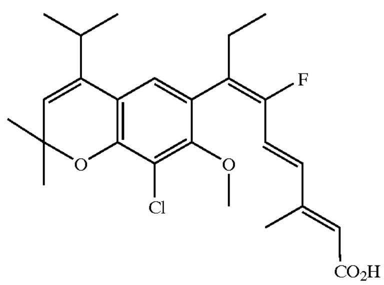 | >1k | 49 (13) | NA | 0.02 (87) | 0.2 (85) | 0.04 (95) |
| | | 47 | 381 | 4.9k | 1.3 | 12 | ND |
| 172 | 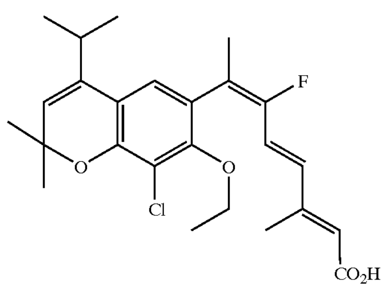 | NA | NA | NA | 5.4 (52) | 52 (45) | 10 (46) |
| | | 404 | 442 | 1.4k | 10 | 85 | ND |
| 173 | 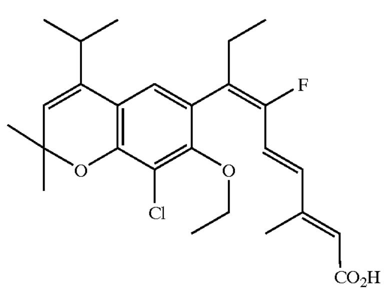 | NA | NA | NA | 4.8 (18) | 18 (21) | 6 (10) |
| | | 102 | 431 | 2.4k | 2 | 36 | ND |

TABLE 4-continued

Receptor Transactivation, Efficacy and Binding Data for Exemplary Compounds of Formula C

| Compound number | Structure | RAR Trans. $EC_{50}$ nM RAR Bind. $K_i$ nM | | | RXR Trans. $EC_{50}$ nM RXR Bind $K_i$ nM | | |
|---|---|---|---|---|---|---|---|
| | | α | β | γ | α | β | γ |
| 174 | 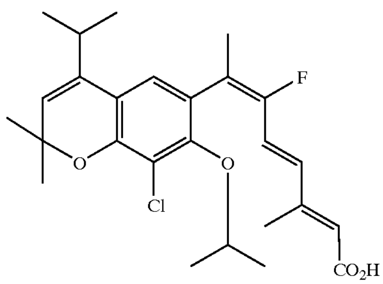 | NA 532 | NA 1.3k | NA 3.4k | 59 (8) 29 | 527 (12) 319 | 114 (6) ND |
| 175 | 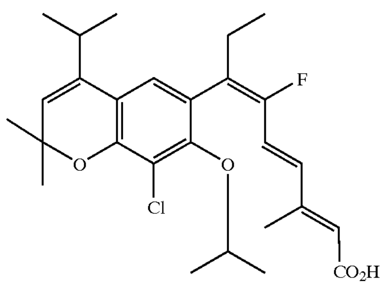 | NA 86 | NA 425 | NA 1.3k | NA 53 | NA 520 | NA ND |

In vivo Data (in ob/ob mice) for Examplary Compounds of Formula C

TABLE 5

| Treat-ment (dose) | Glucose (mg/dl) | | | Triglycerides (mg/dl) | | T4 (µg/dL) |
|---|---|---|---|---|---|---|
| | Day 0 | Day 3, 3 h | Day 6, 3 h | Day 0 | Day 3, 3 h | Day 7 |
| Vehicle (Control Diet) | 296 ± 123 | 279 ± 97 | 367 ± 116 | 90 ± 42 | 98 ± 17 | 3.8 ± 0.3 |
| Standard compound (2.5 mg/kg) | 246 ± 49 | 107 ± 27 | 136 ± 28 | 92 ± 41 | 55 ± 23 | 0.8 ± 0.2 |
| compound 172 (30 mg/kg) | 292 ± 134 | 193 ± 72 | 206 ± 40 | 107 ± 44 | 68 ± 22 | 4.5 ± 0.4 |

In this in vivo assay, the drug was mixed in a control diet and fed to the animals over 7 days. The dose indicates the average amount of drug consumed by each animal per day.

The transient hypertriglyceridemia caused by full RXR agonists is not observed when animals are dosed by this method. Hypothyroidism is the only observed toxicity of RXR full agonists in this assay.

Section D of Specific Embodiments

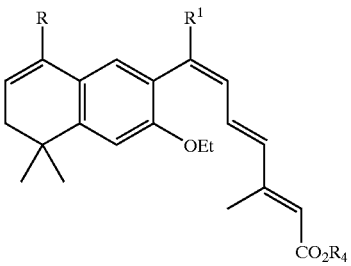

Formula D

Formula D discloses a specific class of preferred and exemplary compounds of the invention. In Formula D:

R represents alkyl of 1 to 8 carbons, more preferably alkyl of 1 to 4 carbons, and most preferably alkyl of 1 to 2 carbons;

$R^1$ represents alkyl of 1 to 8 carbons, more preferably alkyl of 1 to 4 carbons, and $R_4$ represents H, alkyl of 1 to 6 carbons, $CH_2OR_5$ or $CH_2OCOR_5$ where $R_5$ is alkyl of 1 to 3 carbons, or a pharmaceutically acceptable salt of said compound.

The synthetic schemes and the experimental procedures for obtaining compounds within the scope of Formula D are provided below.

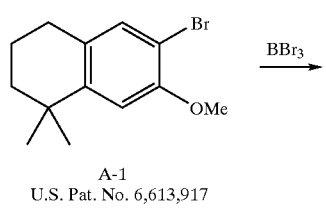
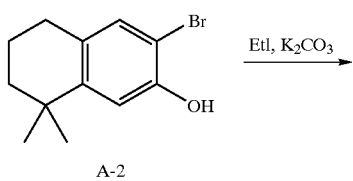
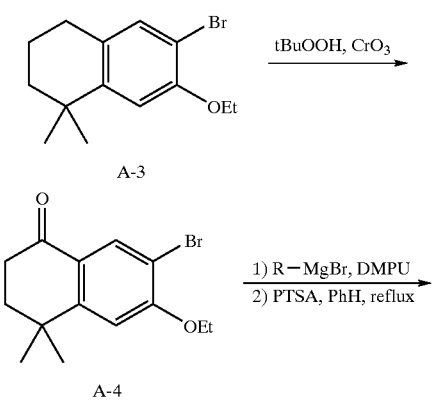
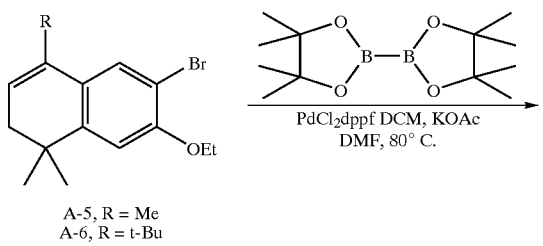
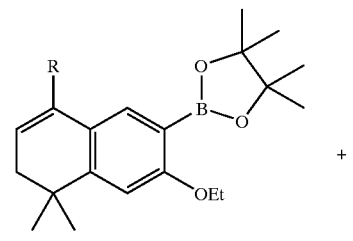
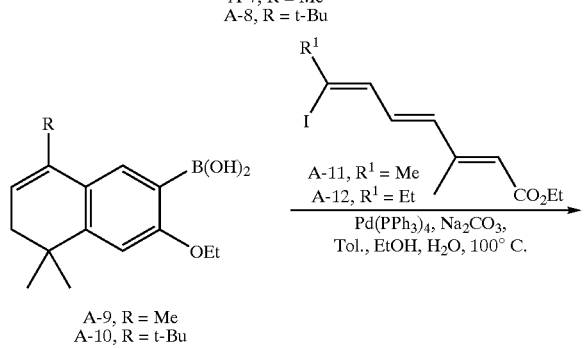
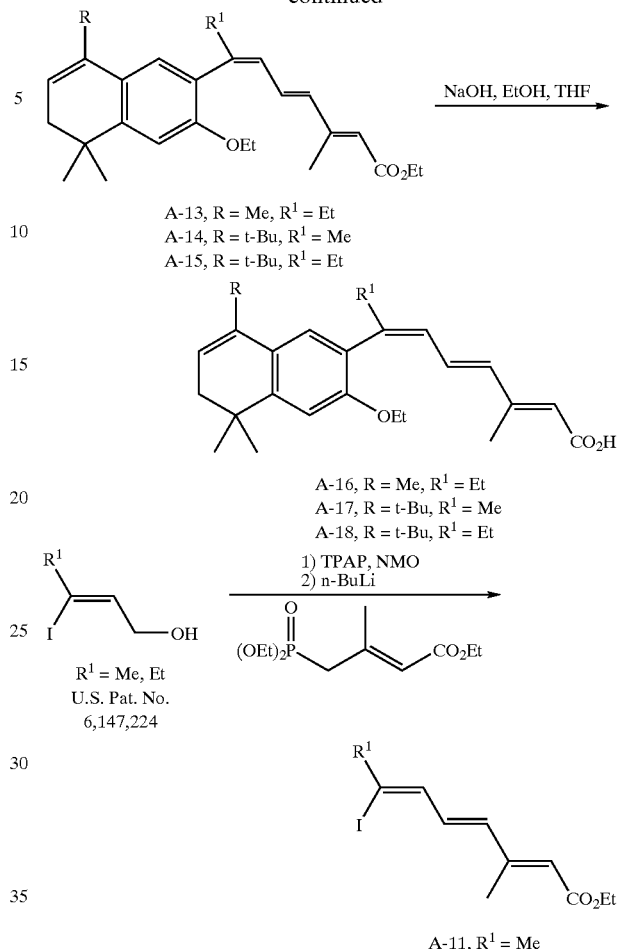

3-Bromo-8,8-dimethyl-5,6,7,8-tetrahydronaphthalen-2-ol (Compound A-2)

To 6-bromo-7-methoxy-1,2-dimethyl-1,2,3,4-tetrahydronaphthalene (Compound A-1 ([U.S. Pat. No. 6,613,917, incorporated herein by reference), 6.34 g, 23.56 mmol) in dichloromethane (10 mL) at −30° C. was added a solution of boron tribromide (1.0 M in dichloromethane, 47 mL, 47 mmol). After warming to 0° C. over 1 h, the reaction mixture was quenched carefully with ice water and extracted with ether. The organic layer was washed successively with water, brine, dried over $Na_2SO_4$, and concentrated in vacuo. Purification by flash column chromatography (silica gel, 5% ethyl acetate/hexane) yielded the title compound as a white solid.

$^1$H NMR (300 MHz, $CDCl_3$): δ 1.25 (s, 6H), 1.60–1.65 (m, 2H), 1.72–1.79 (m, 2H), 2.67 (t, J=6.2 Hz, 2H), 5.24 (s, 1H), 6.98 (s, 1H), 7.13 (s, 1H).

6-Bromo-7-ethoxy-1,1-dimethyl-1,2,3,4-tetrahydronaphthalene (Compound A-3)

A mixture of 3-bromo-8,8-dimethyl-5,6,7,8-tetrahydronaphthalen-2-ol (Compound A-2, 5.77 g, 22.62 mmol); iodoethane (7.2 mL, 90.5 mmol), and potassium carbonate (4.68 g, 34 mmol) in acetone (50 mL) was stirred at 70° C. overnight. The solvent was removed in vacuo. The residue was purified by column chromatography (silica gel, 2.5% ethyl acetate in hexane) to afford the title compound as a pale yellow oil.

$^1$H NMR (300 MHz, CDCl$_3$): δ 1.27 (s, 6H), 1.45 (t, J=7.0 Hz, 3H), 1.62–1.65 (m, 2H), 1.75–1.79 (m, 2H), 2.67 (t, J=6.1 Hz, 2H), 4.09 (q, J=7.0 Hz, 2H), 6.84 (s, 1H), 7.27 (s, 1H).

7-Bromo-6-ethoxy-4,4-dimethyl-3,4-dihydro-2H-naphthalen-1-one (Compound A-4)

To 6-bromo-7-ethoxy-1,1-dimethyl-1,2,3,4-tetrahydronaphthalene (Compound A-3, 5.83 g, 20.6 mmol) in dichloromethane (25 mL) and tert-butyl hydroperoxide (25 mL) at room temperature was added a catalytic amount of chromium (VI) oxide. The reaction was stirred overnight. Quenched the reaction with water and followed by extraction with diethylether. The organic layers were washed with water, brine, dried over Na$_2$SO$_4$ and concentrated in vacuo. Purification by flash column chromatography (silica gel, 2% ethyl acetate/hexane) yielded the title compound as a white solid.

$^1$H NMR (300 MHz, CDCl$_3$): δ 1.38 (s, 6H), 1.52 (t, J=7.0 Hz, 3H), 2.00 (t, J=6.8 Hz, 2H), 2.68 (t, J=6.8 Hz, 2H), 4.18 (q, J=7.0 Hz, 2H), 6.82 (s, 1H), 8.22 (s, 1H).

6-Bromo-7-ethoxy-1,1,4-trimethyl-1,2-dihydronaphthalene (Compound A-5)

To 7-bromo-6-ethoxy-4,4-dimethyl-3,4-dihydro-2H-naphthalen-1-one (Compound A-4, 1.05 g, 3.53 mmol) in THF (12 mL) and 1,3-dimethyl-3,4,5,6-tetrahydro-2(1])-pyrimidinone (2 mL) at 0° C. was added a solution of methylmagnesium bromide (3M in diethylether (3.53 mL, 10.59 mmol). The reaction was allowed to warm up to room temperature and was stirred at 50° C. overnight. The reaction was quenched with ice water and extracted with diethylether. The organic layer was washed successively with water, brine, dried over Na$_2$SO$_4$, and concentrated in vacuo. The crude material was then dissolved in benzene (20 mL). After catalytic amount of p-toluenesulfonic acid was added, the reaction was stirred at reflux for 2 h. The solvent was removed in vacuo. The residue was purified by column chromatography (silica gel, 1% ethyl acetate in hexane) to afford the title compound as a pale yellow oil.

$^1$H NMR (300 MHz, CDCl$_3$): δ 1.22 (s, 6H), 1.47 (t, J=7.0 Hz, 3H), 2.00–2.02 (m, 3H), 2.15–2.17 (m, 2H), 4.13 (q, J=7.0 Hz, 2H), 5.66 (m, 1H), 6.86 (s, 1H), 7.38 (s, 1H).

6-Bromo-4-tert-butyl-7-ethoxy-1,1-dimethyl-1,2-dihydronaphthalene (Compound A-6)

To 7-bromo-6-ethoxy-4,4-dimethyl-3,4-dihydro-2H-naphthalen-1-one (Compound A-4, 2.0 g, 6.73 mmol) in THF (20 mL), ether (20 mL) and 1,3-dimethyl-3,4,5,6-tetrahydro-2(1])-pyrimidinone (8 mL) at −30° C. was added a solution of tert-butylmagnesium bromide (2M in ether, 13.5 mL, 27 mmol). The reaction was allowed to warm to room temperature over 5 h. The reaction was quenched with ice water and extracted with ether. The organic layer was washed successively with water, brine, dried over Na$_2$SO$_4$, and concentrated in vacuo. The crude material was then dissolved in methanol (20 mL). After catalytic amount of p-toluenesulfonic acid was added, the reaction was stirred at 50° C. for 2 h. The solvent was removed in vacuo. The residue was purified by column chromatography (silica gel, 1% ethyl acetate in hexane) to afford the title compound as a pale yellow oil $^1$H NMR (300 MHz, CDCl$_3$): δ 1.19 (s, 6H), 1.32 (s, 9H), 1.46 (t, J=7.0 Hz, 3H), 2.11 (d, J=5.0 Hz, 2H), 4.12 (q, J=7.0 Hz, 2H), 5.85 (t, J=5 Hz, 1H), 6.86 (s, 1H), 7.80 (s, 1H).

Ethyl 7-iodo-3-methyl-nona-2E,4E,6Z-trienoate (Compound A-12)

General Procedure A-1

To a solution of 3-iodo-pent-2-en-1-ol (available as described in U.S. Pat. No. 6,147,224, 3.2 g, 15 mmol) and 4-methylmorpholine N-oxide (3.51 g, 30 mmol) in dichloromethane (20 mL) at 0° C. was added catalytic amount of tetrapropylammonium perruthenate. The reaction was stirred at room temperature for 1.5 h, and then the mixture was loaded directly onto a short pad of silica gel. Elution with 10% ethyl acetate in hexane yielded the corresponding aldehyde as brown oil.

To a solution of ethyl 4(diethoxyphosphoryl)-3-methylbut-2E-enoate (7.92 g, 30 mmol) in 1,3-dimethyl-3,4,5,6-tetrahydro-2(1H-pyrimidinone (12 mL) and THF (40 mL) at −78° C. was added n-butyllithium dropwise (1.6 M in hexane, 19 mL, 30 mmol). After 10 min, the above aldehyde (2.09 g, 9.9 mmol) in THF (5 mL) was added slowly to the reaction mixture. The mixture was stirred at −78° C. for 2 h, quenched with saturated NH$_4$Cl, and extracted with ethyl acetate. The organic layer was washed successively with water, brine, dried over Na$_2$SO$_4$, and concentrated in vacuo. The residue was purified by flash column chromatography (silica gel, 2.5% ethyl acetate in hexane) to yield the title compound as a yellow oil.

$^1$H NMR (300 MHz, CDCl$_3$): δ 1.13 (t, J=7.2 Hz, 3H), 1.19 (t, J=7.0,Hz, 3H), 2.35 (s, 3H), 2.64 (q, J=7.4 Hz, 2H), 4.18 (q, J=7.0 Hz, 2H), 5.81 (s, 1H), 6.24 (d, J=9.8 Hz, 1H), 6.40 (d, J=15.2 Hz, 1H), 6.69 (dd, J=15.1, 9.8 Hz, 1H).

Ethyl 7-iodo-3-methyl-octa-2E,4E,6Z-trienoate (Compound A-11)

Following General Procedure A-1, 3-iodo-but-2-en-1-ol (3.2 g, 15 mmol) and 4-methylmorpholine N-oxide (3.51 g, 30 mmol) in dichloromethane afforded the corresponding aldehyde. Further treatment with a solution of ethyl 4-(diethoxyphosphoryl)-3-methylbut-2E-enoate (7.92 g, 30 mmol) and n-butyl lithium (1.6 M in hexane, 19 mL, 30 mmol) gave rise to the title compound.

$^1$H NMR (300 MHz, CDCl$_3$): δ 1.29 (t, J=7.2 Hz, 3H), 2.35 (s, 3H), 2.64 (s, 3H), 4.18 (q, J=7.2 Hz, 2H), 5.81 (s, 1H), 6.18 (d, J=0 Hz, 1H), 6.38 (d, J=15.2 Hz, 1H), 6.62 (dd, J=15.1, 10 Hz, 1H).

Ethyl 7-(3-ethoxy-5,5,8-trimethyl-5,6-dihydronaphthalen-2-yl)-3-methyl-nona-2E,4E,6Z-trienoate (Compound A-13)

A solution of 6-bromo-7-ethoxy-1,1,4-trimethyl-1,2-dihydronaphthalene (Compound A-5, 980 mg, 3.32 mmol), bis(pinacolato)diboron (1.18 g, 4.65 mmol), and potassium acetate (976 mg, 9.96 mmol) in N,N-dimethylformamide (20 mL) was purged with argon for 15 min. [1,1-bis (disphenylphosphino)-ferrocene]dichloropalladium(II) (1:1 complex with dichloromethane, 270 mg, 0.33 mmol) was added and purged with argon for another 5 min. The reaction was continuously stirred at 80° C. for 4 days under argon. Thereafter the reaction was cooled to room temperature and was quenched with water. The reaction mixture was extracted with ethyl acetate. The organic layer was washed successively with water, brine, dried over Na$_2$SO$_4$, and concentrated in vacuo. Purification by column chromatography (silica gel, 10 to 20% ethyl acetate in hexane) yielded the mixtures (700 mg) of 2-(3-ethoxy-5,5,8-trimethyl-5,6-dihydronaphthalen-2-yl)-4,4,5,5-tetramethyl [1,3,2] dioxaborolane (Compound A-7) and 2-(3-ethoxy-5,5,8-trimethyl-5,6-dihydro-naphthalen-2-yl)boronic acid (Compound A-9). The above mixture of Compounds A-7 and A-9, ethyl 7-iodo-3-methyl-nona-2E,4E,6Z-trienoate (Compound A-12, 0.7 g, 2.14 mmol), tetrakis(triphenylphosphine)palladium(0) (200 mg, 0.17 mmol), and 2 M sodium carbonate (6 mL, 12 mmol) in toluene (18 in L) and ethanol (9 mL) was heated to 100° C. for 36 h. The reaction was cooled to room temperature and extracted with ethyl acetate. The organic layer was washed with brine, dried over $Na_2SO_4$, and concentrated in vacuo. Purification by column chromatography (silica gel, 1% to 2% ethyl acetate in hexane) yielded the title compound as an oil.

$^1$H NMR (300 MHz, $CDCl_3$): δ 1.02 (t, J=7.6 Hz, 3H), 1.24–1.29 (m, 9H), 1.34 (t, J=7.0 Hz, 3H), 1.98–1.99 (m, 3H), 2.14 (s, 3H), 2.18–2.20 (m, 2H), 2.50 (q, J=7.6 Hz, 2H), 4.04 (q, J=7.0 Hz, 2H), 4.16 (q, J=7.3 Hz, 2H), 5.65 (m, 1H), 5.72 (s, 1H), 6.23 (d, J=15.2 Hz, 1H), 6.24 (d, J=10.8 Hz, 1H), 6.56 (dd, J=10.8, 15.2 Hz, 1H), 6.87 (s, 1H), 6.91 (s, 1H).

Ethyl 7-(8-tert-butyl-3-ethoxy-5,5-dimethyl-5,6-dihydronaphthalen-2-yl)-3-methyl-octa-2E,4E,6Z-trienoate (Compound A-14)

General Procedure B

A solution of 6-bromo-4-tert-butyl-7-ethoxy-1,1-dimethyl-1,2-dihydronaphthalene (Compound A-6, 350 mg, 1.04 mmol), bis(pinacolato)diboron (370 mg, 1.46 mmol), and potassium acetate (305 mg, 3.12 mmol) in dimethylformamide (8 mL) was purged with argon for 15 minutes. [1,1-bis(disphenylphosphino)ferrocene]dichloropalladium(II) (1:1 complex with dichloromethane, 82 mg, 0.1 mmol) was added and purged with argon for another 5 min. The reaction was continuously stirred at 80° C. for 4 days under argon. Thereafter the reaction was cooled to room temperature and quenched with water. The reaction mixture was extracted with ethyl acetate. The organic layer was washed successively with water, brine, dried over $Na_2SO_4$, and concentrated in vacuo. Purification by column chromatography (silica gel, 10 to 20% ethyl acetate in hexane) yielded a mixture of 2-(8-tert-butyl-3-ethoxy-5,5-dimethyl-5,6-dihydronaphthalen-2-yl)-4,4,5,5-tetramethyl [1,3,2] dioxaborolane (Compound A-8) and 2-(8-tert-butyl-1-(3-ethoxy-5,5-dimethyl-5,6-dihydro-naphthalen-2-yl)boronic acid (Compound A-10). The above mixture of Compounds A-8 and A-10, ethyl 7-iodo-3-methyl-octa-2E,4E,6Z-trienoate (Compound A-11, 130 mg, 0.43 mmol), tetrakis(triphenylphosphine)palladium(0) (40 mg, 0.03 mmol), and 2M sodium carbonate (1 mL, 2 mmol) in toluene (4 mL) and ethanol (2 mL) was heated to 100° C. for 40 h. The reaction was cooled to room temperature and extracted with ethyl acetate. The organic layer was washed with brine, dried over $Na_2SO_4$, and concentrated in vacuo. Purification by column chromatography (silica gel 1% to 2% ethyl acetate in hexane) yielded the title compound as an oil.

$^1$H NMR (300 MHz, $CDCl_3$): δ 1.23 (s, 6H), 1.27 (t, J=7.0 Hz, 3H), 1.30 (s, 9H), 1.38 (t, J=7.0 Hz, 3H), 2.11 (s, 3H), 2.14 (d, J=5.Hz, 2H), 2.18 (s, 3H), 4.07 (q, J=7.0 Hz, 2H), 4.14 (q, J=7.0 Hz, 2H), 5.72 (s, 1H), 5.84 (t, I=5 Hz, 1H), 6.23 (d, J=15.2 Hz, 1H), 6.24 (d, J=10.8 Hz, 1H), 6.56 (dd, J=10.8, 15.2 Hz, 1H), 6.88 (s, 1H), 7.34 (s, 1H).

Ethyl 7-(8-tert-butyl-3-ethoxy-5,5-dimethyl-5,6-dihydronaphthalen-2-yl)-3-methyl-nona-2E,4E,6Z-trienoate (Compound A-15)

Following General Procedure B-1, 6-bromo-4-tert-butyl-7-ethoxy-1,1-dimethyl-1,2-dihydronaphthalene (Compound A-6, 350 mg, 1.04 mmol) and bis(pinacolato)diboron (370 mg, 1.46 mmol) afforded the corresponding boronic ester. Further treatment with ethyl 7-iodo-3-methyl-nona--2E,4E,6Z-trienoate (Compound A-12,119 mg, 0.36 mmol) yielded the title compound as a pale yellow oil.

$^1$H NMR (300 MHz, $CDCl_3$): δ 1.02 (t, J=7.2 Hz, 3H), 1.23 (s, 6H), 1.27 (t, J=7.0 Hz, 3H), 1.29 (s, 9H), 1.35 (t, J=7.0 Hz, 3H), 2.01(s, 3H), 2.13 (d, J=5.0 Hz, 1H), 2.51 (q, J=7.2 Hz, 2H), 4.05 (q, J=7.0 Hz, 2H), 4.13 (q, J=7.0 Hz, 2H), 5.72 (s, 1H), 5.83 (t, J=5.0 Hz, 1H), 6.23 (d, J=10.8 Hz, 1H), 6.24 (d, J=15.2 Hz, 1H), 6.59 (dd, J=10.8, 15.2 Hz, 1H), 6.87 (s, 1H), 7.29 (s, 1H).

7-(3-Ethoxy-5,5,8-trimethyl-5,6-dihydronaphthalen-2-yl)-3-methyl-nona-2E,4E,6Z-trienoic acid (Compound A-16)

A solution of ethyl 7-(3-ethoxy-5,5,8-trimethyl-5,6-dihydronaphthalen-2-yl)-3-methyl-nona-2E,4E,6Z-trienoate (Compound A-13, 0.82 g, 2.01 mmol) in ethanol (5 mL) and THF (5 mL) was treated with 2M NaOH (5 mL, 10 mmol) and then stirred at 50° C. for 5 h. The mixture was cooled to room temperature, acidified with 10% HCl, and extracted with ethyl acetate. The organic layer was separated, washed with brine, dried over $Na_2SO_4$, and concentrated in vacuo. The residue was purified by recrystallization from acetonitrile to yield the title compound as a white solid.

$^1$H NMR (300 MHz, $CDCl_3$): δ 1.02 (t, J=7.6 Hz), 1.26 (s, 6H), 1.34 (t, J=7.0 Hz, 3M), 1.99–2.00(m, 3H), 2.13 (s, 3H), 2.18–2.20 (m, 2H), 2.51 (q, J=7.6 Hz, 2H), 4.05 (q, J=7.0 Hz, 2H), 5.65 (m, 1H), 5.74 (s, 1H), 6.25 (d, J=10.8 Hz, 1H), 6.26 (d, J=15.2 Hz, 1H), 6.60 (dd,J=10.8, 15.2 Hz, 1H), 6.87 (s, 1H, 6.90 (s, 1H.

7-(8-tert-Butyl-3-ethyloxy-5,5-dimethyl-5,6-dihydronaphthalen-2-yl)-3-methyl-octa-2E,4E,6Z-trienoic acid (Compound A-17)

General
Procedure C-1

A solution of ethyl 7-(8-tert-butyl-3-ethoxy-5,5-dimethyl-5,6-dihydronaphthalen-2-yl)-3-methyl-octa-2E,4E,6Z-trienoate (Compound A-14, 90 mg, 0.21 mmol) in ethanol (2 mL) and THF (2 mL) was treated with 2M NaOH (1 mL, 2 mmol) and then stirred at 50° C. for 5 h. The mixture was cooled to room temperature, acidified with 10% HCl, and extracted with ethyl acetate. The organic layer was separated, washed with brine, dried over $Na_2SO_4$, and concentrated in vacuo. The residue was purified by recrystallization from acetonitrile to yield the title compound as a white solid.

$^1$H NMR (300 MHz, $CDCl_3$): δ 1.23 (s, 6H), 1.30 (s, 9H), 1.38 (t, J=7.0 Hz, 3H), 2.11 (s, 3H), 2.13 (d, J=5.0 Hz, 2H), 2.9 (s, 3H), 4.07 (q, J=7.0 Hz, 2H), 5.74 (s, 1H, 5.84 (t, J=S,0 Hz, 1H), 6.24 (d, J=15.2 Hz, 1H), 6.25 (d, J=10.8 Hz, 1H), 6.65 (dd, J=10.8, 15.2 Hz, 1H), 6.88 (s, 1H), 7.33 (s, 1H).

7-(8-tert-butyl-3-ethyoxy-5,5-dimethyl-5,6-dihydronaphthalen-2-yl)-3-methyl-nona-2E,4E,6Z-trienoic acid (Compound A-18)

Following General Procedure C-1, ethyl 7-(8-tert-butyl-3-ethyoxy-,5,5-dimethyl-5,6-dihydronaphthalen-2-yl)-3-methyl-nona-2E,4E,6Z-trienoate (Compound A-15, 150 mg, 0.33 mmol) and 1 M sodium hydroxide (3 mL, 3 mmol) gave rise to the title compound.

$^1$H NMR Hz, $CDCl_3$): δ 1.02 (t, J=7.6 Hz, 3H), 1.23 (s, 6H), 1.29 (s, 9H), 1.35 (t, J=7.0 Hz, 3H), 2.10(s, 3H), 2.14 (d, 3=5.0 Hz, 1H), 2.52 (q, J=7.6 Hz, 2H), 4.05 (q, J=7.0 Hz,

2H), 5.73 (s, 1H), 5.83 (t, J=5.0 Hz, 1H), 6.25 (d, J=10.8 Hz, 1H), 6.26 (d, J=15.2 Hz, 1H), 6.63 (dd, J=10.8, 15.2 Hz, 1H), 6.87 (s, 1H), 7.28 (s, 1H).

TABLE 6

Receptor Transactivation, Efficacy and Binding Data for Exemplary Compounds of Formula D

| Compound number | Structure | RAR Trans. $EC_{50}$ nM / RAR Bind. $K_i$ nM | | | RXR Trans. $EC_{50}$ nM / RXR Bind $K_i$ nM | | |
|---|---|---|---|---|---|---|---|
| | | α | β | γ | α | β | γ |
| A-16 | | NA | 242 (21) | NA | 12 (39) | 191 (37) | 32 (26) |
| | | 578 | 610 | 3.8k | 8.7 | 49 | ND |
| A-17 | | NA | 50 (7) | NA | 0.6 (85) | 3.2 (72) | 0.9 (73) |
| | | 861 | 401 | 1.9k | 2.4 | 16 | ND |
| A-18 | | NA | 15 (7) | NA | 2.6 (18) | 11 (21) | 2.7 (11) |
| | | 442 | 137 | 537 | 5 | 31 | ND |

In vivo Data (in ob/ob mice) for Exemplary Compounds of Formula D

TABLE 7

| Treatment (dose) | Glucose (mg/dl) | | | Triglycerides (mg/dl) | | T4 (µg/dL) |
|---|---|---|---|---|---|---|
| | Day 0 | Day 3, 3 h | Day 6, 3 h | Day 0 | Day 3, 3 h | Day 7 |
| Vehicle (Corn oil) | 346 ± 73 | 416 ± 116 | 381 ± 85 | 171 ± 34 | 159 ± 35 | 3.5 ± 0.4 |
| Standard compound (5 mg/kg) | 389 ± 138 | 301 ± 94 | 218 ± 43 | 149 ± 51 | 147 ± 41 | 2.7 ± 0.7 |
| compound A-16 (50 mg/kg) | 443 ± 156 | 297 ± 121 | 267 ± 73 | 160 ± 22 | 121 ± 24 | 4.2 ± 0.4 |

Section E of Specific Embodiments

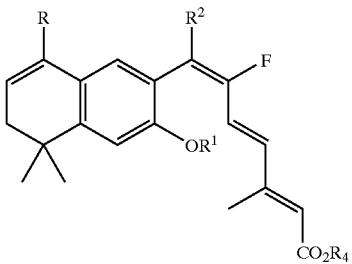

Formula E

Formula E discloses a specific class of preferred and exemplary compounds of the invention. In Formula E:

R represents H, alkyl of 1 to 8 carbons, more preferably alkyl of 1 to 4 carbons;

$R^1$ represents alkyl of 1 to 8 carbons, more preferably alkyl of 1 to 4 carbons;

$R^2$ represents alkyl of 1 to 8 carbons, more preferably alkyl of 1 to 4 carbons, and still more preferably alkyl of 1 to 2 carbons, and $R^4$ represents H, alkyl of 1 to 6 carbons, $CH_2OR_5$ or $CH_2OCOR_5$ where $R_5$ is alkyl of 1 to 3 carbons, or a pharmaceutically acceptable salt of said compound.

The synthetic schemes and the experimental procedures for obtaining compounds within the scope of Formula E are provided below.
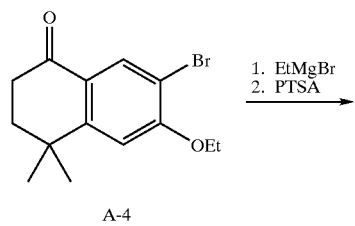
A-4
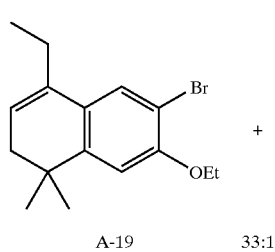
A-19    33:1
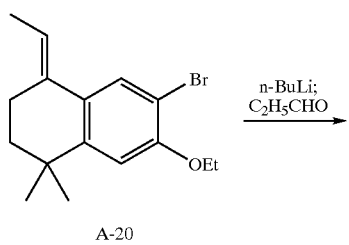
A-20
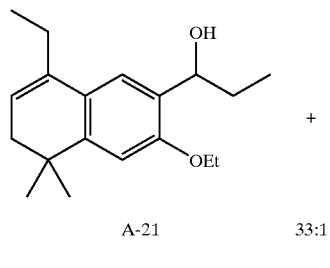
A-21    33:1
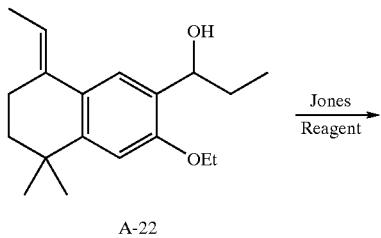
A-22
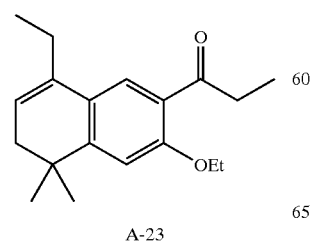
A-23
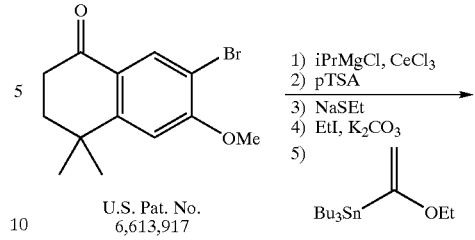
U.S. Pat. No. 6,613,917
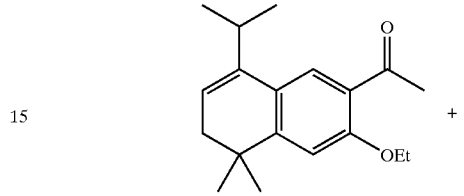
A-24
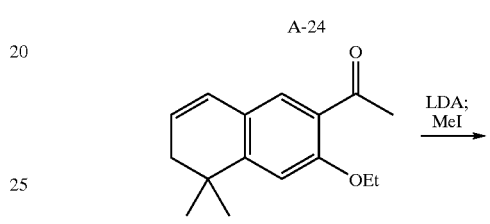
A-25
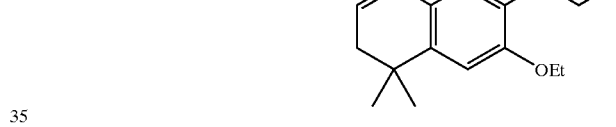
A-26
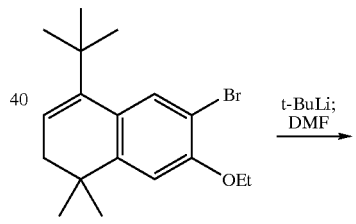
A-6
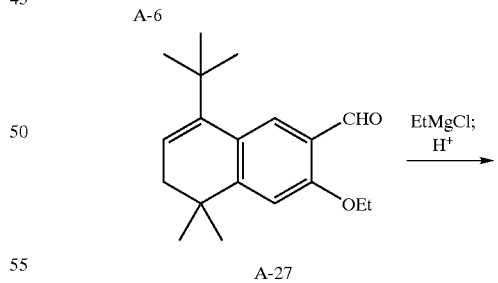
A-27
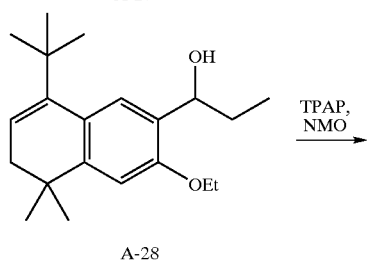
A-28

-continued

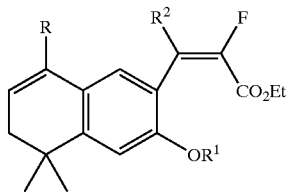

A-29

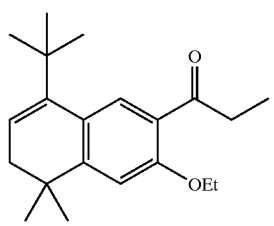

R¹I or R¹Br,
K₂CO₃
acetone

A-30, R = i-Pr
A-31, R = t-Bu

Allergan Docket 17331 (HL)
GLS WILL CHANGE THIS

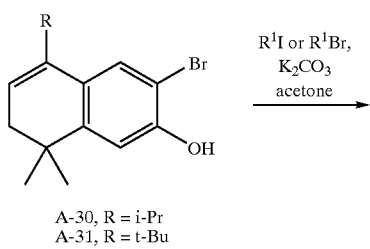

$\overset{OEt}{Bu_3SnC=CH_2}$

PdCl₂(PPh₃)₂

A-32, R = i-Pr, R¹ = Et
A-33, R = i-Pr, R¹ = n-Pr
A-34, R = i-Pr, R¹ = CH₂(c-Pr)
A-6, R = t-Bu, R¹ = Et
A-35, R = t-Bu, R¹ = n-Pr

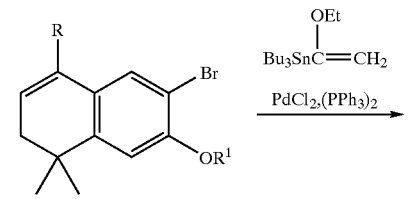

(OEt)₂P(O)CH(F)CO₂Et
LDA, THF

A-25, R = H, R¹ = Et, R² = Me
A-26, R = H, R¹ = Et, R² = Et
A-23, R = Et, R¹ = Et, R² = Et
A-24, R = iPr, R¹ = Et, R² = Me
A-36, R = i-Pr, R¹ = n-Pr, R² = Me
A-37, R = i-Pr, R¹ = CH₂(cPr), R² = Me
A-38, R = t-Bu, R¹ = Et, R² = Me
A-29, R = t-Bu, R¹ = Et, R² = Et
A-39, R = t-Bu, R¹ = n-Pr, R² = Me

-continued

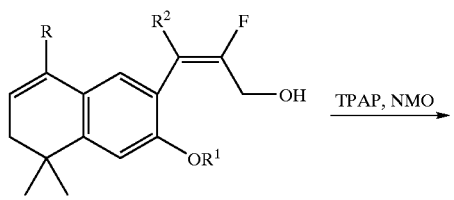

DIBAL

A-40, R = H, R¹ = Et, R² = Me
A-41, R = H, R¹ = Et, R² = Et
A-42, R = Et, R¹ = Et, R² = Et
A-43, R = iPr, R¹ = Et, R² = Me
A-44, R = i-Pr, R¹ = n-Pr, R² = Me
A-45, R = i-Pr, R¹ = CH₂(cPr), R² = Me
A-46, R = t-Bu, R¹ = Et, R² = Me
A-47, R = t-Bu, R¹ = Et, R² = Et
A-48, R = t-Bu, R¹ = n-Pr, R² = Me

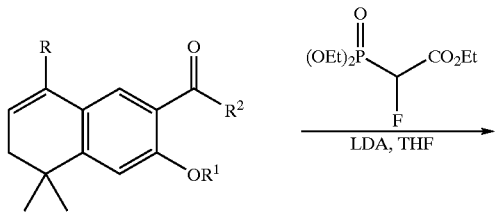

TPAP, NMO

A-49, R = H, R¹ = Et, R² = Me
A-50, R = H, R¹ = Et, R² = Et
A-51, R = Et, R¹ = Et, R² = Et
A-52, R = iPr, R¹ = Et, R² = Me
A-53, R = i-Pr, R¹ = n-Pr, R² = Me
A-54, R = i-Pr, R¹ = CH₂(cPr), R² = Me
A-55, R = t-Bu, R¹ = Et, R² = Me
A-56, R = t-Bu, R¹ = Et, R² = Et
A-57, R = t-Bu, R¹ = n-Pr, R² = Me

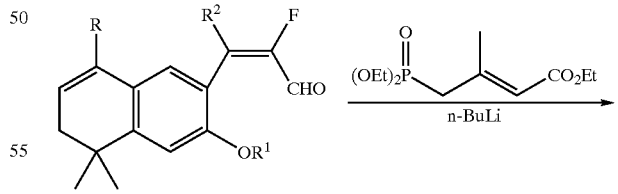

(OEt)₂P(O)CH₂C(Me)=CHCO₂Et
n-BuLi

A-58, R = H, R¹ = Et, R² = Me
A-59, R = H, R¹ = Et, R² = Et
A-60, R = Et, R¹ = Et, R² = Et
A-61, R = iPr, R¹ = Et, R² = Me
A-62, R = i-Pr, R¹ = n-Pr, R² = Me
A-63, R = i-Pr, R¹ = CH₂(cPr), R² = Me
A-64, R = t-Bu, R¹ = Et, R² = Me
A-65, R = t-Bu, R¹ = Et, R² = Et
A-66, R = t-Bu, R¹ = n-Pr, R² = Me

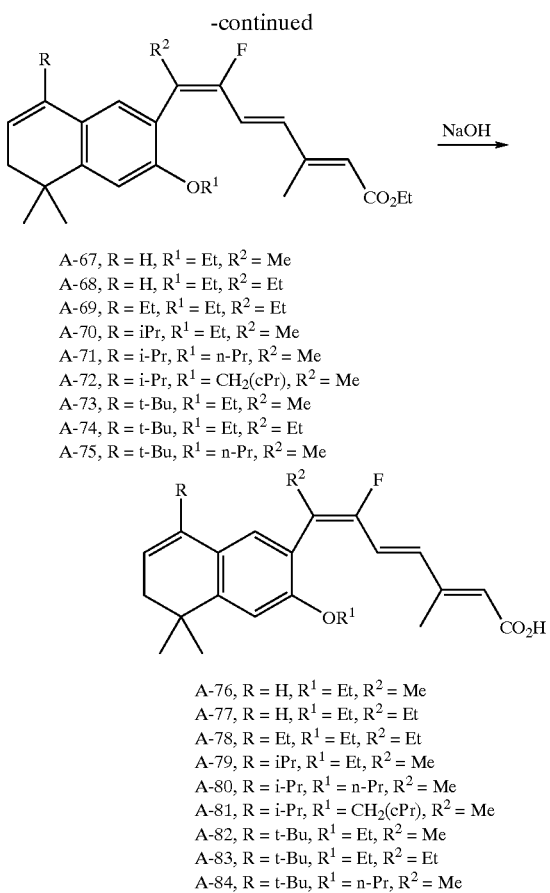

A-67, R = H, R$^1$ = Et, R$^2$ = Me
A-68, R = H, R$^1$ = Et, R$^2$ = Et
A-69, R = Et, R$^1$ = Et, R$^2$ = Et
A-70, R = iPr, R$^1$ = Et, R$^2$ = Me
A-71, R = i-Pr, R$^1$ = n-Pr, R$^2$ = Me
A-72, R = i-Pr, R$^1$ = CH$_2$(cPr), R$^2$ = Me
A-73, R = t-Bu, R$^1$ = Et, R$^2$ = Me
A-74, R = t-Bu, R$^1$ = Et, R$^2$ = Et
A-75, R = t-Bu, R$^1$ = n-Pr, R$^2$ = Me

A-76, R = H, R$^1$ = Et, R$^2$ = Me
A-77, R = H, R$^1$ = Et, R$^2$ = Et
A-78, R = Et, R$^1$ = Et, R$^2$ = Et
A-79, R = iPr, R$^1$ = Et, R$^2$ = Me
A-80, R = i-Pr, R$^1$ = n-Pr, R$^2$ = Me
A-81, R = i-Pr, R$^1$ = CH$_2$(cPr), R$^2$ = Me
A-82, R = t-Bu, R$^1$ = Et, R$^2$ = Me
A-83, R = t-Bu, R$^1$ = Et, R$^2$ = Et
A-84, R = t-Bu, R$^1$ = n-Pr, R$^2$ = Me 1-(3-Ethoxy-8-ethyl-5,5-dimethyl-5,6-dihydro-naphthalen-2-yl)-propan-1-one (Compound A-23)

To a solution of 7-bromo-ethoxy-4,4-dimethyl-3,4-dihydro-2H-naphthalen-1-one (Compound A-4, 1.7 g, 5.7 mmol) in diethyl ether (30 mL) at room temperature was added a solution of ethylmagnesium bromide (3.0 M in ether, 5.7 mL, 17.1 mmol). The reaction was stirred for 2 h, was quenched with aqueous NH$_4$Cl and extracted with diethyl ether. The organic layer was washed with brine, dried over Na$_2$SO$_4$, and concentrated in vacuo. The crude product was dissolved in dichloromethane and was treated with a catalytic amount of p-toluenesulfonic acid for 10 min. The solvent was removed in vacuo and the residue was filtered on a pad of silica gel and eluted with hexane to give a mixture of Compounds A-19 and A-20 as a colorless oil.

To a solution of the mixture of Compounds A-19 and A-20 (1.04 g, 3.37 mmol) at −78° C. in THF (20 mL) was added n-BuLi (1.6 M in hexane, 2.5 mL, 4.0 mmol). The reaction was warmed to room temperature and propionaldehyde (0.49 HL, 6.74 mmol) was added. After the reaction was stirred for 1.5 h, the reaction mixture was quenched with aqueous NH$_4$C) and extracted with ethyl acetate. The organic layer was washed with brine, dried over Na$_2$SO$_4$, and concentrated in vacuo. The crude product was purified by flash column chromatography (silica gel, 100% hexanes to 10% ethyl acetate in hexane) to give a mixture of alcohols Compounds A-21 and A-22 as a yellow oil.

Next, a solution of this mixture in acetone (4 mL) was titrated with Jones' reagent at room temperature until a pale orange color persisted The reaction mixture was diluted with ethyl acetate, washed with brine, dried over Na$_2$SO$_4$, and concentrated in vacuo. The residue was purified by flash column chromatography (silica gel, 10% ethyl acetate in hexane) to give the title compound as nearly colorless oil and a single isomer.

$^1$H NMR (300 MHz, CDCl$_3$): δ 1.14 (t, J=7.4 Hz, 3H), 1.17 (t, J=7.4 Hz, 3H), 1.24 (s, 6H), 1.48 (t, J=6.9 Hz, 3H), 2.17 (m, 2H), 2.48 (in, 2H), 3.02 (q, J=7.3 Hz, 2H), 4.17 (q, J=7.1 Hz, 2H), 5.66 (br t, J=4.7 Hz, 1H), 6.89 (s, 1H), 7.67 (s, 1H).

1-(3-Ethoxy-5,5-dimethyl-5,6-dihydro-naphthalen-2-yl)-ethanone (Compound A-25)

Cerium (III) chloride heptahydrate (18.0 g, 73.0 mmol) was dried at 150° C. under high vacuum for 16 h without stirring and then 3 h with stirring. The white solid in the flask was cooled to room temperature and switched to argon atmosphere. The flask was placed in an ice-water bath and THF (100 mL) was added. The suspension of cerium (III) chloride in THF was stirred for 15 h at room temperature before placing it back into an ice water bath. A solution of 7-bromo-6-methoxy-4,4-dimethyl-3,4-dimethyl-3,4-dihydro-2H-naphthalen-1-one (U.S. Pat. No. 6,613,917, 6.5 g, 23.0 mmol) in THF (30 mL) was added to the suspension at 0° C. and stirred for 1 h. Isopropylmagnesium chloride (2M in THF, 36.5 mL) was then added to the reaction mixture and it was stirred for 10 min at 0° C., then warmed to room temperature. After stirring overnight at room temperature, the reaction mixture was poured onto ice water with 10% HCl, extracted with diethyl ether. The combined organic layers were washed with water, brine, dried (MgSO$_4$), filtered and concentrated in vacuo.

To the crude residue in benzene (60 mL) at room temperature was added p-toluenesulfonic acid (0.26 g, 1.4 mmol). After heating to 100° C. for 38 h, the reaction mixture was cooled to room temperature and concentrated in vacuo. Flash chromatography (silica gel, 100% hexanes) gave a 1:1 mixture of 6-bromo-4-isopropyl-7-methoxy-1,1-dimethyl-1,2-dihydro-naphthalene and 7-bromo-6-methoxy-4,4-dimethyl-3,4-dihydro-2H-naphthalen-1-one (mixture A).

Sodium hydride (0.53 g, 7.56 mmol) was rinsed with hexane and suspended in dry N,N-dimethylformamide (30 mL). To this suspension was added ethanethiol (0.97 mL, 13.10 mmol) and stirred at room temperature for 30 min resulting in the formation of a clear solution. Mixture A (1.05 g, 3.64 mmol) in N,N-dimethylformamide (5 mL) was added to the clear solution and the mixture was heated at 130° C. for 4 h. The mixture was cooled to room temperature, acidified with HCl (10%) and extracted with diethyl ether. The combined ethereal layers were washed with water, brine, dried (Na$_2$SO$_4$), filtered and concentrated in vacuo. The crude residue was purified by flash chromatography (silica gel, 5% ethyl acetate in hexane) to give a 1:1 mixture of the corresponding phenols.

To a solution of the phenol mixture (2.02 g, 7.37 mmol) in acetone (30 mL) were added potassium carbonate (1.6 g, 22.1 mmol) and ethyl iodide (5.9 mL, 73.7 mmol). After heating to reflux for 16 h the reaction mixture was cooled to room temperature, diluted with water and extracted with diethyl ether. The combined ethereal layers were washed with water, brine, dried (Na$_2$SO$_4$), filtered and concentrated in vacuo to give a mixture of 6-bromo-7-ethoxy-4-isopropyl-1,1-dimethyl-1,2-dihydro-naphthalene and 6-bromo-7-ethoxy-1,1-dimethyl-1,2-dihydro-naphthalene (mixture B) as a yellow oil. The material was used in the next step without further purification.

To a solution of mixture B (2.18 g, 7.21 mmol) in THF (40 mL) was added tributyl(1-ethoxyvinyl)tin (3.66 mL, 10.8 mmol). After the mixture was degassed via bubbling argon for 30 min, dichlorobis(triphenylphosphine)palladium (II) (0.25 g, 0.05 mmol) was added. The reaction mixture was heated to reflux for 48 h. Because the reaction was incomplete via TLC, another 0.5 eq tributyl(1-ethoxyvinyl)tin and 0.05 eq dichlorobis(triphenylphosphine)palladium (II) were added and the mixture was heated at reflux for overnight. The reaction mixture was cooled to room temperature and quenched with water and 10% HCl. After stirring at room temperature for 30 min, the mixture was extracted with ether. The combined ethereal layers were washed with water and brine, dried ($Na_2SO_4$), filtered and concentrated in vacuo. Purification by flash chromatography (silica gel, 1% ethyl acetate in hexanes) gave a separable mixture of 1-(3-ethoxy-8-isopropyl-5,5-dimethyl-5,6-dihydro-naphthalen-2-yl)-ethanone (Compound A-24) and the title compound.

$^1$H NMR (300 MHz, $CDCl_3$): δ 1.26 (s, 6H), 1.49 (t, J=6.9 Hz, 3H), 2.22–2.20 (m, 2H), 2.62 (s, 3H), 4.17 (q, J=7.0 Hz, 2H), 5.84 (dt, J=4.5, 9.7 Hz, 1H), 6.43 (d, J=9.4 Hz, 1H), 6.89 (s, 1H), 7.47 (s, 1H, 1-(3-Ethoxy-5,5-dimethyl-5,6-dihydro-naphthalen-2-yl)-propan-1-one (Compound A-26)

To a solution of 1-(3-ethoxy-5,5-dimethyl-5,6-dihydronaphthalen-2-yl)-ethanone (Compound A-25, 0.17 g, 0.68 mmol) in THF (33 mL) at −78° C. was added lithium diisopropylamide (1.5 M in cyclohexane, 0.55 mL 0.82 mmol). The cold bath was removed and the mixture was stirred for 2 h. The mixture was cooled to −78° C. again and methyl iodide (0.13 mL, 2.04 mmol) was added. The mixture was stirred at room temperature for 12 h then quenched with a saturated solution of $NH_4Cl$ and extracted with diethyl ether. The combined ethereal layers were washed with water, brine, dried ($Na_2SO_4$), filtered and concentrated in vacuo. The crude residue was purified by flash chromatography (silica gel, 2% ethyl acetate in hexane) to give the title compound as a yellow oil.

$^1$H NMR (300 MHz, $CDCl_3$): δ 1.16 (t, J=7.3 Hz, 3H), 1.26 (s, 3H), 1.48 (t, J=7.0 Hz, 3H), 2.21 (dd, J=4.4, 1.8 Hz, 2H), 3.00 (q, J=7.2 Hz, 2H), 4.17 (q, J=7.0 Hz, 2H), 5.84 (dt, J=4.5, 9.7 Hz, 1H), 6.43 (d, J=9.7 Hz, 1H), 6.87 (s, 1H), 7.42 (s, 1H)

8-tert-Butyl-3-ethoxy-5,5-dimethyl-5,6-dihydro-naphthalene-2-carbaldehyde (Compound A-27)

To a solution of 6-bromo-4-tert-butyl-7-ethoxy-1,1-dimethyl-1,2-dihydronaphthalene (Compound A-6, 600 mg, 1.78 mmol) in ether (10 mL) at −78° C. was added n-butyllithium (2.3 mL 1.6 M in hexane, 3.9 mmol). After stirring at −78° C. for 25 nm, N,N-dimethylformamide (2 mL) was added and the reaction mixture was allowed to warm to −40° C. over 10 min. The reaction mixture was quenched with water and extracted with ether. The combined organic layers were washed with water and brine, dried over $MgSO_4$, filtered and concentrated under reduced pressure. Purification by flash column chromatography (silica gel, 3% to 10% ethyl acetate in hexane) afforded the title compound as a white solid.

$^1$H NMR (300 MHz, $CDCl_3$): δ 1.22 (s, 6H), 1.34 (s, 9H), 1.48 (t, J=7.0 Hz, 3H), 2.13(d, J=5.0 Hz, 2H), 4.19 (q, J=5.0 Hz, 2H), 5.89 (t, J=5.0 Hz, 1H), 6.92 (s, 1H), 8.11 (s, 1H), 10.47(s, 1H).

1-(8-tert-Butyl-3-ethoxy-5,5-dimethyl-5,6-dihydro-naphthalen-2-yl -propan-1-ol (Compound A-28)

To a solution of 8-tert-butyl-3-ethoxy-5,5-dimethyl-5,6-dihydro-naphthalene-2-carbaldehyde (Compound A-27, 450 mg, 1.57 mmol) in THF (7 mL) and 1,3-dimethyl-3,4,5,6-tetrahydro-2(1H)-pyrimidinone (DMPU, 0.3 mL) was added ethylmagnesium chloride (2 M in THF, 1.6 mL, 3.1 mmol). After stirring at 0° C. for 30 min, the reaction was quenched with 1N HCl. The resulting mixture was diluted with water, extracted with ethyl acetate. The combined organic layers were washed with water and brine, dried ($MgSO_4$), filtered, and concentrated under reduced pressure to give the title compound as a colorless oil after purification by flash chromatography (silica gel, 10% ethyl acetate in hexane).

$^1$H NMR (300 MHz, $CDCl_3$): δ 0.99 (t, J=7.3 Hz, 3H), 1.20 (s, 6H), 1.34 (m, 9H), 1.43 (t, J=7.0 Hz, 3 h), 1.82–1.88 (m. 2H), 2.11 (d, J=5.0 Hz, 2H), 2.67 (d, J=6.1 Hz, 1H), 4.13 (q, J=7.0 Hz, 2H), 4.77 (q, J=6.7 Hz, 1H), 5.83 (t, J=5.0 Hz, 1H), 6.83 (s, 1H), 7.58 (s, 1H). 1-(8-tert-Butyl-3-ethoxy-5,5-dimethyl-5,6 dihydronaphthalen-2-yl)-propan-1-one (Compound A-29)

A solution of 1-(8-tert-butyl-3-ethoxy-5,5-dimethyl-5,6-dihydro-naphthalen-2-yl)-propan-1-ol (Compound A-28, 600 mg, 1.89 mmol), 4 Å molecular sieves (0.5 g), and dichloromethane (8 mL) was treated with tetrapropylammonium peruthenate (PAP, 35 mg, 0.10 mmol) and 4 methylmorpholine N-oxide (442 mg, 3.8 mmol) and acetonitrile (4 mL). The solution was stirred under argon for 30 min and applied directly to flash chromatography (silica gel, 2% to 5% ethyl acetate in hexane) to give rise to the title compound as an oil.

$^1$H NMR (300 MHz, $CDCl_3$): δ 1.17 (t, J=7.3 Hz, 3H), 1.22 (s,6H), 1.34 (s, 9H), 1.49 (t, J=7.0 Hz, 3H), 2.12 (d, J=5.0 Hz, 2H), 3.03(q, J=7.3 Hz, 1H), 4.13 (q, J=7 Hz, 2H), 5.84 (t, J=5.0 Hz, 1H), 6.89 (s, 1H), 8.14 (s, 1H).

7-Bromo-4,4-methyl-6-ethoxy-1-isopropyl-3,4-dihydronaphthalene (Compound A-32)

General Procedure D-1

To a solution of 7-bromo-4,4-dimethyl-6-hydroxy-1-isopropyl-3,4-dihydronaphthalene (Compound A-30, U.S. Pat. No. 6,613,917, 0.251 g, 0.814 mmol) in acetone (10 mL) at room temperature was added potassium carbonate (422 mg) and iodoethane (0.651 mL, 8.14 mmol), and the resulting solution was stirred at 60° C. for 16 h, then cooled to room temperature. The mixture was diluted with water, extracted with hexane, and washed with 2N NaOH, and brine, dried over $MgSO_4$, and filtered. The solvent was removed under reduce pressure, and the residue was purified by flash column chromatography (silica gel, 98:2 hexane/ethyl acetate) to afford the title compound as a clear oil.

$^1$H NMR (300 MHz, $CDCl_3$) δ 1.14 (d, 6H, J=6.5 Hz), 1.20 (s, 6H), 1.47 (t,3H, J=6.0 Hz), 2.15 (d,2H, J=4.5 Hz), 2.85 (m,1H, J=6.5 Hz), 4.13 (q, 2H, J=6.0 Hz), 5.67 (t, 1H, J=4.5 Hz), 6.86 (s,1H), 7.46 (s, 1H).

7-Bromo-4,4-dimethyl-6-n-propoxy-1-isopropyl-3,4-dihydronaphthalene (Compound A-33)

As described in General Procedure D-1, 7-bromo-4,4-dimethyl-6-hydroxy-1-isopropyl-3,4-dihydronaphthalene (Compound A-30, U.S. Pat. No. 6,613,917, 0.100 g, 0.339 mmol), potassium carbonate (140 mg) and 1-iodopropane (0.331 mL, 3.39 mmol), were reacted in acetone (3 mL) to produce the title compound as a clear oil after purification by flash column chromatography (silica gel, 98:2 hexane/ethyl acetate).

$^1$H NMR (300 MHz, $CDCl_3$) δ 1.08 (t, 3H, J=6.3 Hz), 1.14 (d, 6H, J=6.5 Hz), 1.21 (s, 6H), 1.86 (m, 2H, J=6.3 Hz), 2.15 (d, 2H, J=4.5 Hz), 2.85 (m,1H, J=6.5 Hz),4.01 (t,2H, J=6.3 Hz), 5.67 (t,1H, J=4.5 Hz),6.85 (s, 1H), 7.46 (s,1H).

7-Bromo-4,4-dimethyl-6-(cyclopropyl)methoxy-1-isopropyl-3,4-dihydronaphthalene (Compound A-34)

As described in General Procedure D-1, 7-bromo-4,4-dimethyl-6-hydroxy-1-isopropyl-3,44-dihydronaphthalene (Compound A-30, U.S. Pat. No. 6,613,917, 1.00 g, 0.339 mmol), potassium carbonate (141 mg) and 1-bromomethylcyclopropane (0.328 mL, 3.39 mmol), were reacted in acetone (3 mL) to produce the title compound as a clear oil.

$^1$H NMR (300 MHz, CDCl$_3$): δ 0.40 (q, 2H, J=5.5 Hz), 0.65 (q, 2H, J=5.5 Hz), 1.14 (d, 6H, J=6.5 Hz), 1.20 (s, 6H), 1.24 (m, 1H), 2.15 (d, 2H, J=4.5 Hz), 2.85 (m, 1 H, J=6.5 Hz), 3.91 (d, 2H, J=5.5 Hz), 5.68 (t,1H, J=4.5 Hz), 6.86 (s,1H), 7.46 (s, 1H).

7-Bromo-4,4-dimethyl-6-n-propoxy-1-tert-butyl-3,4-dihydronaphthalene (Compound A-35)

As described in General Procedure D-1, 7-bromo-4,4-dimethyl-6-hydroxy-1-tert-butyl-3,4-dihydronaphthalene (Compound A-31, U.S. Pat. No. 6,613,917, 070 g, 0.226 mmol), potassium carbonate (94 mg) and 1-iodopropane (0.220 mL, 2.26 mmol), were reacted in acetone (3 mL) to produce the title compound as a clear oil.

$^1$H NMR (300 MHz, CDCl$_3$): δ 1.08 (t, 3H, J=6.3 Hz), 1.19 (s, 6H), 1.32 (s,9H), 1.85(m,2H, J=6.3 Hz),2.11 (d, 2H, J=4.5 Hz),4.01 (t,2H, J=6.3 Hz), 5;85 (t, 1H, J=4.5 Hz), 6.85 (s, 1H), 7.79 (s,1H).

1-(4,4-dimethyl-6-ethoxy-1-isopropyl-3,4-dihydronaphthalen-7-yl)ethanone (Compound A-24)
General Procedure E-1

To a solution 7-bromo-4,4-dimethyl-6-ethoxy-1-isopropyl-3,4-dihydronaphthalene (Compound A-32, 284 mg, 0.879 mmol) in THF (5 mL) was tributyl(1-ethoxyvinyl) tin (0.445 mL, 1.32 mmol), and the resulting solution was purged with dry argon for 15 min. Dichlorobis(triphenylphosphine)palladium(II) (0.031 g, 0.044 mmol) was added and the solution was refluxed until the reaction was complete by TLC analysis. The reaction was cooled to room temperature. The mixture was diluted with water, extracted with ethyl ether, washed with brine, dried over MgSO$_4$, and filtered. The solvent was removed under reduce pressure, and the residue was purified by flash column chromatography (silica gel, 95:5 hexane/ethyl acetate) to produce the title compound as a colorless solid.

$^1$H NMR (300 MHz, CDCl$_3$): δ 1.14 (d, 6H, J=6.5 Hz), 1.23 (s, 6H), 1.49 (t, 3H, J=6.3 Hz), 2.16 (d, 2H, J=3.5 Hz), 2.63 (s, 3H), 2.95 (m, 1 H, J=6.5 Hz), 4.18 (q, 2H, J=6.3 Hz), 5.68 (t,1H, J=3.5 Hz), 6.90 (s, 1H), 7.76 (s,1H).

1-(4,4-dimethyl-6-n-propoxy-1-isopropyl-3-dihydronaphthalen-7-yl)ethanone (Compound A-36)

As described in General Procedure E-1, 7-bromo-4,4-dimethyl-6-n-propoxy-1-isopropyl-3,4-dihydronaphthalene (Compound A-33, 0.90 g, 0.267 mmol), tributyl (1-ethoxyvinyl) tin (0.14 mL, 0.40 mmol) and dichlorobis(triphenylphosphine)palladium(II) (0.009 g, 0.013 mmol) were reacted in THF (3 mL) to produce the title compound as a yellow oil after purification by flash column chromatography (silica gel, 95:5 hexane/ethyl acetate).

$^1$H NMR (300 MHz, CDCl$_3$) δ 1.10 (t, 3H, J=6.3 Hz), 1.13 (d, 6H, J=6.5 Hz), 1.23 (s,6H), 1.90(m, 2H, J=6.3 Hz), 2.16 (d,2H, J=4.5 Hz), 2.64 (s, 3H), 3.01 (m, 1H, J=6.5 Hz), 4.07 (t, 2H, J=6.3 Hz), 5.68 (t, 1H, J=4.5 Hz), 6.89 (s,1H), 7.77. (s, 1H).

1-(4-dimethyl-6-(cyclopropyl)methoxy-1-isopropyl-3., dihydronaphthalen-7-yl)ethanone (Compound A-37)

As described in General Procedure E-1, 7-bromo-4,4-dimethyl-6 (cyclopropyl)methoxy-1-isopropyl-3,4-dihydronaphthalene (Compound A-34, 0.65 g, 0.19 mmol), tributyl (1-ethoxyvinyl)tin (0.21 mL, 0.63 mol) and dichlorobis(triphenylphosphine)palladium(1) (0.016 g, 0.023 mmol) were reacted in THF (4 mL) to produce the title compound as a yellow oil after purification by flash column chromatography (silica gel, 95:5 hexane/ethyl acetate).

$^1$H NMR (300 MHz, CDCl$_3$): δ 60.39 (q, 2H, J=5.5 Hz), 0.67 (q, 2H, J=5.5 Hz),), 1.14 (d, 6H, J=6.5 Hz), 1.22 (s, 6.H), 1.25 (m, 1H), 2.16 (d, 2H, J=4.5 Hz), 2.68 (s,3H),3.01 (m,1H, J=6.5 Hz),3.95(d,2H, J=6.5 Hz), 5.68 (t,1H, J=4.5 Hz), 6.85 (s, 1H), 7.77 (s, 1H).

1-(4,4-dimethyl-6-ethoxy-1-tert-butyl-3,4-dihydronaphthalen-7-yl)ethanone (Compound A-38)

As described in General Procedure E-1, 7-bromo-4,4-dimethyl-6-ethoxy-1-tert-butyl-3,4-dihydronaphthalene (Compound A-6, 0.075 g, 0.224 mmol), tributyl (1-ethoxyvinyl)tin (0.11 mL, 0.33 mmol) and dichlorobis (triphenylphosphine)palladium(II) (0.008 g, 0.0111 mmol) were reacted in THF (3 mL) to produce the title compound as a yellow oil after purification by flash column chromatography (silica gel, 95:5 hexane/ethyl acetate).

$^1$H NMR (300 MHz, CDCl$_3$) δ 1.21 (s, 6H), 1.34 (s, 9H), 1.49 (t,1H, J=6.3 Hz),2.11 (d,2H, J=4.5 Hz),2.64(s,3H),4.18 (q,2H, J=6.3 Hz), 5.85 (t,1H, J=4.5 Hz), 6.89 (s,1H), 8.13 (s,1H).

1-(4,4-dimethyl-6-n-propoxy-1-tert-butyl-3,4-dihydronaphthalen-7-yl)ethanone (Compound A-39)

As described in General Procedure E-1, 7-bromo-4, dimethyl-6-n-propoxy-1-tert-butyl-3,4-dihydronaphthalene (Compound A-35, 78 mg, 0.22 mmol), tributyl (1-ethoxyvinyl)tin (0.111 mL, 0.33 mmol) and dichlorobis (triphenylphosphine)palladium(1H) (0.008 g, 0.011 In ol) were reacted in THF (3 mL) to produce the title compound as a yellow oil after purification by flash column chromatography (silica gel, 95:5 hexane/ethyl acetate).

$^1$H NMR (300 MHz, CDCl$_3$): δ 1.10 (t, 3H, J=6.3 Hz), 1.22 (s, 6H), 1.34 (s,9H), 1.89(m,2H, J=6.3 Hz),2.12 (d, 2H, J=4.5 Hz), 2.64 (s, 3H), 4.06 (t, 2H, J=6.3 Hz), 5.85 (t,1H, J=4.5 Hz), 6.89 (s, 1H), 8.14 (s, 1H).

Ethyl (2E)-3-(3-ethoxy-5,5-dimethyl-5,6-dihydro-naphthalen-2-yl)-2-fluoro-but-2-enoate (Compound A-40)
General Procedure F-1

To a solution of triethyl 2-fluoro-2-phosphonoacetate (0.61 g, 2.50 mmol) in THF (5 mL) at −78° C. was added n-butyllithium (1.6 M in hexane, 1.6 mL, 2.5 mmol). After 10 min, a solution of 1-(3-ethoxy-5,5-dimethyl-5,6-dihydro-naphthalen-2-yl)-ethanone (Compound A-25, 122 mg, 0.50 mmol) in THF (2 mL) was added and the reaction was stirred for 6 b while warming gradually to room temperature. The reaction was then quenched with aqueous NH$_4$Cl and extracted with ethyl acetate. The combined organic layers were washed with brine, dried over Na$_2$SO$_4$, and concentrated in vacuo. The residue was purified by flash chromatography (silica gel, 2% ethyl acetate in hexanes) to give the title compound as a colorless oil.

$^1$H NMR (300 MHz, CDCl$_3$): δ 0.96 (t, J=7.0 Hz, 3H), 1.25 (s, 6H), 1.34 (t, J=7.0 Hz, 3H), 2.09 (d, J=4.4 Hz, 3H), 2.20 (dd, J=4.3, 1.6 Hz, 2H), 4.01 (q, J=7.0 Hz, 2H), 4.03 (q, J=7.0 Hz, 2H), 5.80 (dt, J=4.5, 9.4 Hz, 1H), 6.35 (d, J=9.7 Hz, 1H), 6.72 (s, 1H), 6.82 (s, 1H).

Ethyl (2E)-3-(3-ethoxy-5,5-dimethyl-5,6-dihydro-naphthalen-2-yl)-2-fluoro-pent-2-enoate (Compound A-41)

Following General Procedure F-1, triethyl-2-fluoro-2-phosphonoacetate (0.52 g, 2.15 mmol) and 1-(3-ethoxy-5,5-dimethyl-5,6-dihydro-naphthalen-2-yl)-ethanone (Compound A-26, 112 mg, 0.43 mmol) were reacted to give the title compound as a clear oil after purification by flash chromatography (silica gel, 2% ethyl acetate in hexanes).

$^1$H NMR (300 MHz, CDCl$_3$) δ 0.93 (t, J=7.2 Hz, 3H), 0.99 (t, J=8.0 Hz, 3H), 1.25 (s, 6H), 1.33 (t, J=7.0 Hz, 3H), 2.20–2.19 (m, 2H), 2.54–2.48 (m, 2H), 3.99 (q, J=7.2 Hz, 2H), 4.02 (q, J=7.0 Hz, 2H), 5.80 (dt, J=4.5, 9.4 Hz, 1H), 6.35 (d, J=9.4 Hz, 1H), 6.67 (s, 1H), 6.81 (s, 1H).

Ethyl (2E)-3-(3-oxy-8-ethyl-5,5-dimethyl-5,6-dihydro-naphthalen-2-yl)-2-fluoro-pent-2-enoate (Compound A-42)

Following General Procedure F-1, triethyl-2-fluoro-2-phosphonoacetate (0.12 mL, 0.58 mmol) and of 1-(3-ethoxy-8-ethyl-5,5-dimethyl-5,6-dihydro-naphthalen-2-yl)-propan-1-one (Compound A-23, 55 mg, 0.19 mmol) were reacted to give the title compound as a clear oil after purification by preparative TLC (5% ethyl acetate in hexane).

$^1$H NMR (300 MHz, CDCl$_3$): δ 0.91 (t, J=7.1 Hz, 3H), 1.00 (t, J=7.5 Hz, 3H), 1.11 (t, J=7.4 Hz, 3H), 1.23 (s, 6H), 1.34 (t, J=7.1 Hz, 3H), 2.16 (m, 2H), 2.40 (m, 2H), 2.54 (m, 2H), 3.97 (q, J=7.1 Hz, 2H), 4.03 (q, J=7.0 Hz, 2H), 5.62 (br t, J=4.5 Hz, 1H), 6.83 (s, 1H), 6.88 (s, 1H).

Ethyl (2E)-2-Fluoro-3-(4,4-dimethyl-6-ethoxy-1-isopropyl-3,4-dihydronaphthalen-7-yl)-2-butenoate (Compound A-43)

As described in General Procedure F-1, 1-(4,4-dimethyl-6-ethoxy-1-isopropyl-3,4-dihydronaphthalen-7-yl)ethanone (Compound A-24, 240 mg, 0.840 mmol) and triethyl 2-fluoro-2-phosphonoacetate (0.51 mL, 2.52 mmol) were reacted with lithium diisopropylamide (2.60 mmol) in THF (2 mL) to produce the title compound after purification by flash column chromatography (silica gel, 97:3 hexane/ethyl acetate).

$^1$H NMR (300 MHz, CDCl$_3$)0.92 (t,3H, J=6.5 Hz), 1.12 (d, 6H, J=6.5 Hz), 1.21 (s, 6H), 1.35 (t, 3H, J=6.3 Hz), 2.11(d, 3H, J=3.5 Hz), 2.15 (d, 2H, J=3.5 Hz),2.85(m,1H, J=6.5 Hz),3.99(q,2H, J=6.5 Hz),4.04 (q,2H, J=6.3 Hz),5.64 (t, 1H, J=3.5 Hz),6.83 (s, 1H),6.97(s,1H).

Ethyl (2E)-2-Fluoro-3-(4,4-methyl-6-n-propoxy-1-isopropyl-3,4-dihydronaphthalen-7-yl)-2-butenoate (Compound A-44)

As described in General Procedure F-1, 1-(7-bromo-4,4-dimethyl-6-n-propoxy-1-isopropyl-3,4-dihydronaphthalen-yl)ethanone (Compound A-36, 0.034 g, 0.113 mmol) and triethyl 2-fluoro-2-phosphonoacetate (0.17 mL, 0.86 mmol) were reacted with lithium diisopropylamide (0.86 mmol) in THF (2 mL) to produce the title compound as a yellow oil after purification by flash column chromatography (silica gel, 97:3 hexane/ethyl acetate).

$^1$H NMR (300 MHz, CDCl$_3$), 0.91 (t, 3H, J=6.5 Hz), 0.99 (t, 3H, J=6.3 Hz), 1.12 (d, 6H, J=6.5 Hz), 1.22 (s, 6H), 1.74 (m, 2H, J=6.3 Hz), 2.11 (d,3H, J=3.5 Hz), 2.16 (d,2H, J=3.5 Hz), 2.85 (m,1H,J=2 6.5 Hz), 3.93 (t,3H, J=6.5 Hz), 3.98(t, 2H, J=6.3 Hz),5.64(t, 1 H, J=3.5 Hz), 6.83(s,1H),6.97(s,1H).

Ethyl (2E)-2-Fluoro-3-(4,4-dimethyl-6(cyclopropyl methoxy-1-isopropyl-3,4-dihydronaphthalen-7-yl)-2-butenoate (Compound A-45)

As described in General Procedure F-1, 1-(7-bromo-4,4-dimethyl-6-(cyclopropyl)methoxy-1-isopropyl-3,4-dihydronaphthalen-yl)ethanone (Compound A-37, 0.029 g, 0.093 mmol) and triethyl 2-fluoro-2-phosphonoacetate (0.17 mL, 0.86 mmol) were reacted with lithium diisopropylamide (0.86 mmol) in THF (2 mL) to produce the title compound as a yellow oil after purification by flash column chromatography (silica gel, 97:3 hexane/ethyl acetate).

$^1$H NMR (300 MHz, CDCl$_3$) δ 0.29 (q, 2H, J=3.5 Hz), 0.67 (q, 2H, 32 4.5 Hz), 0.92 (t, 3H, J=6.5 Hz), 1.14 (d, 6H, J=6.5 Hz), 1.22 (s, 6H), 1.25 (m 1H), 2.14 ((d,3 H, J=3.5 Hz), 2.15 (d, 2H, J=3 Hz), 2.85 (m,1H, 3=6.5 Hz), 3.82 (d, 2H, J=6.5 Hz), 3.99 (q, 2H, J=6.5 Hz), 5.64 (t, 1H, J=3.5 Hz),6.82 (s, 1H), 6.97 (s,1H).

Ethyl (2E)-2-Fluoro-3-(4,4-dimethyl-6-ethoxy-1-tert-butyl-3, dihydronaphthalen-7-yl)-2-butenoate (Compound A-46)

As described in General Procedure F, 1-(7-bromo-4,4-dimethyl-6-ethoxy-1-tert-butyl-3,4-dihydronaphthalen-yl) ethanone (Compound A-38, 43 mg, 0.14 mmol) and triethyl 2-fluoro-2-phosphonoacetate (0.17 μL, 0.86 mmol) were reacted with lithium diisopropylamide (0.86 mmol) in THF (2 mL) to produce the title compound as a yellow oil after purification by flash column chromatography (silica gel, 97:3 hexane/ethyl acetate).

$^1$H NMR (300 MHz CDCl$_3$) δ 0.90 (t, 3H, J=6.5 Hz), 1.20 (s, 6H), 1.29 (s,9H), 1.35(t, 1H,4 6.3 Hz), 2.11 (d, 2H, J=3 Hz), 2.13 (d, 3H,=3.5 Hz), 3.97 (q, 2H, J=6.5 Hz), 4.04 (q, 2H, J=6.3 Hz), 5.82(t, 1 H, J=3.5 Hz), 6.83 (s, 1H), 7.29(s, 1H).

Ethyl(2E63-(8-tert-3-ethoxy-5(5-dimethyl-5,6-dihydronaphthalen-2-yl-2-fluoro-pent-2-enoate (Compound A-47)

As described in General Procedure F-11, 1-(8-tert-butyl-3-ethoxy-5,5-dimethyl-5,6-dihydronaphthalen-2-yl)-propan-1-one (Compound A-29, 550 mg, 1.75 mmol) and triethyl 2-fluoro-2-phosphonoacetate (1.27 g, 5.25 mmol) were reacted with n-butyllithium (1.6 M in hexanes, 3.3 mL, 5.25 mmol) in THF to produce the title compound as an oil after purification by flash chromatography (silica gel, 1% to 2% ethyl acetate in hexane).

$^1$H NMR (300 MHz, CDCl$_3$): δ 0.87 (t, J=7.0 Hz, 3H), 1.02 (t, J=7.1 Hz, 3H), 1.20 (s, 6H), 1.29 (s, 9H), 1.34 (t, J=7.0 Hz, 3H), 2.11 (d, J=4.7 Hz, 2H), 2.55 (m, 2H), 3.95 (q, J=7.0 Hz, 2H), 4.03 (q, J=7.0 Hz, 2H), 5.81 (t, J=4.7 Hz, 1H), 6.82 (s, 1H), 7.24 (s, 1H).

Ethyl (2E)-2-Fluoro-3-(4,4-dimethyl-6-n-propoxy-1-tert-butyl-3,4-dihydronaphthalen-7-yl)-2-butenoate (Compound A-48)

As described in General Procedure F-1, 1-(7-bromo-4,4-dimethyl-6-propoxy-1-tert-butyl-3,4-dihydronaphthalen-yl) ethanone (Compound A-39, 34 mg, 0.11 mmol) and triethyl 2-fluoro-2-phosphonoacetate (0.17 mL, 0.86 mmol) were reacted with lithium diisopropylamide (0.86 mmol) in THF (2 mL) to produce the title compound as a yellow oil after purification by flash column chromatography (silica gel, 97:3 hexane:ethyl acetate).

¹HNMR (300 MHz,CDCl₃)δ0.89(t,3H, J=6.5 Hz), 0.99 (t,3H, J=6.5 Hz), 1.20 (s, 6H), 1.29 (s, 9H), 1.75 (m, 2H, J=6.5 Hz), 2.11 (d, 2H J=3.5 Hz), 2.13 (d, 3H, J=3.5 Hz), 3.94 (q, 2H, J=6.5 Hz), 3.97 (q, 2H, J=6.5 Hz), 5.82 (t, 1H, J=3.5 Hz), 6.82 (s, 1H), 7.29 (s,1H).

(2E)-3-(3-Ethoxy-5,5-dimethyl-5,6-hydro-naphthalen-2-yl)-2-fluoro-but-2-en-1-ol (Compound A-49)

General Procedure G-1

A solution of diisobutylaluminum hydride (1.0 M in dichloromethane, 0.21 mL, 0.21 mmol) was added to a −78° C. solution of ethyl (2E)-3-(3-ethoxy-5,5-dimethyl-5,6-dihydro-naphthalen-2-yl)-2-fluoro-but-2-enoate (Compound A-40, 70 mg, 0.09 mmol) and THF (3 mL). The solution was stirred under argon for 4 h and quenched with methanol (1 mL). After 10 min, the mixture was diluted with saturated aqueous NH₄Cl, and the product was extracted with ethyl ether. The combined ether extracts were washed with brine, dried over MgSO₄, filtered, and concentrated under reduced pressure to give the title compound as a colorless oil after purification by flash chromatography (silica gel, 10% ethyl acetate in hexanes).

¹H NMR (300 MHz, CDCl₃) δ 1.25 (s, 6H), 1.39 (t, J=6.9 Hz, 3H), 1.96 (d, J=3.8 Hz, 3H), 2.21 (dd, J=4.4, 1.8 Hz, 2H), 4.09–3.96 (m, 4H), 5.84 (dt, J=4.6, 9.7 Hz, 1H), 6.36 (d, J=9.4 Hz, 1H), 6.78 (s, 1H), 6.86 (s, 1H).

(2E)-3-(3-Ethoxy-5,5-dimethyl-5,6-dihydro-naphthalen-2-yl)-2-fluoro-pent-2-en-1-ol (Compound A-50)

Following General Procedure G-1, ethyl (2E)-3-(3-ethoxy-5,5-dimethyl-5,6-dihydro-naphthalen-2-yl)-2-fluoro-pent-2-enoate (Compound A-41, 52 mg, 0.15 mmol) and diisobutylaluminum hydride (1M in methylene chloride, 0.36 mL, 0.36 mmol) were reacted to give the title compound as a colorless oil after purification by flash chromatography (silica gel, 10% ethyl acetate in hexanes).

¹H NMR (300 MHz, CDCl₃) δ 0.93 (t, J=7.5 Hz, 3H), 1.25 (s, 6H), 1.38 (t, J=7.0 Hz, 3H), 2.23–2.14 (m, 4H), 2.42 (br s, OH), 4.05–3.91 (m, 4H), 5.83 (dt, J=4.5, 9.2 Hz, 1H), 6.36 (d, J=9.7 Hz, 1H), 6.75 (s, 1H), 6.85 (s, 1H).

(2E)-3-(3-Ethoxy-8-ethyl-5,5-dimethyl-5,6-dihydro-naphthalen-2-yl)-2-fluoro-pent-2-en-1-ol (Compound A-51)

Following General Procedure G-1, ethyl (2E)-3-(3-ethoxy-8-ethyl-5,5-dimethyl-5,6-dihydro-naphthalen-2-yl)-2-fluoro-pent-2-enoate (Compound A-42, 42 mg, 0.11 mmol) in toluene (2 mL) and diisobutylaluminum hydride (1.0 M in hexane, 0.48 mL, 0.48 mmol) were reacted to give the title compound after purification by flash chromatography (silica gel, 2.5% ethyl acetate in hexanes).

¹H NMR (500 MHz, CDCl₃): δ 0.94 (t, J=7.5 Hz, 3H), 1.13 (t, J=7.5 Hz, 3H), 1.24 (s, 6H), 1.38 (t, J=6.9 Hz, 3H), 1.93 (br, 1H), 2.17 (T, 2H), 2.38–2.46 (m, 4H), 3.93–4.10 (m, 4H), 5.66 (br t, J=4.5 Hz, 1H), 6.87 (s, 1H), 6.97 (s, 1H).

(2E)-2-Fluoro-3-(4,4-dimethyl-6-ethoxy-1-isopropyl-3,4-dihydronaphthalen-7-yl)2-butenol (Compound A-52)

Following General Procedure G-1, diisobutylaluminum hydride (1.0 M in hexanes, 2.2 mL, 2.2 mmol) and ethyl (2E)-2-fluoro-3-(4,4-dimethyl-6-ethoxy-1-isopropyl-3,4-dihydronaphthalen-7-yl)-2-butenoate (Compound A-43, 0.205 g, 0.55 mmol) in THF (6 mL) were reacted to give the title compound.

¹H NMR (300 MHz, CDCl₃): δ 1.13 (d, 6H, J=6.5 Hz), 1.21 (s, 6H),1.38 (t,3H, J=6.3 Hz), 1.98(d,3H, J=2 Hz),2.15 (d,2H, J=3 Hz), 2.87(m, 1H, J=6.5 Hz),3.97(br q,2H),4.06 (br q,2H),5.66(t,1H, J=3 Hz), 6.86 (s, 1H), 7.05 (s,1H).

(2E)-2-Fluoro-3-(4,4-dimethyl-6-n-propoxy-1-isopropoxy-3,4-dihydronaphthalen-7-yl)-2-butenol (Compound A-53)

As described in General Procedure G-1, ethyl (2E)-2-fluoro-3-(4,4-dimethyl-6-n-propoxy-1-isopropyl-3,4-dihydronaphthalen-7-yl)-2-butenoate (Compound A-44, 0.041 g, 0.106 mmol) and diisobutylaluminum hydride (1.0 M in hexanes, 0.842 mL, 0.842 mmol) were reacted in THF (1 mL) to produce the title compound as an oil.

¹H NMR (300 MHz, CDCl₃) δ 1.02 (t, 3H, J=6.3 Hz), 1.13 (d, 6H, J=6.5 Hz), 1.21 (s, 6H), 1.80 (m, 2H, J=6.3 Hz), 1.99(d, 3H, J=2 Hz), 2.12 (d, 2H, J=3 Hz),2.85(m,1H, J=6.5 Hz),3.95(t,3H, J=6.3 Hz),4.04(br d,2H, J=24 Hz),5.85(t,1H, J=3 Hz), 6.86 (s, 1H), 7.38 (s, 1H).

(2E)-2-Fluoro-3-(4,4-dimethyl-6-(cyclopropyl) methoxy-1-isopropyl-3,4 dihydronaphthalen-7-yl)2-butenol (Compound A-54)

As described in General Procedure G-1, ethyl (2E)-2-fluoro-3-(4,4-dimethyl-6(cyclopropyl)methoxy-1-isopropyl-3,4-dihydronaphthalen-7-yl)-2-butenoate (Compound A-45, 0.025 g, 0.062 mmol) and diisobutylaluminum hydride (1.0 M in hexanes, 0.50 mL, 0.50 mmol) were reacted in THF (0.5 mL) to produce the title compound as an oil.

¹H NMR (300 MHz, CDCl₃): δ 0.34 (q, 2H, J=4.5 Hz), 0.65 (q, 2H, J=4.5 Hz), 1.14 (d, 6H, J=6.5 Hz), 1.22 (s, 6H), 1.25 (m, 1H), 2.00 (d, 3H, J=3 Hz),2.16(d,2H, J=3 Hz),2.47 (br t,1H), 2.88 (m,1H, J=6.5 Hz), 3.81 (d, 2H, J=6.3 Hz), 4.02 (br d, 2H, J=24 Hz), 5.68 (t, 1H, J=3 Hz), 6.85 (s, 1H), 7.07 (s, 1H).

(2E)-2-Fluoro-3-(4,4-dimethyl-6-ethoxy-1-tert-butyl-3,4 dihydronaphthalen-7-yl)-2-butenol (Compound A-55)

As described in General Procedure G-1, ethyl (2E)-2-fluoro-3-(4,4 dimethyl-6-ethoxy-1-tert-butyl-3,4-dihydronaphthalen-7-yl)-2-butenoate (Compound A-46, 0.037 g, 0.095 mmol) and diisobutylaluminum hydride (1.0 M in hexanes, 0.76 mL, 0.76 mmol) were reacted in THF (0.75 mL) to produce the title compound as an oil.

¹H NMR (300 MHz, CDCl₃): δ 1.21 (s, 6H), 1.32 (s, 9H), 1.40 (t, 1H, J=6.3 Hz), 2.00 (d, 3H, J=2 Hz), 2.12 (d, 2H, J=3.5 Hz), 2.15 (br t, 1H), 4.03(br d,2H, J=18 Hz),4.08(br q,2H),5.85(t,1H, J=3.5 Hz), 6.86 (s, 1H), 7.38 (s,1H).

(2E)-3-(8-tert-Butyl-3-ethoxy-5,5-dimethyl-5-dihydronaphthalen-2-yl)-2-fluoro-pent-2-en-1-ol (Compound A-56)

As described in General Procedure G-1, ethyl (2E)-3-(8-tert-butyl-3-ethoxy-5,5-dimethyl-5,6-dihydronaphthalen-2-yl)-2-fluoro-pent-2-enoate (Compound A-47,650 mg, 1.61 mmol) and diisobutylaluminum hydride (1.0 M in hexanes, 6.5 mL, 16.5 mmol) were reacted in THF to produce the title compound as an oil after purification by flash chromatography (silica gel, 15% ethyl acetate in hexanes).

¹H NMR (300 MHz, CDCl₃): δ 0.95 (t, J=7.5 Hz, 3H), 1.21 (s, 6H), 1.31 (s, 9H), 1.38 (t, J=7.0 Hz, 3H), 2.11–2.15 (m, 3H), 2.45 (bs, 2H), 3.94–4.13 (m, 4H), 5.85 (t, J=5.0 Hz, 1H), 6.85 (s, 1H), 7.34 (s, 1H).

(2E)-2-Fluoro-3-(4,4-dimethyl-6-n-propoxy-1-tert-butyl-3,4-dihydronaphthalen-7-yl)-2-butenol (Compound A-57)

As described in General Procedure G-1, ethyl (2E)-2-fluoro-3-(4,4 dimethyl-6-n-propoxy-1-tert-butyl-3,4-dihydronaphthalen-7-yl)-2-butenoate (Compound A-48, 0.044 g, 0.109 mmol) and diisobutylaluminum hydride (1.0 M in hexanes, 0.87 mL, 0.87 mmol) were reacted in THF (0.87 mL) to produce the title compound as an oil.

¹H NMR (300 MHz, CDCl₃): δ 1.02 (t, 3H, J=6.5 Hz), 1.21 (s, 6H), 1.32 (s, 9H), 1.77 (m, 2H, J=6.5 Hz), 1.99 (d, 3H, J=2.5 Hz), 2.10 (br t, 1H), 2.12(d,2H, J=4.5 Hz),3.95 (br t,2H),4.04(br d,2H, J=18 Hz),5.85 (t, 1 H, J=4.5 Hz), 6.86 (s, 1H), 7.38 (s,1H).

(2E)-3-(3-Ethoxy-5,5-dimethyl-5,6-dihydro-naphthalen-2-yl 2-fluoro-but-2-enal (Compound A-58)

General Procedure H-1

A solution of (2E)-3-(3-ethoxy-5,5-dimethyl-5,6-dihydro-naphthalen-2-yl)-2-fluoro-but-2-en-1-ol (Compound A-49, 18 mg, 0.06 mmol), 4 Å molecular sieves (0.1 g) in dichloromethane (3 mL) was treated with tetrapropylammonium perruthenate (10 mg, 0.028 mmol) and 4 methylmorpholine N-oxide (15 mg, 0.12 mmol). The solution was stirred under argon for 30 min and filtered through a silica gel plug (20% ethyl acetate in hexanes). The filtrate was concentrated under vacuum to give the title compound.

¹H NMR (300 MHz, CDCl₃): δ 1.28 (s, 6H), 1.39 (t, J=7.0 Hz, 3H), 2.25–2.20 (m, 5H), 4.08 (q, J=7.0 Hz, 4H), 5.88 (dt, J=4.5, 10.0 Hz, 1H), 6.37 (d, J=9.7 Hz, 1H), 6.83 (s,1H), 6.88 (s, 1H), 9.23 (d, J=19.6 Hz, 1H)

(2E)-3-(3-Ethoxy-5,5-dimethyl-5,6-dihydro-naphthalen-2-yl)-2-fluoro-pent-2-enal (Compound A-59)

Following General Procedure H-1, (2E)-3-(3-ethoxy-5,5-dimethyl-5,6-dihydro-naphthalen-2-yl)-2-fluoro-pent-2-en-1-ol (Compound A-50, 35 mg, 0.12 mmol) and 4-methylmorpholine N-oxide (27 mg, 0.23 nmol) were reacted to give the title compound as a yellow solid after purification by flash chromatography (silica gel, 10% ethyl acetate in hexanes).

¹H NMR (300 MHz, CDCl₃): δ 1.03 (t, J=7.6 Hz, 3H), 1.28 (s, 6H). 1.37 (t, J=7.0 Hz, 3H), 2.25–2.23 (m, 2H), 2.65 (qd, J=2.8, 7.6 Hz, 2H), 4.07 (q, J=6.8 Hz, 2H), 5.87 (dt, J=4.5, 9.2 Hz, 1H), 6.36 (d, J=9.7 Hz, 1H), 6.79 (s, 1H), 6.87 (s, 1H), 9.17 (d,J=19.6 Hz, 1H).

(2E)-2-Fluoro-3-(4,4-dimethyl-6-ethoxy-1-isopropyl-3,4-dihydronaphthalen-7-yl)-2-butenal (Compound A-61)

As described in General Procedure H-1, (2E)-2-fluoro-3-(4,4-dimethyl-6-ethoxy-1-isopropyl-3,4-dihydronaphthalen-7-yl)-2-butenol (Compound A-52, 0.180 g, 0.54 mmol), tetrapropylammonium perruthenate (0.027 g, 0.081 mmol) and 4-methylmorpholine N-oxide (0.158 g, 1.35 mmol) were reacted in acetonitrile (1.5 mL) and dichloromethane (7.5 mL) to give the title compound.

¹H NMR (300 MHz, CDCl₃): δ 1.13 (d, 6H, J=6.5 Hz), 1.23 (s, 6H), 1.37 (t,3H, J=6.3 Hz),2.17(d,2H, J=3 Hz),2.23 (d,3H, J=2 Hz),2.84(m, 1H, J=6.5 Hz),4.07(q,2H, J=6.3 Hz),5.69(t,1H, J=3 Hz),6.88(s, 1H), 7.06 (s, 1H), 9.22 (d,1H, J=18 Hz).

(2E)-2-Fluoro-3-(4,4-dimethyl-6-n-propoxy-1-isopropyl-3,4-dihydronaphthalen-7-yl)-2-butenal (Compound A-42)

As described in General Procedure H-1, (2E)-2-fluoro-3-(4,4-dimethyl-6-n-propoxy-1-isopropyl-3,4-dihydronaphthalen-7-yl)-2-butenol (Compound A-53, 0.024 g, 0.069 mmol), tetrapropylammonium perruthenate (0.012 g, 0.038 mmol) and 4-methylmorpholine N-oxide (0.022 g, 0.19 mmol) were reacted in acetonitrile (0.2 mL) and dichloromethane (1 mL) to produce the title compound as an oil.

¹H NMR (300 MHz, CDCl₃): δ 1.01 (t, 3H, J=6.3 Hz), 1.13 (d, 6H, J=6.5 Hz), 1.24(s, 6H), 1.79(m,2H, J=6.3 Hz), 2.18 (d,2H, J=2 Hz), 2.24(d,2H, J=3 Hz),2.85(m, 1H, J=6.5 Hz),3.97(t,3H, J=6.3 Hz), 5.85 (t, 1H, J=3 Hz), 6.89 (s, 1H), 7.07 (s, 1H), 9.23 (d, 1H. J=18 Hz).

(2E)-2-Fluoro-3-(4,4-dimethyl-(cyclopropyl)methoxy-1-isopropyl-3,4-dihydronaphthalen-7-yl)-2-butenal (Compound A-63)

As described in General Procedure H-1, (2E)-2-fluoro-3-(4,4-dimethyl-6-(cyclopropyl)methoxy-1-isopropyl-3,4-dihydronaphthalen-7-yl)-2-butenol (Compound A-54, 0.025 g, 0.070 mmol), tetrapropylammonium perruthenate (0.012 g, 0.038 mmol) and 4-methylmorpholine N-oxide (0.022 g, 0.19 mmol) were reacted in acetonitrile (0.2 mL) and dichloromethane (1 mL) to produce the title compound as an oil.

¹H NMR (300 MHz, CDCl₃): δ 0.31 (q, 2H, J=4.5 Hz), 0.62 (q, 2H, J=6.0 Hz), 1.13 (d, 6H, J=6.5 Hz), 1.23 (s, 6H), 1.25 (m, 1H), 2.18 (d, 3H, J=3 Hz),2.27(d,2H, J=3 Hz),2.85 (m,1H, J=6.5 Hz),3.86(d,2H, J=6.3 Hz), 5.70 (t, 1H, J=3 Hz), 6.86 (s, 1H), 7.08 (s,1H), 9.25 (d,1H, J=18 Hz).

(2E)-2-Fluoro-3-(4,4-dimethyl-6-ethoxy-1-tert-butyl-3,4-dihydronaphthalen-7-yl)-2-butenal (Compound A-64)

As described in General Procedure H-1, (2E)-2-fluoro-3-(4,4-dimethyl-6-ethoxy-1-tert-butyl-3,4-dihydronaphthalen-7-yl)-2-butenol (Compound A-55, 0.023 g, 0.066 mmol), tetrapropylammonium perruthenate (0.012 g, 0.038 mmol) and 4-methylmorpholine N-oxide (0.022 g, 0.19 mmol) were reacted in acetonitrile (0.2 mL) and dichloromethane (1 mL) to produce the title compound as an oil.

¹H NMR (300 MHz, CDCl₃): δ 1.21 (s, 6H), 1.32 (s, 9H), 1.40 (t, 1H, J=6.3 Hz), 2.00 (d, 3H, J=2 Hz), 2.12 (d, 2H, J=3.5 Hz), 2.15 (br t,1H), 4.03(br d,2H, J=18 Hz),4.08(br q,2H),5.85(t, 1H, J=3.5 Hz),6.86 (s,1H), 7.38 (s, 1H), 9.26 (d, 1H, J=18 Hz).

(2E)-3-(8-tert-Butyl-3-ethoxy-5,5-dimethyl-5,6-dihydronaphthalen-2-yl)-2-fluoro-pent-2-enal (Compound A-65)

As described in General Procedure H-1, (2E)-3-(8-tert-butyl-3-ethoxy-5,5-dimethyl-5,6-dihydronaphthalen-2-yl)-2-fluoro-pent-2-en-1-ol (Compound A-56, 487 mg, 1.61 mmol), tetrapropylammonium peruthenate (316 mg, 2.7 mmol) and 4-methylmorpholine N-oxide (3.5 mg) were reacted in acetonitrile (4 mL) and dichloromethane (8 mL) to produce the title compound as an oil after flash chromatography (silica gel, 10% ethyl acetate in hexane).

¹H NMR (300 MHz, CDCl₃): δ 1.05 (t, J=7.5 Hz, 3H), 1.22 (s, 6H), 1.30 (s, 9H), 1.37 (t, J=7.0 Hz, 3H), 2.14 (d, J=5.0 Hz, 2H), 2.61–2.68 (m, 2H), 4.07 (q, J=7.0 Hz, 2H), 5.87 (t, J=5.0 Hz, 1H), 6.87 (s, 1H), 7.37 (s, 1H), 9.21 (d, J=19.6 Hz, 1H).

(2E)-2-Fluoro-3-(4,4-dimethyl-6-n-propoxy-1-tert-buyl-3,4-dihydronaphthalen-7-yl)-2-butenal (Compound A-66)

As described in General Procedure H-1, (2E)-2-fluoro-3-(4,4-dimethyl-6-n-propoxy-1-tert-butyl-3,4-dihydronaphthalen-7-yl)-2-butenol (Compound A-57, 0.027 g, 0.075 mmol), tetrapropylammonium perruthenate (12 mg, 0.038 mmol) and 4-methylmorpholine N-oxide (22 mg, 0.19 mmol) were reacted in acetonitrile (0.2 mL) and dichloromethane (1 mL) to produce the title compound as an oil.

¹H NMR (300 MHz, CDCl₃) δ 1.01 (t, 3H, J=6.5 Hz), 1.23 (s, 6H), 1.30 (s, 9H), 1.77 (m, 2H, J=6.5 Hz), 2.14 (d, 2H, J=3.5 Hz), 2.25 (d, 3H, J=3 Hz), 3.96 (t, 2H, J=6.5 Hz), 5.88 (t, 1H, J=3.5 Hz), 6.88 (s, 1H), 7.41 (s, 1H), 9.26 (d, 1H, J=18 Hz).

Ethyl (2E,4E,6E)-7-(3-ethoxy-5,5-dimethyl-5,6-dihydro-naphthalen-2-yl)-6-fluoro-3-methyl-octa-2E,4E,6Z-trienoate (Compound A-47)

General Procedure I-1

A solution of n-butyllithium (1.6 M in hexane, 0.85 mL, 1.36 mmol) was added over 10 min down the side of the flask to a −78° C. solution of ethyl 4(diethylphosphoryl)-3-methylbut-2E-enoate (27 mg, 0.10 mmol), 1,3-dimethyl-3,4,5,6-tetrahydro-2(1H)-pyrimidinone (DMPU, 0.5 mL) and THF (1 mL). After 10 min, a solution of (2E)-3-(3-ethoxy-5,5-dimethyl-5,6-dihydro-naphthalen-2-yl)-2-fluoro-but-2-enal (Compound A-58, 6.0 mg, 0.02 mmol) and THF (1 mL) was added, and the resulting solution was warmed to 0° C. and stirred until the reaction was completed (<2 h). The mixture was diluted with water, and the product was extracted with ethyl ether. The combined ether extracts were washed with brine, dried over MgSO₄, and filtered. The solvent was removed under reduce pressure, and the residue was purified by flash column chromatography (silica gel, 2% ethyl acetate in hexanes) and HPLC (normal phase, 1% ethyl acetate in hexanes) to produce the title compound.

¹H NMR (300 MHz, CDCl₃) δ 1.27 (t, J=7.0 Hz, 3H), 1.27 (s, 6H), 1.36 (t, J=7.0 Hz, 3H), 2.08 (d, J=3.8 Hz, 3H), 2.13 (s, 3H), 2.23 (d, J=2.6 Hz, 2H), 4.05 (q, J=7.0 Hz, 2H), 4.15 (q, J=.7.0 Hz, 2I4), 5.83 (dt, J=4.1, 9.4 Hz, 1H), 5.83 (s, 1H), 6.34 (dd, J=15.6, 25.5 Hz, 1H), 6.35 (d, J=9.7 Hz, 1H), 6.49 (d, J=14.9 Hz, 1H), 6.86 (s, 1H), 6.76 (s, 1H).

Ethyl (2E,4E,6E)-7-(3-ethoxy-5,5-dimethyl-5,6-dihydro-naphthalen-2-yl)-6-fluoro-3-methyl-nona-2E,4E,6Z-trienoate (Compound A-68)

Following General Procedure I-1, ethyl 4-(diethoxyphosphoryl)-3-methyl-but-2E-enoate (92 mg, 0.35 mmol) and (2E)-3-(3-ethoxy-5,5-dimethyl-5,6-dihydro-naphthalen-2-yl)-2-fluoro-pent-2-enal (Compound A-59, 21 mg, 0.07 mmol) were reacted to give the title compound as a colorless oil after purification by column chromatography (silica gel, 2% ethyl acetate in hexane) and HPLC (normal phase, 1% ethyl acetate in hexanes).

¹H NMR (300 MHz, CDCl₃): δ 0.96 (t, J=7.6 Hz, 3H), 1.27 (t, J=7.0 Hz, 3H), 1.27 (s, 6H), 1.35 (t, J=7.0 Hz, 3H), 2.11 (s, 3H), 2.23 (d, J=3.5 Hz, 2H), 2.54 (br s, 2H), 4.05 (q, J=7.0 Hz, 2H), 4.15 (q, J=7.0 Hz, 2H), 5.82 (s, 1H), 5.85–5.79 (m, 1H), 6.26 (dd, J=16, 26 Hz, 1H), 6.35 (d, J=9.7 Hz, 1H), 6.49 (d, J=16 Hz, 1H), 6.73 (s, 1H), 6.85 (s, 1H).

Ethyl (2E,4E,6E)-7-(3-ethoxy-8-ethyl-5,5-dimethyl-5,6-dihydro-naphthalen-2-yl)-6-fluoro-3-methyl-nona-2,4,6-trienoate (Compound A-69)

A mixture of (2E)-3-(3-ethoxy-8-ethyl-5,5-dimethyl-5,6-dihydro-naphthalen-2-yl)-2-fluoro-pent-2-en-1-ol (Compound A-51, 38 mg, 0.11 mmol), 4-methylmorpholine N-oxide (40 mg, 0.33 mmol), and tetrapropylammonium perruthenate (catalytic amount) in dichloromethane (2 mL) was stirred at room temperature for 20 min. The mixture was loaded onto a pad of silica gel and eluted with 10% ethyl acetate-hexane to give the intermediate aldehyde (Compound A-60) as a pale yellow syrup. Next, to a solution of 3-(diethoxy-phosphoryl)-but-2-enoic acid ethyl ester (81 mL, 0.33 mmol) in DMPU (1 mL) and THF (2 mL) at −78° C. was added n-butyllithium (1.6 M in hexane, 0.21 mL, 0.33 mmol) dropwise. After 10 min, a solution of the above intermediate aldehyde (Compound A-60, 37 mg, 0.11 mmol) in THF (1 mL) was added. The reaction was gradually warmed to −5° C. over 2 h and by which time it was complete by TLC analysis. The reaction was quenched with saturated aqueous NH₄Cl and extracted with ethyl acetate. The organic layer was washed with brine, dried over Na₂SO₄, and concentrated in vacuo. The residue was purified by flash column chromatography (silica gel, 3% ethyl acetate in hexanes) followed by preparative TLC (silica gel, 5% ethyl acetate in hexanes) to give the title compound as a yellow syrup.

¹H NMR (300 MHz, CDCl₃): δ 0.96 (t, J=7.7 Hz, 3H), 1.11 (t, J=7.2 Hz, 3H), 1.26 (s, 6H), 1.27(t, J=6.9 Hz, 3H), 1.36(t, J=6.9 Hz, 3H), 2.10 (s, 3H), 2.19 (m, 2H), 2.40 (br q, J=7.0 Hz, 2H), 2.55 (m, 2H), 4.05 (q, J=7.0 Hz, 2H), 4.15 (q, J=7.1 Hz, 2H), 5.65 (br t, J=4.4 Hz, 1H), 5.83 (s, 1H), 6.32 (dd, J=25.8, 15.6 Hz, 1H), 6.50 (d, J=15.6 Hz, 1H), 6.87 (s, 1H), 6.94 (s, 1H).

Ethyl (2E,4E,6E)-6-Fluoro-3-(4,4-dimethyl-6-ethoxy-1-isopropyl-3,4-dihydronaphthalen-7-yl)-3-methyl-2,4,6-octatrienoate (Compound A-70)

As described in General Procedure I-1, (2E)-2-fluoro-3-(4,4 dimethyl-6-ethoxy-1-isopropyl-3,4-dihydronaphthalen-7-yl)-2-butenal (Compound A-61, 0.169 g, 0.51 mmol) in THF (2 mL) reacted with the ylide of ethyl 4-(diethylphosphoryl)-3-methylbut-2Z-enoate (0.36 g, 1.36 mmol), in THF (3 mL) and DMPU (0.065 mL) to produce the title compound after purification by flash column chromatography (silica gel, 97:3 hexane/ethyl acetate)

¹H NMR (300 MHz, CDCl₃) δ 1.12 (d, 6H, J=6.5 Hz), 1.23 (s, 6H), 1.27 (t,3H, J=6.5 Hz), 1.37(t, 3H, J=6.0 Hz), 2.10 (d, 3H, J=I Hz), 2.17 (d, 2H, J=2 Hz), 2.85 (m,1H, J=6.0 Hz), 4.06 (q, 2H, J=6.0 Hz), 4.14 (q, 2H, J=6.5 Hz), 5.66 (t, 1H, J=2 Hz), 5.83 (s,1H), 6.41 (dd,1H, J=16, 26 Hz) 6.51 (d,1H, J=16 Hz), 6.87 (s,1H), 7.02 (s,1H).

Ethyl (2E,4E,6E)-6-Fluoro-3-(4,4-dimethyl-6n-propoxy-1-isopropyl-3,4-dihydronaphthalen-7-yl)-3-methyl-2,4,6-octatrienoate (Compound A-71)

As described in General Procedure I-1, (E)-2-fluoro-3-(4,4-dimethyl-6-n-propoxy-1-isopropyl-3,44-dihydronaphthalen-7-yl)-2-butenal (Compound A-62, 0.018 g, 0.052 mmol) reacted with the ylide of ethyl 4-(diethylphosphoryl)-3-methylbut-2Z-enoate (0.053 g, 0.202 mmol) in THF (1 mL) and DMPU (0.01 mL) to produce the title compound after purification by flash column chromatography silica gel, 97:3 hexane/ethyl acetate).

¹H NMR (300 MHz, CDCl₃) δ 1.01 (t, 3H, J=6.3 Hz), 1.12 (d, 6H, J=6.5 Hz), 1.24 (s, 6H), 1.27(t, 3H, J=7.0 Hz), 1.77(m, 2H, J=6.3 Hz), 2.10 (d,3H, J=2 Hz),2.18(d,2H, J=2 Hz),2.85(m, 1H, J=6.5 Hz),3.95(t, 3H, J=6.3 Hz),4.15(q,2H, J=7.0 Hz),5:66(t,1H, J=2 Hz),5.83(s, 1H), 6.38 (dd, 1H, J=16, 26 Hz), 6.53 (d,1H, J=16 Hz), 6.87 (s,1H), 7.02 (s,1H).

Ethyl (2E,4E,6E)-6-Fluoro-3-(4,4-dimethyl-6-(cyclopropyl)methoxy-1-iso-propyl-3-dihydronaphthalen-7-yl)-3-methyl-2,4,6-octatrienoate (Compound A-72)

As described in General Procedure I-1, (E)-2-fluoro-3-(4,4-dimethyl-6-(cyclopropyl)methoxy-1-isopropyl-3,4-dihydronaphthalen-7-yl)-2-butenal (Compound A-63, (0.018 g, 0.051 mmol) reacted with the ylide of ethyl 4-(diethylphosphoryl)-3-methylbut-2Z-enoate (0.053 g, 0.202 mmol) in THF (1 mL) and DMPU (0.01 mL) to produce the title compound after purification by flash column chromatography (silica gel, 97:3 hexane/ethyl acetate).

$^1$H NMR (300 MHz, CDCl$_3$): δ 0.31 (q, 2H, J=4.5 Hz), 0.59 (q, 2H, J=4.5 Hz), 1.12 (d, 6H, J=36.5 Hz), 1.23 (s, 6H), 1.27 (t, 3H, J=7.0 Hz), 2.12(d,3H, J=1 Hz),2.17(d,2H, J=3 Hz),2.85(m, 1H, J=6.5 Hz), 3.85(br t,2H),4.15(q,2H, J=7.0 Hz),5.66(t,1H, J=3 Hz), 5.83 (s, 1H), 6.40 (dd, 1H, J=16, 26 Hz), 6.55 (d,1H, J=16 Hz), 6.86 (s, 1H), 7.03 (s,1H).

Ethyl (2E4E,6E)-6-Fluoro-3-(4,4-dimethyl-6-ethoxy-1-tert-butyl-3,4 dihydronaphthalen-7-yl)-3-methyl-2,4,6-octatrienoate (Compound A-73)

As described in General Procedure I-1, (E)-2-fluoro-3-(4,4-dimethyl-6-ethoxy-1-tert-butyl-3,4-dihydronaphthalen-7-yl)-2-butenal (Compound A-64, 0.011 g, 0.032 mmol) reacted with the ylide of ethyl 4 (diethylphosphoryl)-3-methylbut-2Z-enoate (0.053 g, 0.202 mmol) in THF (1 mL) and DMPU (0.011 mL) to produce the title compound after purification by flash column chromatography (silica gel, 97:3 hexane/ethyl acetate).

$^1$H NMR (300 MHz, CDCl$_3$) δ 1.23 (s, 6H), 1.28 (t, 3H, J=6.0 Hz), 1.29 (s,9H), 1.38(t,3H, J=7.0 Hz),2.10(d,3H, J=1 Hz), 2.14(d,2H, J=3 Hz), 4.07 (q, 2H, J=6.0 Hz), 4.15 (q, 2H, J=7.0 Hz), 5.83 (s,1H), 5.84 (t, 1H, J=3 Hz), 6.40 (dd,1H, J=16, 26 Hz), 6.53 (d, 1H, J=16 Hz), 6.87 (s,1H), 7.34 (s, 1H).

Ethyl (2E,4E,6E)-7-(8-tert-butyl-3-ethoxy-5,5-dimethyl-5,6-dihydronaphthalen-2-yl)-6-fluoro-3-methyl-nona-2,4,6-trienoate (Compound A-74)

As described in General Procedure I-1, (E)-3-(8-tert-butyl-3-ethoxy-5,5-dimethyl-5,6-dihydronaphthalen-2-yl)-2-fluoro-pent-2-enal (Compound A-65, 435 mg, 1.21 mmol) reacted with the ylide of ethyl 4-(diethylphosphoryl)-3-methylbut-2Z-enoate (1.07 g, 4.05 mmol) in THF (10 mL) and DMPU (5 mL) to produce the title compound as an oil after purification by flash chromatography (silica gel, 1% to 2% ethyl acetate in hexane).

$^1$H NMR (300 MHz, CDCl$_3$): δ 0.98 (t, J=7.4 Hz, 3H), 1.23 (s, 6H), 1.27 (t, J=7.0 Hz, 3H), 1.29 (s, 9H), 1.37 (t, J=7.0 Hz, 3H), 2.08 (s, 3H), 2.14 (d, J=4.7 Hz, 2H), 2.51 (m, 1H), 2.66 (m, 1H), 4.06 (m, 2H), 4.14 (q, J=7.0 Hz, 2H),5.81–5.84 (m, 2H), 6.34 (dd, J=15.5 and 25.5 Hz, 1H), 6.52 (d, J=15.5 Hz, 1H), 6.86 (s, 1H), 7.31 (s, 1H).

Ethyl (2E,4E,6E)-6-Fluoro-3-(4,4-dimethyl-6-n-propoxy-1-tert-butyl-3,4-dihydronaphthalen-7-yl)-3-methyl-2,4,6-octatrienoate (Compound A-75)

As described in General Procedure I-1, (E)-2-fluoro-3-(4,4-dimethyl-6-n-propoxy-1-tert-butyl-3,4-dihydronaphthalen-7-yl)-2-butenal (Compound A-66, 0.024 g, 0.067 mmol) reacted with the ylide of ethyl 4 (diethylphosphoryl)-3-methylbut-2Z-enoate (0.053 g, 0.202 mmol) in THF (1 mL) and DMPU (0.01 mL) to produce the title compound after purification by flash column chromatography (silica gel, 97:3 hexane/ethyl acetate).

$^1$H NMR (300 MHz, CDCl$_3$): δ 1.02 (t, 3H, J=6.3 Hz), 1.23 (s, 6H), 1.27 (t,3H, J=6.0 Hz), 1.29 (s, 9H), 1.79 (m,1H, 6.3 Hz), 2.10 (d, 3H, J=2 Hz), 2.14 (d, 2H, J=3 Hz), 3.95 (br t, 2H), 4.15 (q,2H, J=6.0 Hz), 5.83 (s, 1H), 5.84 (t,1H, J=3 Hz), 6.40 (dd,1H, J=16, 26 Hz), 6.52 (d, 1H, J=16 Hz), 6.87 (s, 1H), 7.34 (s, 1H).

(2E,4E,6E)-7-(3-Ethoxy-5,5-dimethyl-5,6-dihydro-naphthalen-2-yl)-6-fluoro-3-methyl-octa-2,4,6-trienoic acid (Compound A-76)

General Procedure J-1

To a solution of ethyl (2E,4E,6E)-7-(3-ethoxy-5,5-dimethyl-5,6-dihydro-naphthalen-2-yl)-6-fluoro-3-methyl-octa-2,4,6-trienoate (Compound A-67, 4.0 mg, 0.01 mmol) in ethanol (0.2 mL) and THF (1 mL) was added 1M NaOH (0.05 mL, 0.05 mmol). The mixture was heated to 60° C. for 5 h and was cooled to room temperature, acidified with 1M HCl, extracted with ethyl acetate. The organic layer was washed with brine, dried over Na$_2$SO$_4$, and concentrated in vacuo. The residue was purified by flash column chromatography (silica gel, 10% ethyl acetate in hexanes) to give the title compound as a white solid.

$^1$H NMR (300 MHz, CDCl$_3$): δ 1.26 (s, 3H), 1.28 (s, 3H), 1.36 (t, J=7.0 Hz, 3H), 2.09 (d, J=3.2 Hz, 3H), 2.13 (s, 3H), 2.23 (d, J=2.4 Hz, 2H), 4.05 (q, J=7.0 Hz, 2H), 5.86 (s, 1H), 5.88–5.81 (m, 1H), 6.49–6.31 (m, 2H), 6.52 (d, J=15.0 Hz, 1H), 6.76 (s, 1H), 6.86 (s, 1H). (2E,4E,6E)-743-Ethoxy-5,5-dimethyl-5,6-dihydro-naphthalen-2-yl)-6-fluoro-3-methyl-nona-2,4,6-trienoic acid (Compound A-77)

Following General Procedure J-1, ethyl (2E,4E,6E)-7-(3-ethoxy-5,5-dimethyl-5,6-dihydro-naphthalen-2-yl)-6-fluoro-3-methyl-nona-2,4,6-trienoate (Compound A-68, 23 mg, 0.056 mmol) was hydrolyzed with 1M NaOH to yield the title compound as a yellow solid after purification by column chromatography (silica gel, 10% ethyl acetate in hexanes) followed by recrystallization from acetonitrile.

$^1$H NMR (300 MHz, CDCl$_3$): δ 0.96 (t, J=7.5 Hz, 3H), 1.27 (s, 6H), 1.35 (t, J=6.9 Hz, 3H), 2.11 (s, 3H), 2.23 (d, J=2.9 Hz, 2H), 2.55 (br s, 2H), 4.04 (q, J=6.9 Hz, 2H), 5.84 (s, 1H), 5.86–5.80 (m, 1H), 6.30 (dd, J=16, 26 Hz, 1H), 6.36 (d, J=9.7 Hz, 1H), 6.51 (d,J=16 Hz, 1H), 6.72 (s, 1H), 6.85 (s, 1H).

(2E,4E,6E)-7-(3-Ethoxy-8-ethyl-5,5-dimethyl-5,6-dihydro-naphthalen-2-yl)-6-fluoro-3-methyl-nona-2,4,6-trienoic acid (Compound A-78)

Following General Procedure J-1, ethyl (2E,4E,6E)-7-(3-ethoxy-8-ethyl-5,5-dimethyl-5,6-dihydro-naphthalen-2-yl)-6-fluoro-3-methyl-nona-2,4,6-trienoate (Compound A-69, 34 mg, 0.077 mmol) in ethanol (2 mL) was hydrolyzed with 1M NaOH to yield the title compound as a yellow solid after purification by flash column chromatography (silica gel, 3% to 50% ethyl acetate in hexane).

$^1$H NMR (300 MHz, CDCl$_3$): δ 0.96 (t, J=7,7 Hz, 3H), 1.10 (t, J=7.5 Hz, 3H), 1.25 (s, 6H), 1.36 (t, J=6.9 Hz, 3H), 2.10 (s, 3H), 2.19-(m, 2H), 2.40 (r q, J=7.2 Hz, 2H), 2.56 (m, 2H), 4.05 (q, J=6.9 Hz, 2H), 5.65 (br t, J=4.5 Hz, 1H), 5.84 (s, 1H), 6.36 (dd, J=25.5, 15.6 Hz, 1H), 6.53 (d, J=15.6 Hz, 1H), 6.87 (s, 1H), 6.93 (s, 1H).

(2E,4E,6E)-6-Fluoro-3-(4,4-dimethylethoxy-1-isopropyl-3,4-dihydronaphthalen-7-yl)-3-methyl-2.4,6-octa-trienoic acid (Compound A-79)

As described in General Procedure J-1, ethyl (2E,4E,6E)-6-fluoro-3-(4,4-dimethyl-6-ethoxy-1-isopropyl-3,4- dihydronaphthalen-7-yl)-3-methyl-2,4,6-octatrienoate (Compound A-70, 0.165 g, 0.375 mmol) in ethanol (2 mL) was treated with a solution of 2 N KOH (1 mL, 2 mmol) to produce the title compound after purification by recrystallization from acetonitrile.

$^1$H NMR (300 MHz, CDCl$_3$) δ 1.12 (d, 6H, J=6.5 Hz), 1.24 (s, 6H), 1.37 (t,3H, J=6.5 Hz),2.11 (s,3H),2.18(d,2H, J=I Hz), 2.85 (m,1H, J=6.5 Hz), 4.07 (q, 2H, J=6.5 Hz), 5.67 (s,1H), 5.85 (s,1H), 6.43 (dd,1H, J=16, 26 Hz) 6.53 (d,1H, J=16 Hz), 6.88 (s,1H), 7.02 (s, 1H).

(2E,4E,6E)-6-Fluoro-3-(4,4-dimethyl-6-n-propoxy-1-isopropyl-3,4-dihydronaphthalen-7-yl)-3-methyl-2,4,6-octa-trienoic acid (Compound A-80)

As described in General Procedure J-1, ethyl (2E,4E,6E)-2-fluoro-3-(4,4-dimethyl-6-n-propoxy-1-isopropyl-3,4-dihydronaphthalen-7-yl)-2-butenoate (Compound A-71, 0.013 g, 0.029 mmol) reacted with 2N KOH (0.5 mL) in ethanol (1 mL) to produce the title compound.

$^1$H NMR (300 MHz, CDCl$_3$): δ 1.01 (t,3H, J=6.3 Hz), 1.12 (d, 6H, J=6.5 Hz), 1.24(s, 6H), 1.77((m,2H, J=6.3 Hz),2.11 (s,3H),2.18 (d,2H, J=1 Hz), 2.85 (m,1H, J=6.5 Hz), 3.95 (t,3H, J=6.3 Hz), 5.66(t,1H, J=1 Hz), 5.85 (s,1H), 6.42 (dd,1H, J=16, 26 Hz), 6.53 (d,1H, J=16 Hz), 6.87 (s,1H), 7.02 (s,1H). (2E,4E,6E)-6-Fluoro-3-(4-dimethyl-6-(cyclopropyl)methoxy-1-isopropyl-3,4-dihydronaphthalen-7-yl)-3-methyl-2,4.6-octa-trienoic acid (Compound A-81)

As described in General Procedure J-1, ethyl (2E,4E,6E)-2-fluoro-3-(4,4-dimethyl-6-(cyclopropyl)methoxy-1-isopropyl-3,4-dihydronaphthalen-7-yl)-2-butenoate (Compound A-72, 012 g, 0.026 mmol) reacted with 2N KOH (0.5 mL) in ethanol (1 mL) to produce the title compound.

$^1$H NMR (300 MHz, CDCl$_3$): δ 0.31 (q, 2H, J=4.5 Hz), 0.59 (q, 2H. J 4.5 Hz), 1.12 (d, 6H, J=6.5 Hz), 1.24 (s, 6H), 1.25 (t, 3H, J=7.0 Hz), 2.13(d,3H, J=1 Hz),2.17(d,2H, J=2 Hz),2.85 (m,1H, J=6.5 Hz), 3.85 (br t, 2H), 5.67 (t, 1H, J=2 Hz), 5.85 (s,1H), 6.44 (dd, 1H, J=16, 26 Hz), 6.55 (d,1H, J=16 Hz), 6.86 (s,1H), 7.02-(s,1H).

(2E,4E,6E)-6-Fluoro-3-(4,4-dimethyl-6-ethoxy-1-tert-butyl-3,4 dihydronaphthalen-7-yl)-3-methyl-2,4,6-octa-trienoic acid (Compound A-82)

As described in General Procedure J-1, ethyl (2E,4E,6E)-2-fluoro-3-(4,4-dimethyl-6-ethoxy-1-tert-butyl-3,4-dihydronaphthalen-7-yl)-2-butenoate (Compound A-73, 0.007 g, 0.015 mmol) reacted with 2N KOH (0.5 mL) in ethanol (1 mL) to produce the title compound.

$^1$H NMR (300 MHz, CDCl$_3$): δ 1.23 (s, 6H), 1.29 (s, 9H), 1.38 (t, 3H, J=7.0 Hz),2.10(d,3H, J=I Hz),2.14(d,2H, J=I Hz),4.08(q,2H, J=7.0 Hz), 5.84 (s,1H), 5.84 (t,1H, J=I Hz), 6.45 (dd,1H, J=15, 26 Hz), 6.54 (d, 1 H, J=15 Hz), 6.87 (s,1H), 7.34 (s,1H).

(2E,4E,6E)-7-(8-tert-Butyl-3-ethoxy-5,5-dimethyl-5,6-dihydronaphthalen-2-yl)-6-fluoro-3-methyl-nona-2,4,6-trienoic acid (Compound A-83)

As described in General Procedure J-1, ethyl (2E,4E,6E)-7-(8-tert-butyl-3-ethoxy-5,5-dimethyl-5,6-dihydronaphthalen-2-yl)-6-fluoro-3-methyl-nona-2,4,6-trienoate (Compound A-74, 520 mg, 1.111 mmol) in THF (5 mL) and ethanol (5 mL) was hydrolyzed with 1.5 N NaOH (5 mL) to produce the title compound as a yellow solid after purification by recrystallization from acetonitrile.

$^1$H NMR (300 MHz, CDCl$_3$): δ 0.98 (t, J=7.4 Hz, 3H), 1.23 (s, 6H), 1.29 (s, 9H), 1.37 (t, J=7.0 Hz, 3H), 2.08 (s, 3H), 2.14 (d, J=4.7 Hz, 2H), 2.50 (m, 1H), 2.66 (m, 1H), 4.06 (m, 2H), 5.84 (m, 2H), 6.38 (dd, J=15.5 and 25.5 Hz, 1H),6.54 (d, J=15.5 Hz, 1H), 6.86 (s, 1H), 7.30 (s, 1H).

(2E,4E,6E)-6-Fluoro-3-(4,$dimethyl-6-n-propoxy-1-tert-butyl-3,4-dihydronaphthalen-7-yl)-3-methyl-2,4,6-octatrienoic acid (Compound A-84)

As described in General Procedure J-1, ethyl (2E,4E,6E)-2-fluoro-3-(4,4-dimethyl-6-n-propoxy-1-tert-butyl-3,4-dihydronaphthalen-7-yl)-2-butenoate (Compound A-75, 0.021 g, 0.052 mmol) reacted with 2N KOH (0.5 mL) in ethanol (1 mL) to produce the title compound.

$^1$H NMR (300 MHz, CDCl$_3$): δ 1.02 (t; 3H, J=6.3 Hz), 1.23 (s, 6H), 1.29 (s, 9H), 1.79 (m, 1H, 6.3 Hz),2.11 (d, 3H, J=3 Hz), 2.14 (d, 2H, J=1 Hz), 3.95 (br t, 2H), 5.84 (s,1H), 5.84 (t,1H, J=I Hz), 6.46 (dd, 1H, J=15, 26 Hz), 6.53 (d, 1H, J=15 Hz), 6.87 (s,1H), 7.34 (s, 1H).

TABLE 8

Receptor Transactivation, Efficacy and Binding Data for Exemplary Compounds of Formula E

| compound | | RAR Trans. EC$_{50}$ nM | | | RXR Trans. EC$_{50}$ nM | | |
| | | RAR Bind. K$_i$ nM | | | RXR Bind K$_i$ nM | | |
| number | Structure | α | β | γ | α | β | γ |
| --- | --- | --- | --- | --- | --- | --- | --- |
| A-76 | 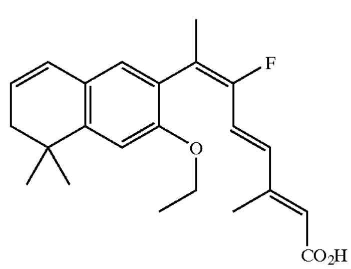 | NA | >10K | >10K | 50 | 368 | 51 |
| | | | | | (104) | (128) | (109) |
| | | 1.6k | 2.6k | 9.2k | 35 | 347 | ND |

TABLE 8-continued

Receptor Transactivation, Efficacy and Binding Data for Exemplary Compounds of Formula E

| compound number | Structure | RAR Trans. EC$_{50}$ nM RAR Bind. K$_i$ nM | | | RXR Trans. EC$_{50}$ nM RXR Bind K$_i$ nM | | |
|---|---|---|---|---|---|---|---|
| | | α | β | γ | α | β | γ |
| A-77 | 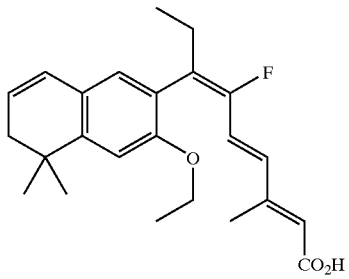 | NA<br>301 | NA<br>371 | 2 | 41<br>(69)<br>6 | >1k<br>63 | 41<br>(73)<br>ND |
| A-78 | 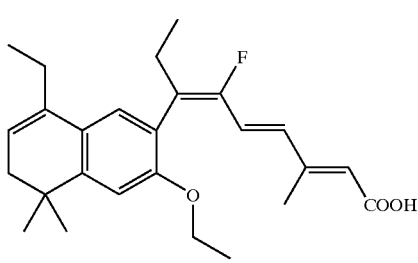 | 29<br>(10)<br>180 | 43<br>(68)<br>477 | NA<br>2.2k | 3<br>(23)<br>3 | 18<br>(23)<br>19 | 4<br>(11)<br>ND |
| A-79 | 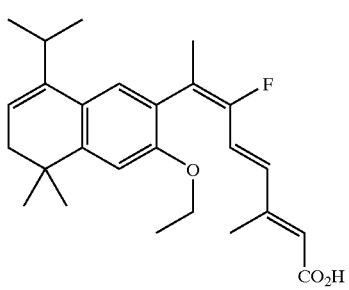 | NA<br>615 | 829<br>(62)<br>1.3k1 | NA<br>3.5k | 1<br>(62)<br>2 | 4<br>(60)<br>13 | 2<br>(59)<br>88 |
| A-80 | 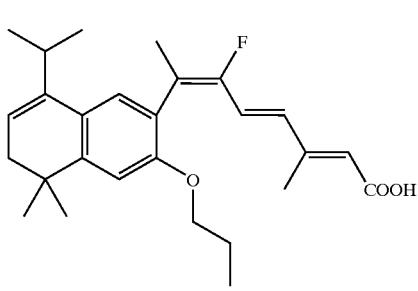 | NA<br>841 | 80<br>(13)<br>552 | NA<br>6.4k | NA<br>10 | NA<br>56 | NA<br>ND |
| A-81 | 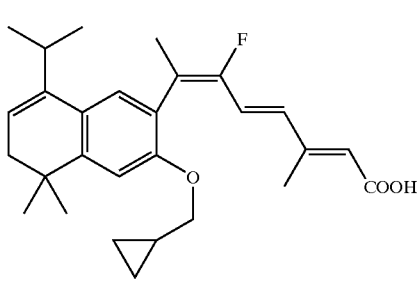 | NA<br>592 | 203<br>(23)<br>927 | NA<br>5.6k | NA<br>12 | NA<br>33 | NA<br>ND |

TABLE 8-continued
Receptor Transactivation, Efficacy and Binding Data for Exemplary Compounds of Formula E
| compound | | RAR Trans. EC$_{50}$ nM RAR Bind. K$_i$ nM | | | RXR Trans. EC$_{50}$ nM RXR Bind K$_i$ nM | | |
|---|---|---|---|---|---|---|---|
| number | Structure | α | β | γ | α | β | γ |
| A-82 | 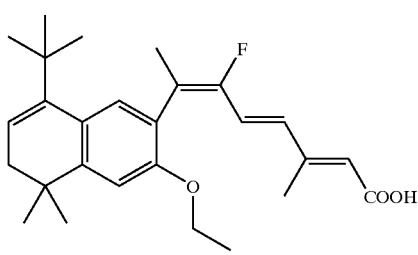 | NA 387 | 170 (9) 400 | NA 1.4k | 1 (43) 2 | 4 (41) 14 | 2 (31) ND |
| A-83 | 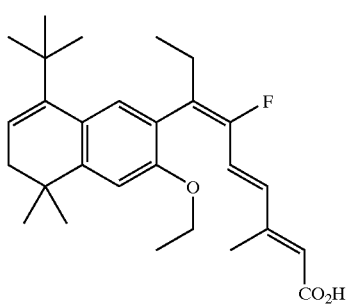 | NA 394 | 31 (12) 261 | NA 698 | 2 (13) 2 | 7 (17) 12 | 2 (7) ND |
| A-84 | 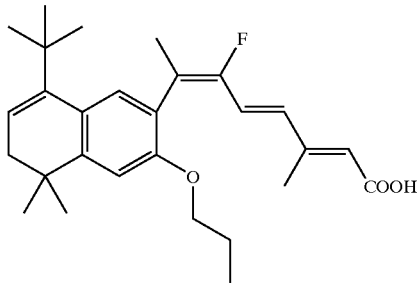 | NA 1.1k | 56 (8) 620 | NA 274 | NA 13 | NA 101 | NA ND |
| | 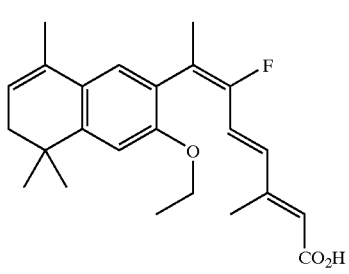 | NA 261 | 316 (26) 359 | NA 1.2k | 3 (62) 2 | 12 (59) 15 | 3 (70) ND |

Section F of Specific Embodiments

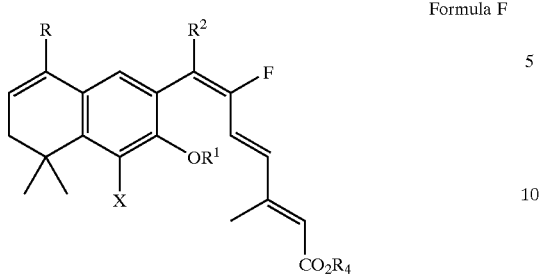

Formula F

Formula F discloses a specific class of preferred and exemplary compounds of the invention. In Formula F:

R represents alkyl of 1 to 8 carbons, more preferably alkyl of 1 to 4 carbons, still more preferably iso-propyl or tert-butyl;

$R^1$ represents alkyl of 1 to 8 carbons, more preferably alkyl of 1 to 4 carbons;

$R^2$ represents alkyl of 1 to 8 carbons, more preferably alkyl of 1 to 4 carbons;

X represents halogen, more preferably Br or Cl, and $R_4$ represents H, alkyl of 1 to 6 carbons, $CH_2OR_5$ or $CH_2OCOR_5$ where $R_5$ is alkyl of 1 to 3 carbons, or a pharmaceutically acceptable salt of said compound.

The synthetic schemes and the experimental procedures for obtaining compounds within the scope of Formula F are provided below.

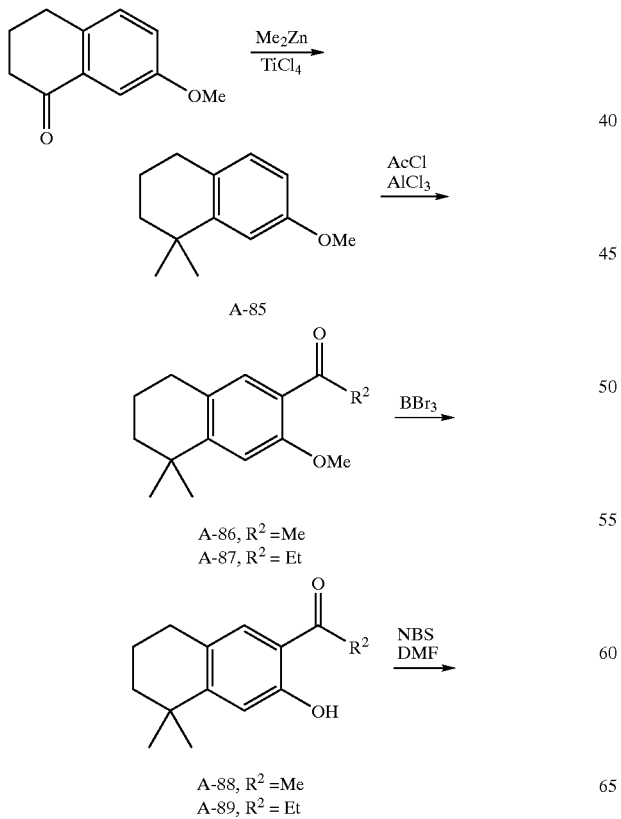

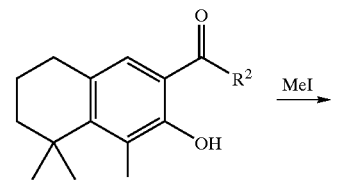

A-91, $R^2$ = Me
A-92, $R^2$ = Et

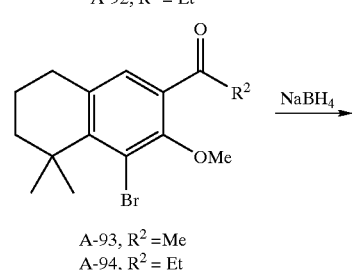

A-93, $R^2$ = Me
A-94, $R^2$ = Et

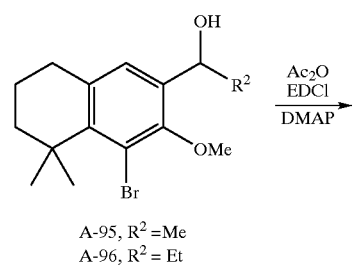

A-95, $R^2$ = Me
A-96, $R^2$ = Et

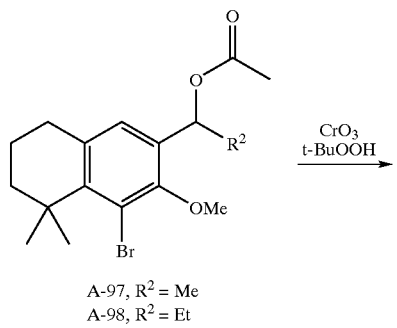

A-97, $R^2$ = Me
A-98, $R^2$ = Et

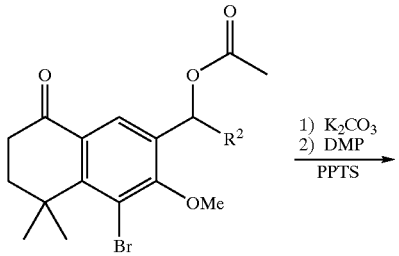

A-99, $R^2$ = Me
A-100, $R^2$ = Et

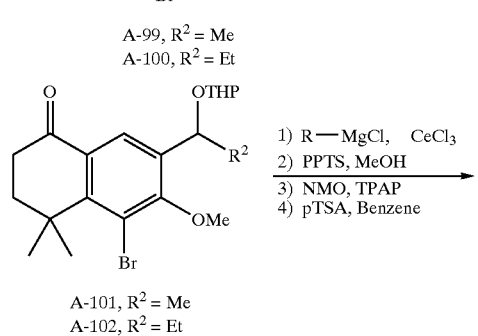

A-101, $R^2$ = Me
A-102, $R^2$ = Et

-continued
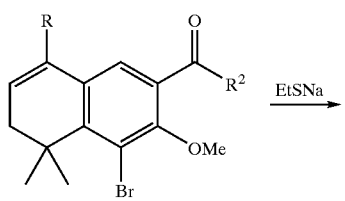
A-103, R = i-Pr, R² = Me
A-104, R = t-Bu, R² = Me
A-105, R = s-Bu, R² = Et
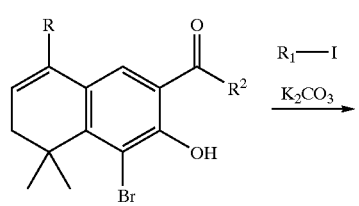
A-106, R = i-Pr, R² = Me
A-107, R = t-Bu, R² = Me
A-108, R = s-Bu, R² = Et
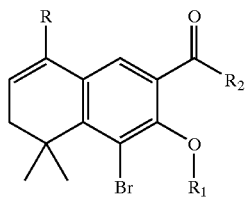
A-109, R = i-Pr, R₁ = Et, R₂ = Me
A-110, R = i-Pr, R₁ = Et, R₂ = Et
A-111, R = i-Pr, R₁ = Et, R₂ = i-Ra
A-112, R = i-Pr, R₁ = i-Pr, R₂ = Me
A-113, R = i-Pr, R₁ = n-Pr, R₂ = Me
A-114, R = t-Bu, R₁ = Et, R₂ = Me
A-115, R = t-Bu, R₁ = i-Pr, R₂ = Me
A-116, R = s-Bu, R₁ = Et, R₂ = Et
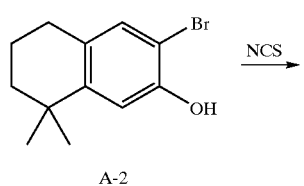
A-2
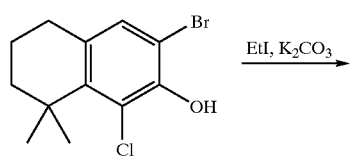
A-117
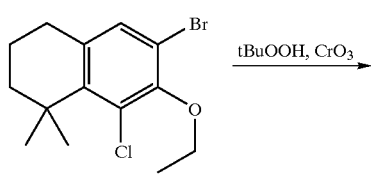
A-118
-continued
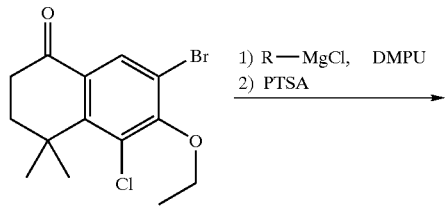
A-119
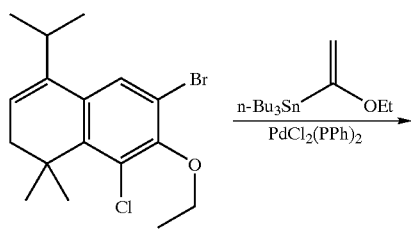
A-120
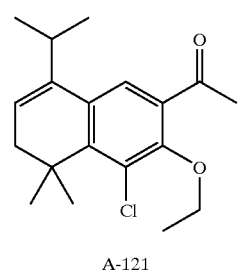
A-121
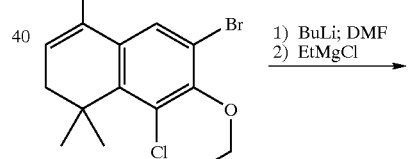
A-120
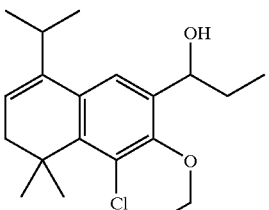
A-122
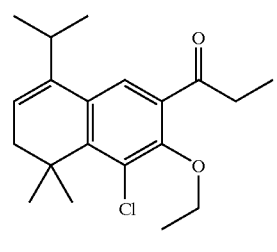
A-123

117

-continued

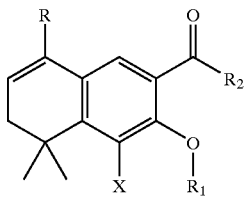

A-108 (R = i-Pr, R₁ = Me, R₂ = Me, X = Br)
A-109 (R = i-Pr, R₁ = Et, R₂ = Me, X = Br)
A-110 (R = i-Pr, R₁ = Et, R₂ = Et, X = Br)
A-111 (R = i-Pr, R₁ = Et, R₂ = i-Pr, X = Br)
A-112 (R = i-Pr, R₁ = i-Pr, R₂ = Me, X = Br)
A-113 (R = i-Pr, R₁ = i-Pr, R₂ = Me, X = Br)
A-114 (R = t-Bu, R₁ = Et, R₂ = Me, X = Br)
A-115 (R = t-Bu, R₁ = i-Pr, R₂ = Me, X = Br)
A-116 (R = s-Bu, R₁ = Et, R₂ = Et, X = Br)
A-121 (R = i-Pr, R₁ = Et, R₂ = Me, X = Cl)
A-123 (R = i-Pr, R₁ = Et, R₂ = Et, X = Cl)

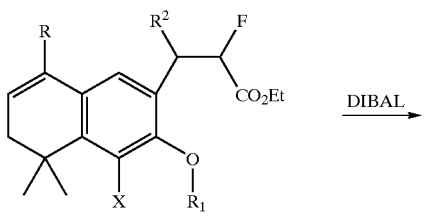

A-124 (R = i-Pr, R₁ = Me, R₂ = Me, X = Br)
A-125 (R = i-Pr, R₁ = Et, R₂ = Me, X = Br)
A-126 (R = i-Pr, R₁ = Et, R₂ = Et, X = Br)
A-127 (R = i-Pr, R₁ = Et, R₂ = i-Pr, X = Br)
A-128 (R = i-Pr, R₁ = i-Pr, R₂ = Me, X = Br)
A-129 (R = i-Pr, R₁ = i-Pr, R₂ = Me, X = Br)
A-130 (R = t-Bu, R₁ = Et, R₂ = Me, X = Br)
A-131 (R = t-Bu, R₁ = i-Pr, R₂ = Me, X = Br)
A-132 (R = s-Bu, R₁ = Et, R₂ = Et, X = Br)
A-133 (R = i-Pr, R₁ = Et, R₂ = Me, X = Cl)
A-134 (R = i-Pr, R₁ = Et, R₂ = Et, X = Cl)

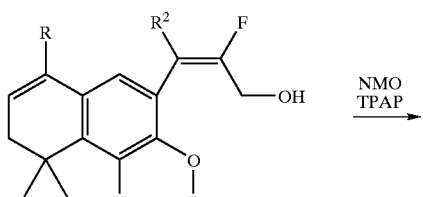

A-135 (R = i-Pr, R₁ = Me, R₂ = Me, X = Br)
A-136 (R = i-Pr, R₁ = Et, R₂ = Me, X = Br)
A-137 (R = i-Pr, R₁ = Et, R₂ = ET, X = Br)
A-138 (R = i-Pr, R₁ = Et, R₂ = i-Pr, X = Br)
A-139 (R = i-Pr, R₁ = i-Pr, R₂ = Me, X = Br)
A-140 (R = i-Pr, R₁ = i-Pr, R₂ = Me, X = Br)
A-141 (R = t-Bu, R₁ = Et, R₂ = Me, X = Br)
A-142 (R = t-Bu, R₁ = i-Pr, R₂ = Me, X = Br)
A-143 (R = s-Bu, R₁ = Et, R₂ = Et, X = Br)
A-144 (R = i-Pr, R₁ = Et, R₂ = Me, X = Cl)
A-145 (R = i-Pr, R₁ = Et, R₂ = Et, X = Cl)

118

-continued

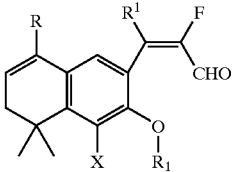

A-146 (R = i-Pr, R₁ = Me, R₂ = Me, X = Br)
A-147 (R = i-Pr, R₁ = Et, R₂ = Me, X = Br)
A-148 (R = i-Pr, R₁ = Et, R₂ = Et, X = Br)
A-149 (R = i-Pr, R₁ = Et, R₂ = i-Pr, X = Br)
A-150 (R = i-Pr, R₁ = i-Pr, R₂ = Me, X = Br)
A-151 (R = i-Pr, R₁ = i-Pr, R₂ = Me, X = Br)
A-152 (R = t-Bu, R₁ = Et, R₂ = Me, X = Br)
A-153 (R = t-Bu, R₁ = i-Pr, R₂ = Me, X = Br)
A-154 (R = s-Bu, R₁ = Et, R₂ = Et, X = Br)
A-155 (R = i-Pr, R₁ = Et, R₂ = Me, X = Cl)
A-156 (R = i-Pr, R₁ = Et, R₂ = Et, X = Cl)

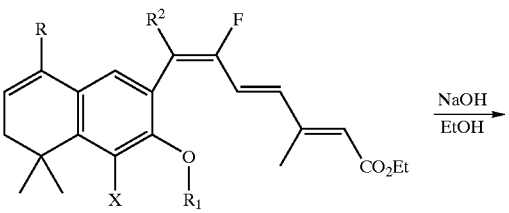

A-157 (R = i-Pr, R₁ = Me, R₂ = Me, X = Br)
A-158 (R = i-Pr, R₁ = Et, R₂ = Me, X = Br)
A-159 (R = i-Pr, R₁ = Et, R₂ = Et, X = Br)
A-160 (R = i-Pr, R₁ = Et, R₂ = i-Pr, X = Br)
A-161 (R = i-Pr, R₁ = i-Pr, R₂ = Me, X = Br)
A-162 (R = i-Pr, R₁ = i-Pr, R₂ = Me, X = Br)
A-163 (R = t-Bu, R₁ = Et, R₂ = Me, X = Br)
A-164 (R = t-Bu, R₁ = i-Pr, R₂ = Me, X = Br)
A-165 (R = s-Bu, R₁ = Et, R₂ = Et, X = Br)
A-166 (R = i-Pr, R₁ = Et, R₂ = Me, X = Cl)
A-167 (R = i-Pr, R₁ = Et, R₂ = Et, X = Cl)

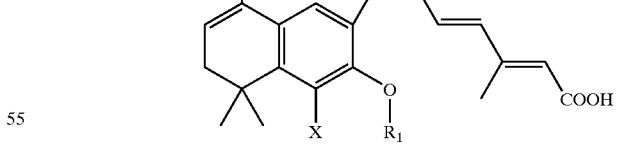

A-168 (R = i-Pr, R₁ = Me, R₂ = Me, X = Br)
A-169 (R = i-Pr, R₁ = Et, R₂ = Me, X = Br)
A-170 (R = i-Pr, R₁ = Et, R₂ = Et, X = Br)
A-171 (R = i-Pr, R₁ = Et, R₂ = i-Pr, X = Br)
A-172 (R = i-Pr, R₁ = i-Pr, R₂ = Me, X = Br)
A-173 (R = i-Pr, R₁ = i-Pr, R₂ = Me, X = Br)
A-174 (R = t-Bu, R₁ = Et, R₂ = Me, X = Br)
A-175 (R = t-Bu, R₁ = i-Pr, R₂ = Me, X = Br)
A-176 (R = s-Bu, R₁ = Et, R₂ = Et, X = Br)
A-177 (R = i-Pr, R₁ = Et, R₂ = Me, X = Cl)
A-178 (R = i-Pr, R₁ = Et, R₂ = Et, X = Cl)

7-Methoxy-1,1-dimethyl-1,2,3,4-tetrahydro-naphthalene (Compound A-85)

To a solution of titanium(IV) chloride (1M in dichloromethane, 205 mL, 205 mmol) at 40° C. under argon was added a solution of dimethylzinc (2 M in toluene, 113.6 mL, 227.2 mmol). The mixture was stirred at 40° C. for 20 min then 7-methoxytetralone (available from Aldrich, 20 g, 113.6 mmol) in dichloromethane (50 mL) was added. After slowly warming to room temperature over 5 h, the mixture was cooled to 0° C. and quenched with methanol and saturated ammonium chloride solution, then extracted with diethyl ether. The combined organic layers were washed with water, brine, dried ($Na_2SO_4$), filtered and concentrated in vacuo. The crude residue was purified by flash chromatography (silica gel, 5% ethyl acetate in hexane) to afford the title compound as a colorless oil.

$^1$H NMR (300 MHz, $CDCl_3$) δ 6.97(d, J=8.5 Hz, 1H), 6.87(d, J=2.6 Hz, 1H), 6.66(dd, J=8.5, 2.6 Hz, 1H) 3.78(s, 3H), 2.70(m, 2H), 1.82–1.74(m, 2H), 1.65–1.63(m, 2H), 1.28(s, 6H)

1-(3-Methoxy-5,5-dimethyl-5,6,7,8-tetrahydro-naphthalen-2-yl)-ethanone (Compound A-86)

To a suspension of aluminum chloride (1–2 g, 90 mmol) in dichloromethane (300 mL) at 0° C. was added acetyl chloride (6.8 ml, 90 mmol). After stirring at 0° C. for 20 min the mixture turned into clear solution. The mixture was then cooled to −78° C. and 7-methoxy-1,1-dimethyl-1,2,3,4-tetrahydro-naphthalene (Compound A-85, 13.2 g, 69 mmol) in dichloromethane (20 mL) was added. After stirring at 78° C. for 2 h the mixture was poured onto ice and extracted with diethyl ether. The combined organic layers were washed with water, brine, dried ($Na_2SO_4$), filtered and concentrated in vacuo. The crude residue was purified by flash chromatography (silica gel, 10% ethyl acetate in hexane) to give the title compound as a white solid.

$^1$H NMR (300 MHz, $CDCl_3$): δ 7.45 (s, 1H), 6.88 (s, 1H), 3.89 (s, 3H), 2.71 (m, 2H), 2.59 (s, 3H), 1.80–1.74 (m, 2H), 1.67–1.63 (m, 2H), 1.30 (s, 6H)

1-(3-Hydroxy-5,5-dimethyl-5,6,7,8-tetrahydro-naphthalen-2-yl)-ethanone (Compound A-88)

To 1-(3-methoxy-5,5-dimethyl-5,6,7,8-tetrahydro-naphthalen-2-yl)-ethanone (Compound A-86, 14.2 g, 61.2 mmol) in dichloromethane (350 mL) at −78° C. was added boron tribromide (1 M in hexane, 80 mL, 80 mmol). After stirring from −78° C. to room temperature over 3 h the reaction mixture was quenched with sodium bicarbonate at −10° C. and extracted with diethyl ether. Combined ethereal layers were washed with water, brine, dried ($Na_2SO_4$), filtered and concentrated in vacuo. Recrystallization from diethyl ether afforded the title compound as a brown solid.

$^1$H NMR (300 MHz, $CDCl_3$): δ 11.90 (s, 1H), 7.40 (s, 1H), 6.93 (s, 1H), 2.72 (m, 2H), 2.59 (s, 3H), 1.82–1.76 (m, 2H), 1.67–1.63 (m, 2H), 1.28 (s, 6H)

1-(4-Bromo-3-hydroxy-5,5-dimethyl-5,6,7,8-tetrahydro-naphthalen-2-yl)-ethanone (Compound A-91)

To a solution of 1-(3-hydroxy-5,5-dimethyl-5,6,7,8-tetrahydro-naphthalen-2-yl)-ethanone (Compound A-88, 13.3 g, 61 mmol) in N,N-dimethylformamide (120 mL) was added N-bromosuccinimide (10.9 mg, 61 mmol). The mixture was stirred at room temperature for 16 h. The mixture was then diluted with water and extracted with diethyl ether. The combined ethereal layers were washed with water, brine, dried ($Na_2SO_4$), filtered and concentrated in vacuo. Recrystallization from diethyl ether and flash column chromatography (silica gel, 5% ethyl acetate in hexane) afforded the title compound as a yellow solid.

$^1$H NMR (300 MHz, $CDCl_3$): δ 12.87 (s, 1H), 7.44 (s, 1H), 2.80 (m, 2H), 2.62 (s, 3H), 1.73 (m, 4H), 1.60 (s, 6H)

1-(4-Bromo-3-methoxy-5,5-dimethyl-5,6,7,8-tetrahydro-naphthalen-2-yl) ethanone (Compound A-93)

To a solution of 1-(4-bromo-3-hydroxy-5,5-dimethyl-5,6,7,8-tetrahydro-naphthalen-2-yl)-ethanone (Compound A-91, 11.8 g, 39.7 mmol), potassium carbonate (14.4 g, 119.1 mmol) in acetone (350 mL) was added methyl iodide (19.8 mL, 317.6 mmol). After heating to reflux for 16 h, the mixture was cooled to room temperature, diluted with water and extracted with diethyl ether. The combined ethereal layers were washed with water, brine, dried ($Na_2SO_4$), filtered and concentrated in vacuo to give the title compound as a yellow oil. The material was used in the next step without further purification.

$^1$HNMR (300 MHz, $CDCl_3$): δ 7.30 (s, 1H), 3.80 (s, 3H), 2.81 (m, 2H), 2.63 (s, 3H), 1.72 (m, 4H), 1.58 (s, 6H)

1-(4-Bromo-3-methoxy-5,5-dimethyl-5,6,7,8-tetrahydro-naphthalen-2-yl)-ethanol (Compound A-95)

To a solution of 1-(4-bromo-3-methoxy-5,5-dimethyl-5,6,7,8-tetrahydro-naphthalen-2-yl)-ethanone (Compound A-93, 12.1 g, 39 mmol) in ethanol (250 mL) was added sodium borohydride (741 mg, 19.5 mmol). After heating to reflux for 2 h the mixture was cooled to room temperature, quenched with 10% HCl and extracted with diethyl ether. The combined ethereal layers were washed with water, brine, dried ($Na_2SO_4$), filtered and concentrated in vacuo to give the title compound as a colorless syrup. The material was used in the next step without further purification.

Acetic acid 1-(4-bromo-3-methoxy-5,5-dimethyl-5,6,7,8-tetrahydro-naphthalen-2-yl)-ethyl ester (Compound A-97)

To a solution of 1-(4-bromo-3-methoxy-5,5-dimethyl-5,6,7,8-tetrahydro-naphthalen-2-yl)-ethanol (Compound A-95, 12.3 g, 39 mmol), 1-(3-dimethylaminopropyl)-3-ethylcarbodiimide hydrochloride (EDCI, 11.2 g, 58.5 mmol) and 4-dimethylaminopyridine (DMAP, 9.5 g, 78 mmol) in dichloromethane (350 mL) at room temperature was added acetic anhydride (3.7 mL, 39 mmol). After stirring at room temperature for 16 h, the mixture was quenched with water and extracted with diethyl ether. The combined ethereal layers were washed with water, brine, dried ($Na_2SO_4$), filtered and concentrated in vacuo. The crude residue was purified by flash chromatography (silica gel, 5% ethyl acetate in hexane) to give the title compound as a colorless oil.

$^1$H NMR (300 MHz, $CDCl_3$): δ 7.03 (s, 1H), 6.12 (q, J=6.5 Hz), 3.86 (s, 3H), 2.79 (m, 2H), 2.08 (s, 3H), 1.69 (m, 4H), 1.56 (s, 6H), 1.49 (d, J=6.5 Hz, 3H)

Acetic acid 1-(4-bromo-3-methoxy-5,5-dimethyl-8-oxo-5,6,7,8-tetrahydro-naphthalen-2-yl)-ethyl ester (Compound A-99)

To a suspension of chromium (VI) oxide (160 mg, 1.6 mmol) in dichloromethane (40 mL) at 0° C. was added tert-butyl hydroperoxide (13 mL, 96 mmol). After stirring at room temperature for 5 min, a solution of acetic acid 1-(4-bromo-3-methoxy-5,5-dimethyl-5,6,7,8-tetrahydro-naphthalen-2-yl)-ethyl ester (Compound A-97, 11.4 g, 32 mmol) in dichloromethane (10 mL) was added. The mixture was stirred at room temperature for 6 days and then quenched with 10% sodium bisulfite.). Organic phase was washed with 10% sodium bisulfite and brine, dried ($Na_2SO_4$), filtered and concentrated in vacuo. Recrystallization from ethyl acetate and flash column chromatography of the mother liquid (silica gel, 10% ethyl acetate in hexane) afforded the title compound as a yellow solid.

$^1$H NMR (300 MHz, $CDCl_3$): 8.13 (s, 1H), 6.11 (q, J=6.5 Hz), 3.95 (s, 3H), 2.67–2.63 (m, 2H), 2.10 (s, 3H), 2.05–2.00 (m, 2H), 1.68 (s, 3H), 1.66 (s, 3H), 1.50 (d, J=6.5 Hz, 3H).

5-Bromo-6-methoxy-4,4-dimethyl-7-[(1-(tetrahydro-pyran-2-yloxy)-ethyl]-3,4-dihydro-2H-naphthalen-1'-one (Compound A-101)

A solution of acetic acid 1-(4-bromo-3-methoxy-5,5-dimethyl-8-oxo-5,6,7,8-tetrahydro-naphthalen-2-yl)-ethyl ester (Compound A-99, 5.88 g, 15.93 mmol), potassium carbonate (4.4 g, 31.86 mmol) in methanol (60 mL) at room temperature was stirred for 1 h. The mixture was diluted with water and extracted with diethyl ether. The ether layer was washed with water, brine, dried ($Na_2SO_4$), filtered and concentrated in vacuo to give crude alcohol as a white solid. To the white solid, pyridium p-toluenesulfonate (128 mg, 0.52 mmol) in dichloromethane (80 mL) was added 3,4-dihydro-2H-pyran (2.9 mL, 31.86 mmol). The mixture was stirred at room temperature for 16 h then concentrated in vacuo. The crude residue was purified by flash chromatography (silica gel, 5% ethyl acetate in hexane) to give the title compound as a colorless syrup.

1-(4-Bromo-8-isopropyl-3-methoxy-5,5-dimethyl-5,6-dihydro-naphthalen-2-yl)-ethanone (Compound A-103)

General Procedure K-1

Cerium (III) chloride heptahydrate (21.5 g, 57.6 mmol) was dried at 150° C. under high vacuum for 16 h without stirring and then 3 h with stirring. The white solid in the flask was cooled to room temperature and switched to argon atmosphere. The flask was placed in an ice-water bath and THF (300 mL) was added. The suspension of cerium (III) chloride was stirred for 16 h at room temperature before placing it back into the ice water bath. A solution of 5-bromo-6-methoxy-4,4-dimethyl-7-[1-(tetrahydro-pyran-2-yloxy)-ethyl]-3,4-dihydro-2H-naphthalen-1-one (Compound A-101, 6.77 g, 16.5 mmol) in THF (30 mL) was added to the suspension of dry cerium chloride in THF at 0° C. and stirred for 1 h. A solution of isopropylmagnesium chloride (2 M in THF, 28.8 mL) was then added to the reaction mixture and stirred for 1 h at 0° C. The reaction mixture was poured onto ice water with 10% HCl, and extracted with diethyl ether. The combined organic layers were washed with water, brine, dried ($Na_2SO_4$), filtered and concentrated in vacuo. The crude residue was purified by flash chromatography (silica gel, 5% ethyl acetate in hexane) to give the corresponding alcohol as a white solid.

To a solution of the white solid (4.2 g 9.23 μmmol) in methanol (80 mL) were added pyridinium p-toluenesulfonate (232 mg, 0.92 mmol) and was heated to reflux for 2 h. The reaction mixture was cooled to room temperature, diluted with water and extracted with diethyl ether. The combined organic layers were washed with water, brine, dried ($Na_2SO_4$), filtered and concentrated in vacuo to give the diol as a yellow syrup. The material was used in the next step without further purification.

To the above syrup in dichloromethane (50 mL) were added 4 Å molecular sieves (1 g), 4-methylmorpholine N-oxide (NMO, 2.7 g, 23.1 mmol), and tetrapropylammonium perruthenate (TPAP, 40 mg). The mixture was stirred at room temperature for 3 h. The mixture was loaded directly onto silica gel column to afford a methyl ketone mixture as a colorless oil.

To a solution of the above ketone mixture and p-toluenesulfonic acid (100 mg) in toluene (100 mL) was heated at 100° C. for 16 h. Toluene was then removed by evaporation. The crude residue was purified by flash chromatography (silica gel, 5% ethyl acetate in hexane) to give the title compound as a yellow oil.

$^1$H NMR (300 MHz, $CDCl_3$): δ 7.56 (s, 1H), 5.81 (t, J=4.8 Hz, 1H), 3.85 (s, 3H), 2.89 (m, 1H), 2.65 (s, 3H), 2.22 (d, J=4.8 Hz, 2H), 1.51 (s, 6H), 1.11 (d, J=6.7 Hz, 6H).

1-(4-Bromo-8-tert-butyl-3-methoxy-5,5-dimethyl-5,6-dihydro-naphthalen-2-yl)-ethanone (Compound A-104)

As described in General Procedure K-1, 5-bromo-6-methoxy-4,4-dimethyl-7-[1-(tetrahydro-pyran-2-yloxy)-ethyl]-3,4-dihydro-2H-naphthalen-1-one (Compound A-101, 2.15 g, 5.23 mmol) gave rise to the title compound in four steps.

$^1$H NMR (300 MHz, $CDCl_3$): δ 7.89 (s, 1H), 5.99 (t, J=4.8 Hz, 1H), 3.84 (s, 3H), 2.64 (s, 3H), 2.14 (d, J=5.2 Hz, 2H), 1.47 (s, 6H), 1.28 (s, 9H)

1-(4-Bromo-3-hydroxy-8-isopropyl-5,5-dimethyl-5,6-dihydro-naphthalen-2-yl)-ethanone (Compound A-106)

General Procedure L-1

Sodium hydride (1.07 g, 26.64 mmol) was rinsed with hexane and suspended in dry N,N-dimethylformamide (80 mL). To the suspension was added ethanethiol (1.9 mL, 26.6 mmol) and stirred at room temperature for 30 min, which resulted in the formation of a clear solution. A solution of 1-(4-bromo-8-isopropyl-3-methoxy-5,5-dimethyl-5,6-dihydronaphthalen-2-yl)-ethanone (Compound A-103, 2.6 g, 7.4 mmol) in N,N-dimethylformamide (10 mL) was added to the solution and the mixture was heated at 130° C. for 5 h. The mixture was cooled to room temperature, acidified with 10% HCl and extracted with diethyl ether. The combined ethereal layers were washed with water, brine, dried ($Na_2SO_4$), filtered and concentrated in vacuo. The crude residue was purified by flash chromatography (silica gel, 5% ethyl acetate in hexane) to yield the title compound as a brown oil.

$^1$H NMR (300 MHz, $CDCl_3$): δ 13.18 (s, 1H), 7.66 (s, 1H; 5.78 (t, J=4.8 Hz, 1H), 2.86 (m, 1H), 2.65 (s, 3H), 2.21 (d, J=4.8 Hz, 2H), 1.51 (s, 6H), 1.14 (d, J=6.7 Hz, 6H).

1-(4-Bromo-8-tert-butyl-3-hydroxy-5,5-dimethyl-5,6-dihydro-naphthalen-2-yl)-ethanone (Compound A-107)

As described in General Procedure L-1, sodium hydride (211 mg, 5.28 mmol) and ethanethiol (0.39 mL, 5.28 mmol) was treated with a solution of 1-(4-bromo-8-tert-butyl-3-methoxy-5,5-dimethyl-5,6-dihydro-naphthalen-2-yl)-ethanone (Compound A-104, 536 mg, 1.47 mmol) in N,N-dimethylformamide to afford the title compound after purification by flash chromatography (silica gel, 5% ethyl acetate in hexane).

¹H NMR (300 MHz, CDCl₃): δ 13.09 (s, 1H), 7.99 (s, 1H), 5.99 (t, J=4.8 Hz, 1H), 2.65 (s, 3H), 2.16 (d, J=5.2 Hz, 2H), 1.49 (s, 6H), 1.31 (s, 9H).

1-(4-Bromo-3-ethoxy-8-isopropyl-5,5-dimethyl-5,6-dihydro-naphthalen-2-yl)-ethanone (Compound A-109)

General Procedure M-1

A mixture of 1-(4-bromo-3-hydroxy-8-isopropyl-5,5-dimethyl-5,6-dihydro-naphthalen-2-yl)-ethanone (Compound A-106, 1.61 g, 4.77 mmol), potassium carbonate (1.97 g, 14.31 mmol) and ethyl iodide (3.8 mL, 47.7 mmol) in acetone (50 mL) was heated to reflux for 16 h. The reaction mixture was cooled to room temperature, diluted with water and extracted with diethyl ether. The combined ethereal layers were washed with water, brine, dried (Na₂SO₄), filtered and concentrated in vacuo to give the title compound as a yellow oil. The material was used in the next step without further purification.

¹H NMR (300 MHz, CDCl₃): δ 7.52 (s, 1H), 5.80 (t, J=4.8 Hz, 1H), 3.96 (q, J=7.0 Hz, 2H), 2.88 (m, 1H), 2.64 (s, 3H), 2.21 (d, J=4.8 Hz, 2H), 1.50 (s, 6H), 1.46 (t, J=7.0 Hz, 3H), 1.11 (d, J=6.7 Hz, 6H).

1-(4-Bromo-3-ethoxy-8-isopropyl-5,5-dimethyl-5,6-dihydro-naphthalen-2-yl)-propan-1-one (Compound A-110)

To a solution of 1-(4-bromo-3-ethoxy-8-isopropyl-5,5-dimethyl-5,6-dihydro-naphthalen-2-yl)-ethanone (Compound A-109, 1.75 g, 4.81 mmol) in THF (33 mL) at −78° C. was added lithium diisopropylamide (1.5 M in cyclohexane, 3.85 mL, 5.78 mmol). The bath was removed and the mixture was stirred for 2.5 h. The mixture was cooled to −78° C. again and methyl iodide was added. The mixture was stirred at room temperature for 16 h, quenched with saturated ammonium chloride, and extracted with diethyl ether. The combined ethereal layers were washed with water, brine, dried (Na₂SO₄), filtered and concentrated in vacuo. The crude residue was purified by flash chromatography (silica gel, 2% ethyl acetate in hexanes) followed by HPLC (normal phase, 2% ethyl acetate in hexanes) to give the title compound as clear oil.

¹H NMR (300 MHz, CDCl₃): δ 7.43 (s, 1H), 5.80 (t, J=4.8 Hz, 1H), 3.96 (q, J=7.0 Hz, 2H), 3.0 (q, J=7.3 Hz, 2H), 2.87 (m, 1H), 2.21 (d, J=4.8 Hz, 2H), 1.50 (s, 6H), 1.43 (t, J=7.0 Hz, 3H), 1.18 (t, J=7.3 Hz, 3H), 1.11 (d, J=6.7 Hz, 6H).

1-(4-Bromo-3-ethoxy-8-isopropyl-5,5-dimethyl-5,6-dihydro-naphthalen-2-yl)2-methyl-propan-1-one (Compound A-111)

To a solution of 1-(4-bromo-3-ethoxy-8-isopropyl-5,5-dimethyl-5,6-dihydro-naphthalen-2-yl)-ethanone (Compound A-109, 512 mg, 1.4 mmol) in THF (10 mL) at −78° C. was added lithium diisopropylamide (1.5 M in cyclohexane, 2.0 mL, 3.0 mmol). The cold bath was removed and the mixture was stirred for 3 h. The mixture was cooled to −78° C. again and methyl iodide (0.52 mL, 8.34 mmol) was added. The mixture was stirred at room temperature for 16 h then quenched with ammonium chloride (sat), extracted with diethyl ether. The combined ethereal layers were washed with water, brine, dried (Na₂SO₄), filtered and concentrated in vacuo. The crude residue was purified by flash chromatography (silica gel, 2% ethyl acetate in hexanes) followed by HPLC (Waters-Nova Pak column, 2% ethyl acetate in hexanes) to give the title compound.

¹H NMR (300 MHz, CDCl₃) δ 7.28 (s, 1H), 5.79 (t, J=4.7 Hz, 1H), 3.92 (q, J=7.0 Hz, 2H), 3.48 (sept, J=6.9 Hz, 1H), 2.84 (sept, J=6.6 Hz, 1H), 2.21 (d, J=3.8, 2H), 1.49 (s, 3H), 1.39 (t, J=7.0 Hz, 3H), 1.50 (d, J=7.0 Hz, 6H), 1.10 (d, J=6.7 Hz, 6H).

1-(4-Bromo-3-isopropoxy-8-isopropyl-5,5-dimethyl-5,6-dihydronaphthalen-2-yl)-ethanone (Compound A-112)

As described in General Procedure M-1, 1-(4-bromo-3-hydroxy-8-isopropyl-5,5-dimethyl-5,6-dihydro-naphthalen-2-yl)-ethanone (Compound A-106, 266 mg, 0.75 mmol), potassium carbonate (314 mg, 2.25 mmol) and 2-iodopropane (0.76 mL, 7.5 mmol) were reacted in acetone to produce the title compound. The crude material was used in the next step without purification.

¹H NMR (300 MHz, CDCl₃): δ 7.42 (s, 1H), 5.80 (t, J=4.8 Hz, 1H), 4.34 (m, 1H), 2.87 (m, 1H), 2.62 (s, 3H), 2.21 (d, J=4.8 Hz, 2H), 1.50 (s, 6H), 1.31 (d, J=6.4 Hz, 6H), 1.10 (d, J=6.7 Hz, 6H).

1-(4-Bromo-8-isopropyl-5,5-dimethyl-3-propoxy-5,6-dihydro-naphthalen-2-yl)-ethanone (Compound A-113)

As described in General Procedure M-1, 1-(4-bromo-3-hydroxy-8-isopropyl-5,5-dimethyl-5,6-dihydro-naphthalen-2-yl)-ethanone (Compound A-106, 210 mg, 0.60 mmol), potassium carbonate (248 mg, 1.8 mmol) and 1-iodopropane (0.58 mL, 6.0 mmol) were reacted in acetone to produce the title compound. The crude material was used in the next step without purification.

¹H NMR (300 MHz, CDCl₃): δ 7.50 (s, 1H), 5.80 (t, J=4.8 Hz, 1H), 3.83 (t, J=7.0 Hz, 2H), 2.88 1H), 2.64 (s, 3H), 2.21 (d, J=4.8 Hz, 2H), 1.89 (m, 2H), 1.50 (s, 6H), 1.11 (d, J=6.7 Hz, 6H), 1.07 (m, 3H).

1-(4-Bromo-8-tert-butyl-3-ethoxy-5,5-dimethyl-5,6-dihydro-naphthalen-2-yl)-ethanone (Compound A-114)

As described in General Procedure M-1, 1-(4-bromo-8-tert-butyl-3-hydroxy-5,5-dimethyl-5,6-dihydro-naphthalen-2-yl)-ethanone (Compound A-107, 223 mg, 0.64 mmol) in acetone was treated with potassium carbonate (263 mg, 1.91 mmol) and iodoethane (0.64 mL, 6.35 mmol) to produce the title compound. The crude material was used in the next step without purification.

¹H NMR (300 MHz, CDCl₃): δ 7.85 (s, 1H), 6.00 (t, J=4.8 Hz, 1H), 3.97 (q, J=6.7 Hz, 2H), 2.65 (s, 3H), 2.15 (d, J=5.2 Hz, 2H), 1.48 (s, 6H), 1.47 (in, 3H), 1.29 (s, 9H).

1-(4-Bromo-8-tert-butyl-3-isopropoxy-5,5-dimethyl-5,6-dihydro naphthalen-2-yl)-ethanone (Compound A-115)

As described in General Procedure M-1, 1-(4-bromo-8-tert-butyl-3-hydroxy-5,5-dimethyl-5,6-dihydro-naphthalen-2-yl)-ethanone (Compound A-1107, 150 mg, 0.43 mmol) in acetone was treated with potassium carbonate (177 mg, 1.28 mmol) and 2-iodopropane (0.43 mL, 4.27 mmol) to produce the title compound. The crude material was used in the next step without purification.

¹H NMR (300 MHz, CDCl₃): δ 7.74 (s, 1H), 5.99 (t, J=4.8 Hz, 1H), 4.33 (m, 1H), 2.62 (s, 3H), 2.17 (r, 2H), 1.48 (s, 6H), 1.2–1.4 (in, 15H).

1-(4-Bromo-8-sec-butyl-3-ethoxy-5,5-dimethyl-5,6-dihydro-naphthalen-2-yl)-propran-1-one (Compound A-116)

As described in General Procedure K-1, 5-bromo-6-ethoxy-4,4 dimethyl-7-{1-[1-(tetrahydro-pyran-2-yloxy)- ethoxy]-propyl}-3,dihydro-2H-naphthalen-1-one (Compound A-102, 2.60 g, 5.92 mmol) gave rise to the title compound in four steps.

$^1$H NMR (300 MHz, CDCl$_3$) δ 7.42 (s, 1H), 5.78 (t, J=4.7 Hz, 1H), 3.94 (q, J=7.0 Hz, 2H), 3.00 (q, J=7.3 Hz, 2H), 2.63 (sext, J=6.6 Hz, 1H), 2.30–2.15 (in 2H), 1.55 (s, 3H), 1.47(s, 3H), 1.43 (t, J=7.0 Hz, 3H), 1.30–1.23 (m, 2H), 1.18 (t, J=7.3 Hz, 3H), 1.11 (d,J=6.7 Hz, 3H), 0.88 (t, J=7.3 Hz, 3H).

3-Bromo-1-chloro-8,8-dimethyl-5,6,7,8-tetrahydro-naphthalene-2-ol (Compound A-117)

To a solution of 3-bromo-8,8-dimethyl-5,6,7,8-tetrahydronaphthale-2-ol (Compound A-2, 3.9 g, 15.39 mmol) in THF (30 mL) was added N-chlorosuccinimide (2.04 g, 15.39 mmol) and stirred at room temperature for 24 h. The reaction was quenched with water and extracted with ether. The organic layers were washed successively with water, brine, dried over Na$_2$SO$_4$, and concentrated in vacuo. Purification by flash column chromatography (silica gel, 2% ethyl acetate/hexane) yielded the title compound as an oil.

$^1$H NMR (300 MHz, CDCl$_3$): δ 1.48 (s, 6H), 1.67–1.72 (m, 4H), 2.70 (t, J=6.2 Hz, 2H), 5.99 (s, 1H), 7.17 (s, 1H).

6-Bromo-8-chloro-7-ethoxy-1'-dimethyl-1,2,3,4-tetrahydronaphthalene (Compound A-118)

A mixture of 3-bromo-1-chloro-8,8-dimethyl-5,6,7,8-tetrahydro-naphthalene-2-ol (Compound A-117, 3.9 g, 13.49 mmol), iodoethane (5 mL, 54 mmol), and potassium carbonate (4.68 g, 18.11 mmol) in acetone (30 mL) was stirred at 70° C. overnight. The solvent was removed in vacuo. The residue was purified by column chromatography (silica gel, 2.5% ethyl acetate in hexane) to afford the title compound as a pale yellow oil.

$^1$H NMR (300 MHz, CDCl$_3$): δ 1.46 (t, J=7.0 Hz, 3H), 1.49 (s, 6H), 1.65–1.71 (m, 4H), 2.71 (t, J=6.1 Hz, 2H), 4.03 (q, J=7.0 Hz, 2H), 7.19 (s, 1H).

7-Bromo-5-chloro-6-ethoxy-4,4-dimethyl-3,4-dihydro-2H-naphthalen-1-one (Compound A-119)

To a solution of 6-bromo-8-chloro-7-ethoxy-1,1-dimethyl-1,2,3,4 tetrahydronaphthalene (Compound A-118, 4.1 g, 12.93 mmol) in dichloromethane (20 mL) and tert-butyl hydroperoxide (20 mL) at room temperature was added a catalytic amount of chromium (VI) oxide. The reaction was stirred overnight. Quenched with the reaction with water followed by extraction with ether. The organic layers were washed with water, brine, dried over Na$_2$SO$_4$ and concentrated in vacuo. Purification by flash column chromatography (silica gel, 2% ethyl acetate/hexane) yielded the title compound as a white solid.

$^1$H NMR (300 MHz, CDCl$_3$): δ 1.50 (t, J=7.0 Hz, 3H), 1.61 (s, 6H), 2.01 (t, J=6.8 Hz, 2H), 2.64 (t, J=6.8 Hz, 2H), 4.11 (q, J=7.0 Hz, 2H), 8.20 (s, 1H).

6-Bromo-8-chloro-7-ethoxy-4-isopropyl-1,1-dimethyl-1,2-dihydronaphthalene (Compound A-120)

To a solution of 7-bromo-5-chloro-6-ethoxy-4,4-dimethyl-3,4-dihydro-2H-naphthalen-1-one (Compound A-119, 0.78 g, 2.35 mmol) in THF (10 mL) and DMPU (3 mL) at −30° C. was added a solution of isopropylmagnesium bromide (2M in THF, 5.8 mL, 11.79 mmol). The reaction was allowed to warm to 10° C. during 3 h. The reaction was quenched with ice water and extracted with ether. The organic layer was washed successively with water, brine, dried over Na$_2$SO$_4$, and concentrated in vacuo. Column chromatography was applied to isolate the desired alcohol product as oil, which was then dissolved in benzene (10 mL). After catalytic amount of p-toluenesulfonic acid was added, the reaction mixture was heated to reflux for 2 h. The solvent was removed in vacuo. The residue was purified by column chromatography (silica gel, 1% ethyl acetate in hexane) to afford the title compound as a pale yellow oil.

$^1$H NMR (300 MHz, CDCl$_3$): δ 10.11 (d, J=6.4 Hz, 6H), 1.43 (s, 6H), 1.47 (t, J=7.0 Hz, 3H), 2.18 (d, J=5.0 Hz, 2H), 2.88 (hept, J=6.4 Hz, 1H), 4.07 (q, J=7.0 Hz, 2H), 5.79 (t, J=5.0 Hz, 1H), 7.40 (s, 1H).

1-(4-Chloro-3-ethoxy-8-isopropyl-5,5-dimethyl-5,6-dihydronaphthalene-2-yl)-ethanone (Compound A-121)

As described in General Procedure E-1, 6-bromo-8-chloro-7-ethoxy-4-isopropyl-1,1-dimethyl-1,2-dihydronaphthalene (Compound A-120, 0.28 g, 0.78 mmol), tributyl(1-ethoxyvinyl)tin (564 mg, 0.52 mmol) and dichlorobis(triphenylphosphine)palladium (II) (0.045 g, 0.062 mmol) were reacted in THF (12 mL) to produce the title compound as a colorless oil after purification by flash chromatography (silica gel, 1% to 4% ethyl acetate in hexane).

$^1$H NMR (300 MHz, CDCl$_3$): δ 1.11 (d, J=6.7 Hz, 6H), 1.45 (t, J=7.0 Hz, 3H), 1.46 (s, 6H), 2.20 (d, J=4.8 Hz, 2H), 2.65 (s, 3H), 2.90 (hept, J=6.7 Hz, 1H), 4.07 (q, J=7.0 Hz, 2H), 5.80 (t, J=4.8 Hz, 1H), 7.50 (s, 1H).

1-(4-Chloro-3-ethoxy-8-isopropyl-5,5-dimethyl-5,6-dihydronaphthalen-2-yl)-propan-1-ol (Compound A-122)

To a solution of 6-bromo-8-chloro-7-ethoxy-4-isopropyl-1 μl-dimethyl-1,2-dihydronaphthalene (Compound A-120, 0.3 g, 0.84 mmol) in ether (5 mL) at −78 DC was added n-butyllithium (1.6 M in hexanes, 1.15 mL, 1.84 mmol) and stirred at −78° C. for 25 min. N,N-dimethylformamide (1 mL) was added and the reaction mixture was allowed to warm up 40° C. during 5 min. The reaction mixture was quenched with water and extracted with ether. The combined organic layers were washed with water and brine, dried over MgSO$_4$ and concentrated under reduced pressure. The crude material was then dissolved in THF (4 mL) at 0° C. A solution of ethylmagnesium bromide (2.0 M in THF, 1.26 mL, 2.52 mmol) was added. The reaction was stirred at 0° C. for 30 min and at room temperature for 1 h. The reaction mixture was quenched with water and extracted with ether. The combined organic layers were washed with water and brine, dried over Na$_2$SO$_4$ and concentrated under reduced pressure. The residue was purified by flash column chromatography (silica gel, 5% to 10% ethyl acetate in hexane) yielding the title compound as an oil.

$^1$H NMR (300 MHz, CDCl$_3$): δ 0.99 (t, J=7.3 Hz, 3H), 1.09–1.13 (m, 6H), 1.43–1.50 (m, 9H), 1.80 (m, 2H), 2.09 (d, J=4.4 Hz, 1H), 2.19 (d, J=4.7 Hz, 2H), 2.89 (m, 1H), 4.03 (m, 2H), 4.90 (m, 1H), 5.75 (t, J=4.7 Hz, 1H), 7.29 (s, 1H).

1-(4-Chloro-3-ethoxy-8-isopropyl-5,5-dimethyl-5,6-dihydronaphthalen-2-yl)-propan-1-one (Compound A-123)

As described in General Procedure H-1, 1-(4-chloro-3-ethoxy-8-isopropyl-5,5-dimethyl-5,6-dihydronaphthalen-2-yl)-propan-1-ol (Compound A-122, 120 mg, 0.36 mmol), 4-methylmorpholine N-oxide (84 mg, 0.72 mmol) were reacted in dichloromethane (4 mL) and acetonitrile (2 mL) to produce the title compound as an r purification by flash chromatography (silica gel, 10% ethyl acetate in hexane).

¹H NMR (300 MHz, CDCl₃): δ 1.03 (s, J=6.7 Hz, 6H), 1.10 (t, J=7.3 Hz, 3H), 1.34(t, J=7.0 Hz, 3H), 1.38(s, 6H), 2.13 (d, J=4.7 Hz, 2H), 2.89 (d, J H), 2.93 (q, J=7.3 Hz, 2H), 3.90 (q, J=7.0 Hz, 2H, 5.72 (t J=4.7 Hz, 1H), 7.34 (s,

Ethyl (2E)-3-(4-bromo-8-isopropyl-3-methoxy-5,5-dimethyl-5,6-dihydro-naphthalen-2-yl)-2-fluoro-but-2-enoate (Compound A-124)

As described in General Procedure F-1, 1-(4-bromo-8-isopropyl-3-methoxy-5,5-dimethyl-5,6-dihydro-naphthalen-2-yl)-ethanone (Compound A-103, 358 mg, 1.02 mmol) and triethyl 2-fluoro-2-phosphonoacetate (0.83 µL, 4.08 mmol) were reacted with n-butyllithium (1.6 M in hexanes, 2.55 mL, 4.08 mmol) in THF to produce the title compound after purification by flash column chromatography (silica gel, 2% ethyl acetate in hexane).

¹H NMR (300 MHz, CDCl₃): δ 6.96(s, 1H), 5.77 (t, J=4.8 Hz, 1H), 4.04 (m, 2H), 3.73 (s, 3H), 2.78 (m, 1H), 2.20 (d, J=4.7 Hz, 2H), 2.14 (d, J=4.7 Hz, 3H), 1.49 (s, 6H), 1.08 (d, J=6.7 Hz, 6H), 0.99 (m, 3H).

Ethyl (2E)-3-(4-bromo-3-ethoxy-8-isopropyl-5,5-dimethyl-5,6,dihydro-naphthalen-2-yl)-2-fluoro-but-2-enoate (Compound A-125)

As described in General Procedure F-1, 1-(4-bromo-3-ethoxy-8-isopropyl-5,5-dimethyl-5,6-dihydro-naphthalen-2-yl)-ethanone (Compound A-109, 1.08 g, 2.96 mmol) and triethyl 2-fluoro-2-phosphonoacetate (2.86 g, 11.84 mmol) were reacted with n-butyllithium (1.6 M in hexanes, 7.4 mL, 11.84 mmol) in THF to produce the title compound after purification by flash column chromatography (silica gel, 2% ethyl acetate in hexane).

¹H NMR (300 MHz, CDCl₃): δ 6.97 (s, 1H), 5.76 (t, J=4.8 Hz, 1H), 4.04 (m, 2H), 3.90 (m, 2H), 2.78 (m, 10H), 2.20 (d, J=4.7 Hz, 2H), 2.15 (d, J=4.7 Hz, 3H), 1.49 (s, 6H), 1.37 (m, 3H), 1.08 (d, J=6.7 Hz, 6H), 0.99 (m, 3H).

Ethyl (2E)3-(4-bromo-3-ethoxy-8-isopropyl-5,5-dihydro-naphthalen-2-yl)-2-fluoro-pent-2-enoate (Compound A-126)

As described in General Procedure F-1, 1-(4-bromo-3-ethoxy-8-isopropyl-5,5-dimethyl-5,6-dihydro-naphthalen-2-yl)-propan-1-one (Compound A-110, 970 mg, 2.56 mmol) and triethyl 2-fluoro-2-phosphonoacetate (2.48 g, 10.24 mmol) were reacted with n-butyllithium (1.6 M in hexanes, 6.4 mL, 10.24 mmol) in THF to produce the title compound after purification by flash column chromatography (silica gel, 2% ethyl acetate in hexane).

¹H-NMR (300 MHz, CDCl₃): δ 6.91 (s, 1H), 5.75 (t, J=4.8 Hz, 1H), 4.08-3.84 (m, 4H), 2.78 (m, 2H), 2.48 (m, 1H), 2.20 (d, J=4.7 Hz, 2H), 1.49 (s, 6H), 1.36 (m, 3H), 1.07 (d, J=6.7 Hz, 6H), 1.03–0.96 (m, 6H).

Ethyl (2E)-3-(4-bromo-3-ethoxy-8-isopropyl-5,5-dimethyl-5,6-dihydro-naphthalen-2-yl)-2-fluoro-4-methyl-pent-2-enoate (Compound A-127)

As described in General Procedure F-1, 1-(4-bromo-3-ethoxy-8-isopropyl-5,5-dimethyl-5,6-dihydro-naphthalen-2-yl)-2-methyl-propan-1-one (Compound A-111, 234 mg, 0.60 mmol) and triethyl 2-fluoro-2-phosphonoacetate (576 mg, 2.38 mmol) were reacted with n-butyllithium (1.6 M in hexanes, 1.48 mL, 2.38 mmol) in THF to produce the title compound as a clear oil after purification by flash column chromatography (silica gel, 2% ethyl acetate in hexane).

¹H NMR (300 MHz, CDCl₃) δ 6.76 (s, 1H, 5.67 (t, J=4.4 Hz, 1H), 3.97–3.69 (m, 4H), 2.99 (sept, J=6.9 Hz, 1 H), 2.69 (sept, J=6.4 Hz, 1H), 2.13 (d, J=5.9 Hz, 2H), 1.43 (s, 3H), 1.40 (s, 3H), 1.29 (t, J=7.0 Hz, 3H), 1.06 (d, J=7.0 Hz, 6H), 0.99 (d, J=6.7 Hz, 6H), 0.88 (t, J=7.2 Hz, 3H).

Ethyl (2E)-3-(4-bromo-3-isopropoxy-8-isopropyl-5,5-dimethyl-5,6-dihydro-naphthalen-2-yl)-2-fluoro-but-2-enoate (Compound A-128)

As described in General Procedure F-1, 1-(4-bromo-3-isopropoxy-8-isopropyl-5,5-dimethyl-5,6-dihydro-naphthalen-2-yl)-ethanone (Compound A-112, 262 mg, 0.69 mmol) and triethyl 2-fluoro-2-phosphonoacetate (669 mg, 2.76 mmol) were reacted with n-butyllithium (1.6 M in hexanes, 1.73 mL, 2.76 mmol) in THF to produce the title compound after purification by flash column chromatography (silica gel, 2% ethyl acetate in hexane).

¹H NMR (300 MHz, CDCl₃): δ 6.98 (s, 1H), 5.76 (t, J=4.8 Hz, 1H), 4.38 (m, 1H), 4.06 (m, 2H), 2.78 (m, 1H), 2.20 (d, J=4.7 Hz, 2H), 2.15 (d, J=4.7 Hz, 3H), 1.50 (s, 6H), 1.27 (s, 6H), 1.09 (d, J=6.7 Hz, 6H), 1.00 (m, 3H).

Ethyl (2E)-3-(4-bromo-3-propoxy-8-isopropyl-5,5-dimethyl-5,6-dihydro-naphthalen-2-yl)-2-fluoro-but-2-enoate (Compound A-129)

As described in General Procedure F-1, 1-(4-bromo-8-isopropyl-5,5-dimethyl-3-propoxy-5,6-dihydro-naphthalen-2-yl)-ethanone (Compound A-113, 202 mg, 0.53 mmol) and triethyl 2-fluoro-2-phosphonoacetate (516 mg, 2.12 mmol) were reacted with n-butyllithium (1.6 M in hexanes, 1.33 mL, 2.12 mmol) in THF to produce the title compound after purification by flash column chromatography (silica gel, 2% ethyl acetate in hexane).

¹H NMR (300 MHz, CDCl₃): δ 6.97 (s, 1H), 5.77 (t, J=4.8 Hz, 1H), 4.37 (br s, 2H), 3.80 (m, 2H), 2.79 (m, 1H), 2.21 (d, J=4.7 Hz, 2H), 2.16 (d, J=4.7 Hz, 3H), 1.77 (m, 2H), 1.50 (s, 6H), 1.09 (d, J=6.7 Hz, 6H), 1.01 (m, 6H).

Ethyl (2E)-3-(4-bromo-8-tert-butyl-3-ethoxy-5,5-dimethyl-5,6-dihydro-naphthalen-2-yl)-2-fluoro-but-2-enoate (Compound A-130)

As described in General Procedure F-1, 1-(4-bromo-8-tert-butyl-3-ethoxy-5,5-dimethyl-5,6-dihydro-naphthalen-2-yl)-ethanone (Compound A-114, 98 mg, 0.26 mmol) and triethyl-2-fluoro-2-phosphonoacetate (250 mg, 1.03 mmol) were reacted with n-butyllithium (1.6 M in hexanes, 0.65 mL, 1.03 mmol) in THF to produce the title compound after purification by flash column chromatography (silica gel, 2% ethyl acetate in hexane).

¹H NM (300 MHz, CDCl₃): δ 7.25 (s, 1H), 5.96 (t, J=4.8 Hz, 1H), 4.00–4.10 (m, 2H), 3.90–4.00 (m, 2H), 2.12–2.16 (m, 5H), 1.47 (s, 6H), 1.36 (m, 3H), 1.25 (s, 9H), 1.00 (m, 3H).

Ethyl (2E)-3-(4-bromo-8-tert-butyl-3-isopropoxy-5,5-dimethyl-5,6-dihydro-naphthalen-2-yl)-2-fluoro-but-2-enoate (Compound A-131)

As described in General Procedure F-1, 1-(4-bromo-8-tert-butyl-3-isopropoxy-5,5-dimethyl-5,6-dihydro-naphthalen-2-yl)-ethanone (Compound A-115, 143 mg, 0.36 mmol) and triethyl 2-fluoro-2-phosphonoacetate (352 mg, 1.46 mmol) were reacted with n-butyllithium (1.6 M in hexanes, 0.91 mL, 1.46 mmol) in THF to produce the title compound after purification by flash column chromatography (silica gel, 2% ethyl acetate in hexane).

¹H NMR (300 MHz, CDCl₃): δ 7.27 (s, 1H), 5.97 (t, J=4.8 Hz, 1H), 4.38 (m, 1H), 4.05 (m, 2H), 2.11–2.16 (m, 5H), 1.48 (s, 3H), 1.46 (s, 3H), 1.20–1.40 (m, 15H), 0.99 (m, 3H)

Ethyl (2E)-3-(4-bromo-8-sec-butyl-3-ethoxy-5,5-dimethyl-5,6-dihydro-naphthalen-2-yl)-2-fluoro-rent-2-enoate (Compound A-132)

As described in General Procedure F-1, 1-(4-bromo-8-sec-butyl-3-ethoxy-5,5-dimethyl-5,6-dihydro-naphthalen-2-yl)-propran-1-one (Compound A-116, 530 mg, 1.35 mmol) and triethyl 2-fluoro-2-phosphonoacetate (1.3 g, 5.4 mmol) were reacted with n-butyllithium (1.6 M in hexanes, 3.4 mL, 5.4 mmol) in THF to produce the title compound as a yellow oil after purification by flash column chromatography (silica gel, 2% ethyl acetate in hexane).

$^1$H NMR (300 MHz, CDCl$_3$) δ 6.90 (s, 1H), 5.74 (t, J=4.7 Hz, 1H), 4.11–3.78 (m, 4H), 2.82–2.68 (m, 1H), 2.57–2.41 (m, 2H), 2.30–2.14 (m, 2H), 1.55 (s, 3H), 1.44 (s, 3H), 1.39–1.26 (m, 2H), 1.36 (t, J=7.0 Hz, 3H), 1.08 (d, J=6.7 Hz, 3H), 0.98 (t, J=7.2 Hz, 3H), 0.85 (t, J=7.3 Hz, 3H).

Ethyl (E)-3-(4-chloro-3-ethoxy-8-isopropyl-5,5-dimethyl-5,6-dihydronaphthalen-2-yl)-2-fluoro-but-2-enoate (Compound A-133)

As described in General Procedure F-1, 1-(4-chloro-3-ethoxy-8-isopropyl-5,5-dimethyl-5,6-dihydronaphthalen-2-yl)-ethanone (Compound A-121, 0.23 g, 0.72 mmol) and triethyl 2-fluoro-2-phosphonoacetate (566 mg, 2.3 μmmol) were reacted with n-butyllithium (1.6 M in hexanes, 1.46 mL, 2.3 mmol) in THF to produce the title compound after purification by flash column chromatography (silica gel, 2% to 4% ethyl acetate in hexane).

$^1$H NMR (300 MHz, CDCl$_3$): δ 0.99 (t, J=7.1 Hz, 3H), 1.10 (d, J=6.7 Hz, 6H), 1.35 (t, J=7.0 Hz, 3H), 1.45 (s, 6H), 2.15(d, J=4.4 Hz, 3H), 2.20 (d, J=4.8 Hz, 2H), 2.79 (hept, J=6.7 Hz, 1H), 3.90 (br, 2H), 4.03 (br, 2H), 5.75 (t, J=4.8 Hz, 1H), 6.92 (s, 1H).

(2E)-3-(4-Bromo-8-isopropyl-3-methoxy-5,5-dimethyl-5,6-dihydro-naphthalen-2-yl)-2-fluoro-but-2-en-1-ol (Compound A-135)

Following General Procedure G-1, ethyl (2E)-3-(4-bromo-8-isopropyl-3-methoxy-5,5-dimethyl-5,6-dihydro-naphthalen-2-yl)-2-fluoro-but-2-enoate (Compound A-124, 313 mg, 0.71 mmol) and diisobutylaluminum hydride (1 M in methylene chloride, 1.7 mL, 1.7 mmol) were reacted to give the title compound as a colorless oil after purification by flash chromatography (silica gel, 10% ethyl acetate in hexanes).

$^1$H NMR (300 MHz, CDCl$_3$): δ 7.07 (s, 1H), 5.80 (t, J=4.8 Hz, 1H), 4.04 (m, 2H), 3.73 (s, 3H), 2.81 (m, 1H), 2.22 (d, J=4.7 Hz, 2H), 2.04 (d, J=4.7 Hz, 3H), 1.50 (s, 6H), 1.10 (d, J=6.7 Hz, 6H).

(2E)-3-(4-Bromo-3-ethoxy-8-isopropyl-5,5-dimethyl-5,6-dihydro-naphthalen-2-yl)-2-fluoro-but-2-en-1-ol (Compound A-136)

Following General Procedure G-1, ethyl (2E)-3-(4-bromo-3-ethoxy-8-isopropyl-5,5 dimethyl-5,6-dihydro-naphthalen-2-yl)-2-fluoro-but-2-enoate (Compound A-125, 1.2 g, 2.65 mmol) and diisobutylaluminum hydride (1 M in methylene chloride, 6.35 mL, 6.35 mmol) were reacted to give the title compound as a colorless oil after purification by flash chromatography (silica gel, 10% ethyl acetate in hexanes).

$^1$H NMR (300 MHz, CDCl$_3$): δ 7.07 (s, 1H), 5.79 (t, J=4.8 Hz, 1H), 3.84.1 (m, 4H), 2.81 (m, 10H), 2.22 (d, J=4.7 Hz, 2H), 2.04 (d, J=4.7 Hz, 3H), 1.49 (s, 6H), 1.41 (m, 3H), 1.10 (d, J=6.7 Hz, 6H)

(2E)-3-(4-Bromo-3-ethoxy-8-isopropyl-5,5-dimethyl-5,6-dihydro-naphthalen-2-yl)-2-fluoro-pent-2-en-1-ol (Compound A-137)

Following General Procedure G-1, ethyl (2E)-3-(4-bromo-3-ethoxy-8-isopropyl-5,5-dimethyl-5,6-dihydro-naphthalen-2-yl)-2-fluoro-pent-2-enoate (Compound A-126, 1.07 g, 2.29 mmol) and diisobutylaluminum hydride (1M in methylene chloride, 5.5 mL, 5.5 mmol) were reacted to give the title compound as a colorless oil after purification by flash chromatography (silica gel, 10% ethyl acetate in hexanes).

$^1$H NMR (300 MHz, CDCl$_3$): δ 7.04 (s, 1H, 5.77 (t, J=4.8 Hz, 1H), 3.63.9 (m, 4H), 2.80 (m, 1H), 2.53 (m, 2H), 2.21 (d, J=4.7 Hz, 2H), 1.49 (s, 6H), 1.41 (m, 3H), 1.09 (d, J=6.7 Hz, 614), 0.99 (m, 3H).

(2E)-3-(4-Bromo-3-ethoxy-8-isopropyl-5,5-dimethyl-5,6-dihydro-naphthalen-2-yl)-2-fluoro-4-methyl-pent-2-en-1-ol (Compound A-138)

Following General Procedure G-1, (2E)-3-(4-bromo-3-ethoxy-8-isopropyl-5,5-dimethyl-5,6-dihydro-naphthalen-2-yl)-2-fluoro-4-methyl-pent-2-enoic acid ethyl ester (Compound A-127, 196 mg, 0.40 mmol) and diisobutylaluminum hydride (1 M in methylene chloride, 1.0 mL, 1.0 mmol) were reacted to give the title compound as a yellow syrup after purification by flash chromatography (silica gel, 10% ethyl acetate in hexanes).

$^1$H NMR (300 MHz, CDCl$_3$) δ 6.92 (s, 1H), 5.71 (t, J=4.4 Hz, 1H), 3.92–3.79 (m, 4H), 2.90 (sept, J=7.0 Hz, 1H), 2.71 (sept, J=6.5 Hz, 1H), 2.40 (br s, 1H), 2.14 (dd, J=5.0, 1.2 Hz, 2H), 1.42 (s, 6H), 1.34 (t, JF7.0 Hz, 3H), 1.11 (dd, J=7.0, 0.9 Hz, 3H), 1.03 (d, J=6.7 Hz, 3H), 1.01 (d, J=6.7 Hz, 6H).

(2E)-3-(4-Bromo-3-isopropoxy-8-isopropyl-5,5-dimethyl-5,6-dihydro naphthalen-2-yl)-2-fluoro-but-2-en-1-ol (Compound A-139)

Following General Procedure G-1, ethyl (2E)-3-(4-bromo-3-isopropoxy-8-isopropyl-5,5-dimethyl-5,6-dihydro-naphthalen-2-yl)-2-fluoro-but-2-enoate (Compound A-128, 282 mg, 0.60 mmol) and diisobutylaluminum hydride (1 M in methylene chloride, 2.4 mL, 2.4 mmol) were reacted to give the title compound as a colorless oil after purification by flash chromatography (silica gel, 10% ethyl acetate in hexanes).

$^1$H NMR (300 MHz, CDCl$_3$): δ 7.06 (s, 1H), 5.79 (t, J=4.8 Hz, 1H), 4.38 (m, 1H), 3.904.10 (n, 2H), 2.70–2.90 (m, 1H), 2.22 (d, J=4.7 Hz, 2H), 2.02 (d, J=4.7 Hz, 3H), 1.50 (s, 6H), 1.27 (s, 6H), 1.10 (d, J=6.7 Hz, 6H).

(2E)-3-(4-Bromo-8-isoprpyl-5,5-ethyl-3-propoxy-5,6-dihydro-naphthalen-2-yl)-2-fluoro-but-2-en-1-ol (Compound A-140)

Following General Procedure G-1, ethyl (2E)-3-(4-bromo-3-propoxy-8-isopropyl-5,5-dimethyl-5,6-dihydro-naphthalen-2-yl)-2-fluoro-but-2-enoate (Compound A-129, 215 mg, 0.46 mmol) and diisobutylaluminum hydride (1 M in methylene chloride, 1.1 mL, 1.1 mmol) were reacted to give the title compound as a colorless oil after purification by flash chromatography (silica gel, 10% ethyl acetate in hexanes).

$^1$H NMR (300 MHz, CDCl$_3$): δ 7.06 (s, 1H), 5.79 (t, J=4.8 Hz, 1H), 3.90–4.10 (m, 2H), 3.77 (m, 2H), 2.81 (m, 1H), 2.22 (d, J=4.7 Hz, 2H), 2.03 (d, J=4.7 Hz, 3H), 1.81 (m, 2H), 1.49 (s, 6H), 1.10 (d, J=6.7 Hz, 6H), 1.01 (m, 3H).

(2E)-3-(4-Bromo-8-tert-butyl-1-3-ethoxy-5,5-dimethyl-5,6-dihydro-naphthalen-2-yl)-2-fluoro-but-2-en-1-ol (Compound A-141)

Following General Procedure G-1, ethyl (2E)-3-(4-bromo-8-tert-butyl-3-ethoxy-5,5-dimethyl-5,6-dihydronaphthalen-2-yl)-2-fluoro-but-2-enoate (Compound A-130, 80 mg, 0.17 mmol) and diisobutylaluminum hydride (1 M in methylene chloride, 0.46 mL, 0.46 mmol) were reacted to give the title compound as a colorless oil after purification by flash chromatography (silica gel, 10% ethyl acetate in hexanes).

$^1$H NMR (300 MHz, CDCl$_3$): δ 7.35 (s, 1H), 5.99 (t, J=4.8 Hz, 1H), 3.80–4.10 (m, 4H), 2.15 (m, 2H), 2.04 (m, 3H), 1.47 (s, 6H), 1.41 (m, 3H), 1.27 (s, 9H).

(2E)-3-(4-Bromo-8-tert-butyl-3-isopropoxy-5,5-dimethyl-5,6-dihydro-naphthalen-2-yl)-2-fluoro-but-2-en-1-ol (Compound A-142)

Following General Procedure G-1, ethyl (2E)-3-(4-bromo-8-tert-butyl-3-isopropoxy-5,5-dimethyl-5,6-dihydro-naphthalen-2-yl)-2-fluoro-but-2-enoate (Compound A-131, 115 mg, 0.24 mmol) and diisobutylaluminum hydride (1M in methylene chloride, 0.64 mL, 0.64 mmol) were reacted to give the title compound as a colorless oil after purification by flash chromatography (silica gel, 10% ethyl acetate in hexanes).

$^1$H NMR (300 MHz, CDCl$_3$): δ 7.36 (s, 1H), 5.98 (t, J=4.8 Hz, 1H), 4.38 (m, 1H), 3.90.4.10 (m, 2H), 2.16 (m, 2H), 2.03 (m, 3H), 1.49 (s, 3H), 1.45 (s, 3H), 1.20–1.40 (m, 15H).

(2E)-3-(4-Bromo-8-sec-butyl-3-ethoxy-5,5-dimethyl-5,6-dihydro-naphthalen-2-yl)-2-fluoro-pent-2-en-1-ol (Compound A-143)

As described in General Procedure G-1, (2E)-3-(4-bromo-8-sec-butyl-3-ethoxy-5,5-dimethyl-5,6-dihydronaphthalen-2-yl)-2-fluoro-pent-2-enoic acid ethyl ester (Compound A-132, 567 mg, 1.18 mmol) and diisobutylaluminum hydride (1M in methylene chloride, 2.84 mL, 2.84 mmol) were reacted to give the title compound as a colorless oil after purification by flash chromatography (silica gel, 10% to 15% ethyl acetate in hexanes).

$^1$H NMR (300 MHz, CDCl$_3$) δ 7.03 (s, 1H); 5.77 (t, J=4.7 Hz, 1H), 4.10–3.84 (m, 4H), 2.30–2.15 (m, 2H), 1.57 (s, 3H), 1.55 (s, 3H), 1.45 (t, J=7.0 Hz, 3H), 1.10(d, J=6.7 Hz, 3H), 1.01 (t, J=7.5 Hz, 3H), 0.87 (t, J=7.3 Hz, 3H).

(2E)-3-(4-Chloro-3-ethoxy-8-isopropyl-5,5-dimethyl-5,6 dihydronaphthalen-2-yl)-2-fluoro-but-2-en-1-ol (Compound A-144)

Following General Procedure G-1, ethyl (2E)-3-(4-chloro-3-ethoxy-8-isopropyl-5,5-dimethyl-5,6-dihydronaphthalen-2-yl)-2-fluoro-but-2-enoate (Compound A-133, 0.27 g, 0.66 mmol) and diisobutylaluminum hydride (1M in methylene chloride, 2.64 mL, 2.64 mmol) were reacted to give the title compound as a colorless oil after purification by flash chromatography (silica gel, 10% to 15% ethyl acetate in hexanes).

$^1$H NMR (300 MHz, CDCl$_3$): δ 1.10 (d, J=6.8 Hz, 6H), 1.39 (t, J=7.0 Hz, 3H), 1.45 (s, 6H), 2.02(d, J=4.0 Hz, 3H), 2.20 (d, J=4.8 Hz, 2H), 2.67 (t, J=36.5 Hz), 2.81 (hept, J=6.7 Hz, 1H), 3.89.4.05 (m, 4H), 5.78 (t, J=4.8 Hz, 1H), 7.02 (s, 1H).

(2E)-3-(4-Chloro-3-ethoxy-8-isopropyl-5,5-dimethyl-5,6-dihydronaphthalen-2-yl)-2-fluoro-pent-2-en-1-ol (Compound A-145)

A solution of n-butyllithium (1.6 M in hexanes, 0.56 mL, 0.90 mmol) was added over 10 min down the side of the flask to a −78° C. solution of ethyl 4-(diethylphosphoryl)-3-methylbut-2Z-enoate (218 mg, 0.90 mmol), 1,3-dimethyl-3,4,5,6-tetrahydro-2(I)-pyrimidinone (DMPU, 0.5 mL) and THF (3 mL). After 10 min, a solution of 1-(4-chloro-3-ethoxy-8-isopropyl-5,5-dimethyl-5,6-dihydronaphthalen-2-yl)-propan-1-one (Compound A-123, 100 mg, 0.3 mmol) and THF (2 mL) was added, and the resulting solution was warmed to 0° C. and stirred until the reaction was completed (<2 h). The mixture was diluted with water, and the product was extracted with ethyl ether. The combined ether extracts were washed with brine, dried over MgSO$_4$, and filtered. Concentration of the filtrate under reduced pressure gave rise to an inseparable mixture of esters.

Following General Procedure G-1, the ester mixture was treated with diisobutylaluminum hydride (1 M in methylene chloride, 1.3 mL, 1.3 mmol) to give the title compound as a colorless oil after purification by HPLC purification (normal phase, 5% ethyl acetate in hexanes).

$^1$H NMR (300 MHz, CDCl$_3$): δ 1.00 (t, J=7.3 Hz, 3H), 1.10 (d, J=6.7 Hz, 6H), 1.40 (t, J=7.0 Hz, 3H), 1.45 (s, 6H), 2.21 (d, J=4.7 Hz, 2H), 2.47–2.56 (r, 2H), 2.80 (m, 1H), 3.95–4.05 (r, 4H), 5.78 (t, J=4.7 Hz, 1H), 7.00 (s, 1H).

(2E)-3-(4-Bromo-8-isopropyl-3-methoxy-5,5-dimethyl-5,6-dihydro-naphthalen-2-yl)-2-fluoro-but-2-enal (Compound A-146)

As described in General Procedure H-1, (2E)-3-(4-bromo-8-isopropyl-3-methoxy-5,5-dimethyl-5,6-dihydro-naphthalen-2-yl)-2-fluoro-but-2-en-1-ol (Compound A-135, 130 mg, 0.33 mmol), tetrapropylammonium perruthenate (10 mg, 0.028 mmol) and 4 methylmorpholine N-oxide (77 mg, 0.66 mmol) were reacted in acetonitrile and dichloromethane to give the title compound after purification by flash column chromatography (silica gel, 5% ethyl acetate in hexane).

$^1$H NMR (300 MHz, CDCl$_3$) δ 9.32(d, J=19.6 Hz, 1H), 7.10(s,1H),5.84(t, J=4.8 Hz, 1H), 3.74(s, 3H), 2.77(m, 1H), 2.29(d, J=3.8 Hz, 3H), 2.24(d, J=4.7 Hz, 2H), 1.51(s, 6H), 1.10(d, J=6.7 Hz, 6H)

(2E)-3-(4-Bromo-3-ethoxy-8-isopropyl-5,5-dimethyl-5,6-dihydro-naphthalen-2-yl)-2-fluoro-but-2-enal (Compound A-147)

As described in General Procedure H-1, (2E>3-(4-bromo-3-ethoxy-8-isopropyl-5,5-dimethyl-5,6-dihydro-naphthalen-2-yl)- 2-fluoro-but-2-en-1-ol (Compound A-136, 908 mg, 2.2 mmol), tetrapropylammonium perruthenate (20 mg, 0.057 mmol) and 4-methylmorpholine N-oxide (516 mg, 4.4 mmol) were reacted in acetonitrile and dichloromethane to give the title compound after purification by flash column chromatography (silica gel, 5% ethyl acetate in hexane).

$^1$H NMR (300 MHz, CDCl$_3$): δ 9.31 (d, J=19.6 Hz, 1H), 7.09 (s, 1H), 5.83 (t, J=4.8 Hz, 1H), 3.88 (m, 2H), 2.77-(m, 1H), 2.28 (d, J=3.8 Hz, 3H), 2.24 (d, J=4.7 Hz, 2H), 1.51 (s, 6H), 1.37 (m, 3H), 1.10 (d, J=6.7 Hz, 6H).

(2E)-3-(4-Bromo-3-ethoxy-8-isopropyl-5,5-dimethyl-5,6-dihydro naphthalen-2-yl)-2-fluoro-pent-2-enal (Compound A-148)

As described in General Procedure H-1, (2E)-3-(4-bromo-3-ethoxy-8-isopropyl-5,5-dimethyl-5,6-dihydro-naphthalen-2-yl)-2-fluoro-pent-2-en-1-ol (Compound A-137, 885 mg, 2.08 mmol), tetrapropylammonium perruthenate (20 mg, 0.057 mmol) and 4-methylmorpholine N-oxide (487 mg, 4.16 mmol) were reacted in acetonitrile and dichloromethane to give the title compound after purification by flash column chromatography (silica gel, 5% ethyl acetate in hexane).

$^1$H NMR (300 MHz, CDCl$_3$): δ 9.29 (d, J=19.6 Hz, 1H), 7.05 (s, 1H), 5.83 (t, J=4.8 Hz, 1H), 3.95 (m, 1H), 3.84 (m, 1H), 2.78 (m, 2H), 2.68 (m, 1H), 2.24 (d, J=4.7 Hz, 2H), 1.51 (d, J=10.3 Hz, 6H), 1.37 (m, 3H), 1.09 (d, J=6.7 Hz, 6H), 1.05 (m, 3H)

(2E)-3-(4-Bromo-3-ethoxy-8-isopropyl-5,5-dimethyl-5,6-dihydro-naphthalen-2-yl)-2-fluoro-4-methyl-pent-2-enal (Compound A-149).

As described in General Procedure H-1, (2E)-3-(4-bromo-3-ethoxy-8-isopropyl-5,5-dimethyl-5,6-dihydro-naphthalen-2-yl)-2-fluoro-4-methyl-pent-2-en-1-ol (Compound A-138, 140 mg, 0.32 mmol), tetrapropylammonium perruthenate (10 mg, 0.028 mmol) and 4 methylmorpholine N-oxide (94 mg, 0.80 mmol) were reacted in acetonitrile and dichloromethane to give the title compound as a white solid after purification by flash column chromatography (silica gel, 5% ethyl acetate in hexane).

$^1$H NMR (300 MHz, CDCl$_3$) δ 9.13 (d, J=18.8 Hz, 1H), 6.92 (s, 1H), 5.75 (t, J=0.4 Hz, 1H), 3.98–3.67 (m, 2H), 3.00 (sept, J=7.0 Hz, 1H), 2.70 (sept, J=6.3 Hz, 1H), 2.23–2.09 (m, 2H), 1.46 (s, 3H), 1.41 (s, 3H), 1.31 (t, J=7.0 Hz, 3H), 1.16 (dd, J-6.9, 1.0 Hz, 3H), 1.12 (d, J=7.0 Hz, 3H), 1.03(d, 6.7 Hz, 3H), 1.02 (d, J=6.7, 1.8 Hz, 3H).

(2E)-3-(4-Bromo-3-isopropoxy-8-isopropyl-5,5-dimethyl-5,6-dihydro-naphthalen-2-yl)-2-fluoro-but-2-enal (Compound A-150)

As described in General Procedure H-1, (2E)-3-(4-bromo-3-isopropoxy-8-isopropyl-5,5-dimethyl-5,6-dihydro-naphthalen-2-yl)-2-fluoro-but-2-en-1-ol (Compound A-139, 220 mg, 0.52 mmol), tetrapropylammonium peruthenate (10 mg, 0.028 mmol) and 4-methylmorpholine N-oxide (151 mg, 1.25 mmol) were reacted in acetonitrile and dichloromethane to give the title compound after purification by flash column chromatography (silica gel, 5% ethyl acetate in hexane).

$^1$H NMR (300 MHz, CDCl$_3$): δ 9.33 (d, J=19.6 Hz, 1H), 7.09 (s,1H), 5.83 (t, J=4.8 Hz, 1H), 4.43 (m, 1H), 2.79 (m, 1H), 2.27 (d, J=3.8 Hz, 3H), 2.24 (d, J=4.7 Hz, 2H), 1.54 (s, 3H), 1.48 (s, 3H), 1.25 (d, J=6.1 Hz, 6H), 1.10 (d, J=6.7 Hz, 6H).

(2E)-3-(4-Bromo-3-propoxy-8-isopropyl-5,5-dimethyl-5,6-dihydro-naphthalen-2-yl)12-fluoro-but-2-enal (Compound A-151)

As described in General Procedure H-1, (2E)-3-(4-bromo-8-isopropyl-5,5-dimethyl-3-propoxy-5,6-dihydro-naphthalen-2-yl)-2-fluoro-but-2-en-1-ol (Compound A-140, 158 mg, 0.37 mmol), tetrapropylammonium perruthenate (10 mg, 0.028 mmol) and 4-methylmorpholine N-oxide (109 mg, 0.93 mmol) were reacted in acetonitrile and dichloromethane to give the title compound after purification by flash column chromatography (silica gel, 5% ethyl acetate in hexane).

$^1$H NMR (300 MHz, CDCl$_3$): δ 9.31 (d, J=19.6 Hz, 1H), 7.10 (s, 1H), 5.83 (t, J=4.8 Hz, 1H), 3.74–3.84 (m, 2H), 2.79 (m, 10H), 2.28 (d, J=3.8 Hz, 3H), 2.24 (d, J=4.7 Hz, 2H), 1.77 (m, 2H), 1.51 (s, 6H), 1.10 (d, J=6.7 Hz, 6H), 1.00 (m, 3H).

(2E)-3-(4-Bromo-8-tert-butyl-3 ethoxy-5,5-dimethyl-5,6-dihydro-naphthalen-2-yl)-2-fluoro-but-2-enal (Compound A-152)

As described in General Procedure H-1, (2E)-3-(4-bromo-8-tert-butyl-3-ethoxy-5,5-dimethyl-5,6-dihydro-naphthalen-2-yl)-2-fluoro-but-2-en-1-ol (Compound A-141, 45 mg, 0.11 mmol), tetrapropylammonium perruthenate (10 mg, 0.028 mmol) and 4-methylmorpholine N-oxide (31 mg, 0.26 mmol) were reacted in acetonitrile and dichloromethane to give the title compound after purification by flash column chromatography (silica gel, 5% ethyl acetate in hexane).

$^1$H NMR (300 MHz, CDCl$_3$): δ 9.33 (d, J=19.3 Hz, 1H), 7.39 (s, 1H), 6.03 (t, J=4.8 Hz, 1H), 3.88 (m, 2H), 2.29 (m, 3H), 2.17 (m, 2H), 1.49 (s, 6H), 1.37 (m, 3H), 1.27 (s, 9H).

(2E)-3-(4-Bromo-8-tert-butyl-3-isopropoxy-5,5-dimethyl-5,6-dihydro-naphthalen-2-yl)-2-fluoro-but-24-enal (Compound A-153)

As described in General Procedure H-1, (2E)-3-(4-bromo-8-tert-butyl-3-isopropoxy-5,5-dimethyl-5,6-dihydro-naphthalen-2-yl)-2-fluoro-but-2-en-1-ol (Compound A-142, 63 mg, 0.14 mmol), tetrapropylammonium perruthenate (10 mg, 0.028 mmol) and 4-methylmorpholine N-oxide (42 mg, 0.36 nmol) were reacted in acetonitrile and dichloromethane to give the title compound after purification by flash column chromatography (silica gel, 5% ethyl acetate in hexane).

$^1$H NMR (300 MHz, CDCl$_3$): δ 9.33 (d, J=19.3 Hz, 1H), 7.39 (s, 1H), 6.02 (t, J=4.8 Hz, 1H), 4.40 (m, 1H), 2.28 (d, J=3.8 Hz, 3H), 2.17 (m, 2H), 1.51 (s, 3H), 1.47 (s, 3H), 1.20–1.40 (m, 15H).

(2E)-3-(4-Bromo-8-sec-butyl-3-ethoxy-5,5-dimethyl-5,6-dihydro-naphthalen-2-yl)-2-fluoro-pent-2-enal (Compound A-154)

As described in General Procedure H-1, (2E)-3-(4-bromo-8-sec-butyl-3-ethoxy-5,5-dimethyl-5,6-dihydro-naphthalen-2-yl)-2-fluoro-pent-2-en-1-ol (Compound A-143, 411 mg, 0.94 mmol), tetrapropylammonium perruthenate (10 mg, 0.028 mmol) and 4-methylmorpholine N-oxide (274 mg, 2.34 mmol) were reacted in acetonitrile and dichloromethane to give the title compound as a yellow oil after purification by flash column chromatography (silica gel, 5% ethyl acetate in hexane).

$^1$H NMR (300 MHz, CDCl$_3$) δ 9.28 (dd, J=19.2, 9.8 Hz,1H), 7.04 (s, 1H), 5.81 (t, J=4.8 Hz, 1H), 4.02–3.77 (m, 2H), 2.90–2.75 (m, 1H), 2.75–2.60 (m, 1H), 2.60–2.49 (m, 1H), 2.33–2.16 (m, 2H), 1.58–1.56 (m, 3H), 1.47(d, J=8.5 Hz, 3H), 1.10 (d, J=6.2 Hz, 3H), 1.05 (t, J=7.3 Hz, 3H), 0.87 (t, J=6.7 Hz, 3H).

(2E)-3-(4-Chloro-3-ethoxy-8-isopropyl-5,5-dimethyl-5,6-dihydronaphthalen-2-yl)-2-fluoro-but-2-enal (Compound A-155)

As described in General Procedure H-1, (2E)-3-(4-chloro-3-ethoxy-8-isopropyl-5,5-dimethyl-5,6-dihydronaphthalen-2-yl)-2-fluoro-but-2-en-1-ol (Compound A-144, 0.18 g, 0.49 mmol), tetrapropylammonium perruthenate (25 mg, 0.071 mmol) and 4-methylmorpholine N-oxide (115 mg, 0.98 mmol) were reacted in acetonitrile and dichloromethane to give the title compound after purification by flash column chromatography (silica gel, 10% ethyl acetate in hexanes).

$^1$H NMR (300 MHz, CDCl$_3$): δ 1.10 (d, J=6.8 Hz, 6H), 1.36 (t, l=7.0 Hz, 3H), 1.47(s, 6H), 2.22(d, J=4.8 Hz, 2H), 2.28 (d, J=4.1 Hz, 3H), 2.77 (m, 1H), 3.88(m, 2H), 5.85 (t, J=4.8 Hz, 1H), 7.05 (s, 1H), 9.31 (d, J=19.6 Hz, 1H).

(2E)-3-(4-Chloro-3-ethoxy-8-isopropyl-5,5-dimethyl-5,6-dihydronaphthalen-2-yl)-2-fluoro-pent-2-enal (Compound A-156)

As described in General Procedure H-1, (2E)-3-(4-chloro-3-ethoxy-8-isopropyl-5,5-dimethyl-5,6-dihydronaphthalen- 2-yl)-2-fluoro-pent-2-en-1-ol (Compound A-145, 34 mg, 0.09 mmol) tetrapropylammonium perruthenate (10 mg, 0.028 mmol) and 4-methylmorpholine N-oxide (21 mg, 0.18 mmol) were reacted in dichloromethane to give the title compound after purification by flash column chromatography (silica gel, 10% ethyl acetate in hexanes).

$^1$H NMR (300 MHz, CDCl$_3$): δ 1.05 (t, J=7.1 Hz, 3H), 1.09 (d, J=6.7 Hz, 6H), 1.35 (t, J=7.0 Hz, 3H), 1.47 (d J=7.3 Hz, 6H), 2.22 (d, J=4.7 Hz, 2H), 2.67 (m, 1H), 2.79–2.83(m, 2H), 3.85(m, 1H), 3.95 (m, 1H), 5.80 (t, J=4.7 Hz, 1H), 7.00 (s, 1H), 9.31 (d, J=19.6 Hz, 1H).

Ethyl (2E,4E,6E)-7-(4-bromo-8-isopropyl-3-methoxy-5,5-dimethyl-5,6-dihydro-naphthalen-2-yl)-6-fluoro-3-methyl-octa-2,4,6-trienoate (Compound A-157)

Following General Procedure I-1, ethyl 4(diethoxyphosphoryl)-3-methyl-but-2E-enoate (233 mg, 0.87 mmol) and (2E)-3-(4-bromo-8-isopropyl-3-methoxy-5,5-dimethyl-5,6-dihydro-naphthalen-2-yl)-2-fluoro-but-2-enal (Compound A-146, 116 mg, 0.29 mmol) were reacted to give the title compound as a colorless oil after purification by flash column chromatography (silica gel, 2% ethyl acetate in hexane) and HPLC (normal phase, 1% ethyl acetate in hexanes).

$^1$H NMR (300 MHz, CDCl$_3$): δ 7.02 (s, 1H), 6.57 (d, J=15.5 Hz, 1H), 6.37 (dd, J=15.5, 25.5 Hz, 1H), 5.87 (s, 1H), 5.80 (t, J=4.8 Hz, 1H), 4.16 (q, J=7.3 Hz, 2H), 3.70 (s, 3H), 2.79 (m, 1H), 2.23 (br s, 2H), 2.11–2.13 (m, 6H), 1.52 (br, 6H), 1.28 (m, 3H), 1.09 (m, 6H).

Ethyl (2E,4E,6E)-7-(4-bromo-3-ethoxy-8-isopropyl-5,5-dimethyl-5,6-dihydro-naphthalen-2-yl)-6-fluoro-3-methyl-octa-2,4,6-trienoate (Compound A-158)

Following General Procedure I-1, ethyl 4-(diethoxyphosphoryl)-3-methyl-but-2E-enoate (1.3 g, 4.95 nmol) and (2E)-3-(4-bromo-3-ethoxy-8-isopropyl-5,5-dimethyl-5,6-dihydro-naphthalen-2-yl)-2-fluoro-but-2-enal (Compound A-147, 675 mg, 1.65 mmol) were reacted to give the title compound as a colorless oil after purification by column chromatography (silica gel, 2% ethyl acetate in hexane).

$^1$H NMR (300 MHz, CDCl$_3$): δ 7.01 (s, 1H), 6.57 (d, J=15.5 Hz, 1H), 6.38 (dd, J=15.5, 25.5 Hz, 1H), 5.87 (s, 1H), 5.79 (t, J=4.8 Hz, 1H), 4.16 (q, J=7.3 Hz, 2H), 3.86 (br s, 2H), 2.79 (m, 1H), 2.23 (br s, 2H), 2.10–2.13 (m, 6H), 1.52 (br, 6H), 1.36 (m, 3H), 1.28 (m, 3H), 1.09 (m, 6H).

Ethyl (2E,4E,6E)-7-(4-bromo-3-ethoxy-8-isopropyl-5,5-dimethyl-5.6 dihydro-naphthalen-2-yl)1)-6-fluoro-3-methyl-nona-2,4,6-trienoate (Compound A-159)

Following General Procedure I-1, ethyl 4(diethoxyphosphoryl)-3-methyl-but-2E-enoate (1.38 g, 5.22 mmol) and (2E)-3-(4-bromo-3-ethoxy-8-isopropyl-5,5-dimethyl-5,6-dihydro-naphthalen-2-yl)-2-fluoro-pent-2-enal (Compound A-148, 736 mg, 1.74 mmol) were reacted to give the title compound as a colorless oil after purification by column chromatography (silica gel, 2% ethyl acetate in hexane).

$^1$H NMR (300 MHz, CDCl$_3$): δ 6.97 (s, 1H), 6.57 (d, J=15.5 Hz, 1H), 6.32 (dd, J=15.5, 25.5 Hz, 1H), 5.86 (s, 1H), 5.79 (t, J=4.8 Hz, 1H), 4.16 (q, J=7.3 Hz, 2H), 3.87–3.94 (m, 1H), 3.76–3.83 (m, 1H), 2.80 (m, 2H), 2.47 (br s, 1H), 2.21–2.27 (m, 2H), 2.13 (s, 3H), 1.56 (s, 3H), 1.48 (s, 3H), 1.35 (m, 3H), 1.28 (m, 3H), 1.11 (d, J=6.7 Hz, 3H), 1.05 (d, J=6.7 Hz, 3H), 0.93 (m, 3H).

Ethyl (2E,4E,6)-7-(4-Bromo-3-ethoxy-8-isopropyl-5,5-dimethyl-5,6-dihydro-naphthalen-2-yl)-6-fluoro-3.8-dimethyl-nona-2,4,6-trienoate (Compound A-160).

Following General Procedure I-1, ethyl 4-(diethoxyphosphoryl)-3-methyl-but-2-enoate (280 mg, 1.06 mmol) and (2E)-3-(4-bromo-3-ethoxy-8-isopropyl-5,5-dimethyl-5,6-dihydro-naphthalen-2-yl)-2-fluoro-4-methyl-pent-2-enal (Compound A-149, 116 mg, 0.27 mmol) were reacted to give the title compound as a colorless oil after purification by column chromatography (silica gel, 2% ethyl acetate in hexane).

$^1$H NMR (300 MHz, CDCl$_3$) δ 6.83 (s, If), 6.46 (d, J=15.5 Hz, if), 6.10 (dd, J=15.7, 25.7 Hz, 1H), 5.77 (s, 1H), 5.70 (t, 0.8 Hz, 1H),4.08 (q, J=7.1 Hz, 2H), 3.80(quint, J=7.0 Hz, 1H), 3.71 (quint, J=7.0 Hz, 1H), 2.91 (sept, J=7.0 Hz, 1H), 2.72 (sept, J=6.8 Hz, 1H),2.23-2.08 (m, 2H), 2.01 (s, 3H), 1.47 (s, 3H), 1.41 (s, 3H), 1.29 (t, J=6.9 Hz, 3H), 1.19 (t, J=7.0 Hz, 3H), 1.06 (d, J=7.0 Hz, 6H), 1.03 (d, J=7.6 Hz, 3H), 0.96 (d, J=6.7 Hz, 3H).

Ethyl (2E,4E,6E)-7-(4-bromo-3-isopropoxy-8-isopropyl-5,5-dimethyl-5,6-dihydro-naphthalen-2-yl)-6-fluoro-3-methyl-octa-2,4,6-trienoate (Compound A-161)

Following General Procedure I-1, ethyl 4-(diethoxyphosphoryl)-3-methyl-but-2E-enoate (417 mg, 1.58 mmol) and (2E)-3-(4-bromo-3-isopropoxy-8-isopropyl-5,5-dimethyl-5,6-dihydro-naphthalen-2-yl)-2-fluoro-but-2-enal (Compound A-150, 167 mg, 0.39 mmol) were reacted to give the title compound as a colorless oil after purification by column chromatography (silica gel, 2% ethyl acetate in hexane).

$^1$H NMR (300 MHz, CDCl$_3$): & 7.01 (s, 1H), 6.57 (d, J=15.5 Hz, 1H), 6.43 (dd, J=15.5, 25.5 Hz, 1H), 5.87 (s, 1H), 5.78 (t, J=4.8 Hz, 1H), 4.38 (m, 1H), 4.16 (q, J=7.3 Hz, 2H), 2.77 (m, 1H), 2.23 (d, J=4.7 Hz, 2H), 2.15 (s, 3H), 2.11 (d, J=3.5 Hz, 3H), 1.51 (s, 6H), 1.28 (m, 3H), 1.24 (d, J=6.2 Hz, 6H), 1.10 (s, 6H).

Ethyl (2E,4E,6E)-7-(bromo-8-isopropyl-5,5-dimethyl-3-propoxy-5,6-dihydro-naphthalen-2-yl)1)-6-fluoro-3-methyl-octa-2,4,6-trienoate (Compound A-162)

Following General Procedure I-1, ethyl 4-(diethoxyphosphoryl)-3-methyl-but-2E-enoate (214 mg, 0.9 mmol) and (2E)-3-(4-bromo-3-propoxy-8-isopropyl-5,5-dimethyl-5,6-dihydro-naphthalen-2-yl)-2-fluoro-but-2-enal (Compound A-151, 129 mg, 0.30 mmol) were reacted to give the title compound as a colorless oil after purification by column chromatography (silica gel, 2% ethyl acetate in hexane).

$^1$H NMR (300 MHz, CDCl$_3$): δ 7.02 (s, 1H), 6.57 (d, J=15.5 Hz, 1H), 6.38 (dd, J=15.5, 25.5 Hz, 1H), 5.87 (s, 1H), 5.79 (t, J=4.8 Hz, 1H), 4.16 (q, J=7.3 Hz, 2H), 3.67–3.86 (br s, 2H), 2.79 (m, 1H), 2.23 (br s, 2H), 2.10–2.13 (m, 6H), 1.79 (m, 2H), 1.52 (br s, 6H), 1.28 (m, 3H), 1.09 (m, 6H) 1.00 (m, 3H).

Ethyl (2E,4E,6E)-7-(4-bromo-8-tert-butyl-3-ethoxy-5,5-dimethyl-5,6-dihydro-naphthalen-2-yl)-6-fluoro-3-methyl-octa-2,4,6-trienoate (Compound A-163)

Following General Procedure I-1, ethyl 4(diethoxyphosphoryl)-3-methyl-but-2E-enoate (92-mg, 0.35 mmol) and (2E)-3-(4-bromo-8-tert-butyl-3-ethoxy-5,5-dimethyl-5,6-dihydro-naphthalen-2-yl)-2-fluoro-but-2-enal (Compound A-152, 37 mg, 0.09 mmol) were reacted to give the title compound as a colorless oil after purification by column chromatography (silica gel, 2% ethyl acetate in hexane).

$^1$H NMR (300 MHz, CDCl$_3$): δ 7.28 (s, 1H), 6.58 (d, J=15.5 Hz, 1H), 6.39 (dd, J=15.5, 25.5 Hz, 1H), 5.99 (t, J=4.8 Hz, 1H), 5.87 (s, 1H), 4.16 (q, J=7.3 Hz, 2H), 3.80–4.00 (m, 2H), 2.13 (m, 8H), 1.56 (s, 3H), 1.43 (s, 3H), 1.37 (m, 3H), 1.28 (m, 3H), 1.26 (s, 9H).

Ethyl (2E,4E,6E)-7-(4-bromo-8-tert-butyl-3-isopropoxy-5,5-dimethyl-5,6-dihydro-naphthalen-2-yl)-6-fluoro-3-methyl-octa-2,4,6-trienoate (Compound A-164)

Following General Procedure I-1, ethyl 4-(diethoxyphosphoryl)-3-methyl-but-2E-enoate (97 mg, 0.36 mmol) and (2E)-3-(4-bromo-8-tert-butyl-3-isopropoxy-5,5-dimethyl-5,6-dihydro-naphthalen-2-yl)-2-fluoro-but-2-enal (Compound A-153, 40 mg, 0.091 mmol) were reacted to give the title compound as a colorless oil after purification by column chromatography (silica gel, 2% ethyl acetate in hexane).

$^1$H NMR (300 MHz, CDCl$_3$): b 7.29 (s, 1H), 6.58 (d, J=15.0 Hz, 1H), 6.44 (dd, J=15.5, 24.9 Hz, 1H), 5.97 (t, J=4.8 Hz, 1H), 5.87 (s, 1H, 4.39 (m, 1H), 4.17 (q, J=7.1 Hz, 2H), 2.11–2.27 (m, 8H), 1.49 (m, 6H), 1.2–1.4 (m, 18H).

Ethyl (2E,4E,6E)-7-(4-Bromo-8-sec-butyl-3-ethoxy-5,5-dimethyl-5,6-dihydro-naphthalen-2-yl)-6-fluoro-3-methyl-nona-2,4,6-trienoate (Compound A-165)

Following General Procedure I-1, ethyl 4(diethoxyphosphoryl)-3-methyl-but-2-enoate (645 mg, 2.44 mmol) and (2E)-3-(4-Bromo-8-sec-butyl-3-ethoxy-5,5-dimethyl-5,6-dihydro-naphthalen-2-yl)-2-fluoro-pent-2-enal (Compound A-154, 333 mg, 0.81 mmol) were reacted to give the title compound as a light yellow syrup after purification by column chromatography (silica gel, 2% ethyl acetate in hexane).

$^1$H NMR (300 MHz, CDCl$_3$) δ 6.97 (s, 1H), 6.57 (d, J=15.6 Hz, 1H), 6.32 (ddd, J=25.6, 15.6, 4.8 Hz, 1H), 5.87(s, 1H), 5.77(t, J=4.7 Hz, 1H), 4.16 (q, J=7.2 Hz, 2H), 3.98–3.87 (m, 1H), 3.83–3.73 (m, 1H), 2.85–2.73 (m, 1H), 2.63–2.41 (m, 2H), 2.29–2.18 (m, 2H), 2.14 (s, 3H), 1.61–1.43 (m, 7H), 1.36 (t, J=7.0 Hz, 3H), 1.28 (t, J=7.0 Hz, 3H), 1.09 (dd, J=1.38, 6.7 Hz, 3H), 0.98–0.79 (m, 6H).

Ethyl] (2E,4E,6E)-7-(4-chloro-3-ethoxy-8-isopropyl-5,5-dimethyl-5,6-dihydronaphthalen-2-yl)-6-fluoro-3-methyl-octa-2,4,6-trienoate (Compound A-166)

Following General Procedure I-1, ethyl 4(diethoxyphosphoryl)-3-methyl-but-2E-enoate (517 mg, 1.96 mmol) and (2E)-3-(4-chloro-3-ethoxy-8-isopropyl-5,5-dimethyl-5,6-dihydronaphthalen-2-yl)-2-fluoro-but-2-enal (Compound A-155, 0.13 g, 0.35 mmol) were reacted to give the title compound as a colorless oil after purification by column chromatography (silica gel, 1% to 2% ethyl acetate in hexanes).

$^1$H NMR (300 MHz, CDCl$_3$): δ 1.09 (m, 6H), 1.28 (t, J=7.3 Hz, 3H), 1.35 (t, J=7.0 Hz, 3H), 1.48 (br s, 6H), 2.12–2.14 (m, 6H), 2.22 (br s, 2H), 2.79 (m, 1H), 3.88 (br s, 2H), 4.16 (q, J=7.4 Hz, 2H), 5.79 (t, J=4.8 Hz, 1H), 5.87 (s, 1H), 6.38 (dd, J=15.5 and 25.5 Hz, 1H), 6.57 (d, J=15.5 Hz, 1H), 6.98 (s, 1H).

Ethyl (2E,4E,6E)-7-(4-chloro-3-ethoxy-8-isopropyl-5,5-dimethyl-5,6 dihydronaphthalen-2-yl)-6-fluoro-3-methyl-nona-2,4,6-trienoate (Compound A-167)

Following General Procedure I-1, ethyl 4-(diethoxyphosphoryl)-3-methyl-but-2E-enoate (139 mg, 0.53 mmol) and (2E)-3-(4-chloro-3-ethoxy-8-isopropyl-5,5-dimethyl-5,6-dihydronaphthalen-2-yl)-2-fluoro-pent-2-enal (Compound A-156, 32 mg, 0.09 mmol) were reacted to give the title compound as a colorless oil after purification by column chromatography (silica gel, 1% to 2% ethyl acetate in hexane).

$^1$H NMR (300 MHz, CDCl$_3$): 30.94 (t, J=7.4 Hz, 3H), 1.05–1.13 (m, 6H), 1.28 (t, J=7.0 Hz, 3H), 1.34 (t, J=7.0 Hz, 3H), 1.50 (s, 3H),1.56 (s, 3H), 2.13 (s, 3H), 2.24 (m, 2H), 2.46 (m, 1H), 2.80 (m, 2H), 3.81 (m, 1H), 3.91 (m, 1H), 4.16 (q, J=7.3 Hz, 2H), 5.78 (t, J=4.8 Hz, 1H), 5.86 (s, if), 6.31 (dd, J=15.5 and 25.5 Hz, 1H), 6.56 (d, J=15.5 Hz, 1H), 6.93 (s, 1H).

(2E,4E,6E)-7-(4-Bromo-8-isopropyl-3-methoxy-5,5-dimethyl-5,6-dihydro-naphthalen-2-yl)-6-fluoro-3-methyl-nona-2,4,6-trienoic acid (Compound A-168)

As described in General Procedure J-1, ethyl (2E,4E,6E)-7-(4-bromo-8-isopropyl-3-methoxy-5,5-dimethyl-5,6-dihydro-naphthalen-2-yl)-6-fluoro-3-methyl-octa-2,4,6-trienoate (Compound A-157, 43 mg, 0.085 mmol) in ethanol was treated with a solution of 1 N NaOH to produce the title compound after purification by recrystallization from acetonitrile.

$^1$H NMR (300 MHz, CDCl$_3$): δ 7.02 (s, 1H), 6.60 (d, J=15.5 Hz, 1H), 6.41 (dd, J=15.5, 25.5 Hz, 1H), 5.89 (s, 1H), 5.80 (t, J=4.8 Hz, 1H), 3.71 (s, 3H), 2.79 (m, 1H), 2.23 (br s, 2H), 2.12–2.15 (m, 6H), 1.52 (br s, 6H), 1.09 (m, 6H).

(2E,4E,6E)-7-(4-Bromo-3-ethoxy-8-isopropyl-5,5-dimethyl-5,6-dihydro-naphthalen-2-yl)-6-fluoro-3-methyl-octa-2,4,6-trienoic acid (Compound A-169)

As described in General Procedure J-1, ethyl (2E,4E,6E)-7-(4 bromo-3-ethoxy-8-isopropyl-5,5-dimethyl-5,6-dihydro-naphthalen-2-yl)-6 fluoro-3-methyl-octa-2,4,6-trienoate (Compound A-158, 860 mg, 1.65 mmol) in ethanol was treated with a solution of 1 N NaOH to produce the title compound after purification by recrystallization from acetonitrile.

$^1$H NMR (300 MHz, CDCl$_3$): δ 7.01 (s, 1H), 6.59 (d, J=15.5 Hz, 1H), 6.42 (dd, J=15.5, 25.5 Hz, 1H), 5.89 (s, 1H), 5.79 (t, J=4.8 Hz,1H), 3.70–3.90 (br s, 2H), 2.78 (m, 1H), 2.22 (br s, 2H), 2.12–2.18 (m, 6H), 1.52 (br s, 6H), 1.36 (m, 3H), 1.09 (m, 6H).

(2E,4E,6E)-7-(4-Bromo-3-ethoxy-8-isopropyl-5,5-dimethyl-5,6-dihydro-naphthalen-2-yl)-6-fluoro-3-methyl-nona-2,4,6-trienoic acid (Compound A-170)

As described in General Procedure J-1, ethyl (2E,4E,6E)-7-(4-bromo-3-ethoxy-8-isopropyl-5,5-dimethyl-5,6-dihydro-naphthalen-2-yl)-6-fluoro-3-methyl-nona-2,4,6-trienoate (Compound A-159, 930 mg, 1.74 mmol) in ethanol was treated with a solution of 1 N NaOH to produce the title compound after purification by recrystallization from acetonitrile.

$^1$H NMR (300 MHz, CDCl$_3$): δ 6.97 (s, 1H), 6.59 (d, J=15.5 Hz, 1H), 6.37 (dd, J=15.5, 25.5 Hz, 1H), 5.89 (s, 1H), 5.79 (t, J=4.8 Hz, 1H), 3.87–3.94 (m, 1H), 3.76–3.83 (m, 1H), 2.80 (m, 2H), 2.47 (br s, 1H), 2.20–2.26 (m, 2H), 2.14 (s, 3H), 1.56 (s, 3H), 1.48 (s, 3H), 1.36 (m, 3H), 1.11 (d, J=6.7 Hz, 3H), 1.05 (d, J=6.7 Hz, 3H), 0.93 (m, 3H).

(2E,4E,6E)-7-(4-Bromo-3-ethoxy-8-isopropyl-5,5-dimethyl-5,6-dihydro-naphthalen-2-yl)-6-fluoro-3,8-dimethyl-nona-2,4,6-trienoic acid (Compound A-171)

As described in General Procedure J-1, ethyl (2E,4E,6E)-7-(4-bromo-3-ethoxy-8-isopropyl-5,5-dimethyl-5,6-dihydro-naphthalen-2-yl)-6-fluoro-3,8-dimethyl-nona-2,4,6-trienoate (Compound A-160, 134 mg, 0.25 mmol) in ethanol was treated with a solution of 1 N aqueous NaOH to produce the title compound as a white solid after purification by recrystallization from acetonitrile.

$^1$H NMR (300 MHz, CDCl$_3$) δ 6.90 (s, 1H), 6.56 (d, J=15.8 Hz, 1H), 6.22 (dd, J=15.8, 25.5 Hz, 1H), 5.86 (s, 1H), 5.78 (t, J=4.5 Hz, 1H), 3.92 (quint, J=7.0 Hz, 1H), 3.78 (quint, J=7.0 Hz, 1H), 2.99 (sept, J=7.0 Hz, 1H), 2.79 (sept, J=6.6 Hz, 1H), 2.31–2.14 (m, 2H), 2.09 (s, 3H), 1.54 (s, 3H), 1.49 (s, 3H), 1.37 (t, J=7.0 Hz, 3H), 1.14 (t, J=7.0 Hz, 6H), 1.11 (d, J=6.7 Hz, 3H), 1.03 (d, J=6.7 Hz, 3H).

(2E,4E,6E)-7-(4-Bromo-3-isopropoxy-8-isopropyl-5,5-dimethyl-5,6-dihydro-naphthalen-2-yl)-6-fluoro-3-methyl-octa-2,4,6-trienoic acid (Compound A-172)

As described in General Procedure J-1, ethyl (2E,4E,6E)-7-(4-bromo-3-isopropoxy-8-isopropyl-5,5-dimethyl-5,6-dihydro-naphthalen-2-yl)-6-fluoro-3-methyl-octa-2,4,6-trienoate (Compound A-161, 189 mg, 0.35 mmol) in ethanol was treated with a solution of 1 N NaOH to produce the title compound after purification by recrystallization from acetonitrile.

$^1$H NMR (300 MHz, CDCl$_3$): δ 7.00 (s, 1H), 6.59 (d, J=15.5 Hz, 1H), 6.47 (dd, J=15.5, 25.5 Hz, 1H), 5.89 (s, 1H), 5.79 (t, J=4.8 Hz, 1H), 4.38 (m, 1H), 2.77 (m, 1H), 2.24 (d, J=4.1 Hz, 2H), 2.16 (s, 3H), 2.12 (d, J=3.5 Hz, 3H), 1.52 (s, 6H), 1.24 (d, J=6.2 Hz, 6H), 1.10 (s, 6H).

(2E,4E,6E)-7-(4-Bromo-8-isopropyl-5,5-dimethyl-3-propoxy-5,6-dihydro-nahthalen-2-yl)-6-fluoro-3-methyl-octa-2,4,6-trienoic acid (Compound A-173)

As described in General Procedure J-1, ethyl (2E,4E,6E)-7-(4-bromo-8-isopropyl-5,5-dimethyl-3-propoxy-5,6-dihydro-naphthalen-2-yl)-6-fluoro-3-methyl-octa-2,4,6-trienoate (Compound A-162, 160 mg, 0.30 mmol) in ethanol was treated with a solution of 1 N NaOH to produce the title compound after purification by recrystallization from acetonitrile.

$^1$H NMR (300 MHz, CDCl$_3$): δ 7.02 (s, 1H), 6.59 (d, J=15.5 Hz, 1H), 6.43 (dd, J=15.5, 25.5 Hz, 1H), 5.89 (s, 1H), 5.79 (t, J=4.8 Hz, 1H), 3.60–3.80 (br s, 2H), 2.79 (m, 1H), 2.23 (br s, 2H), 2.12–2.16 (m, 6H), 1.79 (m, 2H), 1.52 (br s, 6H), 1.09 (br s, 6H), 1.00 (m, 3H).

(2E,4E,6E)-7-(4-Bromo-8-tert-butyl-3-ethoxy-5,5-dimethyl-5,6-dihydro-naphthalen-2-yl)-6-fluoro-3-methyl-octa-2,4,6-trienoic acid (Compound A-174)

As described in General Procedure J-1, ethyl (2E,4E,6E)-7-(4 bromo-8-tert-butyl-3-ethoxy-5,5-dimethyl-5,6-dihydro-naphthalen-2-yl)-6-fluoro-3-methyl-octa-2,4,6-trienoate (Compound A-163, 46 mg, 0.086 mmol) in ethanol was treated with a solution of 1 N NaOH to produce the title compound after purification by recrystallization from acetonitrile.

$^1$H NMR (300 MHz, CDCl$_3$): δ 7.28 (s, 1H), 6.60 (d, J=15.5 Hz, 1H), 6.43 (dd, J=15.5, 25.5 Hz, 1H), 5.99 (t, J=4.8 Hz, 1H), 5.89 (s, 1H), 3.84.0 (m, 2H), 2.13 (m, 8H), 1.56 (s, 3H), 1.43 (s, 3H), 1.37 (m, 3H), 1.26 (s, 9H).

(2E,4E,6E)-7-(4 Bromo-8-tert-butyl-3-isopropoxy-5,5-dimethyl-5,6 dihydro-naphthalen-2-yl)-6-fluoro-3-methyl-octa-2,4,6-trienoic acid (Compound A-175)

As described in General Procedure J-1, ethyl (2E,4E,6E)-7-(4-bromo-8-tert-butyl-3-isopropoxy-5,5-dimethyl-5,6-dihydro-naphthalen-2-yl)-6-fluoro-3-methyl-octa-2,4,6-trienoate (Compound A-164, 46 mg, 0.08 mmol) in ethanol was treated with a solution of 1 N NaOH to produce the title compound after purification by recrystallization from acetonitrile.

$^1$H NMR (300 MHz, CDCl$_3$): δ 7.29 (s, 1H), 6.60 (d, J=14.1 Hz, 1H), 6.49 (dd, J=14.3, 24.3 Hz, 1H), 5.97 (t, J=4.8 Hz, 1H), 5.89 (s, 1H), 4.39 (m, 1H), 2.01–2.18 (m, 8H), 1.49 (s, 6H), 1.20–1.40 (m, 15H).

(2E,4E,6E)-7-(4-Bromo-8-sec-butyl-3-ethoxy-5,5-methyl-5,6-dihydro-naphthalen-2-yl)-6-fluoro-3-methyl-nona-2,4,6-trienoic acid (Compound A-176).

As described in General Procedure J-1, ethyl (2E,4E,6E)-7-(4-bromo-8-sec-butyl-3-ethoxy-5,5-dimethyl-5,6-dihydro-naphthalen-2-yl)-6-fluoro-3-methyl-nona-2,4,6-trienoate (Compound A-165, 370 mg, 0.67 mmol) in ethanol and THF was treated with a solution of 1 N aqueous NaOH to produce the title compound after purification by recrystallization from acetonitrile.

$^1$H NMR (300 MHz, CDCl$_3$) δ 6.95 (s, 1H), 6.59 (d, J=15.5 Hz, 1H), 6.36 (ddd, J=25.3, 15.9, 4.8 Hz,1H), 5.77(t, J=4.5 Hz, 1H), 5.88 (s, 1H), 5.77 (t, J=4.5 Hz, 1H), 3.97–3.87 (m, 1H), 3.83–3.73 (m, 1H), 2.79 (quintet, 1H), 2.62–2.41 (m, 2H), 2.29–2.19 (m, 2H), 2.14 (s, 3H), 1.60–1.45 (m, 8H), 1.36 (t, J=7.0 Hz, 3H), 1.08 (dd, J=15.2, 6.7 Hz, 3H), 0.97–0.78 (m, 6H).

(2E,4E,6E)-7-(4-Chloro-3-ethoxy-8-isopropyl-5,5-dimethyl-5,6-dihydronaphthalen-2-yl)6-fluoro-3-methyl-octa-2,4,6-trienoic acid (Compound A-177)

As described in General Procedure J-1, ethyl (2E,4E,6E)-7-(4-chloro-3-ethoxy 8-isopropyl-5,5-dimethyl-5,6-dihydronaphthalen-2-yl)-6-fluoro-3-methyl-octa-2,4,6-trienoate (Compound A-166, 0.14 g, 0.30 mmol) was hydrolyzed with 1 N NaOH to produce the title compound as a yellow solid after recrystallization from acetonitrile.

$^1$H NMR (300 MHz, CDCl$_3$): δ 1.09 (m, 6H), 1.35 (t, J=7.0 Hz, 3H), 1.47 (br s. 6H), 2.12–2.14 (m, 6H), 2.22 (br s, 2H), 2.79 (m, 1H), 3.87 (br s, 2H), 5.79 (t, J=4.8 Hz, 1H), 5.89 (s, 1H), 6.41 (dd, J=15.5 and 25.5 Hz, 1H), 6.59 (d, J=15.5 Hz, 1H), 6.97 (s, 1H).

(2E,4E,6E)-7-(4-Chloro-3-ethoxy-8-isopropyl-5,5-dimethyl-5,6-dihydronaphthalen-2-yl)-6-fluoro-3-methyl-nona-2,4,6-trienoic acid (Compound A-178)

As described in General Procedure J-1, ethyl (2E,4E,6E)-7-(4-chloro-3-ethoxy-8-isopropyl-5,5-dimethyl-5,6-dihydronaphthalen-2-yl)-6-fluoro-3-methyl-nona-2,4,6-trienoate (Compound A-167, 30 mg, 0.06 mmol) was hydrolyzed with 1 N NaOH to produce the title compound as a solid after recrystallization from acetonitrile.

$^1$HNMR (300 MHz, CDCl$_3$): δ 0.94 (t, J=7.3 Hz, 3H), 1.05–1.13 (m, 6H), 1.34 (t, J=7.0 Hz, 3H), 1.45 (s, 3H), 1.50 (s, 3H), 2.13 (s, 3H), 2.22 (m, 2H), 2.47 (m, 1H), 2.77–2.84 (m, 2H), 3.81–3.88 (m, 1H), 3.89–3.94 (m, 1H), 5.78 (t, l=4.8 Hz, 1H), 5.88 (s, 1H), 6.35 (dd, J=15.5 and 25.5 Hz, 1H), 6.58 (d, J=15.5 Hz, 1H), 6.93 (s, 1H).

TABLE 9

Receptor Transactivation, Efficacy and Binding Data for Exemplary Compounds of Formula F

| Cmpd # | Structure | | RAR α | RAR β | RAR γ | RXR α | RXR β | RXR γ |
|---|---|---|---|---|---|---|---|---|
| A-168 | 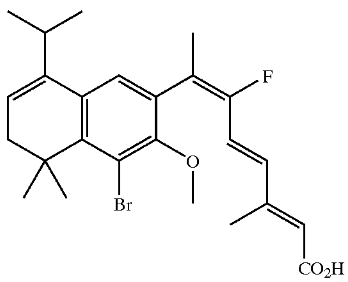 | EC$_{50}$ (% Eff) K$_d$ | NA<br>98 | 231<br>(8)<br>579 | NA<br>2.8k | 0.02<br>(95)<br>1.2 | 0.13<br>(99)<br>11 | 0.01<br>(101)<br>ND |
| A-169 | 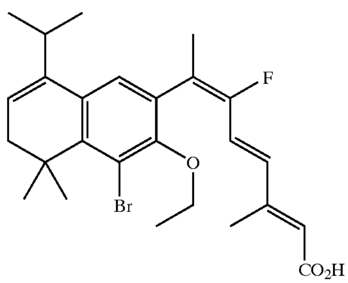 | EC$_{50}$ (% Eff) K$_d$ | NA<br>70 | NA<br>252 | NA<br>1k | 0.4<br>(66)<br>3 | 2.2<br>(68)<br>16 | 0.6<br>(71)<br>ND |
| A-170 | 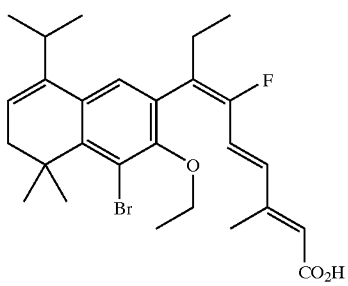 | EC$_{50}$ (% Eff) K$_d$ | NA<br>12 | 3.5<br>(8)<br>56 | NA<br>507 | 0.2<br>(60)<br>2 | 1.0<br>(59)<br>14 | 0.4<br>(53)<br>29 |
| A-171 | 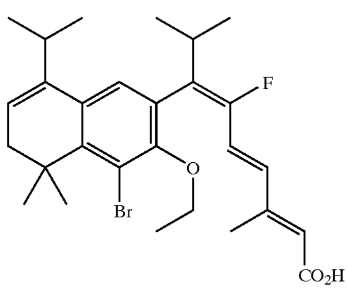 | EC$_{50}$ (% Eff) K$_d$ | 3<br>(13)<br>29 | 2<br>(12)<br>37 | NA<br>272 | 0.9<br>(24)<br>2 | 3<br>(30)<br>15 | 2<br>(16)<br>112 |
| A-172 | 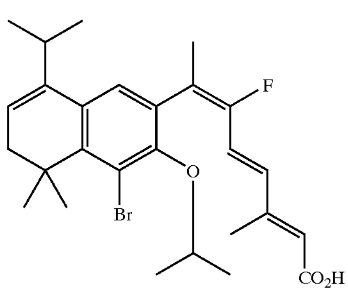 | EC$_{50}$ (% Eff) K$_d$ | NA<br>141 | NA<br>212 | NA<br>834 | 19<br>(31)<br>8 | 83<br>(39)<br>41 | 18<br>(12)<br>221 |

TABLE 9-continued

Receptor Transactivation, Efficacy and Binding Data for Exemplary Compounds of Formula F

| Cmpd # | Structure | | RAR | | | RXR | | |
|---|---|---|---|---|---|---|---|---|
| | | | α | β | γ | α | β | γ |
| A-173 | 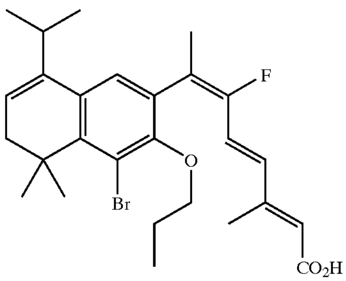 | $EC_{50}$ (% Eff) $K_d$ | NA<br>91 | NA<br>192 | NA<br>810 | 1<br>(5)<br>2 | NA<br>11 | NA<br>ND |
| A-174 | 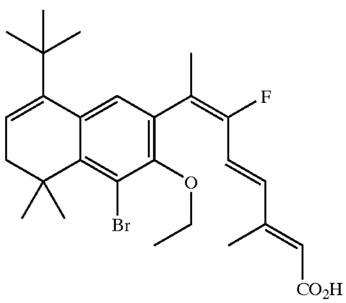 | $EC_{50}$ (% Eff) $K_d$ | NA<br>997 | NA<br>517 | NA<br>1.6k | 1<br>(24)<br>2 | 7<br>(25)<br>12 | 2<br>(12)<br>34 |
| A-175 | 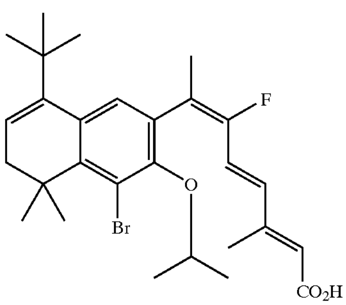 | $EC_{50}$ (% Eff) $K_d$ | NA<br>458 | NA<br>280 | NA<br>866 | NA<br>9 | NA<br>31 | NA<br>ND |
| A-176 | 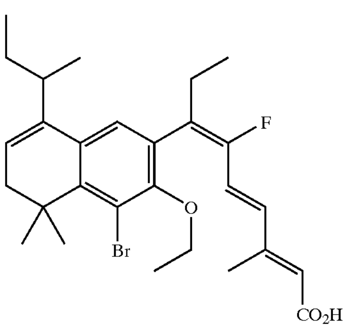 | $EC_{50}$ (% Eff) $K_d$ | NA<br>32 | 14<br>(19)<br>112 | NA<br>517 | 0.9<br>(58)<br>ND | 4<br>(58)<br>23 | 3<br>(53)<br>122 |
| A-177 | 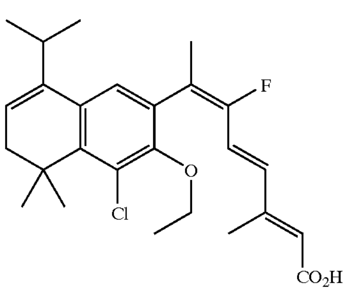 | $EC_{50}$ (% Eff) $K_d$ | NA<br>60 | NA<br>443 | NA<br>1.2k | 0.1<br>(72)<br>2 | 0.5<br>(66)<br>12 | 0.2<br>(73)<br>NA |

TABLE 9-continued

Receptor Transactivation, Efficacy and Binding Data for Exemplary Compounds of Formula F

| Cmpd # | Structure | | RAR α | RAR β | RAR γ | RXR α | RXR β | RXR γ |
|---|---|---|---|---|---|---|---|---|
| A-178 | 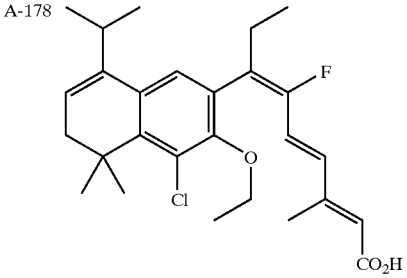 | $EC_{50}$ (% Eff) $K_d$ | 1<br>(8)<br>9.9 | 9<br>(26)<br>79 | >10K<br>449 | 0.1<br>(43)<br>1 | 0.5<br>(53)<br>11 | 0.3<br>(46)<br>61 |

In vivo Data (in ob/ob mice) for Exemplary Compounds of Formula F

TABLE 9

| Treatment (dose) | Glucose (mg/dl) | | | Triglycerides (mg/dl) | | T4 (μg/dL) |
|---|---|---|---|---|---|---|
| | Day 0 | Day 3, 3 h | Day 6, 3 h | Day 0 | Day 3, 3 h | Day 7 |
| Vehicle (Corn oil) | 417 ± 109 | 491 ± 78 | 482 ± 145 | 236 ± 85 | 274 ± 140 | 2.9 ± 0.4 |
| Standard compound (4 mg/kg) | 544 ± 83 | 312 ± 156 | 291 ± 110 | 261 ± 88 | 309 ± 122 | 0.5 ± 0.0 |
| Compound A-170 (80 mg/kg) | 423 ± 93 | 294 ± 107 | 255 ± 85 | 168 ± 44 | 195 ± 33 | 2.7 ± 0.4 |

What is claimed is:

1. A compound of the formula

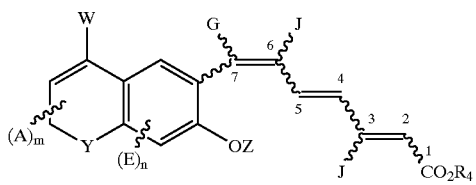

wherein
A is independently an alkyl group of 1 to 6 carbons, halogen, or alkoxy of 1 to 6 carbons;
m is an integer having the values of 0 to 3;
W is H, alkyl of 1 to 8 carbons or phenyl;
E is independently an alkyl group of 1 to 6 carbons, halogen, or alkoxy of 1 to 6 carbons;
n is an integer having the values of 0 to 2;
Z is an alkyl group of 1 to 8 carbons;
G is H or an alkyl group of 1 to 8 carbons;
J is independently H, halogen, or alkyl of 1 to 6 carbons;
Y is O, or $[C(R_3)-2]_o$ where $R_3$ independently is H or alkyl of 1 to 6 carbons and o is an integer having the value of zero (0) or one (1), and $R^4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

2. A compound in accordance with claim 1 where Y is O.
3. A compound in accordance with claim 2 where $(A)_m$ represents a geminal dimethyl group in the 2 position of the chromene nucleus.
4. A compound in accordance with claim 1 where Y is $[C(R_3)-2]_o$.
5. A compound in accordance with claim 4 where Y is $C(CH_3)-2$.
6. A compound in accordance with claim 5 where m is zero (0).
7. A compound in accordance with claim 1 where n is one (1) and E is Cl or Br.
8. A compound in accordance with claim 1 where W is alkyl of 1 to 4 carbons.
9. A compound in accordance with claim 8 where W is isopropyl or tertiary-butyl.
10. A compound in accordance with claim 1 where Z is alkyl of 1 to 4 carbons.
11. A compound in accordance with claim 1 where J is independently F or alkyl of 1 to 2 carbons.
12. A compound of the formula

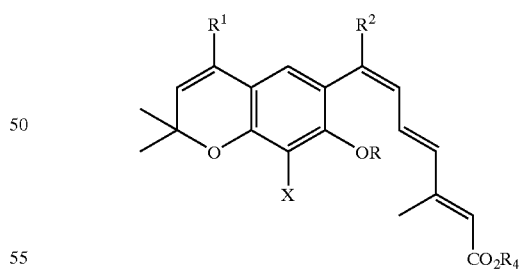

wherein
R is alkyl of 1 to 8 carbons;
$R^1$ is alkyl of 1 to 8 carbons;
$R^2$ is alkyl of 1 to 8 carbons;
$R_4$ is H, alkyl of 1 to 6 carbons, $CH_2OR_5$ or $CH_2OCOR_5$ where $R_5$ is alkyl of 1 to 3 carbons, and
X is H or halogen, or a pharmaceutically acceptable salt of said compound.
13. A compound in accordance with claim 12 wherein R is methyl or ethyl.

14. A compound in accordance with claim 2 wherein $R^1$ is alkyl of 1 to 3 carbons.

15. A compound in accordance with claim 12 wherein $R^2$ is methyl or ethyl.

16. A compound in accordance with claim 12 wherein X is H or Cl.

17. A compound in accordance with claim 12 wherein $R_4$ is H or a pharmaceutically acceptable salt.

18. A compound in accordance with claim 12 wherein R is methyl or ethyl, $R^1$ is alkyl of 1 to 3 carbons, $R^2$ is methyl or ethyl, and X is H or Cl.

19. A compound in accordance with claim 18 wherein $R_4$ is H or a pharmaceutically acceptable salt.

20. A compound in accordance with claim 12 that has the formula

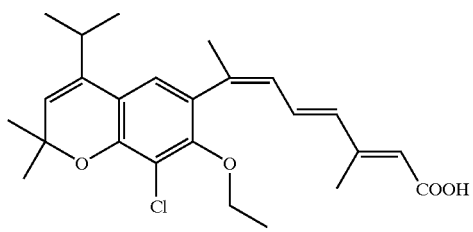

or a pharmaceutically acceptable salt of said compound.

21. A compound of the formula

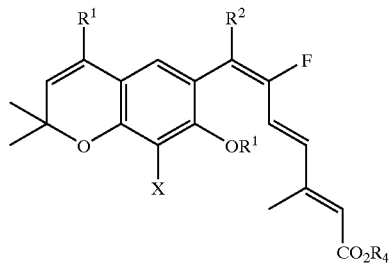

wherein

R is alkyl of 1 to 8 carbons;

$R^1$ is phenyl, or alkyl of 1 to 8 carbons;

$R^2$ is alkyl of 1 to 8 carbons, and $R^4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

22. A compound in accordance with claim 21 wherein R is alkyl of 1 to 4 carbons.

23. A compound in accordance with claim 21 wherein $R^1$ is alkyl of 1 to 4 carbons.

24. A compound in accordance with claim 21 wherein $R^2$ is methyl or ethyl.

25. A compound in accordance with claim 21 wherein $R_4$ is H or a pharmaceutically acceptable salt.

26. A compound in accordance with claim 21 wherein R is alkyl of 1 to 4 carbons, $R^1$ is alkyl of 1 to 4 carbons, and $R^2$ is methyl or ethyl.

27. A compound in accordance with claim 26 wherein $R_4$ is H or a pharmaceutically acceptable salt.

28. A compound of the formula

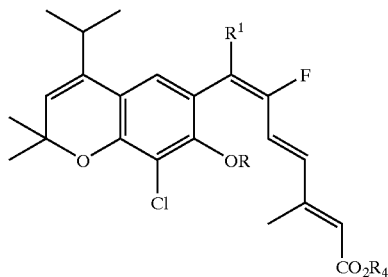

wherein

R is alkyl of 1 to 8 carbons;

$R^1$ is alkyl of 1 to 8 carbons, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

29. A compound in accordance with claim 28 wherein R is alkyl of 1 to 3 carbons.

30. A compound in accordance with claim 28 wherein $R^1$ is methyl or ethyl.

31. A compound in accordance with claim 28 wherein $R_4$ is H or a pharmaceutically acceptable salt.

32. A compound in accordance with claim 28 wherein R is alkyl of 1 to 3 carbons and $R^1$ is methyl or ethyl.

33. A compound in accordance with claim 32 wherein $R_4$ is H or a pharmaceutically acceptable salt.

34. A compound in accordance with claim 28 that has the formula

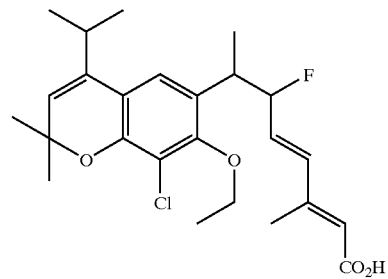

or a pharmaceutically acceptable salt of said compound.

35. A compound of the formula

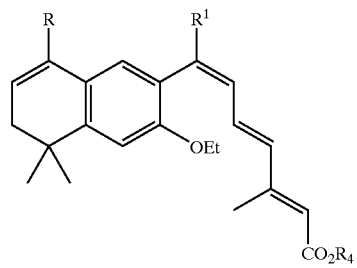

wherein

R is alkyl of 1 to 8 carbons;

$R^1$ is alkyl of 1 to 8 carbons, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

36. A compound in accordance with claim 35 wherein R is methyl or ethyl.

37. A compound in accordance with claim 35 wherein $R^1$ is alkyl of 1 to 4 carbons.

38. A compound in accordance with claim 35 wherein $R_4$ is H or a pharmaceutically acceptable salt.

39. A compound in accordance with claim 35 wherein R is methyl or ethyl and $R^1$ is alkyl of 1 to 4 carbons.

40. A compound in accordance with claim 39 wherein $R_4$ is H or a pharmaceutically acceptable salt.

41. A compound in accordance with claim 35 that has the formula

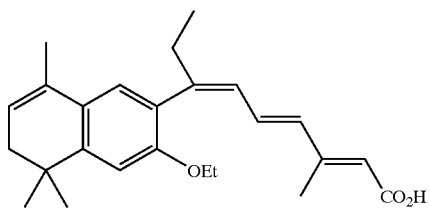

or a pharmaceutically acceptable salt of said compound.

42. A compound of the formula

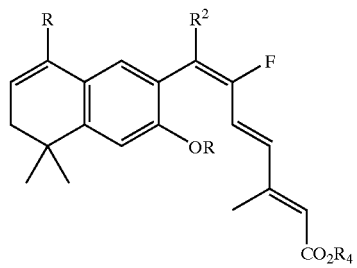

wherein

R is H, or alkyl of 1 to 8 carbons;

$R^1$ is alkyl of 1 to 8 carbons;

$R^2$ is alkyl of 1 to 8 carbons, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

43. A compound in accordance with claim 42 wherein R is alkyl of 1 to 4 carbons.

44. A compound in accordance with claim 42 wherein $R^1$ is alkyl of 1 to 4 carbons.

45. A compound in accordance with claim 42 wherein $R^2$ is methyl or ethyl.

46. A compound in accordance with claim 42 wherein $R_4$ is H or a pharmaceutically acceptable salt.

47. A compound in accordance with claim 42 wherein R is alkyl of 1 to 4 carbons, $R^1$ is alkyl of 1 to 4 carbons and $R^2$ is methyl or ethyl.

48. A compound in accordance with claim 47 wherein $R_4$ is H or a pharmaceutically acceptable salt.

49. A compound of the formula

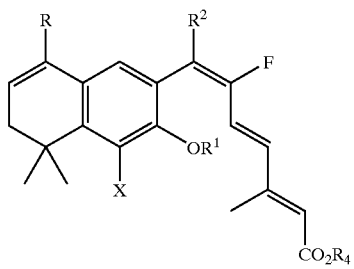

wherein

R represents alkyl of 1 to 8 carbons;

$R^1$ is alkyl of 1 to 8 carbons;

$R^2$ is alkyl of 1 to 8 carbons;

X is halogen, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

50. A compound in accordance with claim 49 wherein R is iso-propyl or tertiary-butyl.

51. A compound in accordance with claim 49 wherein $R^1$ is alkyl of 1 to 4 carbons.

52. A compound in accordance with claim 49 wherein $R^2$ is alkyl of 1 to 4 carbons.

53. A compound in accordance with claim 49 wherein X is Br or Cl.

54. A compound in accordance with claim 49 wherein $R_4$ is H or a pharmaceutically acceptable salt.

55. A compound in accordance with claim 49 wherein R is iso-propyl or tertiary-butyl, $R^1$ is alkyl of 1 to 4 carbons, $R^2$ is alkyl of 1 to 4 carbons and X is Br or Cl.

56. A compound in accordance with claim 55 wherein $R_4$ is H or a pharmaceutically acceptable salt.

57. A compound in accordance with claim 49 that has the formula

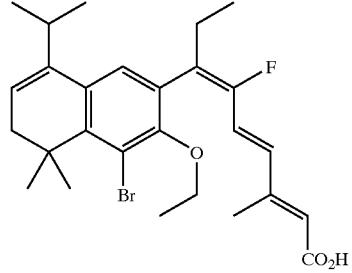

or a pharmaceutically acceptable salt of said compound.

58. A process for administering to a diabetic mammal to reduce the serum glucose level of said mammal a compound of the formula

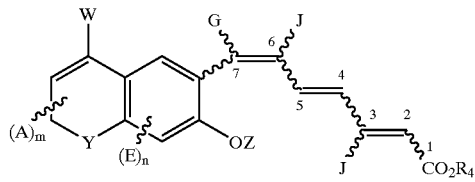

wherein

A is independently an alkyl group of 1 to 6 carbons, halogen, or alkoxy of 1 to 6 carbons;

m is an integer having the values of 0 to 3;

W is H, alkyl of 1 to 8 carbons or phenyl;

E is independently an alkyl group of 1 to 6 carbons, halogen, or alkoxy of 1 to 6 carbons;

n is an integer having the values of 0 to 2;

Z is an alkyl group of 1 to 8 carbons;

G is H or an alkyl group of 1 to 8 carbons;

J is independently H, halogen, or alkyl of 1 to 6 carbons;

Y is O, or $[C(R_3)\text{-}2]_o$ where $R_3$ independently is H or alkyl of 1 to 6 carbons and o is an integer having the value of zero (0) or one (1), and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

59. A process in accordance with claim 58 where the compound used in the process is in accordance with the formula wherein R is alkyl of 1 to 8 carbons;

$R^1$ is alkyl of 1 to 8 carbons;

$R^2$ is alkyl of 1 to 8 carbons, and

X is H or halogen, or a pharmaceutically acceptable salt of said compound.

60. A process in accordance with claim 59 where the compound used in the process has the formula or a pharmaceutically acceptable salt of said compound.

61. A process in accordance with claim 58 where the compound used in the process is in accordance with the formula wherein R is alkyl of 1 to 8 carbons;

$R^1$ is phenyl, or alkyl of 1 to 8 carbons, and $R^2$ is alkyl of 1 to 8 carbons or a pharmaceutically acceptable salt of said compound.

62. A process in accordance with claim 58 where the compound used in the process is in accordance with the formula wherein R is alkyl of 1 to 8 carbons, and $R^1$ is alkyl of 1 to 8 carbons or a pharmaceutically acceptable salt of said compound.

63. A process in accordance with claim 59 where the compound used in the process has the formula or a pharmaceutically acceptable salt of said compound.

64. A process in accordance with claim 58 where the compound used in the process is in accordance with the formula

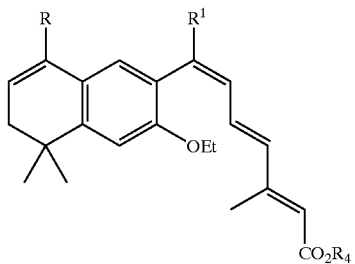

wherein

R is alkyl of 1 to 8 carbons, and $R^1$ is alkyl of 1 to 8 carbons, or a pharmaceutically acceptable salt of said compound.

65. A process in accordance with claim 64 where the compound used in the process has the formula

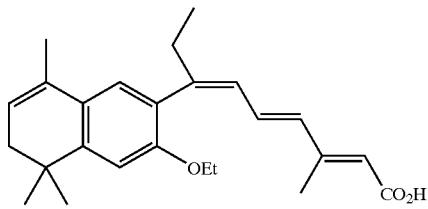

or a pharmaceutically acceptable salt of said compound.

66. A process in accordance with claim 58 where the compound used in the process is in accordance with the formula

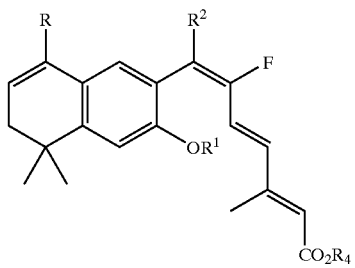

wherein

R is H, or alkyl of 1 to 8 carbons;

$R^1$ is alkyl of 1 to 8 carbons, and $R^2$ is alkyl of 1 to 8 carbons or a pharmaceutically acceptable salt of said compound.

67. A process in accordance with claim 58 where the compound used in the process is in accordance with the formula

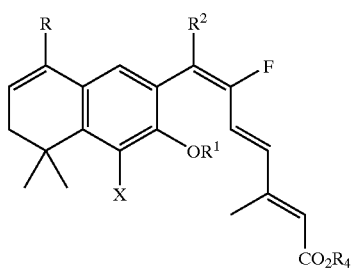

wherein

R represents alkyl of 1 to 8 carbons;

$R^1$ is alkyl of 1 to 8 carbons;

$R^2$ is alkyl of 1 to 8 carbons, and

X is halogen or a pharmaceutically acceptable salt of said compound.

68. A process in accordance with claim 67 where the compound used in the process has the formula

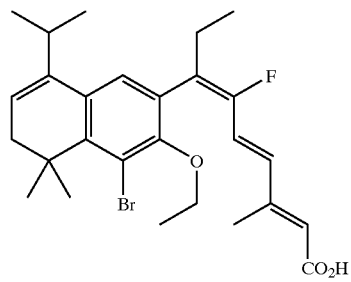

or a pharmaceutically acceptable salt of said compound.

* * * * *

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 4, Line 17, "shown un"
should be --shown in--

Column 12, Line 54, "MinoxidilR"
should be --Minoxidil$^R$--

Column 21, Line 48, "61)." should be --6H).--

Column 23, Line 3, "tetrahydro-2(]-pyrimidinone"
should be -- tetrahydro-2(1H)-pyrimidinone --

Column 23, Line 20, "dichloropalladium (l)"
should be --dichloropalladium (II)--

Column 24, Line 17, "(Compound 16,335"
should be --(Compound 16, 355--

Column 25, Line 54, "2.742.84"
should be --2.74-2.84--

Column 27, Line 7, "36.89" should be --δ 6.89--

Column 27, Line 30, "6.106.24"
should be --6.10-6.24--

Column 28, Line 50, "2.642.75"
should be --2.64-2.75--

Column 29, Line 46, "2.742.83"
should be --2.74-2.83--

Column 29, Line 55, "dimethyl-2H-chromen-6yl)$_3$"
should be --dimethyl-2H-chromen-6yl-3--

Column 30, Line 20, "methoxy-22-dimethyl"
should be -- methoxy-2,2-dimethyl --

Column 41, Line 10, "(s, 10H)"
should be --(s, 1H)--

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 41, Line 22, "(m, If,"
should be --m, 1H),--
Column 41, Line 32, "(s, if),"
should be --(s, 1H),--

Column 41, Line 46, "(t, J 57.2 Hz, 3H)"
should be --(t, J=7.2 Hz, 3H) --

Column 41, Line 55, "-78DC." should be -- -78°C --

Column 41, Line 63, "2.0μM" should be --2.0M --

Column 42, Line 12, "I-(Isopropyl"
should be -- I-(4-Isopropyl --

Column 42, Line 58, "(s, If),"
should be --(s, 1H),--

Column 45, Line 17-18, "Ethyl (2E)-2-fluoro-3-[(4-isopropyl-2,2-dimethyl-7yl)-but-2-enoate (Compound 73)"
should be --Ethyl (2E)-2-fluoro-3-[(4-isopropyl-2,2-dimethyl-7-propoxy-*2H*-chromen-6-yl)-but-2-enoate (Compound 73)--

Column 45, Line 45, "(s, 1 ul)," should be --(s, 1H),--

Column 45, Line 48, "(2E)$_3$" should be --(2E)-3--

Column 46, Line 10, "Ethyl (2E)$_2$-fluoro-3-(7-methoxy-22,4" should be -- Ethyl (2E)-2-fluoro-3-(7-methoxy-2,2,4--

Column 47, Line 35, "(m, 10H)" should be --(m, 1H)--

Column 48, Line 28, "11.0" should be --1.10--

Column 48, Line 50, "chromen-6yl)$_2$"
should be --chromen-6yl)-2--

Column 51, Line 3, "6.50 (s, 1H,"
should be --6.50 (s, 1H), --

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 52, Line 48, "1.35 (s, 614),"
should be --1.35 (s, 6H),--

Column 52, Line 66, "6.42 (s, 1 ul),"
should be --6.42 (s, 1H),--

Column 53, Line 16, "(dd, J 15.5, 25.5 Hz, 1H),"
should be --(dd, J=15.5, 25.5 Hz, 1H),--
Column 55, Line 23, "(in, 21), 2.05 (s, 31)"
should be --(m, 2H), 2.05 (s, 3H),--

Column 55 , Line 53, "(300 M-z" should be --(300 MHz--

Column 56, Line 8, "2.46" should be --2,4,6--

Column 57, Line 33, "11.25 br s, 1H),"
should be --11.25 (br s, 1H),--

Column 58, Line 17, "ten-butyl" should be -- *tert*-butyl --

Column 58, Line 26, "2.402.60" should be --2.40-2.60--

Column 58, Line 40, "11.25 br s, 1H),"
should be --11.25 (br s, 1H),--

Column 60, table 3, compound no. 121, RAR Bind. Ki nM under β, table 3, compound no.121, RAR Bind. Ki nM under β), "46620"
should be --4662(0)--????????

UNITED STATES PATENT AND TRADEMARK OFFICE
CERTIFICATE OF CORRECTION

PATENT NO.        : 6,887,896 B1
APPLICATION NO.   : 10/696748
DATED             : May 3, 2005
INVENTOR(S)       : Beard et al.

It is certified that error appears in the above-identified patent and that said Letters Patent is hereby corrected as shown below:

Column 63, compound no.131 in TABLE 3

" 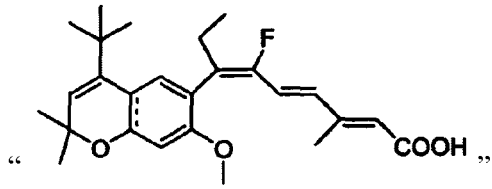 ,"

should be

-- 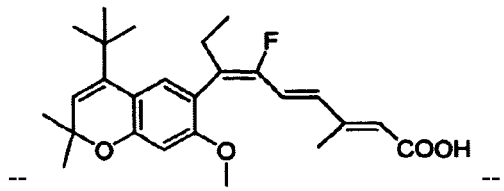 --

Column 67, Line 67, "(sept, 36.2 Hz"
should be --(sept. J=6.2 Hz --

Column 68, Line 26, "2.842.87" should be --2.84-2.87--

Column 68, Line 36, "2.842.87" should be --2.84-2.87--

Column 70, Line 7, "3.984.02" should be --3.98-4.02--

Column 70, Line 7, "2.742.76" should be --2.74-2.76--

Column 70, Line 32, "1) and" should be --) and--

Column 71, Line 40, "(d, J=6.8Hz, 6-H),"
should be --(d, J=6.8Hz, 6 H),--

Column 71, Line 42, "1.H)," should be --1 H),--

Column 71, Line 52, "0.101" should be --0.10--
Column 71, Line 57, "8 ppm" should be --δ ppm--

Column 71, Line 59, "4.44-(sept," should be --4.44 (sept,--

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 72, Line 54, "6-Y1)" should be --6-yl)--
Column 73, Line 23, "(m, 21H)," should be --(m, 2H),--

Column 73, Line 37, "66.83" should be --δ 6.83--

Column 74, Line 6, "(in, 1H)" should be --(m, 1H)--

Column 74, Line 7, "3.75-(s, 3H)"
should be --3.75 (s, 3H)--

Column 74, Line 29, "7L(8" should be --7-(8--

Column 74, Line 57, "7-isopropoxy-2,2-methyl"
should be --4-isopropoxy-2,2-dimethyl --

Column 81, Line 55, "2(1])-pyrimidinone"
should be --2(*1H*)-pyrimidinone --

Column 82, Line 47, "J=0 Hz"
should be -- J=10 Hz --

Column 83, Line 25, "General Procedure B"
should be --General Procedure B-1--

Column 83, Line 59, "I=5Hz" should be -- J=5Hz --

Column 84, Line 33, "(s, 1H." should be --(s, 1H).--

Column 84, Line 52, "(s, 1H." should be --(s, 1H).--

Column 87, Line 46, "33:1" should be --3.3 :1--

Column 91, Line 39, "7-bromo-ethoxy"
should be --7-bromo-6-ethoxy--

Column 91, Line 58, "NH$_4$C)" should be --NH$_4$Cl--

Column 94, Line 13, "(m. 2H)" should be --(m, 2H)--

Column 96, Line 1, "1-(4-dimethyl"
should be --1-(4,4-dimethyl --

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 96, Line 2, "isopropyl-3.,"
should be -- isopropyl-3,4--

Column 96, Line 8 "palladium (1)"
should be -- palladium (II)--

Column 96, Line 12, "δ 60.39" should be --δ 0.39--

Column 96, Line 40, "In ol)" should be --mmol--

Column 98, Line 17, "0.67 (q, 2H, 32 4.5 Hz),"
should be --0.67 (q, 2H, J=4.5 Hz),--

Column 98, Line 18, "2.14 ((d" should be --2.14 (d --

Column 98, Line 19, "3=6.5Hz" should be --J=6.5Hz--

Column 98, Line 41, "Ethyl (2E63"
should be --Ethyl (2E)-3--

Column 98, Line 45, "F-11" should be --F-1--

Column 99, Line 3, "60.89" should be --δ 0.89--

Column 99, Line 60, "(T, 2H)" should be --(m, 2H)--

Column 102, Line 7, "(Compound A-42)"
should be --(Compound A-62)--

Column102, Line 23, "dimethyl-(cyclopropyl)"
should be -- dimethyl-6-(cyclopropyl)--

Column 103, Line 24, "(Compound A-47)"
should be --(Compound A-67) --

Column 104, Line 3, "2,4.6" should be --2,4,6--

Column 104, Line 59, "3,44" should be --3,4--

UNITED STATES PATENT AND TRADEMARK OFFICE
CERTIFICATE OF CORRECTION

PATENT NO.         : 6,887,896 B1
APPLICATION NO. : 10/696748
DATED                 : May 3, 2005
INVENTOR(S)       : Beard et al.

It is certified that error appears in the above-identified patent and that said Letters Patent is hereby corrected as shown below:

Column 105, Line 3, "5:66" should be --5.66--

Column 105, Line 20, "J=36.5 Hz" should be --J=6.5 Hz--

Column 105, Line 26, "Ethyl (2E4E,6E)"
should be --Ethyl (2E,4E,6E)--

Column 105, Line 34, "0.011mL" should be --0.01mL --

Column 106, Line 14, "2,4.6" should be --2,4,6--

Column 106, Line 31, "743-Ethoxy"
should be --7-(3-Ethoxy --

Column 106, Line 58, "2.19-(m, 2H)"
should be --2.19 (m, 2H)--

Column 106, Line 58, "2.40 (r q" should be --2.40 (br q --

Column 106, Line 63, "4,4-dimethylethoxy"
should be --4,4-dimethyl-6-ethoxy --

Column 106, Line 64, "methyl-2.4"
should be --methyl-2,4--

Column 107, Line 26, "3-(4-dimethyl"
should be --3-(4,4-dimethyl --

Column 107, Line 28, "2,4.6" should be --2,4,6--

Column 107, Line 40, "7.02-(s, 1H)."
should be --7.02 (s, 1H).--

Column 108, Line 19, "1.111 mmol"
should be --1.11 mmol--

Column 108, Line 28, "(4,$dimethyl"
should be --(4,4-dimethyl --

Column 108, Line 36, "(t; 3H" should be --(t, 3H --

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 114, Line 50,

" 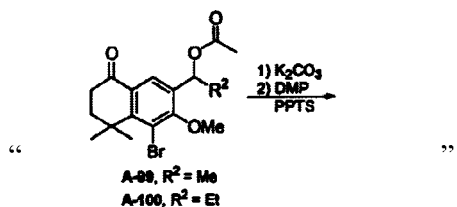 "

should be -- 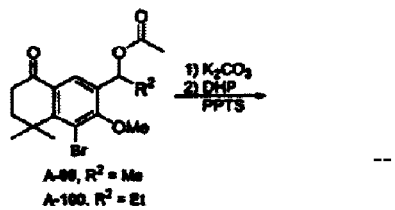 --

Column 115, Lines 36-40 in the reaction scheme,

" 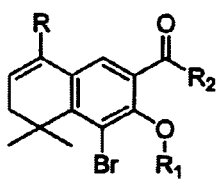 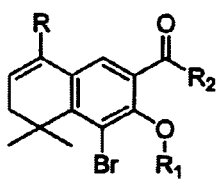 "

UNITED STATES PATENT AND TRADEMARK OFFICE
CERTIFICATE OF CORRECTION

PATENT NO.      : 6,887,896 B1
APPLICATION NO. : 10/696748
DATED           : May 3, 2005
INVENTOR(S)     : Beard et al.

It is certified that error appears in the above-identified patent and that said Letters Patent is hereby corrected as shown below:

Column 117, Lines 25-34 in the reaction scheme, should be --

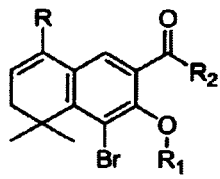

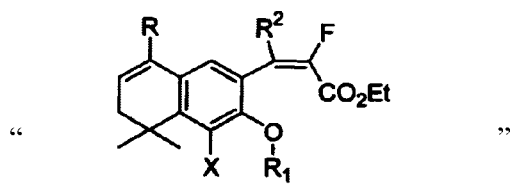

"  "  should be --

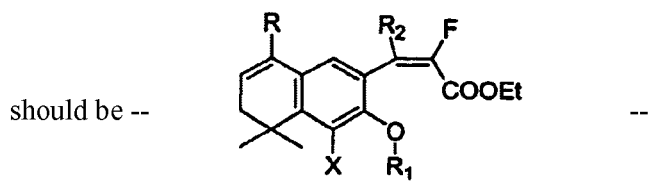

--

Column 118, in the reaction scheme row 1,

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

" 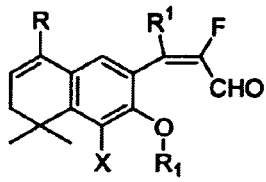

A-146 (R=i-Pr, R₁=Me, R₂=Me, X=Br)
A-147 (R=i-Pr, R₁=Et, R₂=Me, X=Br)
A-148 (R=i-Pr, R₁=Et, R₂=Et, X=Br)
A-149 (R=i-Pr, R₁=Et, R₂=i-Pr, X=Br)
A-150 (R=i-Pr, R₁=i-Pr, R₂=Me, X=Br)
A-151 (R=i-Pr, R₁=n-Pr, R₂=Me, X=Br)
A-152 (R=t-Bu, R₁=Et, R₂=Me, X=Br)
A-153 (R=t-Bu, R₁=i-Pr, R₂=Me, X=Br)
A-154 (R=s-Bu, R₁=Et, R₂=Et, X=Br)
A-155 (R=i-Pr, R₁=Et, R₂=Me, X=Cl)
A-156 (R=i-Pr, R₁=Et, R₂=Et, X=Cl)
"

should be --
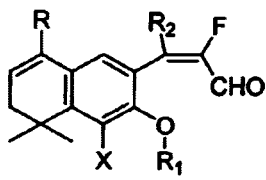

A-146 (R=i-Pr, R₁=Me, R₂=Me, X=Br)
A-147 (R=i-Pr, R₁=Et, R₂=Me, X=Br)
A-148 (R=i-Pr, R₁=Et, R₂=Et, X=Br)
A-149 (R=i-Pr, R₁=Et, R₂=i-Pr, X=Br)
A-150 (R=i-Pr, R₁=i-Pr, R₂=Me, X=Br)
A-151 (R=i-Pr, R₁=n-Pr, R₂=Me, X=Br)
A-152 (R=t-Bu, R₁=Et, R₂=Me, X=Br)
A-153 (R=t-Bu, R₁=i-Pr, R₂=Me, X=Br)
A-154 (R=s-Bu, R₁=Et, R₂=Et, X=Br)
A-155 (R=i-Pr, R₁=Et, R₂=Me, X=Cl)
A-156 (R=i-Pr, R₁=Et, R₂=Et, X=Cl)
--

Column 119, Line 25, "1-2 g" should be --12g--

Column 124, Line 31, "2.881H)" should be --2.88 (m, 1H)--

Column 124, Line 47, "(in, 3H)" should be --(m, 3H)--

Column 124, Line 60, "(r, 2H)" should be --(m, 2H)--

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 125, Line 1, "3, dihydro"
should be --3,4-dihydro --

Column 125, Line 25, "1'-dimethyl
should be --1,1-dimethyl --

Column 126, Line 35, "1 µl-dimethyl"
should be --1,1-dimethyl--

Column 126, Line 66, "r purification"
should be --after purification--

Column 127, Line 4, "7.34 (s," should be --7.34 (s,1H)--

Column 127, Line 12, "µl" should be --mL--

Column 127, Line 66, "(s,1H," should be --(s,1H),--

Column 128, Line 49, "$^1$H NM" should be --$^1$H NMR--

Column 129, Line 25, "2.3 µmmol"
should be --2.3 mmol--

Column 129, Line 65, "3.84.1" should be --3.8-4.1--

Column 130, Line 13, "3.63.9" should be --3.6-3.9--

Column 130, Line 15, "614" should be --6H--

Column 130, Line 30, "JF7.0 Hz"
should be --J=7.0 Hz--

Column 130, Line 44, "3.904.10 (n"
should be --3.90-4.10 (m --

Column 130, Line 47, "8-isoprpyl"
should be --8-isopropyl --

Column 130, Line 63, "butyl-1-3-ethoxy"

UNITED STATES PATENT AND TRADEMARK OFFICE
CERTIFICATE OF CORRECTION

| | | |
|---|---|---|
| PATENT NO. | : 6,887,896 B1 | Page 12 of 14 |
| APPLICATION NO. | : 10/696748 | |
| DATED | : May 3, 2005 | |
| INVENTOR(S) | : Beard et al. | |

It is certified that error appears in the above-identified patent and that said Letters Patent is hereby corrected as shown below:

should be -- butyl-3-ethoxy --

Column 131, Line 24, "3.904.10"
should be --3.90-4.10--

Column 131, Line 58, "3.894.05"
should be --3.89-4.05--

Column 132, Line 1, "2(I)-pyrimidinone"
should be --2(*1H*)-pyrimidinone --

Column 132, Line 21, "(r, 4H)" should be --(m, 4H)--

Column 132, Line 44, "(2E>3" should be --(2E)3--

Column 134, Line 13, "24-enal" should be --2-enal--

Column 135, Line 51, "2-yl)1-6" should be --2-yl)-6--

Column 136, Line 4, "4E,6)" should be --4E,6E)--

Column 136, Line 18, "0.8 Hz" should be --J=4.8Hz--

Column 136, Line 44, "7-(bromo"
should be --7-(4-bromo --

Column 136, Line 45, "2-yl)1)-6-fluoro"
should be --2-yl)-6-fluoro--

Column 138, Line 13, "30.94" should be --δ 0.94--

Column 138, Line 17, "(s, if)" should be --(s, 1H)--

Column 139, Line 37, "2E" should be --2Z--

Column 139, Line 67, "3.84.0" should be --3.8-4.0--

Column 140, Line 18, "methyl" should be --dimethyl--

Column 145, Line 67, in Claim 1, below the structure "$R^4$" should be --$R_4$--

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

Column 147, Line 40, claim no.21 21),

"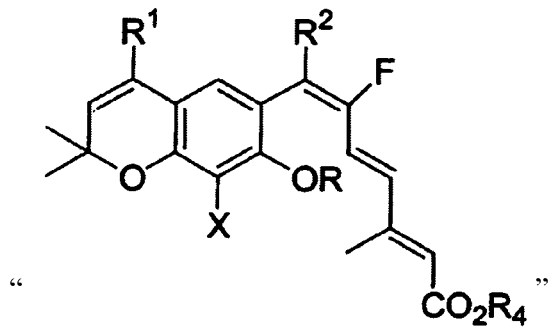"

should be --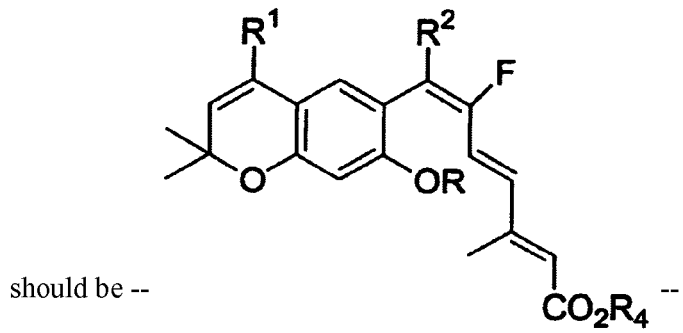--

Column 149, claim no. 42,

UNITED STATES PATENT AND TRADEMARK OFFICE
CERTIFICATE OF CORRECTION

PATENT NO. : 6,887,896 B1
APPLICATION NO. : 10/696748
DATED : May 3, 2005
INVENTOR(S) : Beard et al.

It is certified that error appears in the above-identified patent and that said Letters Patent is hereby corrected as shown below:

" 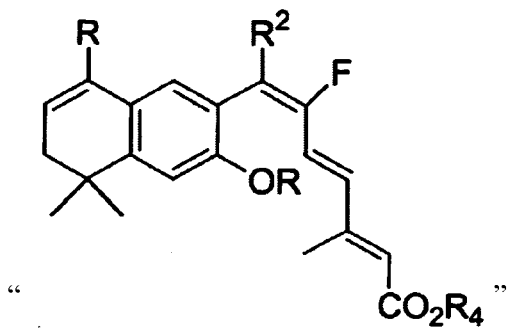 "

should be -- 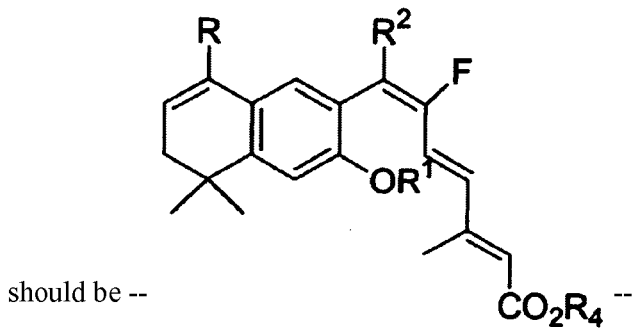 --

Signed and Sealed this

Twenty-fourth Day of October, 2006

JON W. DUDAS
*Director of the United States Patent and Trademark Office*

Disclaimer

6,887,896—Richard L. Beard, Newport Beach, CA (US); Tien T. Duong, Irvine, CA (US); Janet A. Takeuchi, Anaheim, CA (US); Ling Li, Irvine, CA (US); Kwok Yin Tsang, Irvine, CA (US); Xiaoxia Liu, Tustin, CA (US); Jayasree Vasudevan, Anaheim, CA (US); Liming Wang, Irvine, CA (US); Santosh C. Sinha, Irvine, CA (US); Haiqing Yuan, Irvine, CA (US); Roshantha A. Chandraratna, Laguna Hills, CA (US). 7-[(07-ALKOXY)-CHROM-3-EN-6-YL]-HEPTATRIENOIC ACID AND 7-[(3-ALKOXY)-5,6-DIHYDRONAPHTHALEN-2YL]-HEPTATRIENCOIN ACID DERIVATIVES HAVING SERUM GLUCOSE REDUCING ACTIVITY. Patent dated May 3, 2005. Disclaimer filed August 8, 2011, by the assignee, Allergan, Inc., Irvine, CA (US).

Hereby disclaims all of the claims 1-68 of said patent.
*(Official Gazette November 22, 2011)*